United States Patent
Pfau et al.

(10) Patent No.: US 12,421,218 B2
(45) Date of Patent: Sep. 23, 2025

(54) SUBSTITUTED PYRAZINE-CARBOXAMIDE DERIVATIVES

(71) Applicant: Boehringer Ingelheim International GmbH, Ingelheim am Rhein (DE)

(72) Inventors: Roland Pfau, Mittelbiberach (DE); Georg Dahmann, Biberach (DE); Johann Faustus Du Hoffmann, Biberach an der Riss (DE); Kai Gerlach, Mittelbiberach (DE); Riccardo Giovaninni, Biberach an der Riss (DE); Christoph Hohn, Freiburg (DE); Stefan Just, Biberach an der Riss (DE); Thorsten Lehmann, Biberach (DE); Anton Pekcec, Biberach (DE); Stefan Peters, Biberach an der Riss (DE); Julia Schlichtiger, Biberach (DE); Heiko Sommer, Warthausen (DE); Christian Specker, Hochdorf (DE); Dieter Wiedenmayer, Biberach an der Riss (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 18/804,311

(22) Filed: Aug. 14, 2024

(65) Prior Publication Data
US 2024/0417394 A1 Dec. 19, 2024

Related U.S. Application Data

(63) Continuation of application No. 18/384,393, filed on Oct. 27, 2023.

(30) Foreign Application Priority Data

Oct. 28, 2022 (EP) .................................... 22204281

(51) Int. Cl.
C07D 403/12 (2006.01)
A61P 25/18 (2006.01)
C07D 405/14 (2006.01)

(52) U.S. Cl.
CPC ............ C07D 405/14 (2013.01); A61P 25/18 (2018.01); C07D 403/12 (2013.01)

(58) Field of Classification Search
CPC ...................... C07D 403/12; C07D 405/14
See application file for complete search history.

(56) References Cited

U.S. PATENT DOCUMENTS

2024/0174652 A1   5/2024   Pfau et al.

FOREIGN PATENT DOCUMENTS

| WO | 2004072047 A1 | 8/2004 |
| WO | 2016054491 A1 | 4/2016 |
| WO | 2019138017 A1 | 7/2019 |
| WO | 2021028512 A1 | 2/2021 |

OTHER PUBLICATIONS

Berge, Stephen et al. "Pharmaceutical Salts" Journal of Pharmaceutical Sciences, 1977, vol. 66, 1-19.
Blackshaw, L. Ashley et al. "Metabotropic glutamate receptors as novel therapeutic targets on visceral sensory pathways" Frontiers in Neuroscience, 2011, vol. 5, Article 40, 1-7.
Chang, Hee Jin et al. Metabotropic Glutamate Receptor 4 Expression in Colorectal Carcinoma and its Prognostic Significance, Clin. Cancer Res., 2005, vol. 11, 3288-3295.
Conn, P. Jeffrey et al., "Pharmacology and Functions of Metabolic Glutamate Receptors", Annual Review Pharmacol. Toxicol, 1997, vol. 37, 205-237.
Davis, Matthew et al. "Role of mGluR4 in acquisition of fear learning and memory", Neuropharmacology, 2013, vol. 66, 365-372.
Iscru, E. et al. "Improved spatial learning is associated with increased hippocampal but not prefrontal long-term potentiation in mGluR4 knockout mice", Genes Brain and Behavior, 2013, vol. 12, 615-625.
Isherwood, Sarah et al. "Selective and interactive effects of D2 receptor antagonism and positive allosteric mGluR4 modulation, on waiting impulsivity" Neuropharmacology, 2017, vol. 123, 249-260.
Makoff, Andrew et al. "Molecular characterization and localization of human metabotropic glutamate receptor type 4", Molecular Brain Research, 1996, vol. 37, 239-248.

(Continued)

*Primary Examiner* — Brian E McDowell
(74) *Attorney, Agent, or Firm* — David L. Kershner

(57) ABSTRACT

The present invention relates to compounds of formula I

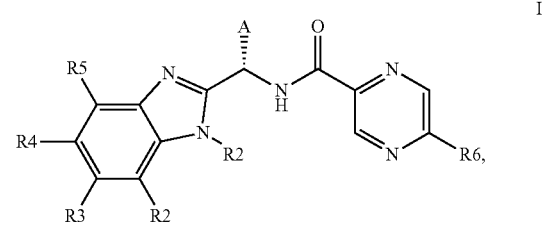

a process for their manufacture, pharmaceutical compositions containing them and their use in therapy, particularly in the treatment and/or prevention of conditions having an association with the function of metabotropic glutamate receptor subtype 4 (mGluR4). A, $R^1$, $R^2$, $R^3$, $R^4$, $R^5$ and $R^6$ have meanings given in the description.

14 Claims, No Drawings

(56) References Cited

OTHER PUBLICATIONS

Szczurowska, E. et al. "Positive Allosteric Modulator of MGluR4 PHCCC Exhibits Proconvulsant Action in Three Models of Epileptic Seizures in Immature Rats," Physiol., Res., 2012, vol. 61, 619-628.
Marino, Michael et al. "Modulation of Inhibitory Transmission in the Rat Globus Pallidus by Activation of mGluR4", Ann NY Acad. Sci., 2003, vol. 1003, 435-437.
Page, Amanda et al. "Peripheral neural targets in obesity", British Journal of Pharmacology, 2012, 166, 1537-1558.
Nunez-Salces, Maria et al, "Nutrient sensing components of the mouse stomach and the gastric ghrelin cell", Neurogastroenterol., 2020, vol. 32, 1-13.
Schoepp, Darryle "Unveiling the Functions of Presynaptic Metabotropic Glutamate Receptors in the Central Nervous System," Journal of Pharmacology and Experimental Therapeutics, 2001, vol. 299, No. 1, 12-20.
Uhera, Shunseuke, et al, Metabotropic Glutamate Receptor Type 4 is Involved in Autoinhibitor Cascade for Glucagon Secretion by a-cells of Islet of Langerhans, Diabetes, 2004, vol. 53, 998-1006.
Unitt, John et al. "Discovery of small molecule human FPR1 receptor antagonists", Bioorganic & Medicinal Chem Letters, 2011, vol. 21, 2991-2997.
International Search Report PCT/EP2023/080028 mailed Feb. 5, 2024.

SUBSTITUTED PYRAZINE-CARBOXAMIDE DERIVATIVES

FIELD OF THE INVENTION

The present invention relates to substituted pyrazine-carboxamide derivatives, pharmaceutical compositions containing them and their use in therapy, particularly in the treatment and/or prevention of neuronal and non-neuronal conditions having an association with mGluR4 function and/or in the treatment of obesity by means of mGluR4 modulation.

BACKGROUND OF THE INVENTION

L-glutamate (here referred to as glutamate) is among the most abundant excitatory neurotransmitters within the vertebrate brain. Malfunction of the brain glutamate system often leads to neurological or psychiatric disorders. Therefore, modulation of the glutamatergic system is considered as attractive therapeutic direction.

Glutamate acts via different types of glutamate receptor, which are located on the cell surface. Glutamate receptors include AMPA receptors, kainate receptors, NMDA receptors, and metabotropic glutamate receptors. The metabotropic glutamate receptors (mGluR) exert their action via coupling to G proteins and activation of second messenger systems.

The mGluR subtypes are classified into three groups (distinction by sequence homology, pharmacology, second messenger system) with Group III being the largest group (mGluR4, mGluR6, mGluR7, mGluR8) [Conn and Pin, Annu Rev Pharmacol Toxicol, 1997, 37: 205-237]. Group III mGlu receptors share mainly presynaptic expression Schoepp, Pharmacol Exp Ther, 2001, 299: 12-20) where they modulate glutamatergic as well as GABAergic transmission. Activation of Group III receptors (including mGluR4) reduces transmitter release due to its activation of the Gαi/o which leads to attenuated adenylate cyclase activity.

The mGluR4 receptor is mainly located in presynaptic endings of nerve endings. Expression of mGluR4 has been demonstrated in multiple brain regions with high expression within the basal ganglia and cerebellum among other brain regions. Due to expression of mGluR4 within relevant brain circuitries and its role to modulate transmitter release, mGluR4 modulators are considered to have impact on motor control (including Parkinsons Disease), impulse control, learning and memory, cognition, anxiety, pain, cerebellar functions, epilepsy, modulation of excitation/inhibition balance, which is of crucial importance for information processing (Marino et al. Ann NY Acad Sci, 2003, 1003: 435-437; Isherwood et al. Neuropharmacology 2017, 123: 249-260; Makoff et al. Mol Brain Res, 1996, 37: 239-248; Davis et al. Neuropharmacology 2013, 66: 365-372; Iscru et al. Genes Brain Behav. 2013, 12: 615-625; Szczurowska and Mareš, Physiol Res, 2012, 61: 619-628) but is not limited to these actions.

As mGluR4 has been reported to be also expressed in peripheral tissue like islets of Langerhans, but not limited to, it is considered that antagonists of mGluR4 function may also have therapeutic effect in disorders including but not limited to metabolic disorders, gastro-intestinal disorders, and cancer (Chang et al. Clin Cancer Res. 2005, 11: 3288-3295; Uhera et al. Diabetes 2004, 53: 998-1006; Nunez-Salces et al. Neurogastroenterol Motil 2020, 32).

As mGluR4 has been reported to be also expressed in vagal afferents as well as within central satiety pathways and brain circuits, it is considered that antagonists of mGluR4 function may also have therapeutic effect in disorders including but not limited to overweight and obesity (Blackshow et al. Front Neurosci 2011, 5: 40; 1-7; Page et al. Br J Pharmacol. 2012, 166: 1537-1558).

WO21028512 describes arylsulfonamides as mGluR4 NAMs. However, the activity of those compounds seems too low to be applicable as a drug, especially so since acidic arylsulfonamides might additionally be subject to efflux at the blood brain barrier, which limits their brain exposure for CNS applications.

DETAILED DESCRIPTION OF THE INVENTION

The present invention provides novel substituted pyrazine-carboxamide derivatives that unexpectedly are potent mGluR4 negative modulators, namely compounds of formula I Embodiment 1

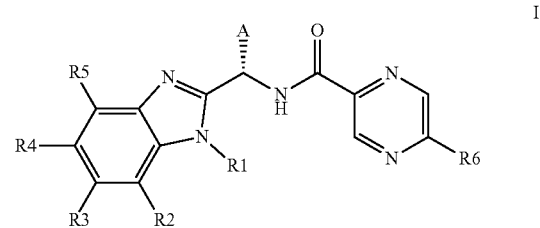

in which
A represents $C_1$-$C_6$-alkyl, $C_3$-$C_6$-cycloalkyl, $C_3$-$C_5$-cycloalkyl-$C_1$-$C_2$-alkyl-, $C_1$-$C_3$-alkyl-O—$C_1$-$C_3$-alkyl-, 4-6-membered heterocycloalkyl-, 4-6-membered heterocycloalkyl-$C_1$-$C_3$-alkyl-, which latter groups are optionally substituted with 1-4 substituents chosen from $C_1$-$C_4$-alkyl, $C_1$-$C_4$-alkoxy, hydroxy, fluoro;

$R^1$ represents $C_1$-$C_7$-alkyl, $C_1$-$C_3$-alkyl-O— $C_1$-$C_3$-alkyl-, $C_3$-$C_7$-cycloalkyl, 4-6-membered heterocycloalkyl, $C_3$-$C_7$-cycloalkyl-$C_1$-$C_3$-alkyl-, 4-6-membered heterocycloalkylmethyl-, $C_5$-$C_6$-heterocycloalkylethyl-, which latter groups are optionally substituted with 1-4 substituents chosen from $C_1$-$C_4$-alkyl, $C_1$-$C_4$-alkoxy, $C_3$-$C_7$-cycloalkoxy, hydroxy, fluoro;

$R^2$, $R^3$, $R^4$ and $R^5$ independently of each other represent hydrogen, halogen, cyano, $C_1$-$C_4$-alkyl, $C_1$-$C_3$-alkyl-O—$C_1$-$C_3$-alkyl-, $C_3$-$C_6$-cycloalkyl, 4-6-membered $C_4$-$C_6$-heterocycloalkyl, $C_1$-$C_4$-alkoxy-, $C_3$-$C_6$-cycloalkoxy-, which latter six groups are optionally substituted with 1-4 substituents chosen from $C_1$-$C_4$-alkyl, $C_1$-$C_4$-alkoxy, hydroxy, fluoro; provided that at least one of the groups $R^2$, $R^3$, $R^4$ and $R^5$ is not hydrogen;

$R^6$ represents halogen, $C_1$-$C_3$-alkyl optionally substituted with 2-3 fluorine atoms;

or a physiologically acceptable salt thereof.

In another embodiment, in the general formula I, according to any one of the preceding embodiments
A represents $C_1$-$C_3$-alkyl, $C_3$-$C_6$-cycloalkyl, $C_3$-$C_5$-cycloalkylmethyl-, tetrahydrofuranyl-, tetrahydropyranyl-, 1,4-dioxanyl, tetrahydrofuranylmethyl-, tetrahydropyranylmethyl-, 1,4-dioxan-ylmethyl-, $C_1$-$C_2$-alkyl-O—$C_1$-$C_2$-alkyl-, which latter groups are optionally substituted with 1-4 substituents chosen from methyl, methoxy, hydroxy, fluoro.

In a further embodiment, in the general formula I, according to any one of the preceding embodiments $R^1$ represents $C_1$-$C_3$-alkyl, $C_1$-$C_2$-alkyl-O— $C_1$-$C_3$-alkyl-, $C_3$-$C_4$-cycloalkyl, $C_4$-$C_5$-heterocycloalkyl, $C_3$-$C_4$-cycloalkyl-O—$C_1$-$C_3$-alkyl-, which latter groups are optionally substituted with 1-4 substituents chosen from $C_1$-$C_4$-alkyl, $C_1$-$C_4$-alkoxy, $C_3$-$C_4$-cycloalkoxy, hydroxy, fluoro.

In a further embodiment, in the general formula I, according to any one of the preceding embodiments $R^2$, $R^3$, $R^4$ and $R^5$ independently of each other represent hydrogen, fluoro, chloro, bromo, cyano, methyl, cyclopropyl, methoxy, which latter three groups are optionally substituted with 2-3 fluoro substituents, provided that at least one of the groups $R^2$, $R^3$, $R^4$ and $R^5$ is not hydrogen.

In a further embodiment, in the general formula I, according to any one of the preceding embodiments $R^6$ represents $C_1$-$C_3$-alkyl optionally substituted with 2-3 fluorine atoms.

In another embodiment, in the general formula I, according to any one of the preceding embodiments A represents a group chosen from the group comprising

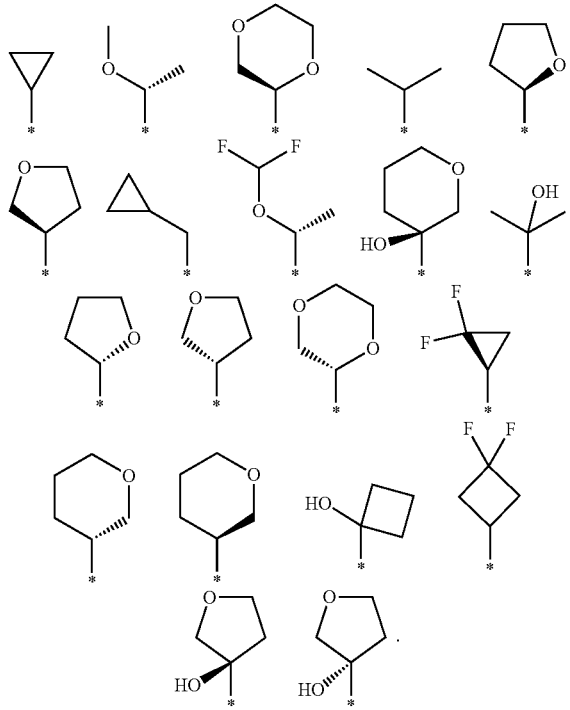

In another embodiment, in the general formula I, according to any one of the preceding embodiments $R^1$ represents a substituent chosen from the group consisting of

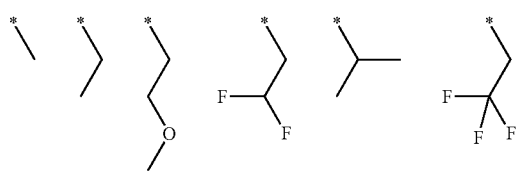

-continued

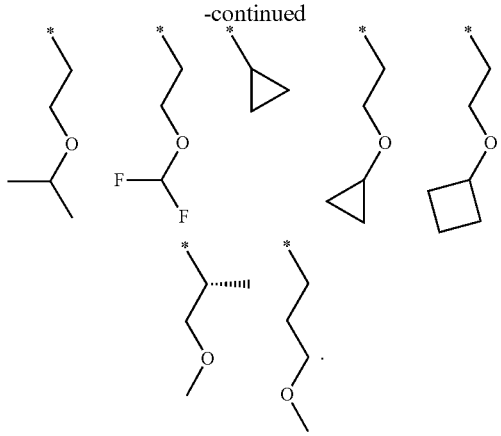

In another embodiment, in the general formula I, according to any one of the preceding embodiments $R^2$ represents hydrogen.

In another embodiment, in the general formula I, according to any one of the preceding embodiments $R^3$ represents hydrogen, fluoro, bromo and trifluromethyl.

In another embodiment, in the general formula I, according to any one of the preceding embodiments $R^4$ represents hydrogen, fluoro, chloro, bromo, cyano, methyl, trifluromethyl, $CF_3O$—, and $CHF_2O$—.

In another embodiment, in the general formula I, according to any one of the preceding embodiments $R^5$ represents hydrogen, fluoro, chloro, methyl, ethyl, cyclopropyl and methoxy.

In another embodiment, in the general formula I, according to any one of the preceding embodiments $R^6$ represents methyl, trifluromethyl and —$CF_2H$.

Compounds of the present invention are potent mGluR4 negative modulators inhibiting the function of mGluR4 thereby blocking glutamate induced intracellular cAMP lowering.

The present invention thus provides compounds for use in the treatment of a mGluR4 mediated disorder.

The present invention further provides methods of treating a mGluR4 mediated disorder in a human subject comprising administering to the subject a compound or composition of a compound of the present invention or a pharmaceutically acceptable salt thereof.

In one aspect, the invention relates to a method for treating a condition for which reduced mGluR4 activity can reduce the severity of the condition, by administering a compound inhibiting mGluR4 function, such as a compound as described herein that inhibits glutamate induced intracellular cAMP lowering. Described herein are compounds, which are antagonists of mGluR4 function that have a measured $IC_{50}$ for inhibition of mGluR4 of 100 nanomolar, preferred 50 nM or less.

In another aspect, the compounds described herein, which are antagonists of mGluR4 function can be used to inhibit a function of mGluR4, for example a mGluR4-mediated glutamate induced intracellular cAMP lowering. In some embodiments, the compounds described herein can be used to inhibit a mGluR4 mediated glutamate induced intracellular cAMP lowering in vitro, for example in cells in culture. In other embodiments, the compounds described herein can be used to inhibit a mGluR4 mediated glutamate induced intracellular cAMP lowering in vivo.

Definitions

Terms not specifically defined herein should be given the meanings that would be given to them by one skilled in the art in the light of the disclosure and the context.

The terms "negative modulator", "antagonist" and "inhibitor" are used interchangeably to refer to an agent that decreases or suppresses a biological activity such as the reduction of an activity of a receptor, and comprise negative allosteric modulators (NAM). mGluR4 receptors as described herein include homomultimeric and heteromultimeric structures (e.g. homomultimeric mGluR4 and heteromeric mGluR4-mGluR2). Inhibitors of mGluR4 function include inhibitors having any combination of the structural and/or functional properties disclosed herein.

An "effective amount" of a (mGluR4) antagonist, with respect to the subject methods of inhibition or treatment, refers to an amount of the antagonist in a preparation which, when applied as part of a desired dosage regimen brings about a desired clinical or functional result. Without being bound by theory, an effective amount of a mGluR4 antagonist for use in the methods of the present invention includes an amount of a mGluR4 antagonist effective to decrease one or more in vitro or in vivo functions of a mGluR4 receptor. Exemplary functions include, but are not limited to, changed intracellular cAMP, or synaptic transmitter release, or changed neuronal activity or modulation of impulsive behavior. Compounds that antagonize mGluR4 function include compounds that antagonize an in vitro or in vivo functional activity of mGluR4. When a particular functional activity is only readily observable in an in vitro assay, the ability of a compound to inhibit mGluR4 function in that in vitro assay serves as a reasonable proxy for the activity of that compound. In certain embodiments, an effective amount is an amount sufficient to inhibit a mGluR4-mediated cellular function.

The mGluR4 antagonists for use in the methods of the present invention may be characterized according to their activity, or lack of activity, against one or more receptors. When other receptors are referred to, inhibition of a function of such other receptors is defined similarly. For example, inhibition of a receptor or an activity of a receptor means the antagonist inhibits one or more functional activities of the other receptor. Such functions include, for example, signal transduction across a cellular membrane and/or changes in the intracellular concentration of intracellular substances like cAMP mediated by the particular receptor and subsequent functions like e.g. neurotransmitter release.

The terms "compound" and "agent" are used interchangeably to refer to the negative modulators of the invention.

In the groups, radicals, or moieties defined below, the number of carbon atoms is often specified preceding the group, for example, C1-6-alkyl means an alkyl group or radical having 1 to 6 carbon atoms. In general, for groups comprising two or more subgroups, the last named subgroup is the radical attachment point, for example, the substituent "aryl-C1-3-alkyl-" means an aryl group which is bound to a C1-3-alkyl-group the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

Stereochemistry/Solvates/Hydrates

The compounds described herein can be chiral (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

Resolution of racemic mixtures of compounds can be carried out by any of numerous methods known in the art. An example method includes fractional recrystallizaion using a "chiral resolving agent" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S- and R-forms, or diastereomerically pure forms), 2-phenylglycinol, norephedrine, ephedrine, N-methylephedrine, cyclohexylethylamine, and 1,2-diaminocyclohexane.

Resolution of racemic mixtures can also be carried out by elution on a column packed with an optically active resolving agent (e.g., dinitrobenzoylphenylglycine). Suitable elution solvent composition can be determined by one skilled in the art. Compounds of the invention also include tautomeric forms, such as keto-enol tautomers.

Unless specifically indicated, throughout the specification and the appended claims, a given chemical formula or name shall encompass tautomers and all stereo, optical and geometrical isomers (e.g. enantiomers, diastereoisomers, E/Z isomers) and racemates thereof, as well as mixtures in different proportions of the separate enantiomers, mixtures of diastereoisomers, or mixtures of any of the foregoing forms where such isomers and enantiomers exist.

Compounds of the invention can also include all isotopes of atoms occurring in the intermediates or final compounds. For example, the compound of the invention may be radiolabeled with radioactive isotopes, such as for example tritium ($^3H$) or carbon-14 ($^{14}C$). All isotopic variations, whether radioactive or not, are intended to be encompassed within the scope of the present invention.

Salts

The phrase "pharmaceutically acceptable" is employed herein to refer to those compounds, materials, compositions, and/or dosage forms which are, within the scope of sound medical judgment, suitable for use without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid. Also included are the salts of amino acids such as arginate, and salts of organic acids like glucuronic or galactunoric acids (see, for example, Berge et al., "Pharmaceutical Salts", Journal of Pharmaceutical Science, 1977, 66, 1-19).

The neutral form of the compounds of the invention is preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Halogen

The term halogen generally denotes fluorine, chlorine, bromine and iodine.

Alkyl

The term "$C_1$-n-alkyl", wherein n is an integer from 2 to n, either alone or in combination with another radical denotes an acyclic, saturated, branched or linear hydrocarbon radical with 1 to n C atoms. For example the term $C_1$-$C_5$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Cycloalkyl

The term "C3-n-cycloalkyl", wherein n is an integer from 4 to n, either alone or in combination with another radical denotes a cyclic, saturated, unbranched hydrocarbon radical with 3 to n C atoms. For example, the term C3-7-cycloalkyl includes cyclopropyl, cyclobutyl, cyclopentyl, cyclohexyl and cycloheptyl.

Heterocycloalkyl

The term "heterocycloalkyl" means a saturated or unsaturated mono- or polycyclic-ring systems including aromatic ring system containing one or more heteroatoms selected from N, O or S(O)r, wherein r=0, 1 or 2, consisting of 3 to 14 ring atoms wherein none of the heteroatoms is part of the aromatic ring.

Many of the terms given above may be used repeatedly in the definition of a formula or group and in each case have one of the meanings given above, independently of one another.

According to the invention the compounds of general formula (I) are obtained by methods known per se, for example by the following methods:

(a) The preparation of a compound of general formula (I)

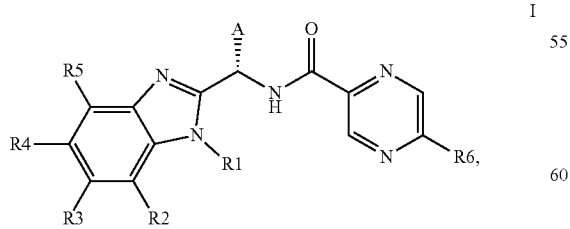

wherein A and $R^1$ to $R^6$ are defined as described in embodiment 1, and which may optionally be protected at any amino, hydroxy, carboxy or thiol groups through common protective groups such as for example those described in T. W. Greene, P. G. M. Wuts in "Protective Groups in Organic Synthesis", Wiley, 1991 and 1999, and protective groups which may be cleaved by methods known from the literature, is described in the examples or may be carried out for example according to combinations of reaction steps of the following formulae in Scheme 1.

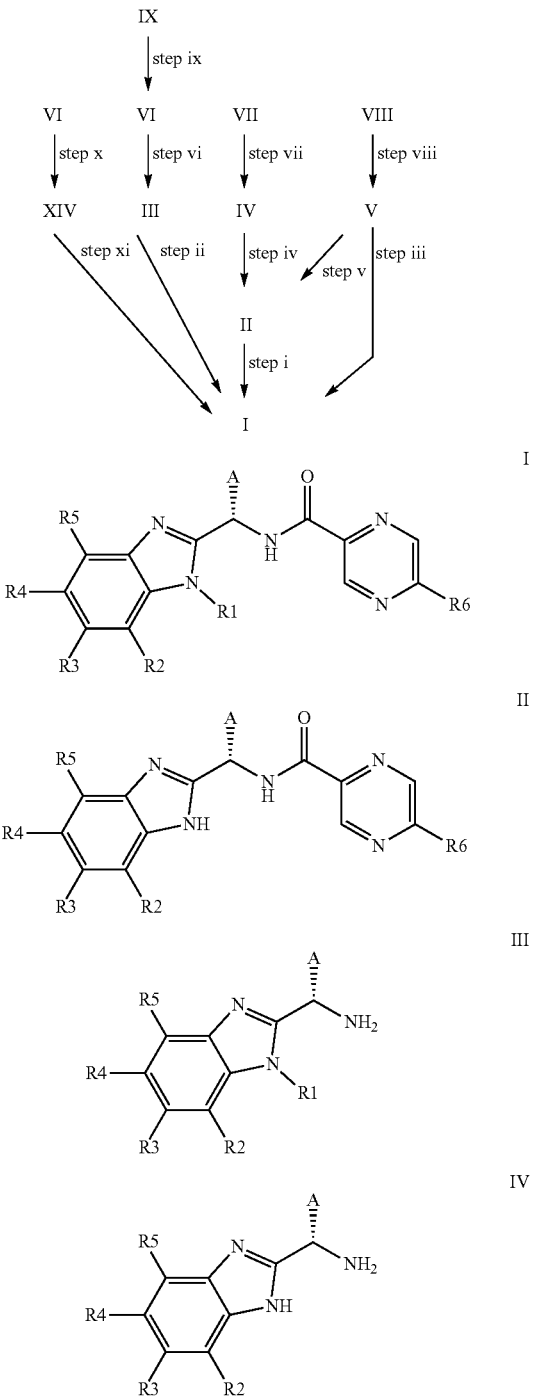

-continued

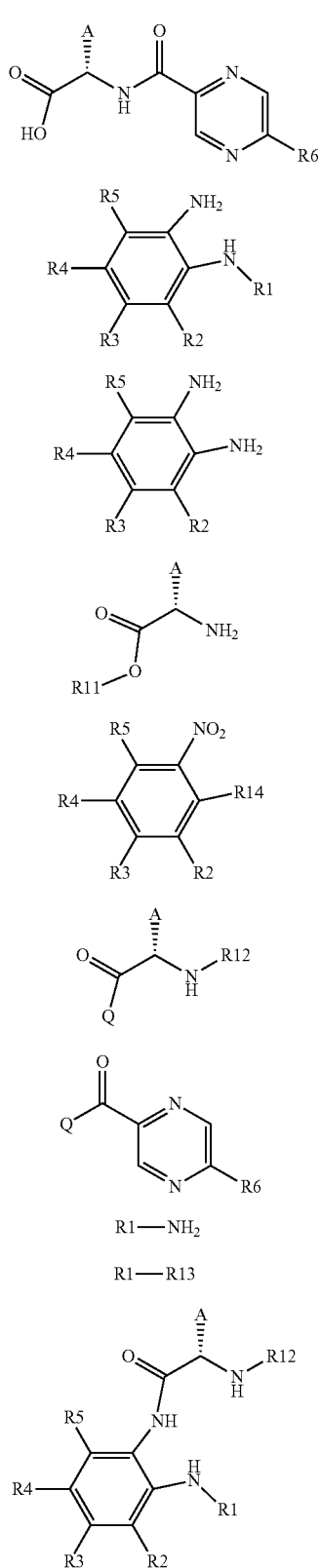

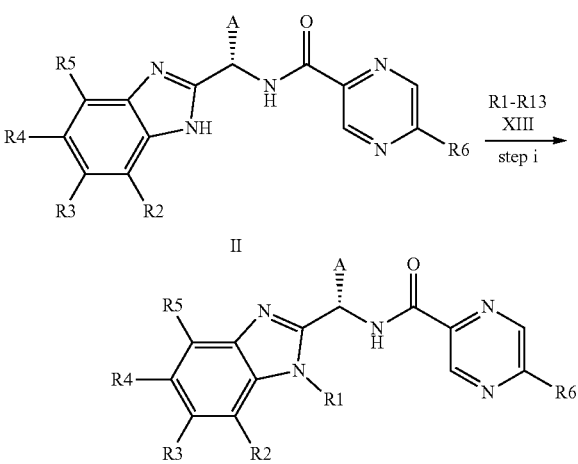

wherein
Q denotes a leaving group or a group which may be converted in-situ into a leaving group, such as for example a halogen atom, a hydroxy, $C_{1-4}$-alkyloxy, alkyloxycarbonyloxy, 4-pentafluorophenyloxy, nitrophenyloxy, a trichloromethyl or acyloxy group or together with the carbonyl group denotes an alkali carboxylate group, and R11 denotes a protective group for the carboxylate function known from the literature, such as for example a tert-butyl, methyl, ethyl, allyl or benzyl group, and R12 denotes a protective group for the amino function known from the literature, such as for example a tert-butoxycarbonyl, benzyloxycarbonyl or a trifluoroacetyl group, and R13 denotes a leaving group for alkylating reactions, such as for example an iodine or bromine atom or tosylate or mesylate group, and R14 denotes a leaving group for nucleophilic aromatic substitution reactions, such as for example a fluorine or chlorine atom.

The reaction step i (substitution) shown in Scheme 1 may be carried out in the manner described in the Examples or according to the conditions known from the literature, for example as follows:

Compounds of general formula II are mixed with compounds of general formula XIII in a solvent such as dichloromethane, chloroform, carbon tetrachloride, diethylether, tetrahydrofuran, 1,4-dioxane, benzene, toluene, acetonitrile, dimethylformamide, dimethylsulfoxide, sodium hydroxide solution or sulfolane, optionally in the presence of an inorganic or organic base like potassium carbonate, sodium hydride, triethylamine or Hunig's base at temperatures between −20 and 200° C., but preferably at temperatures between −10 and 100° C.

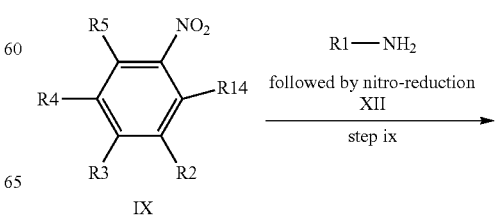

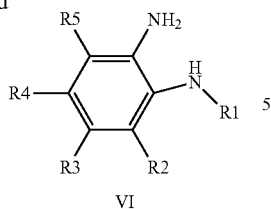

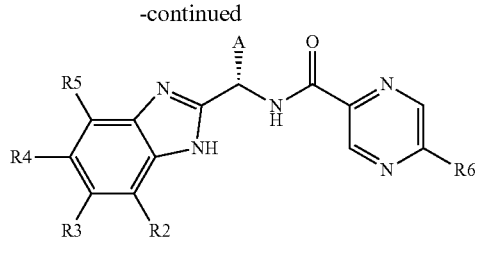

The reaction step ix (substitution followed by nitro-reduction) shown in Scheme 1 may be carried out in the manner described in the Examples or according to the conditions known from the literature, for example as follows:

Substitution of a substrate IX with an amine XII like described above, followed by a nitro-reduction like described below:

A nitro reduction to an amine group can be achieved in an aqueous solvent, e.g. in water, isopropanol/water, tetrahydrofuran/water or 1,4-dioxane/water, or in a solvent such as diethylether, tetrahydrofuran, 1,4-dioxane, benzene, toluene, in the presence of an acid such as trifluoroacetic acid, hydrochloric acid or sulfuric acid and in the presence of a reductive metal like zinc, iron, magnesium or calcium or in the presence of an reductive agent like triphenyl phosphine or lithium alanate, at temperatures between −40 and 100° C., preferably at temperatures between −10 and 50° C. Alternatively, reduction can be achieved with hydrogen in the presence of a catalyst such as Palladium/charcoal, Raney nickel or Platinum in a solvent such as tetrahydrofuran, methanol, ethanol, ethyl acetate, dimethylformamide, dimethylformamide/acetone or glacial acetic acid, optionally with the addition of an acid such as hydrochloric acid at temperatures between −20 and 50° C., but preferably at 0° C. to ambient temperature, and at a hydrogen pressure of 1 to 7 bar, but preferably, 1 to 5 bar.

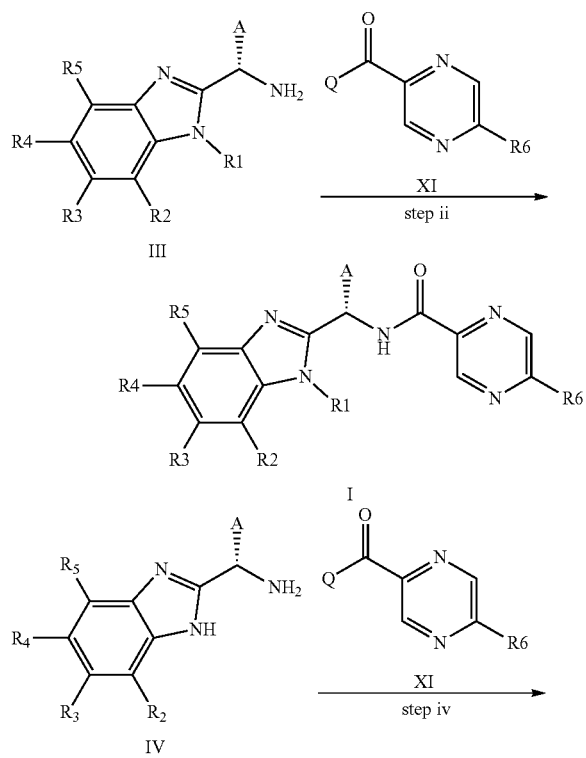

The reaction steps ii and iv (acylation) may be carried out in the manner described in the Examples or according to the conditions known from the literature, for example as follows:

by acylating an amine (III or IV) with an optionally activated carboxylic acid (XI):

The acylation is conveniently carried out with a corresponding halide or anhydride in a solvent such as dichloromethane, chloroform, carbon tetrachloride, diethylether, tetrahydrofuran, 1,4-dioxane, benzene, toluene, acetonitrile, dimethylformamide, dimethylsulfoxide, sodium hydroxide solution or sulfolane, optionally in the presence of an inorganic or organic base like potassium carbonate, sodium hydride, triethylamine or Hünig's base at temperatures between −20 and 200° C., but preferably at temperatures between −10 and 100° C.

The acylation may however also be carried out with the free acid optionally in the presence of an acid-activating agent or a dehydrating agent, for example in the presence of ethyl-1-ethoxy-1,2-dihydroquinoline-1-carboxylate, isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, propanephosphonic acid cycloanhydride, N,N'-dicyclohexylcarbodiimide, N,N'-dicyclohexylcarbodiimide/camphorsulphonic acid, N,N'-dicyclohexylcarbodiimide/N-hydroxysuccinimide or 1-hydroxy-benzotriazole, N,N'-carbonyldiimidazole, O-(benzotriazol-1-yl)-N,N,N',N'-tetramethyl-uronium tetrafluoroborate/N-methylmorpholine, O-(benzotriazol-1-yl)-N,N,N',N'-tetramethyl-uronium tetrafluoroborate/N-ethyldiisopropylamine, O-(7-azabenzotriazol-1-yl)-N,N,N',N'-tetramethyluronium-hexafluorophosphate/N-methylmorpholine, O-pentafluorophenyl-N,N,N',N'-tetramethyluronium-hexafluorophosphate/triethylamine, N,N'-thionyldiimidazole or triphenylphosphine/carbon tetrachloride, optionally with the addition of an auxiliary base such as sodium hydroxide solution, caesium, potassium or sodium carbonate or hydrogen carbonate or an amine base such as pyridine, triethylamine, N-methylmorpholine or diisopropylethylamine, at temperatures between −20 and 200° C., but preferably at temperatures between −10 and 160° C.

Other methods of amide coupling are described for example in P. D. Bailey, I.D. Collier, K. M. Morgan in "Comprehensive Functional Group Interconversions", Vol. 5, page 257ff., Pergamon 1995, or in the Houben-Weyl Supplementary Volume 22, published by Thieme, 2003, and the literature cited therein.

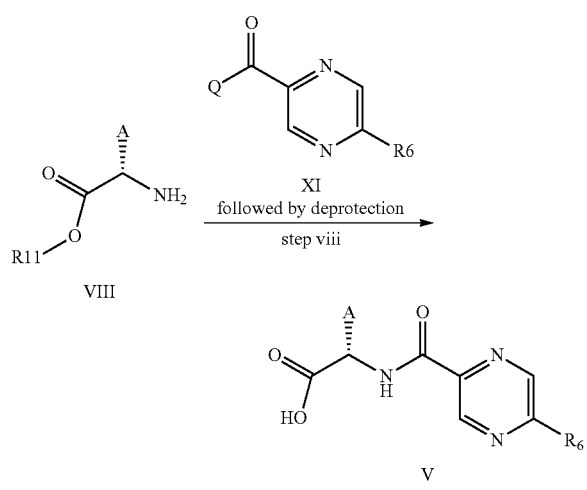

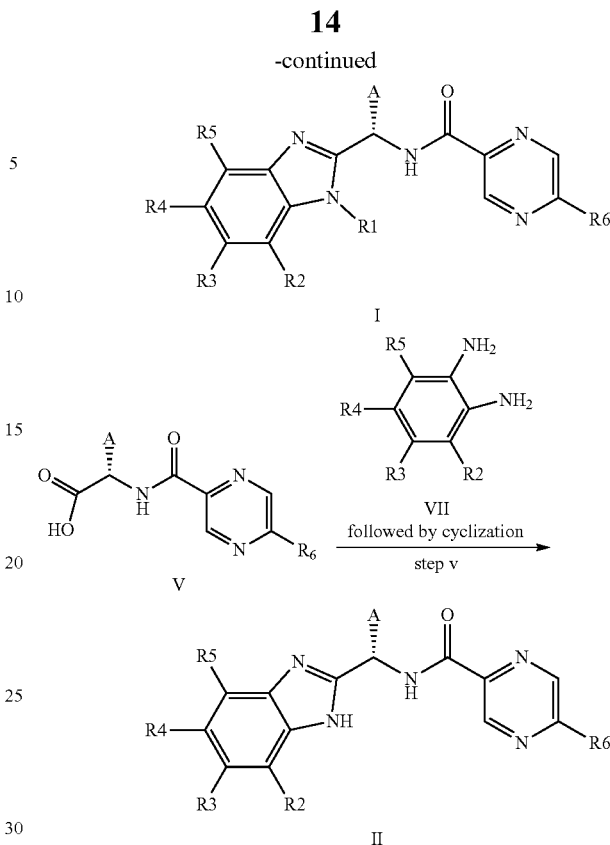

The reaction steps viii (acylation followed by deprotection) may be carried out in the manner described in the Examples or according to the conditions known from the literature, for example as follows:

Acylation of an amine-carrying substrate VIII with a reagent XI like described above, followed by cleaving a protective group like described below:

Any protecting group used may optionally subsequently be cleaved for example by hydrolysis in an aqueous solvent, e.g. in water, isopropanol/water, tetrahydrofuran/water or 1,4-dioxane/water, in the presence of an acid such as trifluoroacetic acid, hydrochloric acid or sulfuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 1° and 50° C.

However, a benzyl, methoxybenzyl or benzyloxycarbonyl group is cleaved hydrogenolytically, for example, e.g. with hydrogen in the presence of a catalyst such as palladium/charcoal in a solvent such as tetrahydrofuran, methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 1 to 5 bar.

However, a protective group may also be cleaved by the methods described by T. W. Greene, P. G. M. Wuts in "Protective Groups in Organic Synthesis", Wiley, 1991 and 1999.

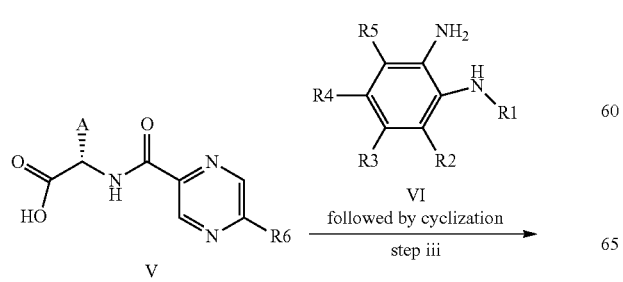

The reaction steps iii and v (acylation followed by cyclization) may be carried out in the manner described in the Examples or according to the conditions known from the literature, for example as follows:

Acylation of an amine-carrying substrate VI or VII with a free carboxylic acid V like described above, followed by cyclization like described below:

The cyclisation is conveniently carried out in a solvent or mixture of solvents such as ethanol, isopropanol, acetic acid, benzene, chlorobenzene, toluene, xylene, glycol, glycolmonomethylether, diethyleneglycol dimethylether, sulfolane, dimethylformamide or tetraline, dimethylsulfoxide, dichloromethane, chloroform, tetrachloromethane, for example at temperatures between 0 and 250° C., but preferably between 2° and 100° C., optionally in the presence of a condensing agent such as phosphorus oxychloride, thionyl chloride, sulfuryl chloride, sulfuric acid, p-toluenesulfonic acid, methanesulfonic acid, hydrochloric acid, phosphoric acid, polyphosphoric acid, acetic acid, acetic anhydride, N,N'-dicyclohexylcarbodiimide or optionally also in the presence of a base such as potassium methoxide or potassium tert-butoxide or in the presence of a metal salt like lithium bromide, aluminum bromide, zinc bromide or aluminum-doped montmorillonite clay. However, the cyclisation may also be carried out without a solvent and/or condensing agent.

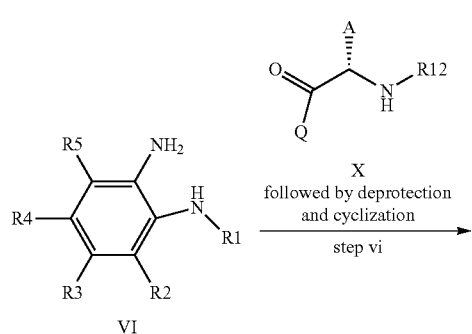

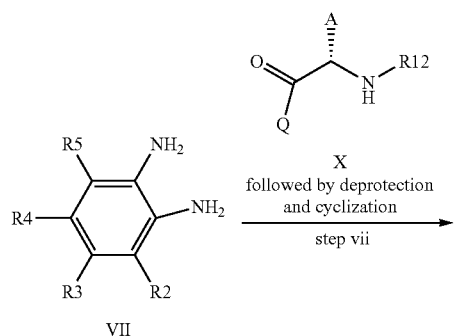

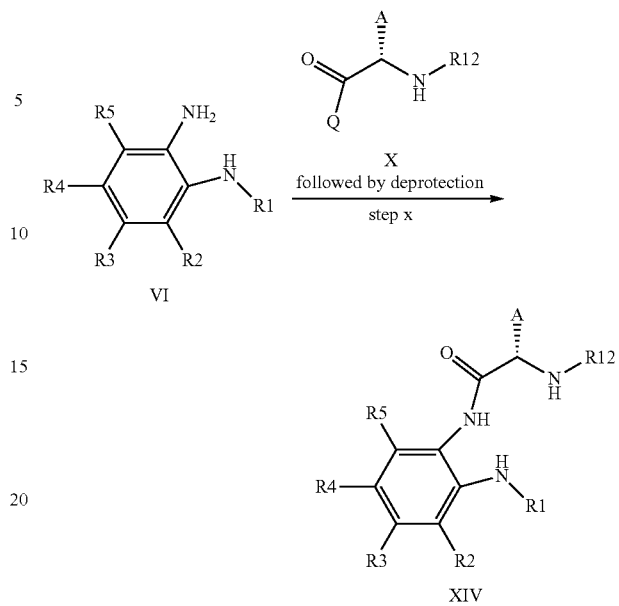

The reaction step x (acylation followed by deprotection) shown in Scheme 1 may be carried out in the manner described in the Examples or according to the conditions known from the literature, for example as follows:

Acylation of a substrate VI with a carboxylic acid or carboxylic acid derivative X like described above, followed by deprotection like described above.

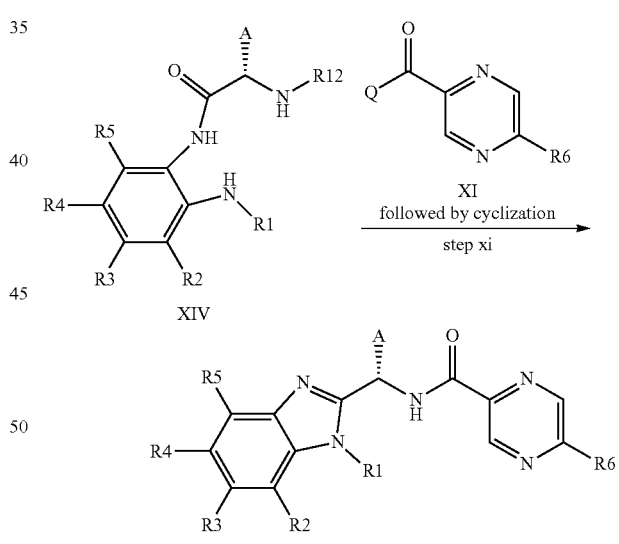

The reaction steps vi and vii (acylation followed by deprotection and cyclization) may be carried out in the manner described in the Examples or according to the conditions known from the literature, for example as follows:

Acylation of an amine-carrying substrate VI with a reagent X like described above, followed by cleaving a protective group like described above, followed by cyclization like described above.

The reaction step xi (acylation followed by cyclization) shown in Scheme 1 may be carried out in the manner described in the Examples or according to the conditions known from the literature, for example as follows:

Acylation of substrate XIV with a carboxylic acid or carboxylic acid derivative XI like described above, followed by cyclization like described above.

The terms "mGluR4", "mGluR4 protein", and "mGluR4 receptor" are used interchangeably throughout the application. Unless expressly stated, the term mGluR4 includes homomultimeric structures (e.g. homomultimeric mGluR4) and heteromultimeric structures (e.g. heteromultimeric mGluR4-mGluR2).

Biological Assays

The biological activity of compounds is determined by the following methods:

A. In Vitro Testing of mGluR4 Potency

The in vitro activity of the compounds according to the invention may be investigated as follows:

The HEK293 cell overexpressing the human metabotropic Glutamate 4 receptor are thawed at 37° C. and immediately diluted with cell culture medium. After centrifugation, the cell pellet is re-suspended in medium and then distributed from a stirred spinner flask into the wells of the assay plate. The plates are incubated for one hour at room temperature before they are incubated for 24 hours at 37° C./5% CO2. After washing the cells in the plate three times with 80 uL HBSS/HEPES buffer (10 uL buffer remained in the wells after washing), 5 uL per well of compounds diluted in HBSS/HEPES buffer containing 0.2% BSA (final concentration: 0.1%) and 1 mM IBMX (final concentration: 0.5 mM) are added to the wells of the assay plate. Thereafter 5 uL per well of L-Glutamic acid (final concentration: 10 uM), forskolin (final concentration: 1 uM) and 1 mM IBMX (final concentration: 0.5 mM) dissolved in HBSS/HEPES buffer containing 0.2% BSA (final concentration: 0.1%) are added to the assay plate (final DMSO concentration: 1%). Several wells of the assay plate are used either for the positive and the negative controls or for the cAMP standard curve. The assay plate is incubated for 30 minutes at room temperature. Then 5 ul per well of Anti-cAMP-Antibody-d2 solution and 5 ul per well of cAMP-Europium Cryptate dilution are added to all wells of the plate and the plate is incubated another 60 minutes light protected at room temperature. The emission at 615 nm and 665 nm (Excitation wavelength: 320 nm) are measured on the EnVision™ reader (PerkinElmer). The ratio between the emission at 665 nm and 615 is calculated by the reader. The whole assay is performed in the dark or under green light.

The cAMP standard is prepared by diluting the cAMP stock solution with HBSS/Hepes buffer: 5 µl/well of the cAMP dilutions (in HBSS/Hepes buffer containing 1 mM IBMX and 0.2% BSA-final concentration: 0.5 mM IBMX and 0.1% BSA) are added to 10 ul/well HBSS/Hepes buffer plus 5 ul/well 4% DMSO in HBSS/Hepes containing 0.2% BSA (final DMSO concentration: 1%-like in the wells containing compounds) in the wells of the assay plate. The final cAMP concentrations in the assay plate are: 0, 0.17, 0.69, 2.78, 11.1, 44.5, 178, and 712 nM (two wells/cAMP concentration).

Each assay microtiter plate contained also wells with vehicle controls instead of compound as controls for L-Glutamic acid induced signal (negative control; 100% CTL; 10 uM L-Glutamic acid+1 uM forskolin+0.5 mM IBMX+1% DMSO) and wells with vehicle controls without L-Glutamic acid as controls for non-specific changes in signal (positive control; 0% CTL; 0 uM L-Glutamic acid+1 uM forskolin+0.5 mM IBMX+1% DMSO).

The analysis of the data is performed by the calculation the ratio between the emission at 665 nm and the emission at 615 nm (Em665/Em615 ratio). Thereafter the signals of the compounds are normalized using the positive and negative controls by the following formula:

$PoC = 100 \times (Signal\ Sample - Positive\ Control)$

/(Negative Control − Positive Control)]

B. Assessment of Metabolic Stability in Human Liver Microsomes (Human MST)

The metabolic stability of the compounds according to the invention may be investigated as follows:

The metabolic degradation of the test compound is assayed at 37° C. with pooled human liver microsomes. The final incubation volume of 100 µL per time point contains TRIS buffer pH 7.6 at room temperature (0.1 M), $MgCl_2$ (5 mM), microsomal protein (1 mg/mL) and the test compound at a final concentration of 1 µM. Following a short pre-incubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LC-MS/MS for the amount of parent compound. The half-life ($t_{1/2}$) is determined by the slope of the semi-logarithmic plot of the concentration-time profile.

C. Assessment of Efflux in Madin-Darby Canine Kidney (MDCK) Cells Transfected with the Human MDR1 Gene Apparent permeability coefficients (PE) of the compounds across the MDCK-MDR1 cell monolayers are measured (pH 7.4, 37° C.) in apical-to-basal (AB) and basal-to-apical (BA) transport direction. AB permeability (PEAB) represents drug absorption from the blood into the brain and BA permeability (PEBA) drug efflux from the brain back into the blood via both passive permeability as well as active transport mechanisms mediated by efflux and uptake transporters that are expressed on the MDCK-MDR1 cells, predominantly by the overexpressed human MDR1 P-gp. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB indicates the involvement of active efflux mediated by MDR1 P-gp. Active transport is concentration-dependently saturable.

MDCK-MDR1 cells (1-2×10e5 cells/1 cm2 area) are seeded on filter inserts (Costar transwell polycarbonate or PET filters, 0.4 µm pore size) and cultured (DMEM) for 7 days. Subsequently, the MDR1 expression is boosted by culturing the cells with 5 mM sodium butyrate in full medium for 2 days. Compounds are dissolved in appropriate solvent (like DMSO, 1–20 mM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_4 \times 7H_2O$, 0.41 mM $NaH_2PO_4 \times H_2O$, 15 mM HEPES, 20 mM glucose, 0.25% BSA, pH 7.4) to prepare the transport solutions (0.1-300 µM compound, final DMSO<=0.5%). The transport solution (TL) is applied to the apical or basolateral donor side for measuring A-B or B-A permeability (3 filter replicates), respectively. The receiver side contains the same buffer as the donor side. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

D. Assessment of Efficacy on Impulsive Behavior Tested in the Rat Five Choice Serial Reaction Time Task 5-CSRTT Assessment of efficacy on motor impulsive behavior may be investigated as follows:

5-CSRTT task training took place according to standard protocols (Isherwood et al. Neuropharmacology 2017, 123: 249-260). Briefly, rats were trained to nose poke at the location of a light cue presented at 1 of 5 locations on a curved wall of an operant box (Med Associates Inc, St. Albans, Vermont). If a nose poke occurred at the illuminated location during or up to 1 s after stimulus presentation a sugar pellet was delivered in a reward receptacle located across the chamber. Infrared beams in each choice aperture and the reward receptacle allowed for precise detection of the rat at this task associated operanda. Motor impulsive behavior was defined as a response at any nose poke aperture which occurred before onset of the light cue (premature response).

After reaching stable performance, a new analytical approach was applied which revealed trait-like (long-term) stability in the number of premature responses individual animals made across several months. In general, this analysis made it possible to robustly stratify animals into high- and low-impulsive groups based on longitudinal assessment of the number of premature responses they made during training.

Experiments were performed in cross-over such that all experiment subjects received both vehicle and compound, on separate days, with each administration separated by ~2 weeks. The order of vehicle and compound administration was randomized within experimental subjects, while a third group was administered Atomoxetine on both experimental days as a technical control.

As a standardized numerical threshold for impulsivity levels, animals with >40 and <40 premature responses (out of 200 initiated trials) in vehicle were labeled as high and low impulsive, respectively. Importantly, this numerical threshold-based labeling overlapped >80% with the longitudinal analysis of the training data (described above). The high convergence of these two approaches towards stratification allowed us to robustly compare compound effects in stably high- vs stably low-impulsive rats in the 5-CSRTT.

Biological Data

TABLE 1

In vitro potencies of the structurally closest compounds disclosed in WO2019/138017 (as determined in Assay A)

| Example | Structure | Assay A mGluR4 IC50 |
|---|---|---|
| Example 8 in WO2019/138017 | 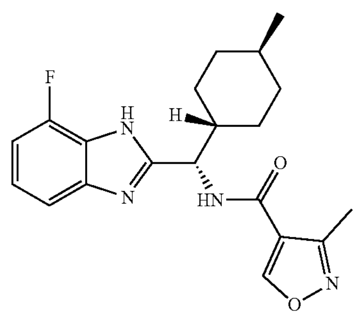 [SMILES: Cc1nocc1C(=O)N[C@H](c1nc2cccc(F)c2[nH]1)[C@H]1CC[C@H](C)CC1] | 9.85 μM |
| Example 12 in WO2019/138017 | 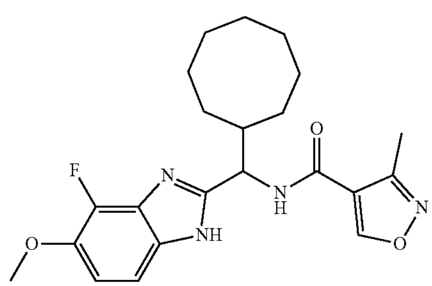 [SMILES: COc1ccc2[nH]c(C(NC(=O)c3conc3C)C3CCCCCCC3)nc2c1F] | >10 μM |
| Example 125 in WO2019/138017 | 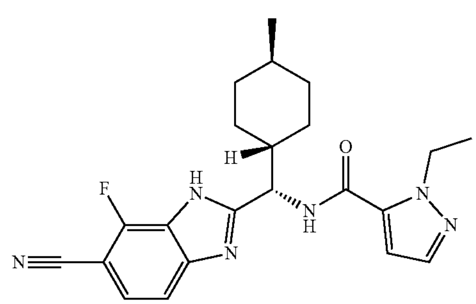 [SMILES: CCn1nccc1C(=O)N[C@H](c1nc2ccc(C#N)c(F)c2[nH]1)[C@H]1CC[C@H](C)CC1] | 5.6 μM |

TABLE 1-continued

In vitro potencies of the structurally closest compounds disclosed in WO2019/138017 (as determined in Assay A)

| Example | Structure | Assay A mGluR4 IC50 |
|---|---|---|
| Intermediate 250 in WO2019/138017 (regioisomere 1) | [structure: 4-F, 5-Br benzimidazole with N-methyl, cyclohexyl-CH linked via NH to N-methylpyrazole-5-carboxamide] | 6.3 µM |
| Intermediate 250 in WO2019/138017 (regioisomere 2) | [structure: 4-F, 5-Br benzimidazole with N-methyl, cyclohexyl-CH linked via NH to N-methylpyrazole-5-carboxamide, opposite stereochemistry] | 4.0 µM |

Compounds of the present invention differ structurally from the structurally closest compounds in the prior art (i.e. Examples 8, 12, 125 and Intermediate 250 in WO 2019/138017) in that the heteromonocycle bound as an carboxamide is a pyrazine (6-membered heteroaryl) group rather than a pyrazole or isoxazole moiety (5-membered heteroaryl). Whereas the structurally closest compounds disclosed in WO2019/138017 are as disclosed therein immunomodulators (IL-17 modulators), compounds of the present invention unexpectedly are highly potent mGluR4 negative modulators (see Table 2). The structurally closest compounds disclosed in WO2019/138017 were tested in Assay A and found to have no therapeutically relevant activity as mGluR4 modulators (Table 1). Unexpectedly, compounds of the present invention are >100 times more potent in Assay A. (Compare data in Tables 1 and 2).

TABLE 2

In vitro potencies of compounds of the present invention as determined in Assay A

| Example | Structure | Assay A mGluR4 IC$_{50}$ [μM] |
|---|---|---|
| 1 | 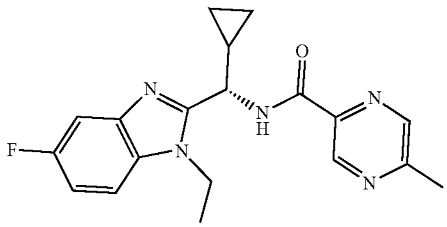 [SMILES: CCn1c([C@@H](NC(=O)c2cnc(C)cn2)C2CC2)nc2cc(F)ccc21] | 0.004 |
| 2 | 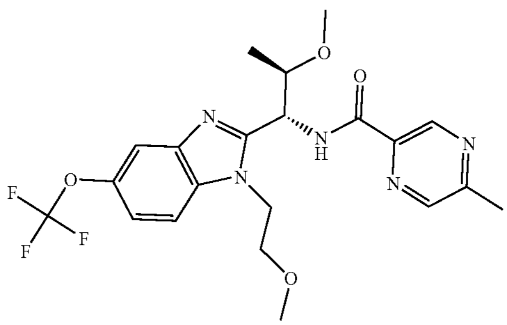 [SMILES: COCCn1c([C@@H](NC(=O)c2cnc(C)cn2)[C@@H](C)OC)nc2cc(OC(F)(F)F)ccc21] | 0.002 |
| 3 | 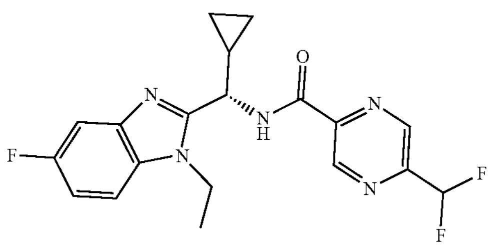 [SMILES: CCn1c([C@@H](NC(=O)c2cnc(C(F)F)cn2)C2CC2)nc2cc(F)ccc21] | 0.003 |
| 4 | 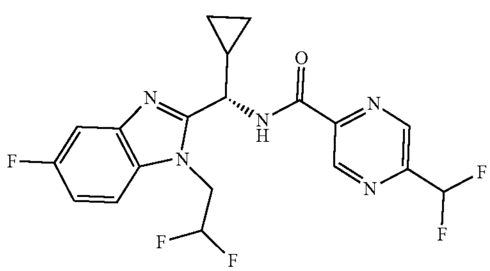 [SMILES: O=C(N[C@H](c1nc2cc(F)ccc2n1CC(F)F)C1CC1)c1cnc(C(F)F)cn1] | 0.004 |
| 5 | 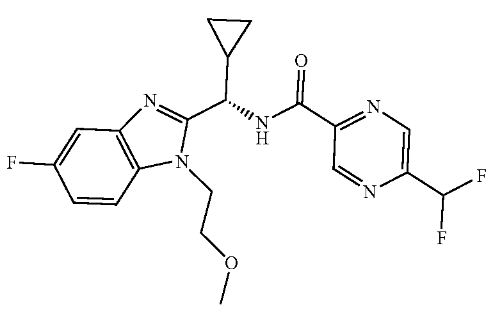 [SMILES: COCCn1c([C@@H](NC(=O)c2cnc(C(F)F)cn2)C2CC2)nc2cc(F)ccc21] | 0.005 |

TABLE 2-continued

In vitro potencies of compounds of the present invention as determined in Assay A

| Example | Structure | Assay A mGluR4 IC$_{50}$ [μM] |
|---|---|---|
| 6 | 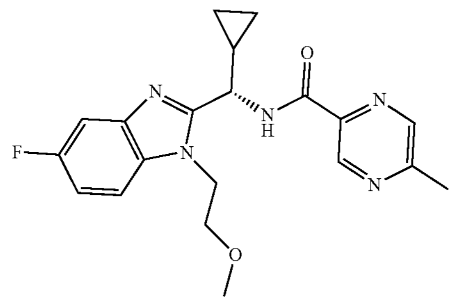 [SMILES: COCCn1c([C@@H](NC(=O)c2cnc(C)cn2)C2CC2)nc2cc(F)ccc21] | 0.007 |
| 7 | 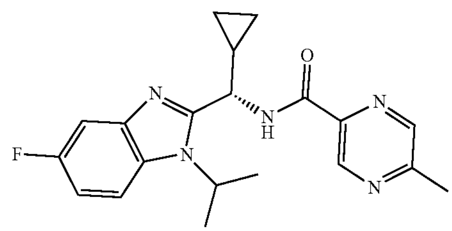 [SMILES: Cc1cnc(C(=O)N[C@H](c2nc3cc(F)ccc3n2C(C)C)C2CC2)cn1] | 0.004 |
| 8 | 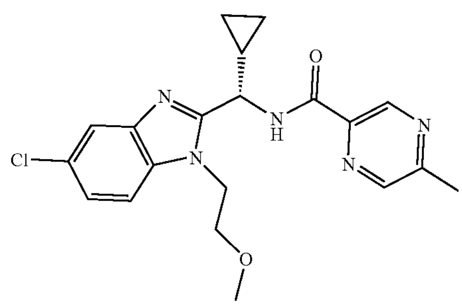 [SMILES: COCCn1c([C@@H](NC(=O)c2cnc(C)cn2)C2CC2)nc2cc(Cl)ccc21] | 0.003 |
| 9 | 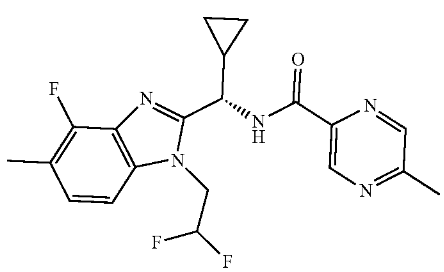 | 0.004 |
| 10 | 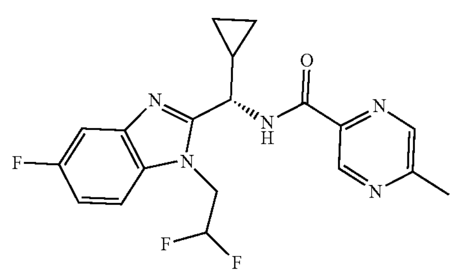 [SMILES: Cc1cnc(C(=O)N[C@H](c2nc3cc(F)ccc3n2CC(F)F)C2CC2)cn1] | 0.005 |

TABLE 2-continued

In vitro potencies of compounds of the present invention as determined in Assay A

| Example | Structure | Assay A mGluR4 IC$_{50}$ [μM] |
|---|---|---|
| 11 | 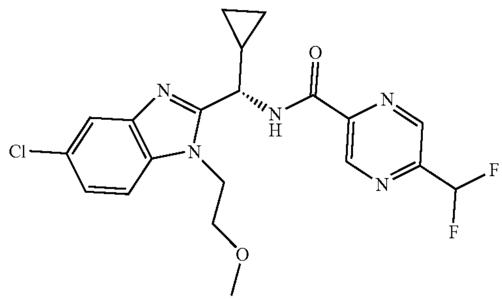 [SMILES: COCCn1c([C@@H](NC(=O)c2cnc(C(F)F)cn2)C2CC2)nc2cc(Cl)ccc21] | 0.003 |
| 12 | 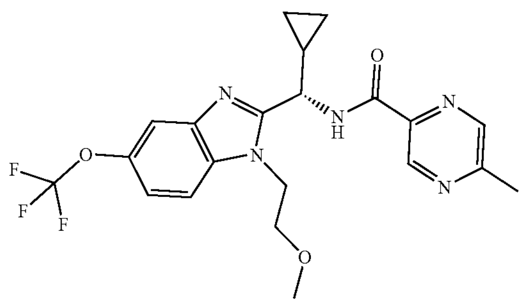 [SMILES: COCCn1c([C@@H](NC(=O)c2cnc(C)cn2)C2CC2)nc2cc(OC(F)(F)F)ccc21] | 0.002 |
| 13 | 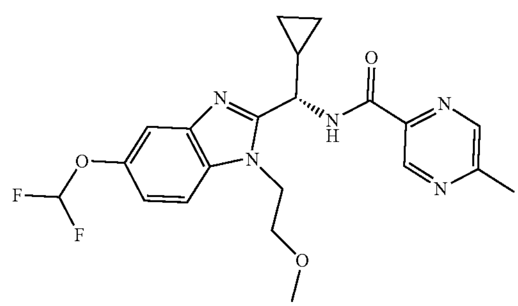 [SMILES: COCCn1c([C@@H](NC(=O)c2cnc(C)cn2)C2CC2)nc2cc(OC(F)F)ccc21] | 0.007 |
| 14 | 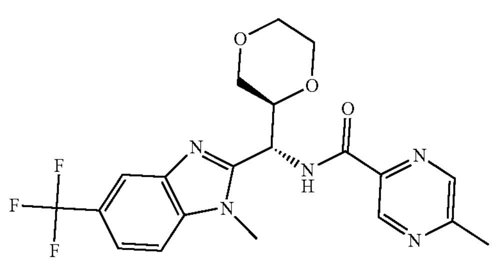 [SMILES: Cc1cnc(C(=O)N[C@H](c2nc3cc(C(F)(F)F)ccc3n2C)[C@H]2COCCO2)cn1] | 0.020 |
| 14-1 | 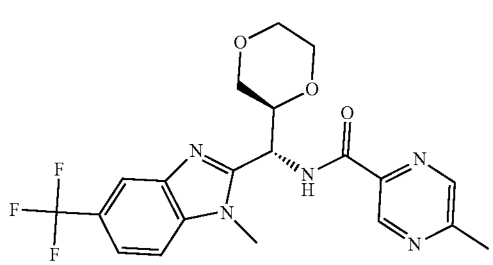 [SMILES: Cc1cnc(C(=O)N[C@H](c2nc3cc(C(F)(F)F)ccc3n2C)[C@H]2COCCO2)cn1] | 0.067 |

TABLE 2-continued

In vitro potencies of compounds of the present invention as determined in Assay A

| Example | Structure | Assay A mGluR4 IC$_{50}$ [μM] |
|---|---|---|
| 15 | 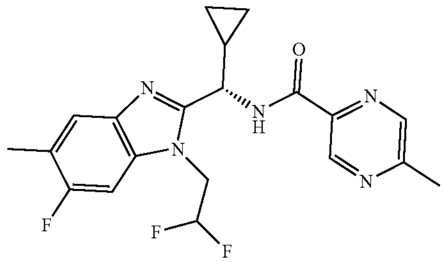 | 0.003 |
| 16 | 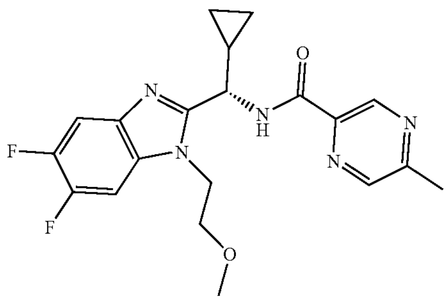 [SMILES: COCCn1c([C@@H](NC(=O)c2cnc(C)cn2)C2CC2)nc2cc(F)c(F)cc21] | 0.005 |
| 17 | 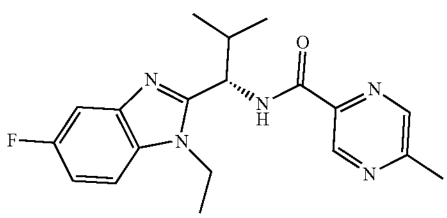 [SMILES: CCn1c([C@@H](NC(=O)c2cnc(C)cn2)C(C)C)nc2cc(F)ccc21] | 0.004 |
| 18 | 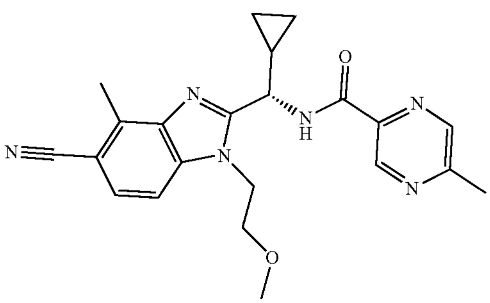 [SMILES: COCCn1c([C@@H](NC(=O)c2cnc(C)cn2)C2CC2)nc2c(C)c(C#N)ccc21] | 0.007 |
| 19 | 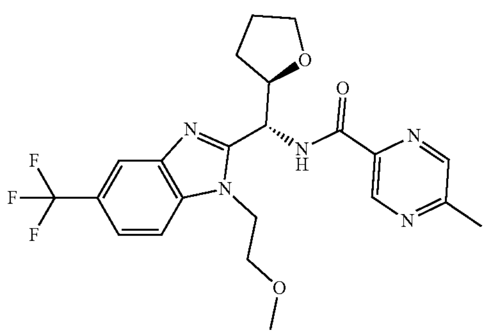 [SMILES: COCCn1c([C@@H](NC(=O)c2cnc(C)cn2)[C@H]2CCCO2)nc2cc(C(F)(F)F)ccc21] | 0.003 |

TABLE 2-continued

In vitro potencies of compounds of the present invention as determined in Assay A

| Example | Structure | Assay A mGluR4 IC$_{50}$ [μM] |
|---|---|---|
| 19-1 | 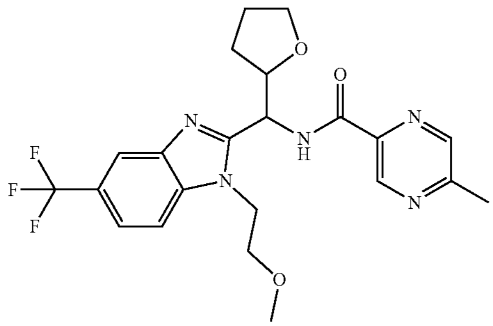 [SMILES: COCCn1c(C(NC(=O)c2cnc(C)cn2)C2CCCO2)nc2cc(C(F)(F)F)ccc21] | 0.013 |
| 19-2 | 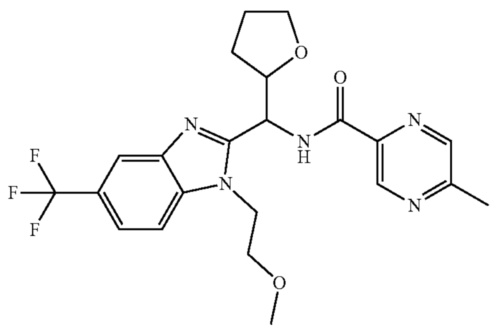 [SMILES: COCCn1c(C(NC(=O)c2cnc(C)cn2)C2CCCO2)nc2cc(C(F)(F)F)ccc21] | 0.062 |
| 20 | 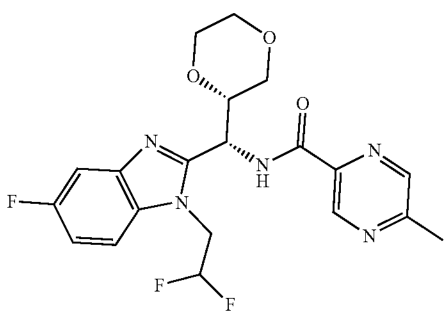 [SMILES: Cc1cnc(C(=O)N[C@H](c2nc3cc(F)ccc3n2CC(F)F)[C@H]2COCCO2)cn1] | 0.014 |
| 21 | 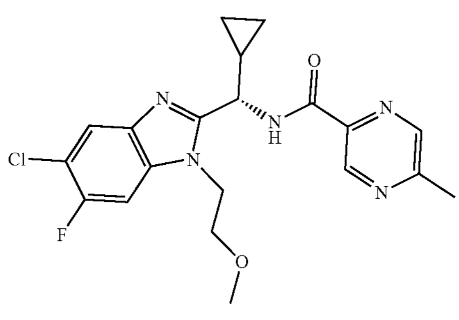 [SMILES: COCCn1c([C@@H](NC(=O)c2cnc(C)cn2)C2CC2)nc2cc(Cl)c(F)cc21] | 0.003 |
| 22 | 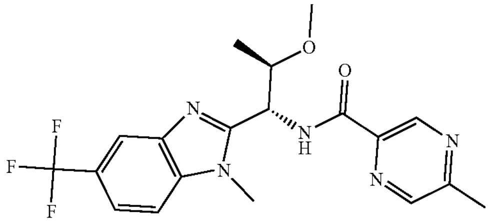 [SMILES: CO[C@H](C)[C@H](NC(=O)c1cnc(C)cn1)c1nc2cc(C(F)(F)F)ccc2n1C] | 0.006 |

TABLE 2-continued
In vitro potencies of compounds of the present invention as determined in Assay A
| Example | Structure | Assay A mGluR4 IC$_{50}$ [μM] |
|---|---|---|
| 23 | 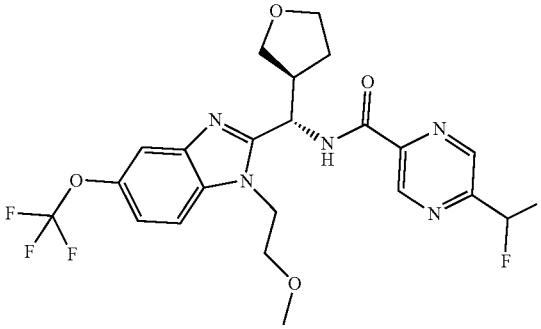 | 0.004 |
| 24 | 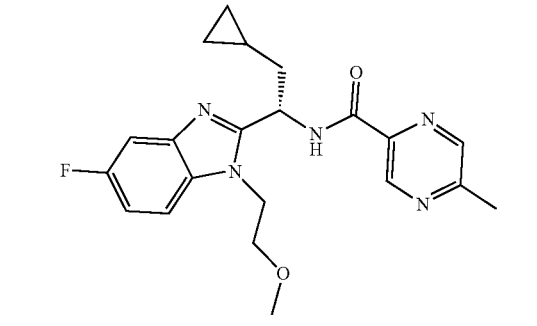 [SMILES: COCCn1c([C@H](CC2CC2)NC(=O)c2cnc(C)cn2)nc2cc(F)ccc21] | 0.007 |
| 25 | 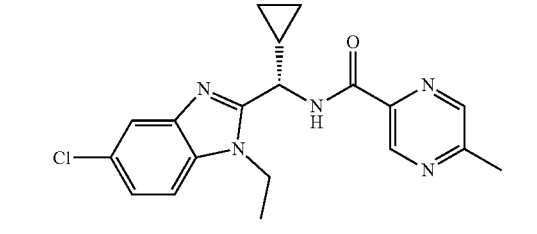 [SMILES: CCn1c([C@@H](NC(=O)c2cnc(C)cn2)C2CC2)nc2cc(Cl)ccc21] | 0.003 |
| 26 | 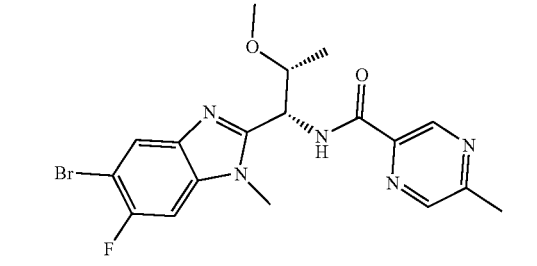 [SMILES: CO[C@H](C)[C@H](NC(=O)c1cnc(C)cn1)c1nc2cc(Br)c(F)cc2n1C] | 0.007 |
| 27 | 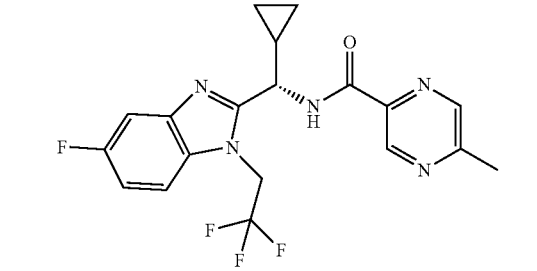 [SMILES: Cc1cnc(C(=O)N[C@H](c2nc3cc(F)ccc3n2CC(F)(F)F)C2CC2)cn1] | 0.005 |

TABLE 2-continued

In vitro potencies of compounds of the present invention as determined in Assay A

| Example | Structure | Assay A mGluR4 IC$_{50}$ [μM] |
|---|---|---|
| 28 | 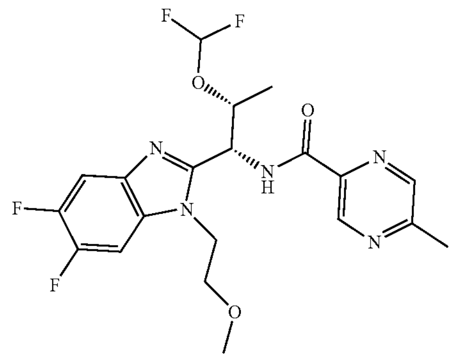 [SMILES: COCCn1c([C@@H](NC(=O)c2cnc(C)cn2)[C@@H](C)OC(F)F)nc2cc(F)c(F)cc21] | 0.010 |
| 29 | 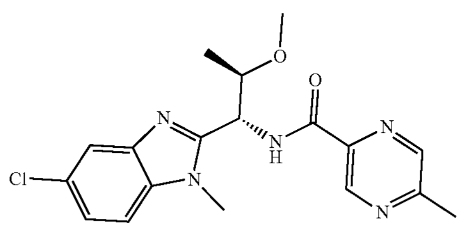 [SMILES: CO[C@H](C)[C@H](NC(=O)c1cnc(C)cn1)c1nc2cc(Cl)ccc2n1C] | 0.011 |
| 30 | 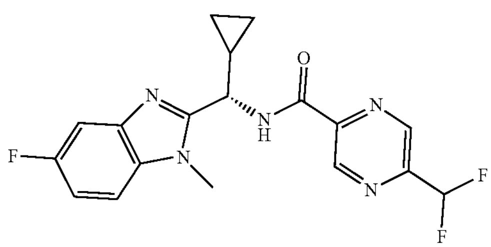 [SMILES: Cn1c([C@@H](NC(=O)c2cnc(C(F)F)cn2)C2CC2)nc2cc(F)ccc21] | 0.018 |
| 31 | 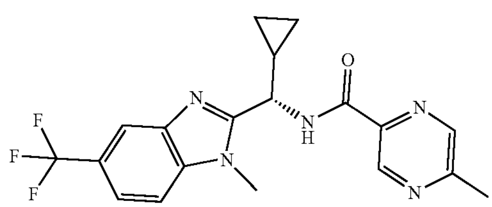 [SMILES: Cc1cnc(C(=O)N[C@H](c2nc3cc(C(F)(F)F)ccc3n2C)C2CC2)cn1] | 0.006 |
| 32 | 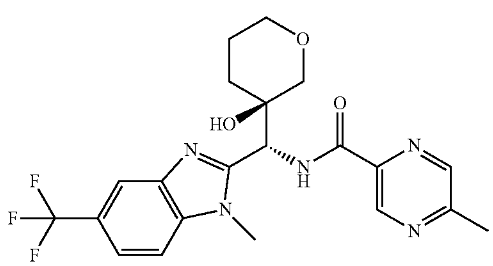 [SMILES: Cc1cnc(C(=O)N[C@H](c2nc3cc(C(F)(F)F)ccc3n2C)[C@]2(O)CCCOC2)cn1] | 0.016 |

TABLE 2-continued

In vitro potencies of compounds of the present invention as determined in Assay A

| Example | Structure | Assay A mGluR4 IC$_{50}$ [μM] |
|---|---|---|
| 33 | 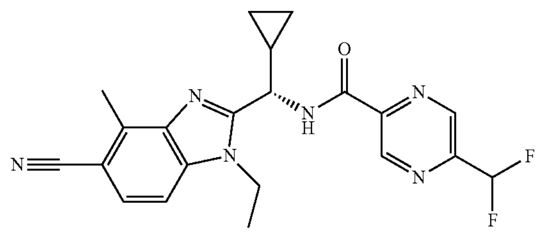 [SMILES: CCn1c([C@@H](NC(=O)c2cnc(C(F)F)cn2)C2CC2)nc2c(C)c(C#N)ccc21] | 0.004 |
| 34 | 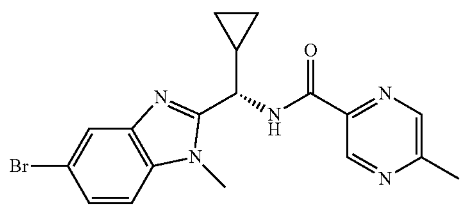 [SMILES: Cc1cnc(C(=O)N[C@H](c2nc3cc(Br)ccc3n2C)C2CC2)cn1] | 0.005 |
| 35 | 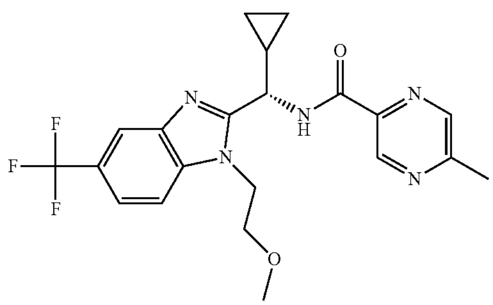 [SMILES: COCCn1c([C@@H](NC(=O)c2cnc(C)cn2)C2CC2)nc2cc(C(F)(F)F)ccc21] | 0.002 |
| 36 | 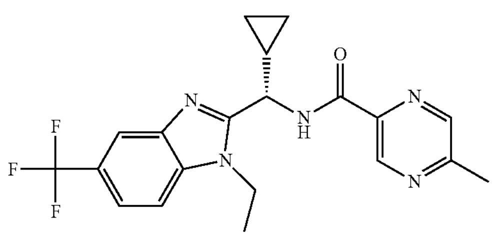 [SMILES: CCn1c([C@@H](NC(=O)c2cnc(C)cn2)C2CC2)nc2cc(C(F)(F)F)ccc21] | 0.003 |
| 37 | 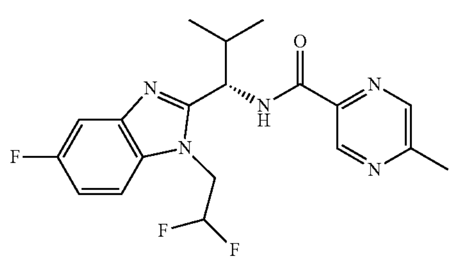 [SMILES: Cc1cnc(C(=O)N[C@H](c2nc3cc(F)ccc3n2CC(F)F)C(C)C)cn1] | 0.009 |
| 38 | 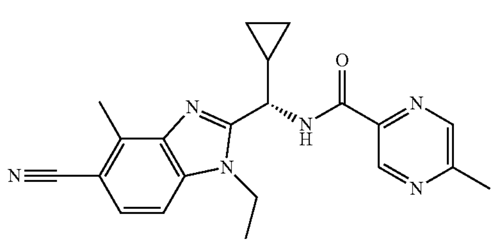 [SMILES: CCn1c([C@@H](NC(=O)c2cnc(C)cn2)C2CC2)nc2c(C)c(C#N)ccc21] | 0.005 |

TABLE 2-continued

In vitro potencies of compounds of the present invention as determined in Assay A

| Example | Structure | Assay A mGluR4 IC$_{50}$ [µM] |
|---|---|---|
| 39 | 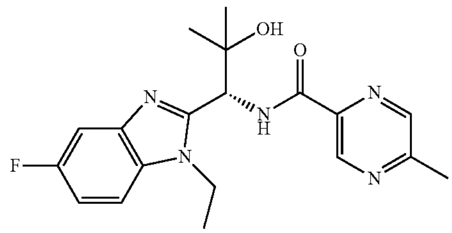 [SMILES: CCn1c([C@@H](NC(=O)c2cnc(C)cn2)C(C)(C)O)nc2cc(F)ccc21] | 0.028 |
| 40 | 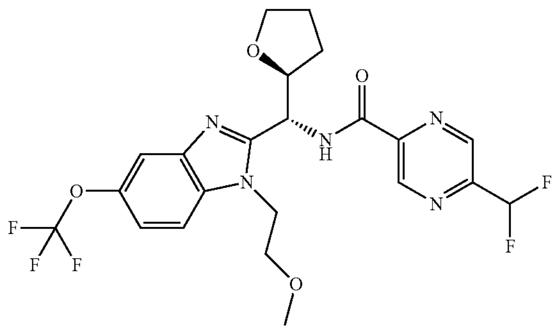 [SMILES: COCCn1c([C@@H](NC(=O)c2cnc(C(F)F)cn2)[C@@H]2CCCO2)nc2cc(OC(F)(F)F)ccc21] | 0.002 |
| 41 | 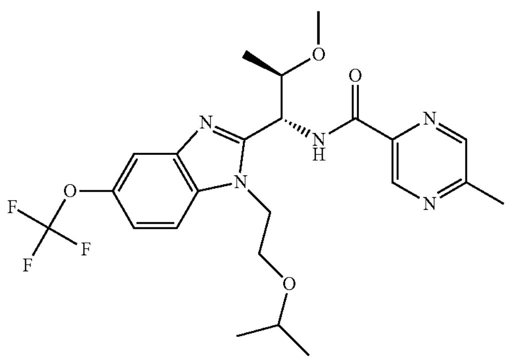 [SMILES: CO[C@H](C)[C@H](NC(=O)c1cnc(C)cn1)c1nc2cc(OC(F)(F)F)ccc2n1CCOC(C)C] | 0.002 |
| 42 | 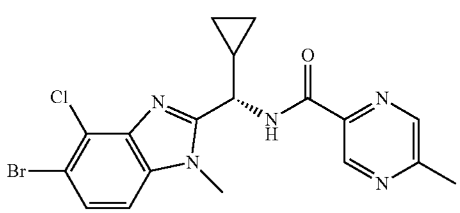 [SMILES: Cc1cnc(C(=O)N[C@H](c2nc3c(Cl)c(Br)ccc3n2C)C2CC2)cn1] | 0.002 |
| 43 | 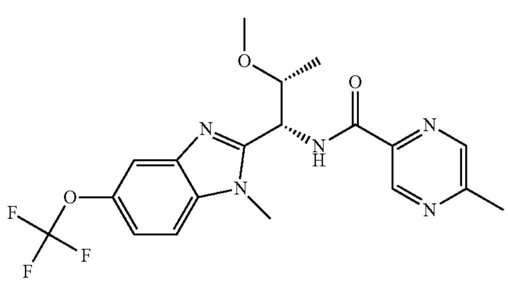 [SMILES: CO[C@H](C)[C@H](NC(=O)c1cnc(C)cn1)c1nc2cc(OC(F)(F)F)ccc2n1C] | 0.010 |

TABLE 2-continued

In vitro potencies of compounds of the present invention as determined in Assay A

| Example | Structure | Assay A mGluR4 IC$_{50}$ [μM] |
|---|---|---|
| 44 | 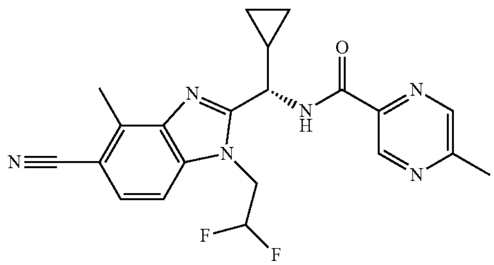 [SMILES: Cc1cnc(C(=O)N[C@H](c2nc3c(C)c(C#N)ccc3n2CC(F)F)C2CC2)cn1] | 0.005 |
| 45 | 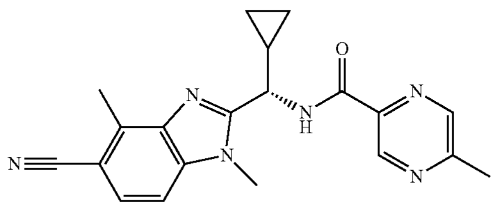 [SMILES: Cc1cnc(C(=O)N[C@H](c2nc3c(C)c(C#N)ccc3n2C)C2CC2)cn1] | 0.026 |
| 46 | 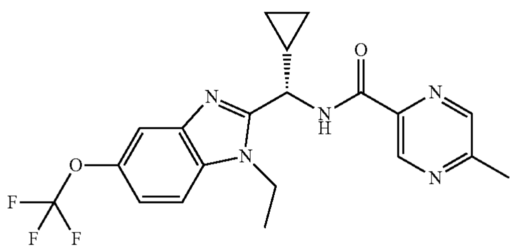 [SMILES: CCn1c([C@@H](NC(=O)c2cnc(C)cn2)C2CC2)nc2cc(OC(F)(F)F)ccc21] | 0.002 |
| 47 | 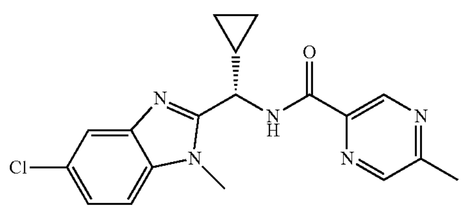 [SMILES: Cc1cnc(C(=O)N[C@H](c2nc3cc(Cl)ccc3n2C)C2CC2)cn1] | 0.009 |
| 48 | 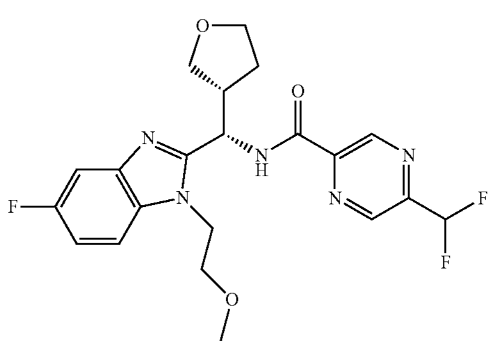 [SMILES: COCCn1c([C@@H](NC(=O)c2cnc(C(F)F)cn2)[C@H]2CCOC2)nc2cc(F)ccc21] | 0.021 |

TABLE 2-continued

In vitro potencies of compounds of the present invention as determined in Assay A

| Example | Structure | Assay A mGluR4 IC$_{50}$ [μM] |
|---|---|---|
| 48-2 | 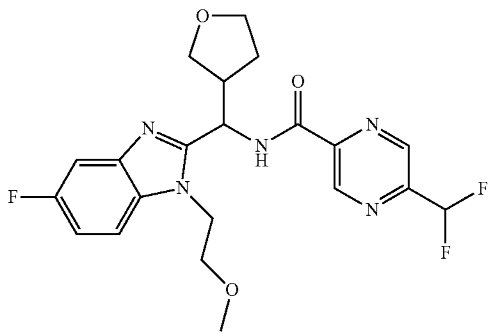 [SMILES: COCCn1c(C(NC(=O)c2cnc(C(F)F)cn2)C2CCOC2)nc2cc(F)ccc21] | 0.06 |
| 49 | 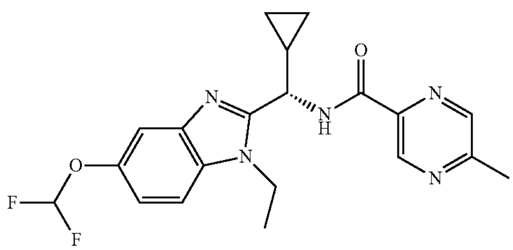 [SMILES: CCn1c([C@@H](NC(=O)c2cnc(C)cn2)C2CC2)nc2cc(OC(F)F)ccc21] | 0.007 |
| 50 | 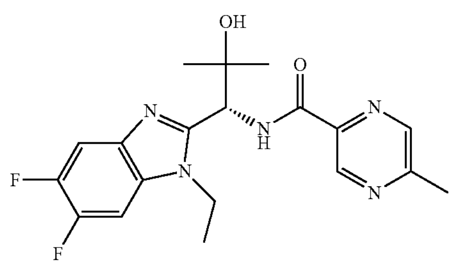 [SMILES: CCn1c([C@@H](NC(=O)c2cnc(C)cn2)C(C)(C)O)nc2cc(F)c(F)cc21] | 0.024 |
| 51 | 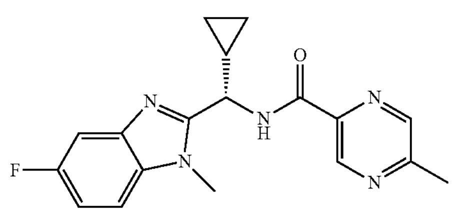 [SMILES: Cc1cnc(C(=O)N[C@H](c2nc3cc(F)ccc3n2C)C2CC2)cn1] | 0.028 |
| 52 | 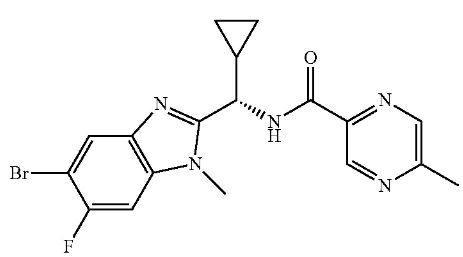 [SMILES: Cc1cnc(C(=O)N[C@H](c2nc3cc(Br)c(F)cc3n2C)C2CC2)cn1] | 0.005 |

TABLE 2-continued

In vitro potencies of compounds of the present invention as determined in Assay A

| Example | Structure | Assay A mGluR4 IC$_{50}$ [μM] |
|---|---|---|
| 53 | 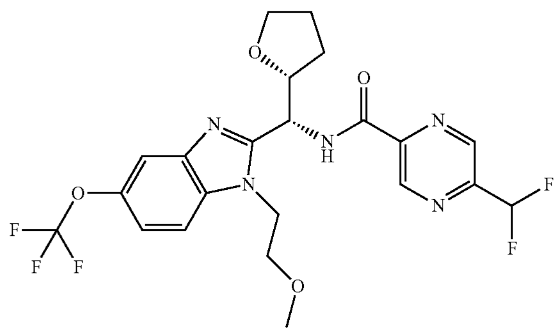 | 0.006 |
| 54 | 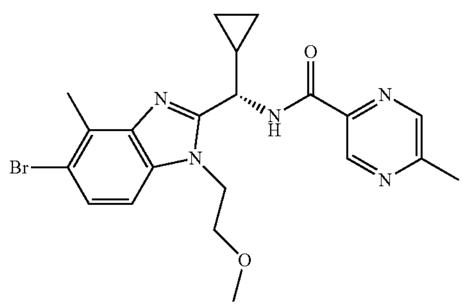 [SMILES: COCCn1c([C@@H](NC(=O)c2cnc(C)cn2)C2CC2)nc2c(C)c(Br)ccc21] | 0.001 |
| 55 | 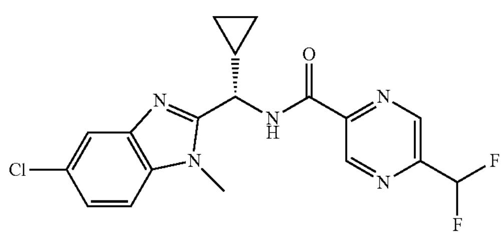 [SMILES: Cn1c([C@@H](NC(=O)c2cnc(C(F)F)cn2)C2CC2)nc2cc(Cl)ccc21] | 0.007 |
| 56 | 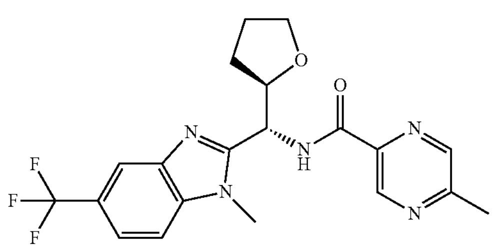 [SMILES: Cc1cnc(C(=O)N[C@H](c2nc3cc(C(F)(F)F)ccc3n2C)[C@H]2CCCO2)cn1] | 0.013 |
| 57 | 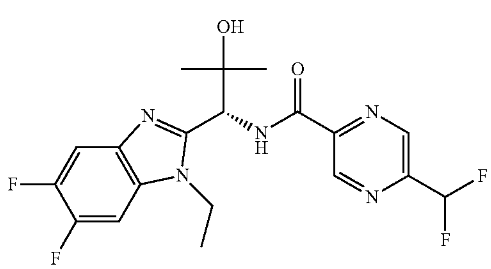 [SMILES: CCn1c([C@@H](NC(=O)c2cnc(C(F)F)cn2)C(C)(C)O)nc2cc(F)c(F)cc21] | 0.019 |

TABLE 2-continued

In vitro potencies of compounds of the present invention as determined in Assay A

| Example | Structure | Assay A mGluR4 IC$_{50}$ [μM] |
|---|---|---|
| 58 | 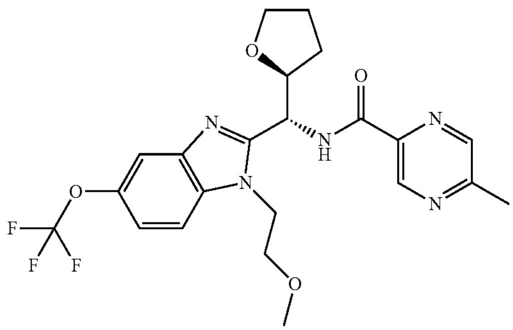 [SMILES: COCCn1c([C@@H](NC(=O)c2cnc(C)cn2)[C@@H]2CCCO2)nc2cc(OC(F)(F)F)ccc21] | 0.004 |
| 59 | 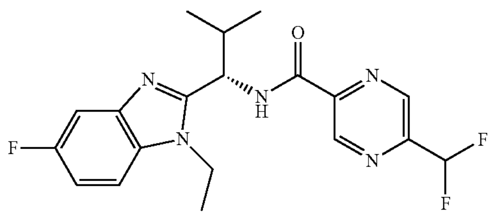 [SMILES: CCn1c([C@@H](NC(=O)c2cnc(C(F)F)cn2)C(C)C)nc2cc(F)ccc21] | 0.004 |
| 60 | 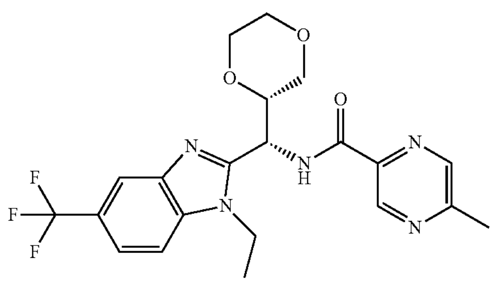 [SMILES: CCn1c([C@@H](NC(=O)c2cnc(C)cn2)[C@H]2COCCO2)nc2cc(C(F)(F)F)ccc21] | 0.005 |
| 61 | 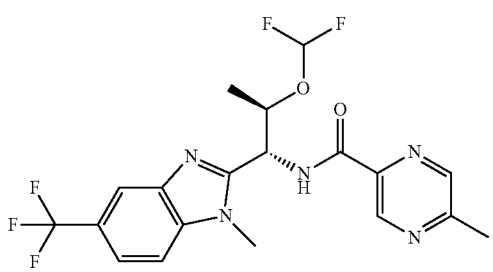 [SMILES: Cc1cnc(C(=O)N[C@H](c2nc3cc(C(F)(F)F)ccc3n2C)[C@@H](C)OC(F)F)cn1] | 0.008 |
| 62 | 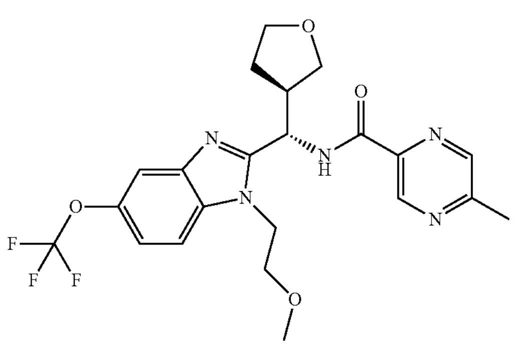 [SMILES: COCCn1c([C@@H](NC(=O)c2cnc(C)cn2)[C@H]2CCOC2)nc2cc(OC(F)(F)F)ccc21] | 0.009 |

TABLE 2-continued

In vitro potencies of compounds of the present invention as determined in Assay A

| Example | Structure | Assay A mGluR4 IC$_{50}$ [µM] |
|---|---|---|
| 62-2 | 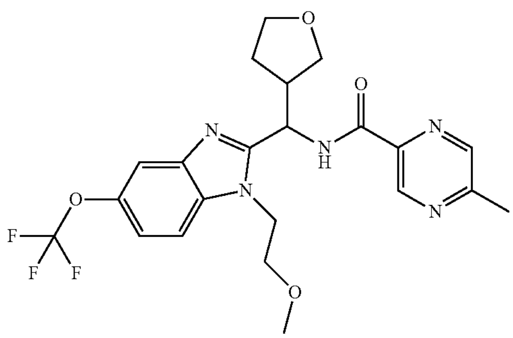 [SMILES: COCCn1c(C(NC(=O)c2cnc(C)cn2)C2CCOC2)nc2cc(OC(F)(F)F)ccc21] | 0.028 |
| 63 | 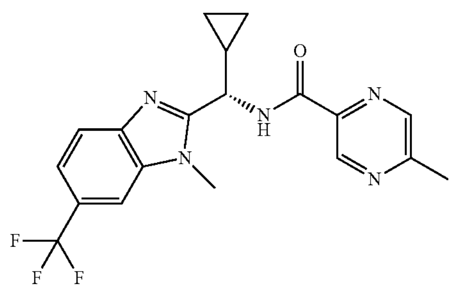 [SMILES: Cc1cnc(C(=O)N[C@H](c2nc3ccc(C(F)(F)F)cc3n2C)C2CC2)cn1] | 0.014 |
| 64 | 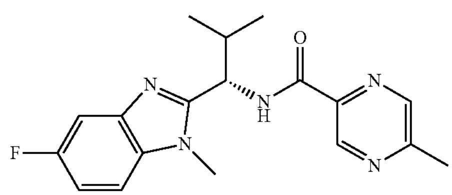 [SMILES: Cc1cnc(C(=O)N[C@H](c2nc3cc(F)ccc3n2C)C(C)C)cn1] | 0.019 |
| 65 | 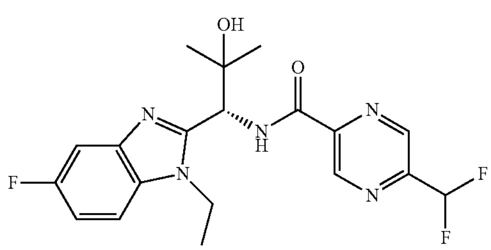 [SMILES: CCn1c([C@@H](NC(=O)c2cnc(C(F)F)cn2)C(C)(C)O)nc2cc(F)ccc21] | 0.016 |
| 66 | 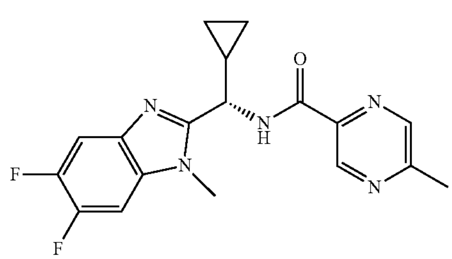 [SMILES: Cc1cnc(C(=O)N[C@H](c2nc3cc(F)c(F)cc3n2C)C2CC2)cn1] | 0.023 |

TABLE 2-continued
In vitro potencies of compounds of the present invention as determined in Assay A
| Example | Structure | Assay A mGluR4 IC$_{50}$ [μM] |
|---|---|---|
| 67 | 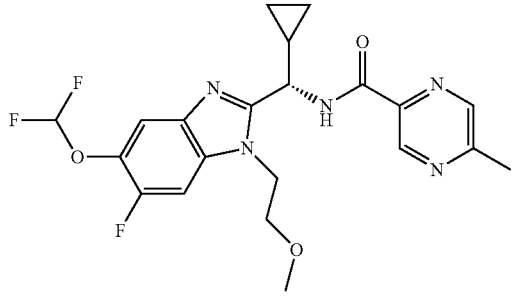 [SMILES: COCCn1c([C@@H](NC(=O)c2cnc(C)cn2)C2CC2)nc2cc(OC(F)F)c(F)cc21] | 0.010 |
| 68 | 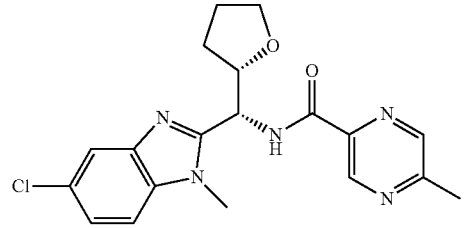 [SMILES: Cc1cnc(C(=O)N[C@H](c2nc3cc(Cl)ccc3n2C)[C@@H]2CCCO2)cn1] | 0.019 |
| 69 | 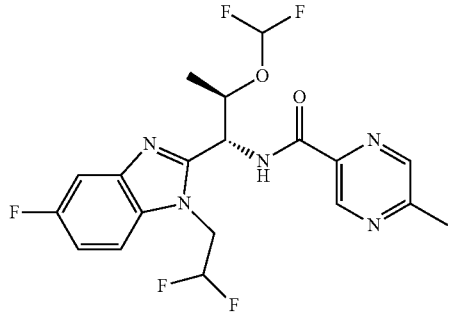 [SMILES: Cc1cnc(C(=O)N[C@H](c2nc3cc(F)ccc3n2CC(F)F)[C@@H](C)OC(F)F)cn1] | 0.018 |
| 70 | 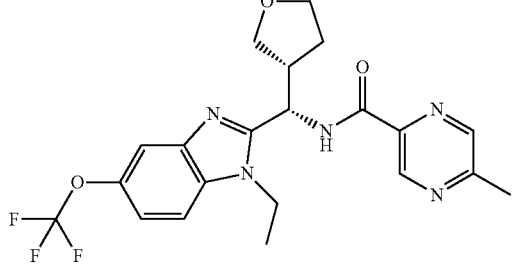 | 0.012 |
| 70-2 | 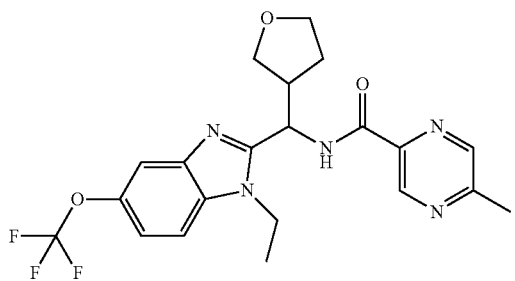 [SMILES: CCn1c(C(NC(=O)c2cnc(C)cn2)C2CCOC2)nc2cc(OC(F)(F)F)ccc21] | 0.020 |

TABLE 2-continued

In vitro potencies of compounds of the present invention as determined in Assay A

| Example | Structure | Assay A mGluR4 IC$_{50}$ [μM] |
|---|---|---|
| 71 | 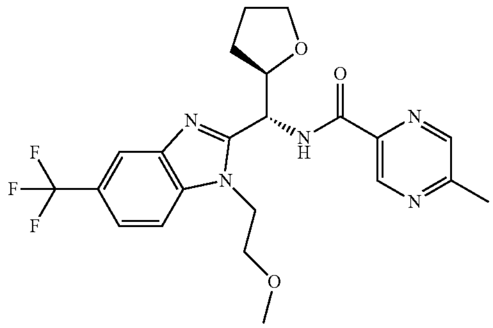 [SMILES: COCCn1c([C@@H](NC(=O)c2cnc(C)cn2)[C@H]2CCCO2)nc2cc(C(F)(F)F)ccc21] | 0.013 |
| 71-2 | 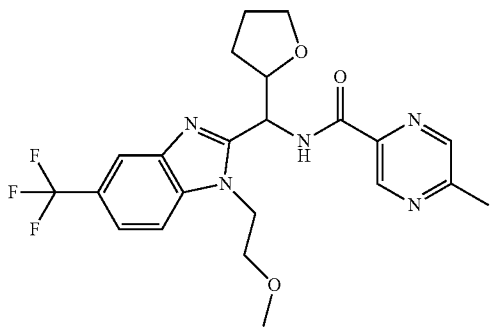 [SMILES: COCCn1c(C(NC(=O)c2cnc(C)cn2)C2CCCO2)nc2cc(C(F)(F)F)ccc21] | 0.003 |
| 71-3 | 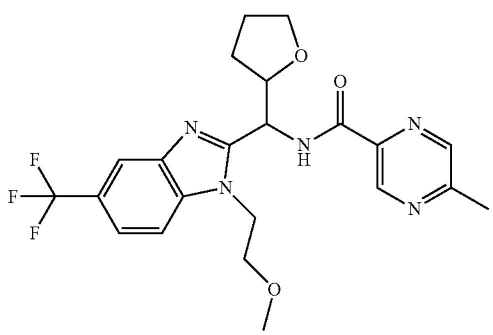 [SMILES: COCCn1c(C(NC(=O)c2cnc(C)cn2)C2CCCO2)nc2cc(C(F)(F)F)ccc21] | 0.062 |
| 72 | 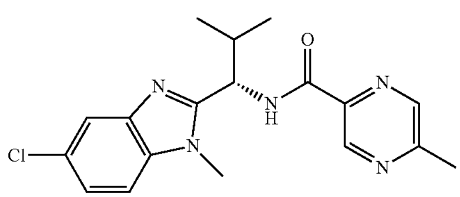 [SMILES: Cc1cnc(C(=O)N[C@H](c2nc3cc(Cl)ccc3n2C)C(C)C)cn1] | 0.008 |
| 73 | 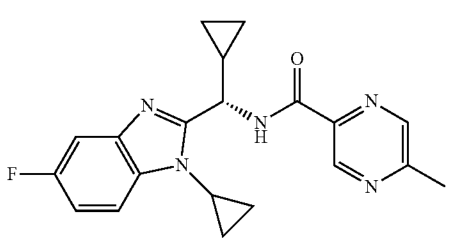 [SMILES: Cc1cnc(C(=O)N[C@H](c2nc3cc(F)ccc3n2C2CC2)C2CC2)cn1] | 0.018 |

TABLE 2-continued

In vitro potencies of compounds of the present invention as determined in Assay A

| Example | Structure | Assay A mGluR4 IC$_{50}$ [µM] |
|---|---|---|
| 74 | 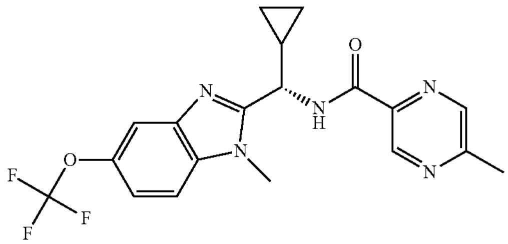 [SMILES: Cc1cnc(C(=O)N[C@H](c2nc3cc(OC(F)(F)F)ccc3n2C)C2CC2)cn1] | 0.006 |
| 75 | 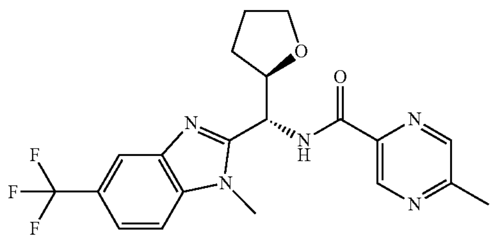 [SMILES: Cc1cnc(C(=O)N[C@H](c2nc3cc(C(F)(F)F)ccc3n2C)[C@H]2CCCO2)cn1] | 0.019 |
| 76 | 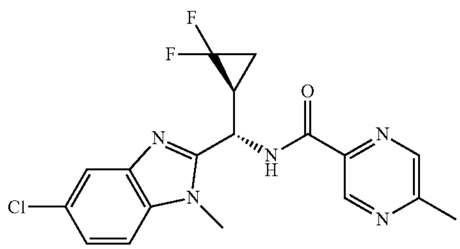 [SMILES: Cc1cnc(C(=O)N[C@H](c2nc3cc(Cl)ccc3n2C)[C@@H]2CC2(F)F)cn1] | 0.012 |
| 77 | 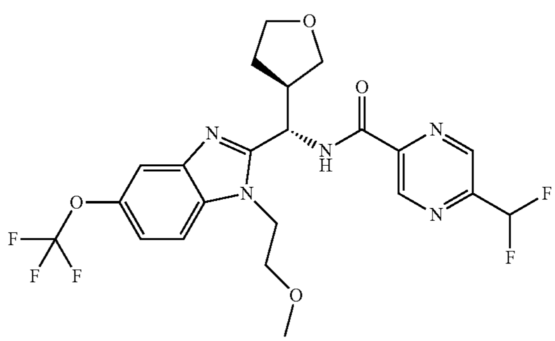 [SMILES: COCCn1c([C@@H](NC(=O)c2cnc(C(F)F)cn2)[C@H]2CCOC2)nc2cc(OC(F)(F)F)ccc21] | 0.012 |
| 78 | 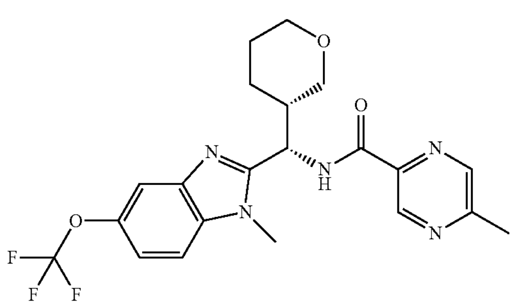 | 0.013 |

TABLE 2-continued

In vitro potencies of compounds of the present invention as determined in Assay A

| Example | Structure | Assay A mGluR4 IC$_{50}$ [μM] |
|---|---|---|
| 78-2 | 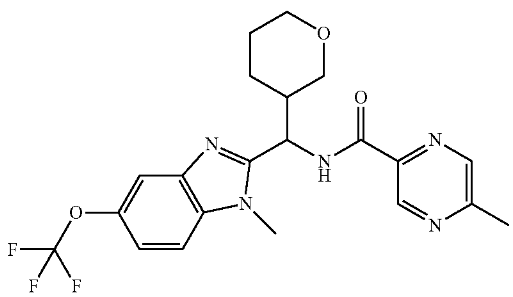 | 0.025 |
| 79 | 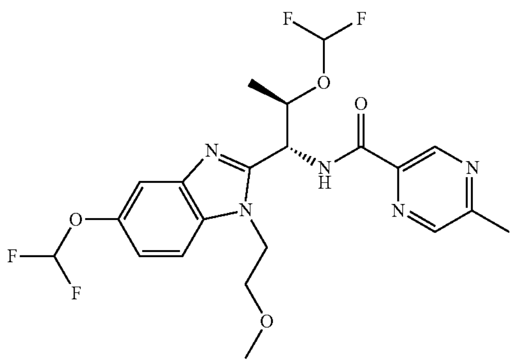 [SMILES: COCCn1c([C@@H](NC(=O)c2cnc(C)cn2)[C@@H](C)OC(F)F)nc2cc(OC(F)F)ccc21] | 0.019 |
| 80 | 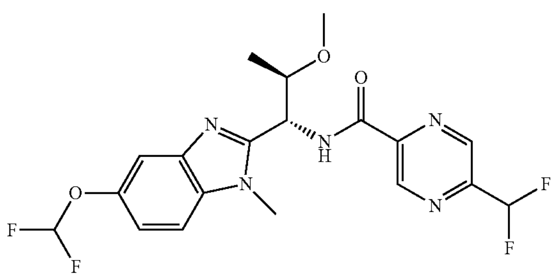 [SMILES: CO[C@H](C)[C@H](NC(=O)c1cnc(C(F)F)cn1)c1nc2cc(OC(F)F)ccc2n1C] | 0.029 |
| 81 | 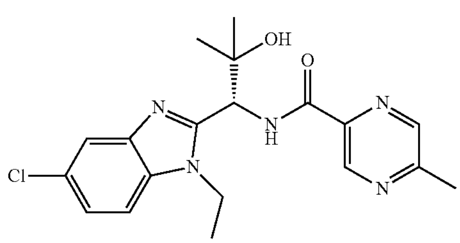 [SMILES: CCn1c([C@@H](NC(=O)c2cnc(C)cn2)C(C)(C)O)nc2cc(Cl)ccc21] | 0.014 |
| 82 | 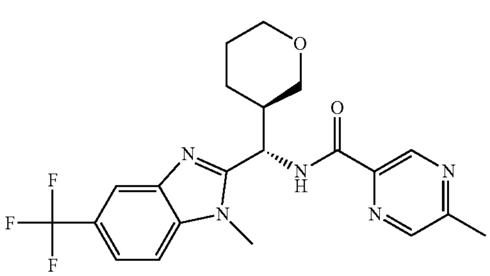 [SMILES: Cc1cnc(C(=O)N[C@H](c2nc3cc(C(F)(F)F)ccc3n2C)[C@H]2CCCOC2)cn1] | 0.013 |

TABLE 2-continued

In vitro potencies of compounds of the present invention as determined in Assay A

| Example | Structure | Assay A mGluR4 IC$_{50}$ [μM] |
|---|---|---|
| 82-2 | 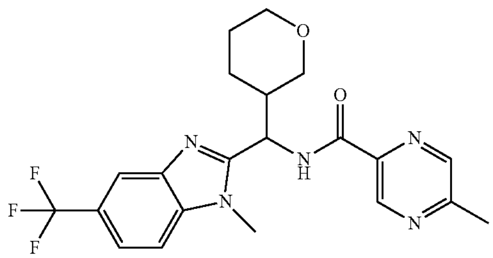 [SMILES: Cc1cnc(C(=O)NC(c2nc3cc(C(F)(F)F)ccc3n2C)C2CCCOC2)cn1] | 0.032 |
| 83 | 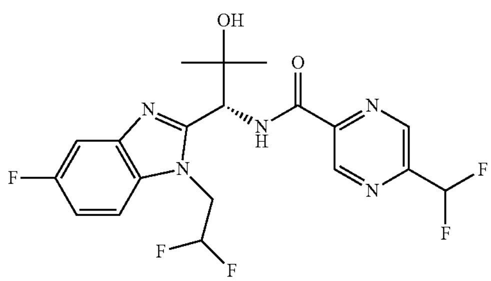 [SMILES: CC(C)(O)[C@H](NC(=O)c1cnc(C(F)F)cn1)c1nc2cc(F)ccc2n1CC(F)F] | 0.038 |
| 84 | 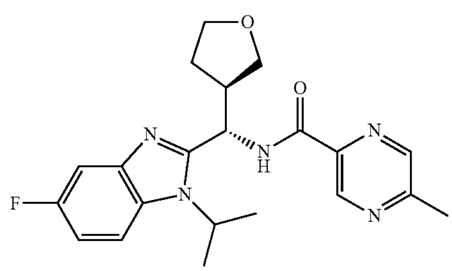 [SMILES: Cc1cnc(C(=O)N[C@H](c2nc3cc(F)ccc3n2C(C)C)[C@H]2CCOC2)cn1] | 0.026 |
| 85 | 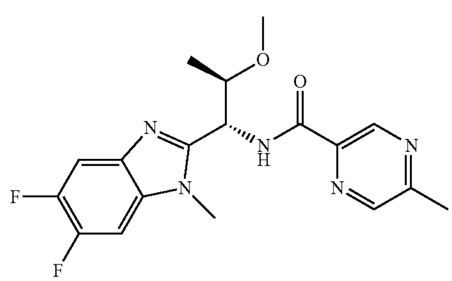 [SMILES: CO[C@H](C)[C@H](NC(=O)c1cnc(C)cn1)c1nc2cc(F)c(F)cc2n1C] | 0.048 |
| 86 | 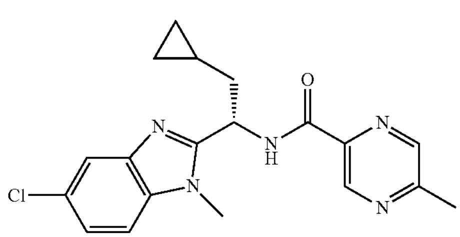 [SMILES: Cc1cnc(C(=O)N[C@@H](CC2CC2)c2nc3cc(Cl)ccc3n2C)cn1] | 0.010 |

TABLE 2-continued

In vitro potencies of compounds of the present invention as determined in Assay A

| Example | Structure | Assay A mGluR4 IC$_{50}$ [µM] |
|---|---|---|
| 87 | 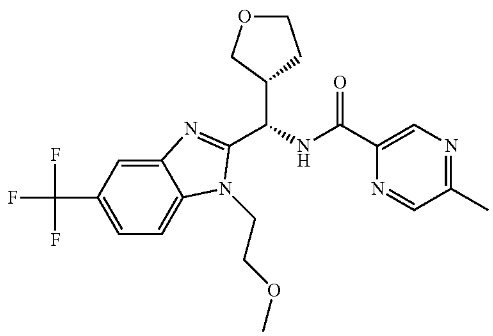 [SMILES: COCCn1c([C@@H](NC(=O)c2cnc(C)cn2)[C@H]2CCOC2)nc2cc(C(F)(F)F)ccc21] | 0.012 |
| 87-1 | 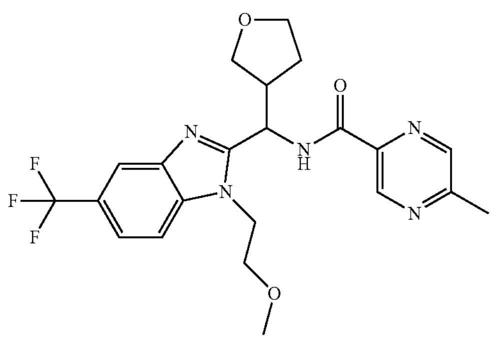 [SMILES: COCCn1c(C(NC(=O)c2cnc(C)cn2)C2CCOC2)nc2cc(C(F)(F)F)ccc21] | 0.021 |
| 88 | 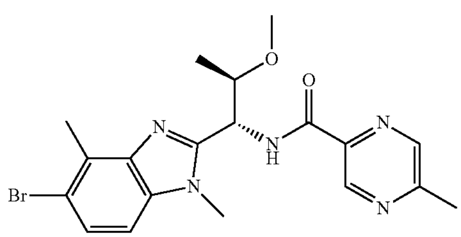 [SMILES: CO[C@H](C)[C@H](NC(=O)c1cnc(C)cn1)c1nc2c(C)c(Br)ccc2n1C] | 0.003 |
| 89 | 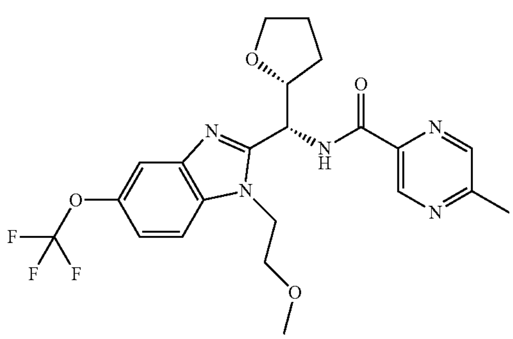 [SMILES: COCCn1c([C@@H](NC(=O)c2cnc(C)cn2)[C@H]2CCCO2)nc2cc(OC(F)(F)F)ccc21] | 0.010 |

TABLE 2-continued

In vitro potencies of compounds of the present invention as determined in Assay A

| Example | Structure | Assay A mGluR4 IC$_{50}$ [µM] |
|---|---|---|
| 89-2 | 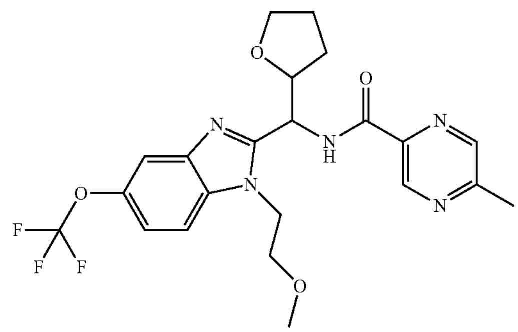 [SMILES: COCCn1c(C(NC(=O)c2cnc(C)cn2)C2CCCO2)nc2cc(OC(F)(F)F)ccc21] | 0.004 |
| 90 | 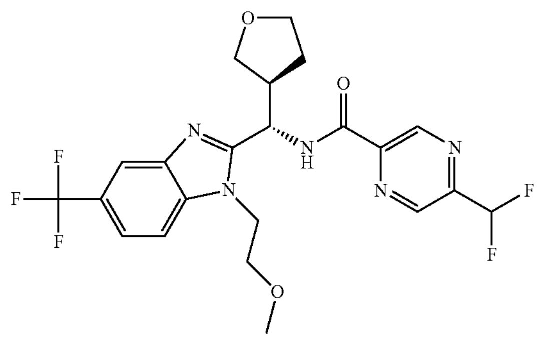 [SMILES: COCCn1c([C@@H](NC(=O)c2cnc(C(F)F)cn2)[C@@H]2CCOC2)nc2cc(C(F)(F)F)ccc21] | 0.006 |
| 90-3 | 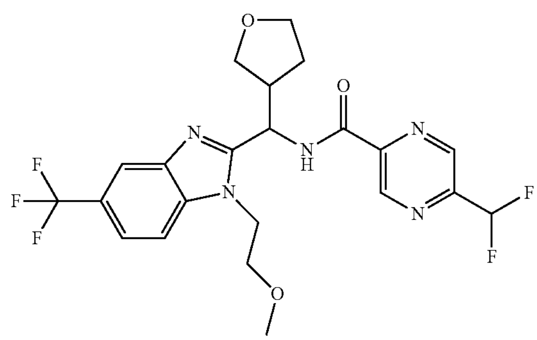 [SMILES: COCCn1c(C(NC(=O)c2cnc(C(F)F)cn2)C2CCOC2)nc2cc(C(F)(F)F)ccc21] | 0.013 |
| 91 | 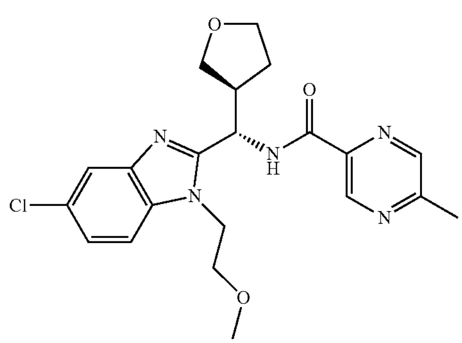 [SMILES: COCCn1c([C@@H](NC(=O)c2cnc(C)cn2)[C@@H]2CCOC2)nc2cc(Cl)ccc21] | 0.011 |

TABLE 2-continued
In vitro potencies of compounds of the present invention as determined in Assay A
| Example | Structure | Assay A mGluR4 IC$_{50}$ [μM] |
|---|---|---|
| 91-1 | 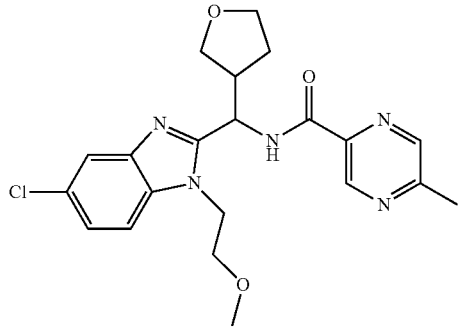 [SMILES: COCCn1c(C(NC(=O)c2cnc(C)cn2)C2CCOC2)nc2cc(Cl)ccc21] | 0.032 |
| 92 | 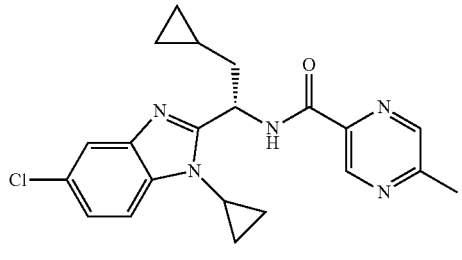 [SMILES: Cc1cnc(C(=O)N[C@@H](CC2CC2)c2nc3cc(Cl)ccc3n2C2CC2)cn1] | 0.018 |
| 93 | 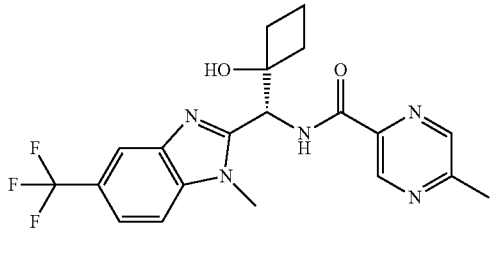 [SMILES: Cc1cnc(C(=O)N[C@H](c2nc3cc(C(F)(F)F)ccc3n2C)C2(O)CCC2)cn1] | 0.009 |
| 94 | 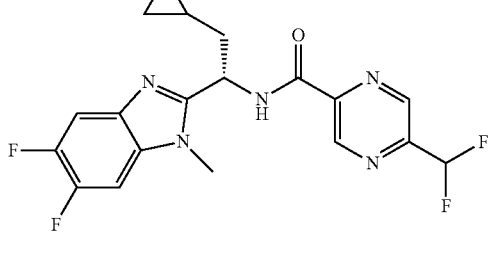 | 0.016 |
| 95 | 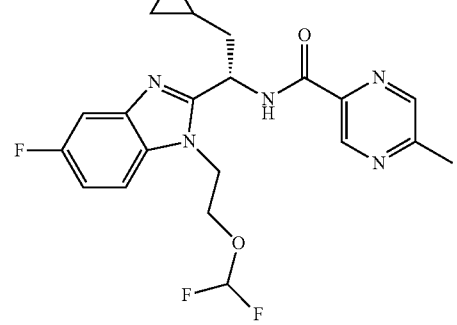 | 0.013 |

TABLE 2-continued

In vitro potencies of compounds of the present invention as determined in Assay A

| Example | Structure | Assay A mGluR4 IC$_{50}$ [µM] |
|---|---|---|
| 96 | 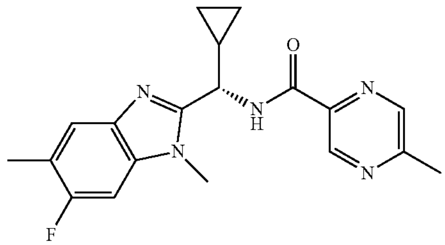 | 0.015 |
| 97 | 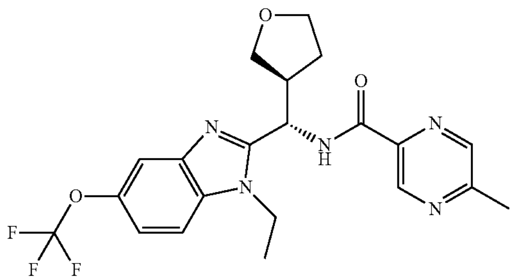 [SMILES: CCn1c([C@@H](NC(=O)c2cnc(C)cn2)[C@@H]2CCOC2)nc2cc(OC(F)(F)F)ccc21] | 0.020 |
| 97-1 | 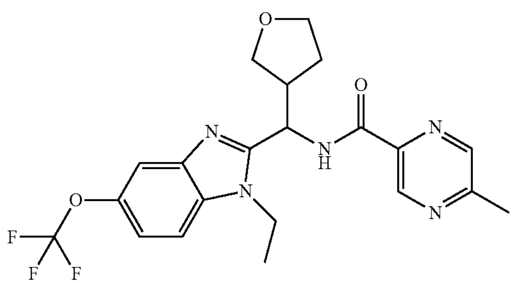 [SMILES: CCn1c(C(NC(=O)c2cnc(C)cn2)C2CCOC2)nc2cc(OC(F)(F)F)ccc21] | 0.012 |
| 98 | 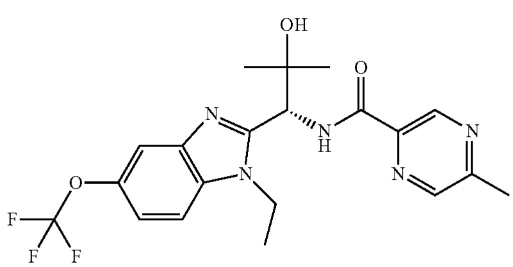 [SMILES: CCn1c([C@@H](NC(=O)c2cnc(C)cn2)C(C)(C)O)nc2cc(OC(F)(F)F)ccc21] | 0.010 |
| 99 | 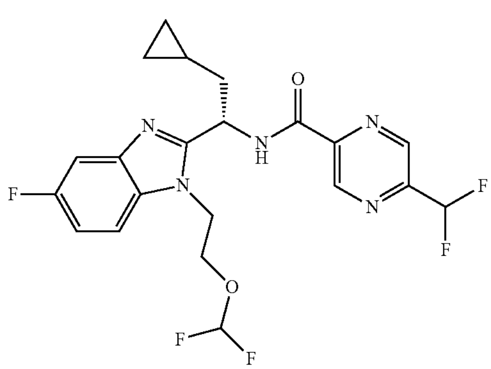 [SMILES: O=C(N[C@@H](CC1CC1)c1nc2cc(F)ccc2n1CCOC(F)F)c1cnc(C(F)F)cn1] | 0.009 |

TABLE 2-continued
In vitro potencies of compounds of the present invention as determined in Assay A
| Example | Structure | Assay A mGluR4 IC$_{50}$ [μM] |
|---|---|---|
| 100 | 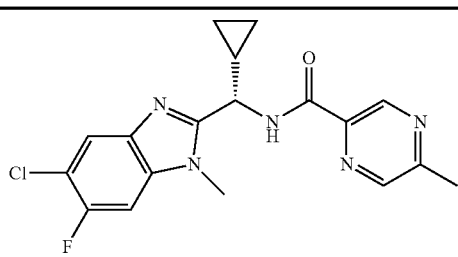 | 0.019 |
| 101 | 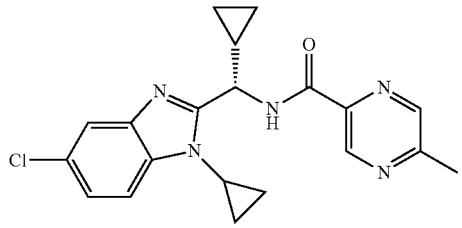 [SMILES: Cc1cnc(C(=O)N[C@H](c2nc3cc(Cl)ccc3n2C2CC2)C2CC2)cn1] | 0.009 |
| 102 | 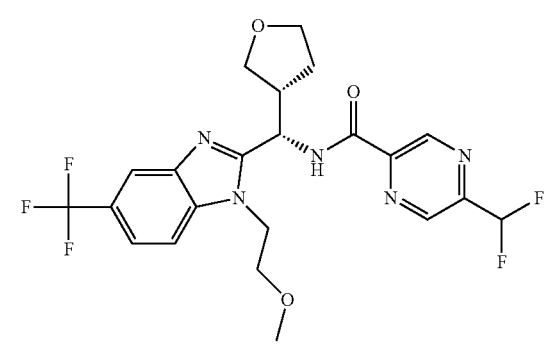 [SMILES: COCCn1c([C@@H](NC(=O)c2cnc(C(F)F)cn2)[C@H]2CCOC2)nc2cc(C(F)(F)F)ccc21] | 0.013 |
| 103 | 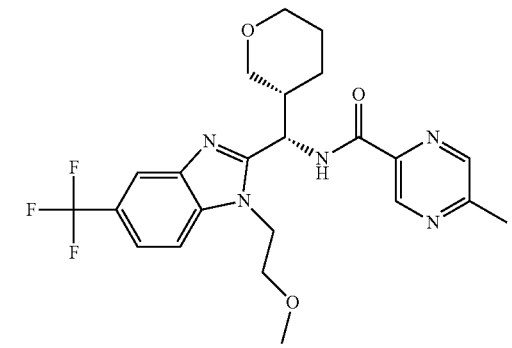 [SMILES: COCCn1c([C@@H](NC(=O)c2cnc(C)cn2)[C@H]2CCCOC2)nc2cc(C(F)(F)F)ccc21] | 0.008 |
| 103-1 | 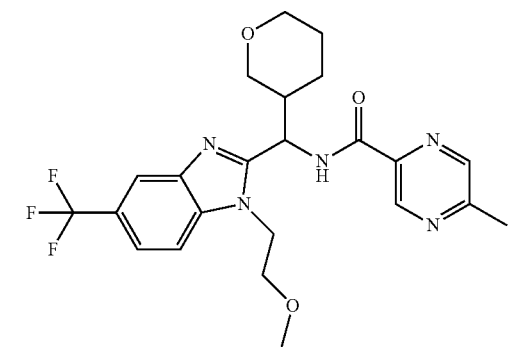 [SMILES: COCCn1c(C(NC(=O)c2cnc(C)cn2)C2CCCOC2)nc2cc(C(F)(F)F)ccc21] | 0.022 |

TABLE 2-continued

In vitro potencies of compounds of the present invention as determined in Assay A

| Example | Structure | Assay A mGluR4 IC$_{50}$ [μM] |
|---|---|---|
| 104 | 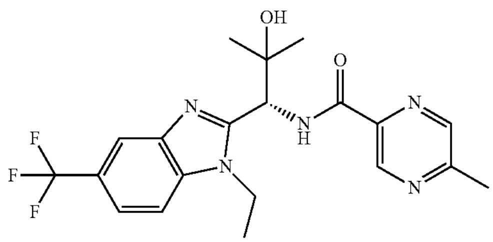 [SMILES: CCn1c([C@@H](NC(=O)c2cnc(C)cn2)C(C)(C)O)nc2cc(C(F)(F)F)ccc21] | 0.017 |
| 105 | 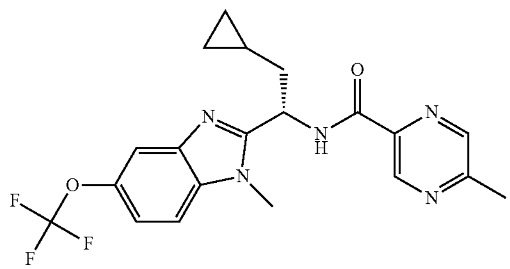 [SMILES: Cc1cnc(C(=O)N[C@@H](CC2CC2)c2nc3cc(OC(F)(F)F)ccc3n2C)cn1] | 0.008 |
| 106 | 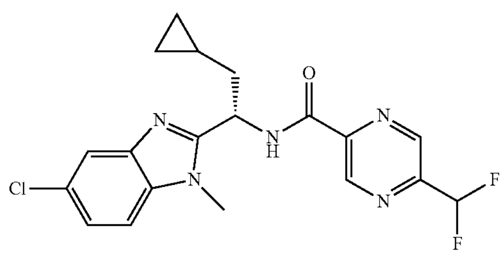 [SMILES: Cn1c([C@H](CC2CC2)NC(=O)c2cnc(C(F)F)cn2)nc2cc(Cl)ccc21] | 0.011 |
| 107 | 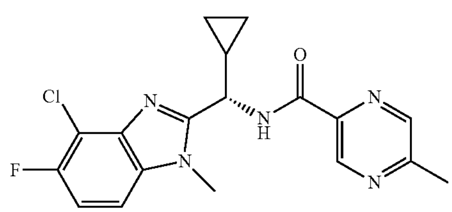 [SMILES: Cc1cnc(C(=O)N[C@H](c2nc3c(Cl)c(F)ccc3n2C)C2CC2)cn1] | 0.013 |
| 108 | 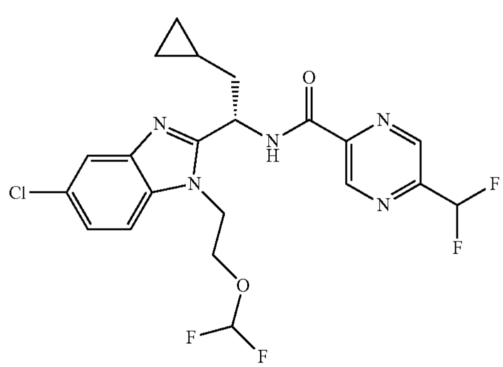 [SMILES: O=C(N[C@@H](CC1CC1)c1nc2cc(Cl)ccc2n1CCOC(F)F)c1cnc(C(F)F)cn1] | 0.006 |

TABLE 2-continued
In vitro potencies of compounds of the present invention as determined in Assay A
| Example | Structure | Assay A mGluR4 IC$_{50}$ [μM] |
|---|---|---|
| 109 | 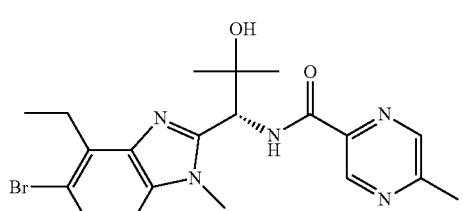 | 0.006 |
| 110 | 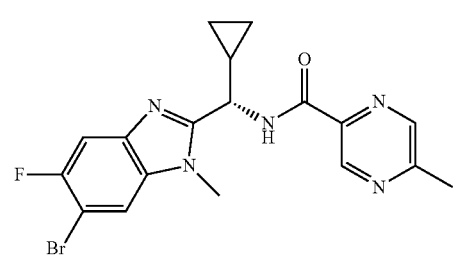 [SMILES: Cc1cnc(C(=O)N[C@H](c2nc3cc(F)c(Br)cc3n2C)C2CC2)cn1] | 0.014 |
| 111 | 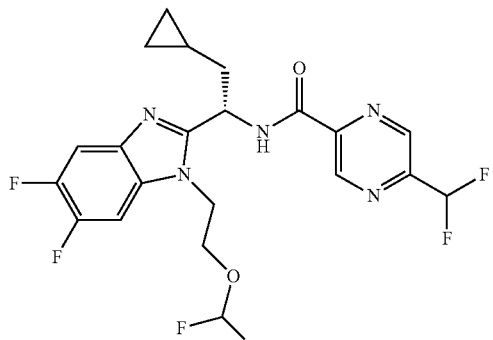 | 0.010 |
| 112 | 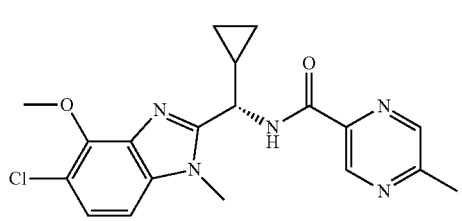 [SMILES: COc1c(Cl)ccc2c1nc([C@@H](NC(=O)c1cnc(C)cn1)C1CC1)n2C] | 0.015 |
| 113 | 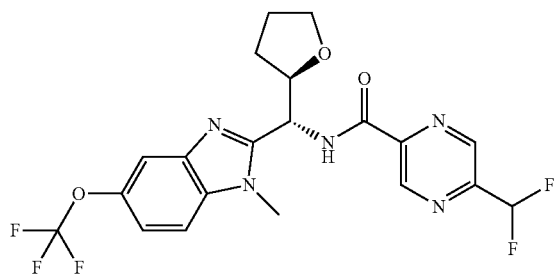 [SMILES: Cn1c([C@@H](NC(=O)c2cnc(C(F)F)cn2)[C@H]2CCCO2)nc2cc(OC(F)(F)F)ccc21] | 0.017 |

TABLE 2-continued

In vitro potencies of compounds of the present invention as determined in Assay A

| Example | Structure | Assay A mGluR4 IC$_{50}$ [µM] |
|---|---|---|
| 113-1 | 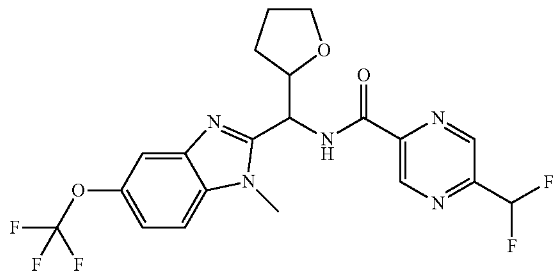 [SMILES: Cn1c(C(NC(=O)c2cnc(C(F)F)cn2)C2CCCO2)nc2cc(OC(F)(F)F)ccc21] | 0.045 |
| 114 | 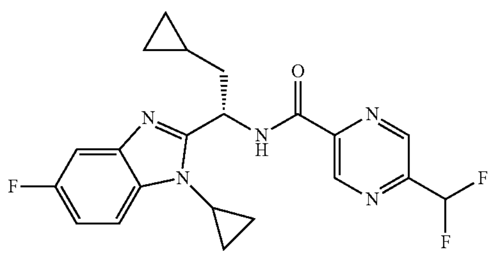 [SMILES: O=C(N[C@@H](CC1CC1)c1nc2cc(F)ccc2n1C1CC1)c1cnc(C(F)F)cn1] | 0.015 |
| 115 | 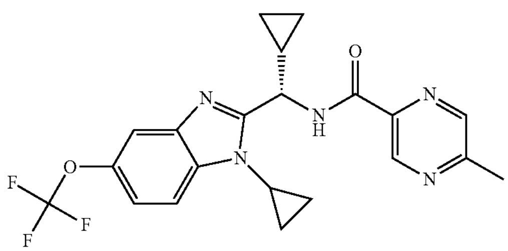 [SMILES: Cc1cnc(C(=O)N[C@H](c2nc3cc(OC(F)(F)F)ccc3n2C2CC2)C2CC2)cn1] | 0.009 |
| 116 | 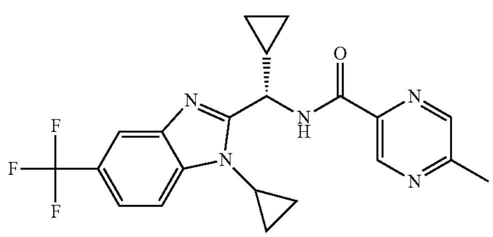 [SMILES: Cc1cnc(C(=O)N[C@H](c2nc3cc(C(F)(F)F)ccc3n2C2CC2)C2CC2)cn1] | 0.013 |
| 117 | 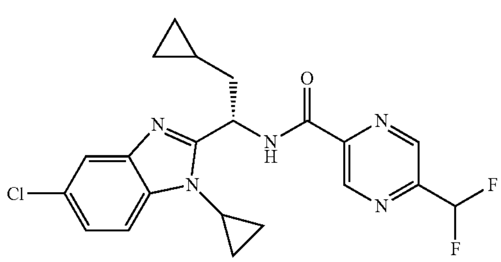 [SMILES: O=C(N[C@@H](CC1CC1)c1nc2cc(Cl)ccc2n1C1CC1)c1cnc(C(F)F)cn1] | 0.008 |

TABLE 2-continued
In vitro potencies of compounds of the present invention as determined in Assay A
| Example | Structure | Assay A mGluR4 IC$_{50}$ [µM] |
|---|---|---|
| 118 | 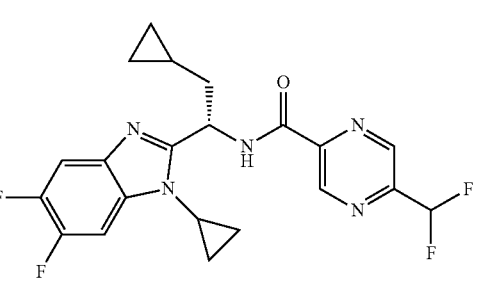 | 0.014 |
| 119 | 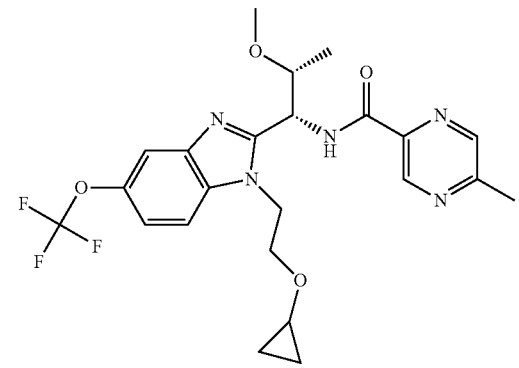 [SMILES: CO[C@H](C)[C@H](NC(=O)c1cnc(C)cn1)c1nc2cc(OC(F)(F)F)ccc2n1CCOC1CC1] | 0.001 |
| 120 | 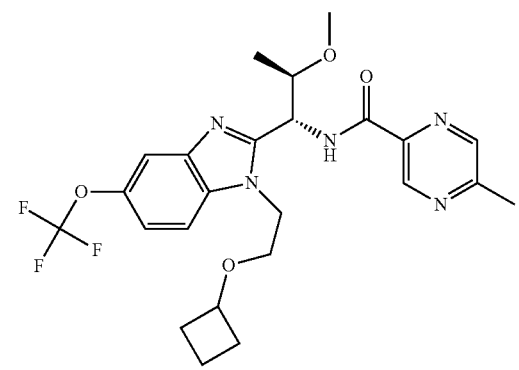 [SMILES: CO[C@H](C)[C@H](NC(=O)c1cnc(C)cn1)c1nc2cc(OC(F)(F)F)ccc2n1CCOC1CCC1] | 0.001 |
| 121 | 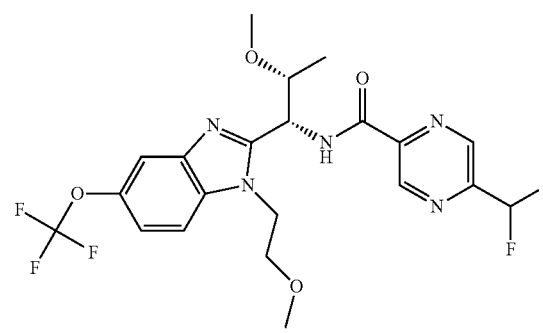 | 0.001 |

TABLE 2-continued

In vitro potencies of compounds of the present invention as determined in Assay A

| Example | Structure | Assay A mGluR4 IC$_{50}$ [μM] |
|---|---|---|
| 122 | 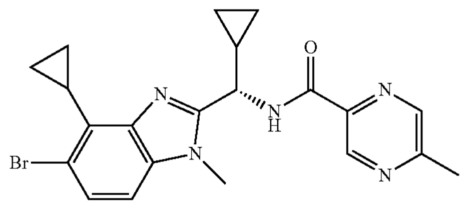 [SMILES: Cc1cnc(C(=O)N[C@H](c2nc3c(C4CC4)c(Br)ccc3n2C)C2CC2)cn1] | 0.001 |
| 123 | 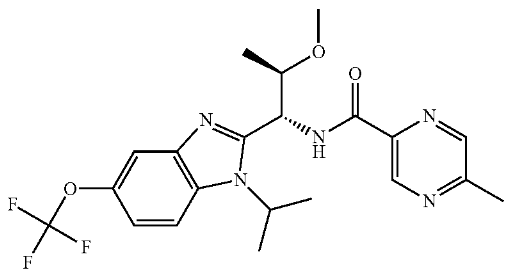 [SMILES: CO[C@H](C)[C@H](NC(=O)c1cnc(C)cn1)c1nc2cc(OC(F)(F)F)ccc2n1C(C)C] | 0.003 |
| 124 | 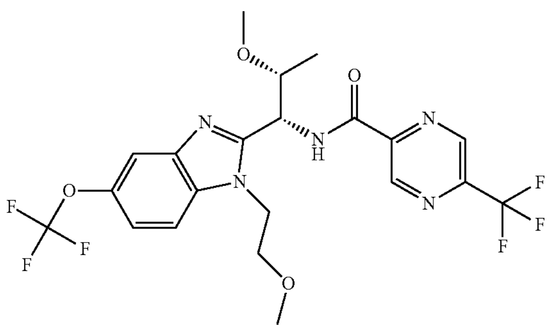 [SMILES: COCCn1c([C@@H](NC(=O)c2cnc(C(F)(F)F)cn2)[C@@H](C)OC)nc2cc(OC(F)(F)F)ccc21] | 0.004 |
| 125 | 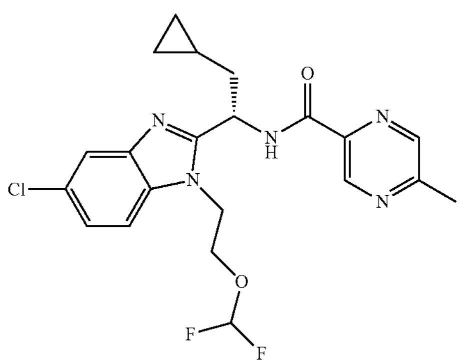 [SMILES: Cc1cnc(C(=O)N[C@@H](CC2CC2)c2nc3cc(Cl)ccc3n2CCOC(F)F)cn1] | 0.007 |
| 126 | 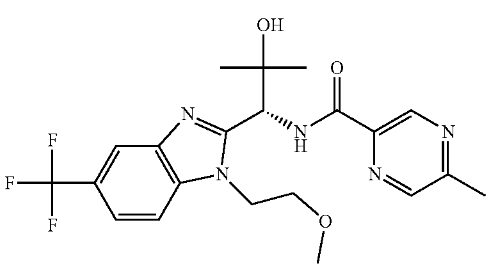 [SMILES: COCCn1c([C@@H](NC(=O)c2cnc(C)cn2)C(C)(C)O)nc2cc(C(F)(F)F)ccc21] | 0.014 |

TABLE 2-continued

In vitro potencies of compounds of the present invention as determined in Assay A

| Example | Structure | Assay A mGluR4 IC$_{50}$ [μM] |
|---|---|---|
| 127 | 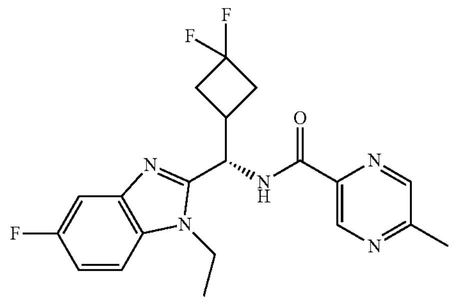 [SMILES: CCn1c([C@@H](NC(=O)c2cnc(C)cn2)C2CC(F)(F)C2)nc2cc(F)ccc21] | 0.008 |
| 128 | 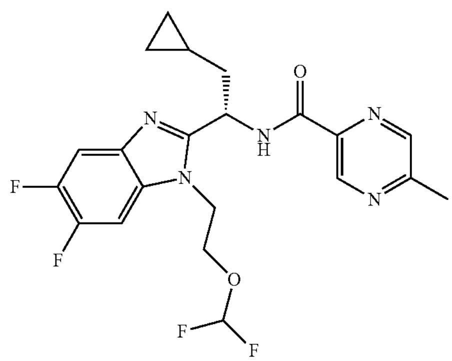 [SMILES: Cc1cnc(C(=O)N[C@@H](CC2CC2)c2nc3cc(F)c(F)cc3n2CCOC(F)F)cn1] | 0.008 |
| 129 | 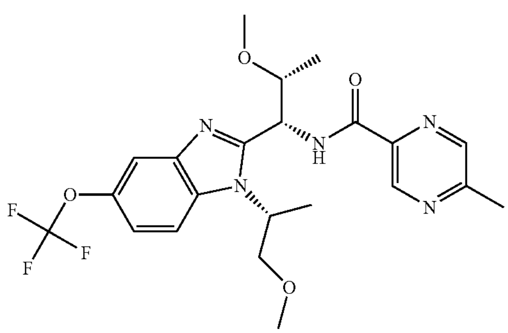 [SMILES: COC[C@@H](C)n1c([C@@H](NC(=O)c2cnc(C)cn2)[C@@H](C)OC)nc2cc(OC(F)(F)F)ccc21] | 0.009 |
| 130 | 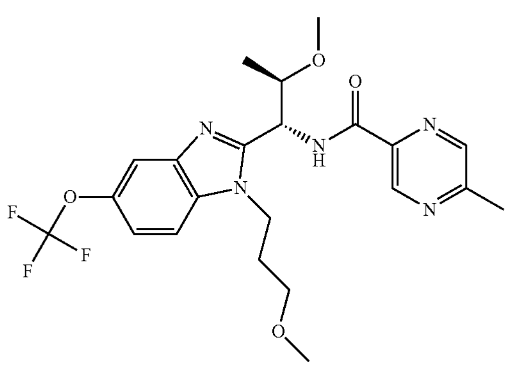 [SMILES: COCCCn1c([C@@H](NC(=O)c2cnc(C)cn2)[C@@H](C)OC)nc2cc(OC(F)(F)F)ccc21] | 0.013 |

TABLE 2-continued

In vitro potencies of compounds of the present invention as determined in Assay A

| Example | Structure | Assay A mGluR4 IC$_{50}$ [µM] |
|---|---|---|
| 131 | 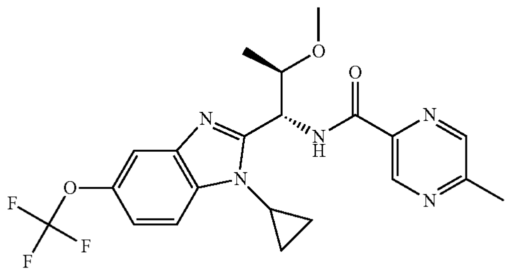 [SMILES: CO[C@H](C)[C@H](NC(=O)c1cnc(C)cn1)c1nc2cc(OC(F)(F)F)ccc2n1C1CC1] | 0.014 |
| 132 | 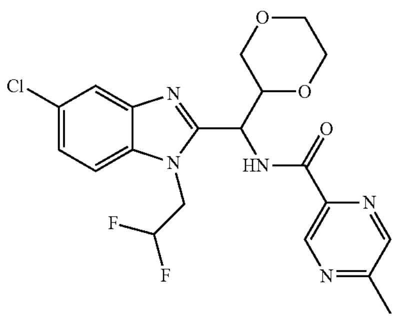 [SMILES: Cc1cnc(C(=O)NC(c2nc3cc(Cl)ccc3n2CC(F)F)C2COCCO2)cn1] | 0.007 |
| 133 | 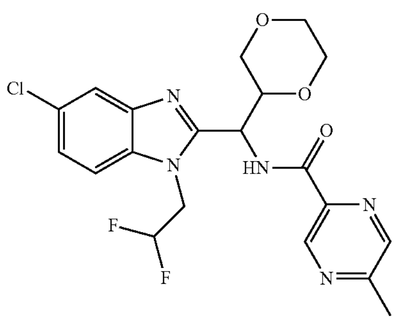 [SMILES: Cc1cnc(C(=O)NC(c2nc3cc(Cl)ccc3n2CC(F)F)C2COCCO2)cn1] | 0.062 |
| 134 | 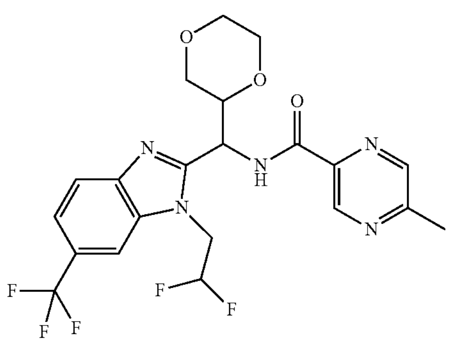 [SMILES: Cc1cnc(C(=O)NC(c2nc3ccc(C(F)(F)F)cc3n2CC(F)F)C2COCCO2)cn1] | 0.006 |

TABLE 2-continued

In vitro potencies of compounds of the present invention as determined in Assay A

| Example | Structure | Assay A mGluR4 IC$_{50}$ [μM] |
|---|---|---|
| 135 | 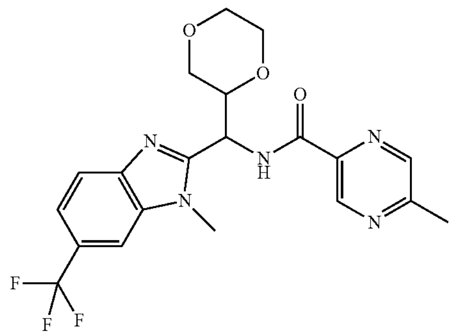 [SMILES: Cc1cnc(C(=O)NC(c2nc3ccc(C(F)(F)F)cc3n2C)C2COCCO2)cn1] | 0.07 |
| 136 | 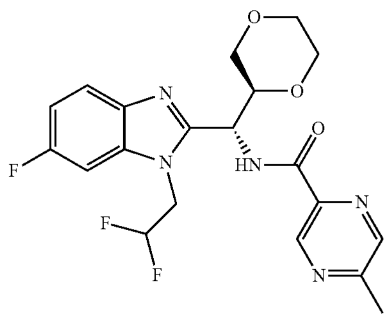 [SMILES: Cc1cnc(C(=O)N[C@H](c2nc3ccc(F)cc3n2CC(F)F)[C@H]2COCCO2)cn1] | 0.031 |
| 137 | 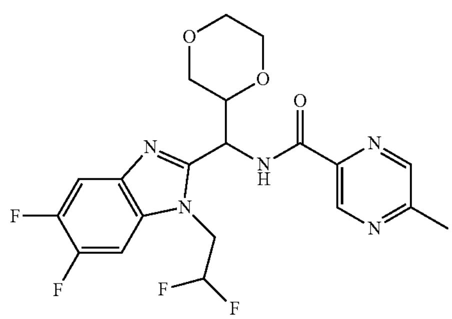 [SMILES: Cc1cnc(C(=O)NC(c2nc3cc(F)c(F)cc3n2CC(F)F)C2COCCO2)cn1] | 0.011 |
| 138 | 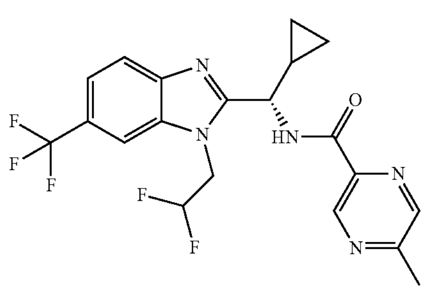 [SMILES: Cc1cnc(C(=O)N[C@H](c2nc3ccc(C(F)(F)F)cc3n2CC(F)F)C2CC2)cn1] | 0.003 |
| 139 | 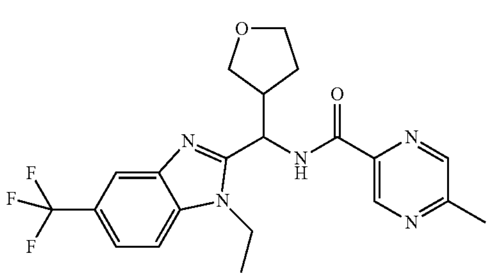 [SMILES: CCn1c(C(NC(=O)c2cnc(C)cn2)C2CCOC2)nc2cc(C(F)(F)F)ccc21] | 0.011 |

TABLE 2-continued

In vitro potencies of compounds of the present invention as determined in Assay A

| Example | Structure | Assay A mGluR4 IC$_{50}$ [μM] |
|---|---|---|
| 140 | 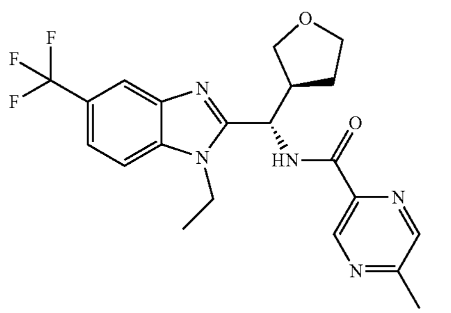 [SMILES: CCn1c([C@@H](NC(=O)c2cnc(C)cn2)[C@@H]2CCOC2)nc2cc(C(F)(F)F)ccc21] | 0.012 |
| 141 | 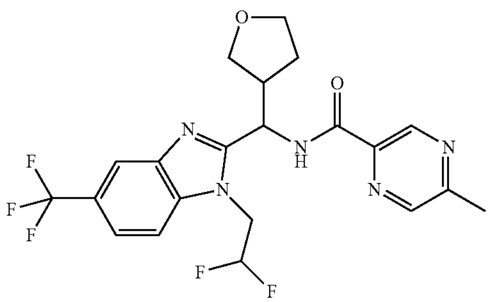 [SMILES: Cc1cnc(C(=O)NC(c2nc3cc(C(F)(F)F)ccc3n2CC(F)F)C2CCOC2)cn1] | 0.031 |
| 142 | 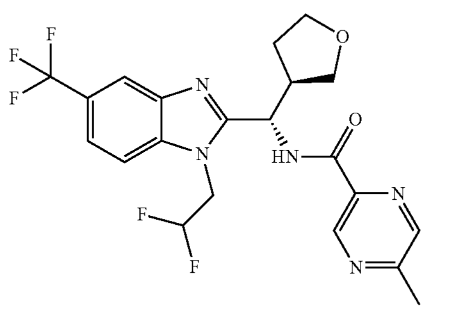 [SMILES: Cc1cnc(C(=O)N[C@H](c2nc3cc(C(F)(F)F)ccc3n2CC(F)F)[C@H]2CCOC2)cn1] | 0.008 |
| 143 | 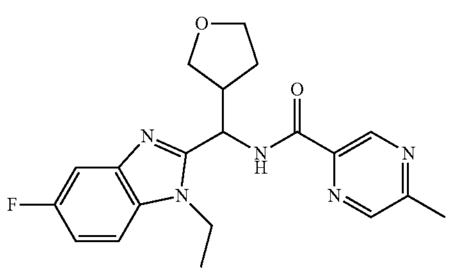 [SMILES: CCn1c(C(NC(=O)c2cnc(C)cn2)C2CCOC2)nc2cc(F)ccc21] | 0.066 |
| 144 | 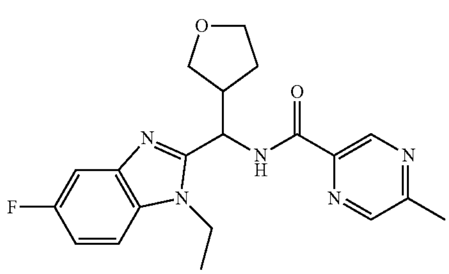 [SMILES: CCn1c(C(NC(=O)c2cnc(C)cn2)C2CCOC2)nc2cc(F)ccc21] | 0.041 |

TABLE 2-continued

In vitro potencies of compounds of the present invention as determined in Assay A

| Example | Structure | Assay A mGluR4 IC$_{50}$ [μM] |
|---|---|---|
| 145 | 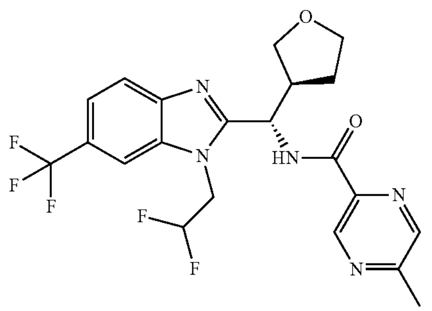 [SMILES: Cc1cnc(C(=O)N[C@H](c2nc3ccc(C(F)(F)F)cc3n2CC(F)F)[C@@H]2CCOC2)cn1] | 0.041 |
| 146 | 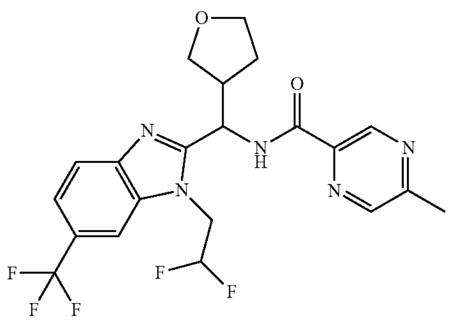 [SMILES: Cc1cnc(C(=O)NC(c2nc3ccc(C(F)(F)F)cc3n2CC(F)F)C2CCOC2)cn1] | 0.016 |
| 147 | 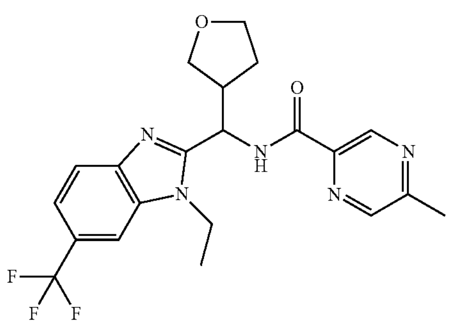 [SMILES: CCn1c(C(NC(=O)c2cnc(C)cn2)C2CCOC2)nc2ccc(C(F)(F)F)cc21] | 0.011 |
| 148 | 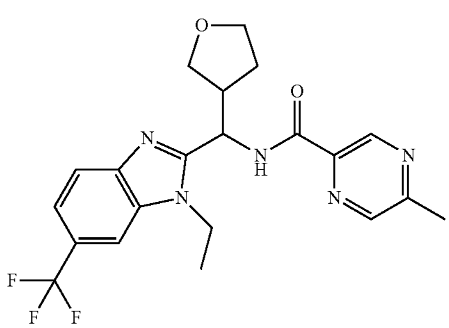 [SMILES: CCn1c(C(NC(=O)c2cnc(C)cn2)C2CCOC2)nc2ccc(C(F)(F)F)cc21] | 0.014 |

TABLE 2-continued

In vitro potencies of compounds of the present invention as determined in Assay A

| Example | Structure | Assay A mGluR4 IC$_{50}$ [μM] |
|---|---|---|
| 149 | 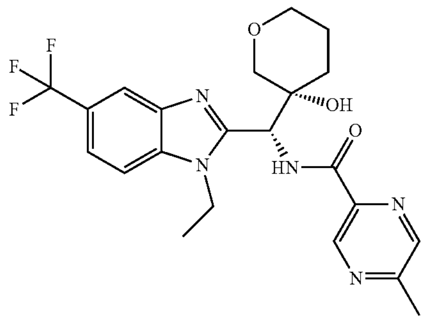 [SMILES: CCn1c([C@@H](NC(=O)c2cnc(C)cn2)[C@]2(O)CCCOC2)nc2cc(C(F)(F)F)ccc21] | 0.003 |
| 150 | 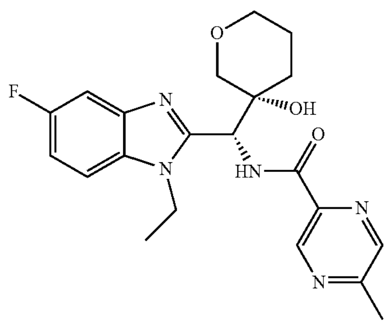 [SMILES: CCn1c([C@@H](NC(=O)c2cnc(C)cn2)[C@]2(O)CCCOC2)nc2cc(F)ccc21] | 0.014 |
| 151 | 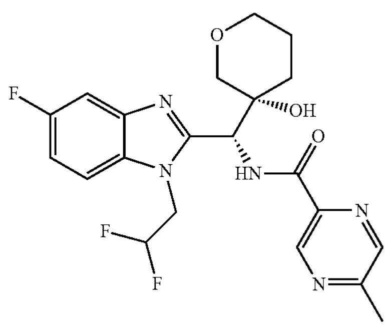 [SMILES: Cc1cnc(C(=O)N[C@H](c2nc3cc(F)ccc3n2CC(F)F)[C@]2(O)CCCOC2)cn1] | 0.058 |
| 152 | 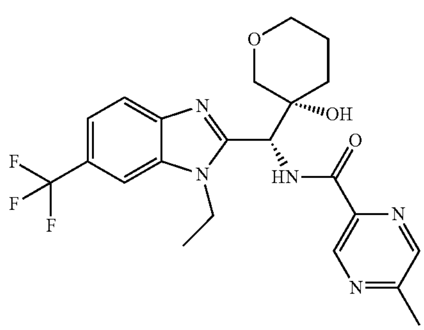 [SMILES: CCn1c([C@@H](NC(=O)c2cnc(C)cn2)[C@]2(O)CCCOC2)nc2ccc(C(F)(F)F)cc21] | 0.014 |

TABLE 2-continued

In vitro potencies of compounds of the present invention as determined in Assay A

| Example | Structure | Assay A mGluR4 IC$_{50}$ [μM] |
|---|---|---|
| 153 | 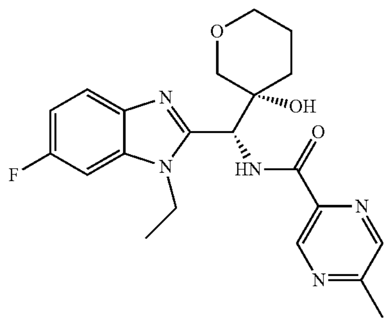 [SMILES: CCn1c([C@@H](NC(=O)c2cnc(C)cn2)[C@]2(O)CCCOC2)nc2ccc(F)cc21] | 0.03 |
| 154 | 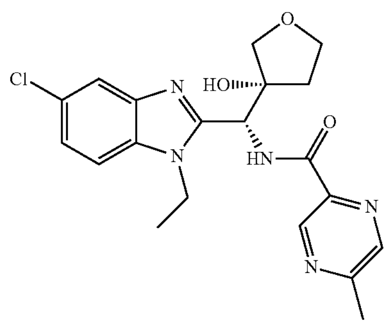 [SMILES: CCn1c([C@@H](NC(=O)c2cnc(C)cn2)[C@]2(O)CCOC2)nc2cc(Cl)ccc21] | 0.084 |
| 155 | 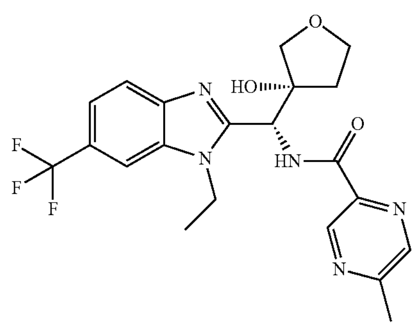 [SMILES: CCn1c([C@@H](NC(=O)c2cnc(C)cn2)[C@]2(O)CCOC2)nc2ccc(C(F)(F)F)cc21] | 0.063 |
| 156 | 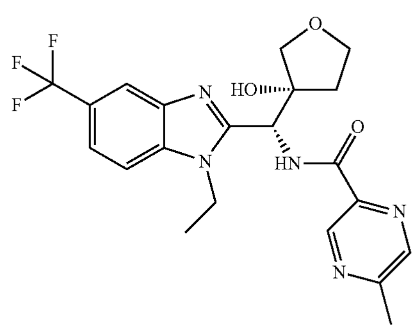 [SMILES: CCn1c([C@@H](NC(=O)c2cnc(C)cn2)[C@]2(O)CCOC2)nc2cc(C(F)(F)F)ccc21] | 0.039 |

TABLE 2-continued

In vitro potencies of compounds of the present invention as determined in Assay A

| Example | Structure | Assay A mGluR4 IC$_{50}$ [μM] |
|---|---|---|
| 157 | 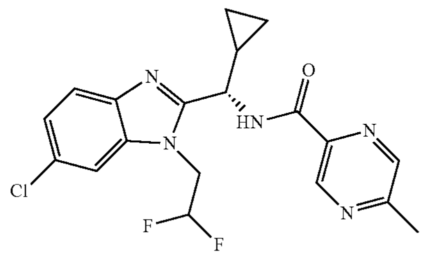 [SMILES: Cc1cnc(C(=O)N[C@H](c2nc3ccc(Cl)cc3n2CC(F)F)C2CC2)cn1] | 0.006 |
| 158 | 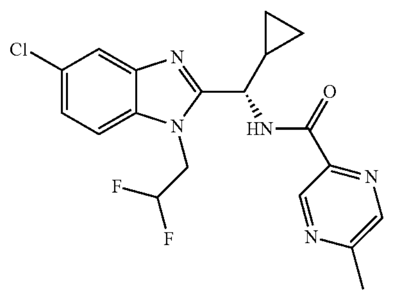 [SMILES: Cc1cnc(C(=O)N[C@H](c2nc3cc(Cl)ccc3n2CC(F)F)C2CC2)cn1] | 0.003 |
| 159 | 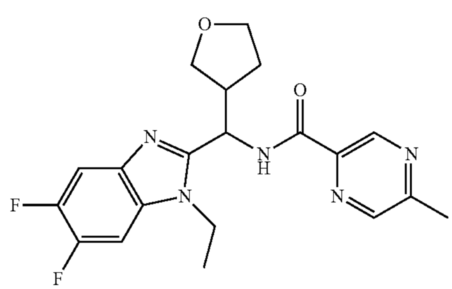 [SMILES: CCn1c(C(NC(=O)c2cnc(C)cn2)C2CCOC2)nc2cc(F)c(F)cc21] | 0.030 |
| 160 | 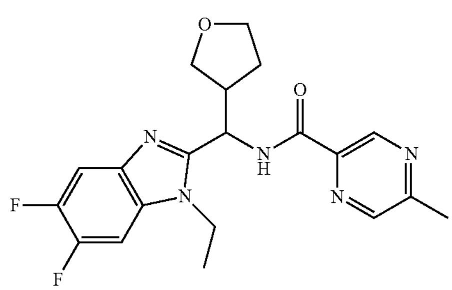 [SMILES: CCn1c(C(NC(=O)c2cnc(C)cn2)C2CCOC2)nc2cc(F)c(F)cc21] | 0.047 |
| 161 | 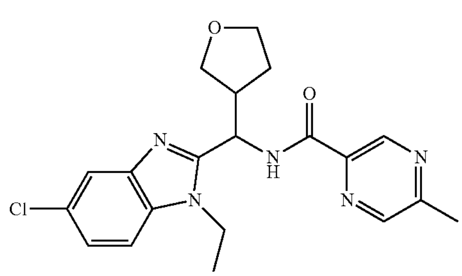 [SMILES: CCn1c(C(NC(=O)c2cnc(C)cn2)C2CCOC2)nc2cc(Cl)ccc21] | 0.014 |

TABLE 2-continued

In vitro potencies of compounds of the present invention as determined in Assay A

| Example | Structure | Assay A mGluR4 IC$_{50}$ [µM] |
|---|---|---|
| 162 | 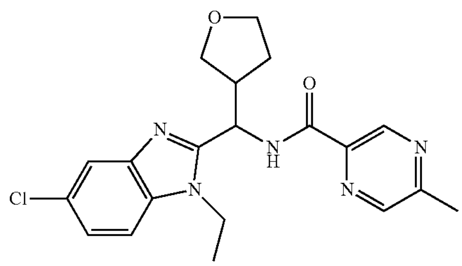 [SMILES: CCn1c(C(NC(=O)c2cnc(C)cn2)C2CCOC2)nc2cc(Cl)ccc21] | 0.030 |
| 163 | 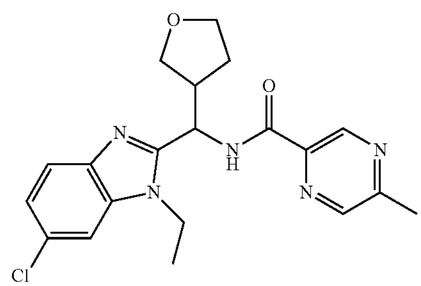 [SMILES: CCn1c(C(NC(=O)c2cnc(C)cn2)C2CCOC2)nc2ccc(Cl)cc21] | 0.027 |
| 164 | 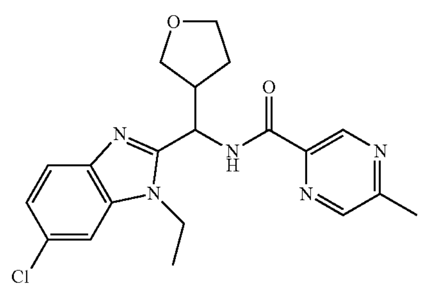 [SMILES: CCn1c(C(NC(=O)c2cnc(C)cn2)C2CCOC2)nc2ccc(Cl)cc21] | 0.035 |
| 165 | 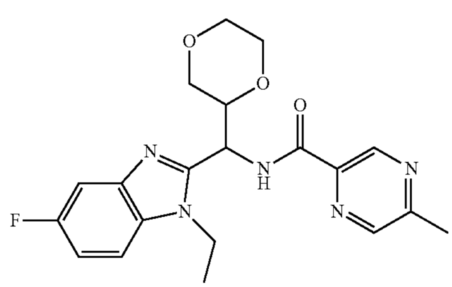 [SMILES: CCn1c(C(NC(=O)c2cnc(C)cn2)C2COCCO2)nc2cc(F)ccc21] | 0.020 |
| 166 | 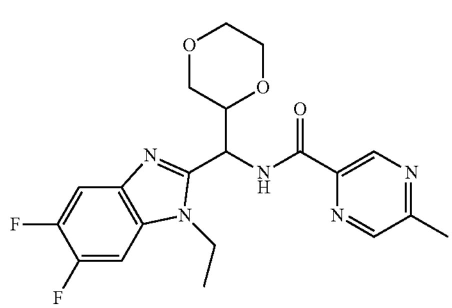 [SMILES: CCn1c(C(NC(=O)c2cnc(C)cn2)C2COCCO2)nc2cc(F)c(F)cc21] | 0.015 |

TABLE 2-continued

In vitro potencies of compounds of the present invention as determined in Assay A

| Example | Structure | Assay A mGluR4 IC$_{50}$ [μM] |
|---|---|---|
| 167 | 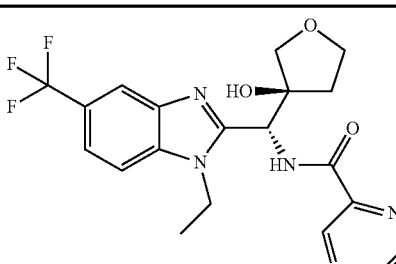 | 0.055 |

Use in Treatment/Method of Use

The present invention is directed to compounds which are useful in the treatment and/or prevention of a disease, disorder and condition wherein the inhibition of mGluR4 activity is of therapeutic benefit, including but not limited to the treatment of psychiatric and neurological conditions associated with impulse control deficits or maladaptive impulsivity. Such impulse control deficits are seen in addictions including substance use disorders; personality disorders such as borderline personality disorder, antisocial personality disorder, conduct disorder, eating disorders such as binge eating disorder, attention deficit hyperactivity disorder, bipolar disorder, stress related disorders such as post-traumatic stress disorder, tic disorders like Tourerett's syndrome, other movement disorders such as restless legs syndrome. According to a further aspect of the invention, compounds of the present invention are useful in the treatment of mGluR4 related pathophysiological disturbances, cognition, motivated behaviours/reward, mood and stress, aggression. In addition, there is therapeutic benefit in cancer and related disorders associated with maladaptive tumorgenesis like osteosarcoma. According to a further aspect of the invention, compounds of the present invention are useful in the treatment of metabolic disorders by mGluR4-related modulation of satiety pathways and/or signaling, to treat disorders including but not limited to obesity.

In view of their pharmacological effect, compounds of the present invention are suitable for use in the treatment and/or prevention of a disease or condition selected from the list consisting of (1) Disorders associated with malfunction in impulse control such as pathological gambling, trichotillomania, intermittent explosive disorder, conduct disorder, antisocial personality disorder, kleptomania, pyromania, compulsive shopping, internet addiction, sexual compulsion, sexual disorder, sexual dysfunction, psychosexual disorder, eating disorders, such as binge eating, bulimia nervosa, anorexia nervosa, other specified feeding or eating disorders, obesity, overweight, cachexia, appetite/taste disorders, vomiting, nausea, Prader-Willi-syndrome, hyperphagia, appetite/taste disorders, bipolar disorder, post-traumatic stress disorder;

(2) Substance abuse/dependence/seeking or addiction as well as relapse prevention (including but not limited to drugs, such as cocaine, opiates such as morphine, barbiturates, benzodiazepines, amphetamines, nicotine/tobacco and other psychostimulants), alcoholism and alcohol-related disorders, drug abuse or addiction or relapse, tolerance to narcotics or withdrawal from narcotics;

(3) Psychiatric and neurological conditions like attention deficit hyperactivity disorder, conduct disorders, attention problems and related disorders, sleep disorders, anxiety disorders such as generalized anxiety disorder, panic disorder, phobias, post-traumatic stress disorder, schizophrenia, Alzheimer's disease, Parkinson's disease, Huntington's disease and Gilles de la, restless legs syndrome, dementia, dyskinesia, severe mental retardation, neurodegenerative disorders including nosological entities such as disinhibition-dementia-parkinsonism-amyotrophy complex, pallido-ponto-nigral degeneration, Mood disorders, bipolar disorder, mania, depression, manic depression, borderline personality disorder, antisocial personality disorder, aggression such as impulsive aggression, suicidality, frontotemporal dementia, obsessive compulsive disorder, delirium, affective neurosis/disorder, depressive neurosis/disorder, anxiety neurosis, dysthymic disorder, neurological diseases, such as cerebral oedema and angioedema, cerebral dementia like e.g. Parkinson's and Alzheimer's disease, senile dementia; multiple sclerosis, epilepsy, temporal lobe epilepsy, drug resistant epilepsy, seizure disorders, stroke, myasthenia gravis, brain and meningeal infections like encephalomyelitis, meningitis, HIV as well as schizophrenia, delusional disorders, autism, affective disorders and tic disorders including but not limited to Tourette Syndrome and other movement disorders, dpilepsia, chronic pain;

(4) Cognitive dysfunction in psychiatric or neurological disorder, cognitive impairments associated with schizophrenia, Alzheimer's disease and other neurological and psychiatric disorders;

(5) Personality disorders such as borderline personality disorder, antisocial personality disorder, paranoid personality disorder, schizoid and schizotypal personality disorder, histrionic personality disorder, narcissistic personality disorder, avoidant personality disorder, dependent personality disorder, other specified and non-specified personality disorders;

(6) sleep disorders such as narcolepsy, jetlag, sleep apnea, insomnia, parasomnia, disturbed biological and circadian rhythms, sleep disturbances associated with psychiatric and neurological disorders;
(7) Non-neuronal conditions including metabolic conditions like diabetes, insulin resistance, metabolic syndrome, overweight, obesity, as well as use for weight reduction, cosmetic weight loss, relapse prevention during or after obesity treatment, body weight maintenance, emesis, disorders associated with malfunction of the cardiovascular-vascular system and disorders associated with maladaptive blood pressure control like hypertension or hypotension;
(8) Cancer and related disorders associated with maladaptive tumorgenesis like osteosarcoma, breast cancer, ependymoma, bladder cancer, colorectal cancer.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable compositions for administering the compounds of the present invention will be apparent to those with ordinary skill in the art and include for example tablets, pills, capsules, suppositories, lozenges, troches, solutions, syrups, elixirs, sachets, injectables, inhalatives, and powders. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and compressing the resulting mixture to tablets.

Combination Therapy

Compounds according to the present invention can be combined with other treatment options known to be used in the art in connection with a treatment of any of the indications the treatment of which is in the focus of the present invention.

Among such active pharmaceutical ingredients or treatment options that are considered suitable for combination with the compounds and the treatment according to the present invention are antidepressants, mood stabilizers, typical and atypical antipsychotics, anxiolytics, antiepileptic drugs, anti-Parkinsons medication, sleeping agents, cognitive enhancers, stimulants, medication for attention deficit hyperactivity disorder, additional psychoactive drugs, anti-inflammatory drugs, analgesic drugs, chemotherapeutic drugs, as well as combination with treatment options used for metabolic disorders, liver diseases and kidney diseases.

Experimental Section

List of Abbreviations

% Sol percentage of solvent
μL microliter
ACN acetonitrile
AcOH acetic acid
aq. aqueous
Boc tert-butyloxycarbonyl
$Boc_2O$ di-tert-butyl-dicarbonate
chir. chiral
CIP 2-chloro-1,3-dimethyl-2-imidazolinium hexafluorophosphate
conc. concentrated
d day
DA diode Array
DAD diode array detector
DCM dichloromethane
DMF N,N-dimethylformamide
ELSD Evaporative Light Scattering Detector
EtOAc ethyl acetate
ETOH ethanol
g gram
h hour
half-conc. half concentrated
HPLC high performance liquid chromatography
i. vac. in vacuo
IPA Isopropylic Alcohol
M molar
MeOH methanol
MEOH methanol
mg milligram
min minute
ml milliliter
mL milliliter
MS Mass Spectrometer
N normal
NBS N-bromo-succinimide
NMM N-methyl-morpholine
NMP N-Methylpyrrolidone
PE petrolether
PPA 1-propanephosphonic acid cyclic anhydride
prep. Preparative
PSI pound per square inch
quant. quantitative
Rf retarding front
RT retention time
sat. saturated
$scCO2$ supercritical carbon dioxide
SFC supercritical fluid chromatography
TBTU O-(Benzotriazol-1-yl)-N,N,N,N-tetramethyluronium-tetrafluoroborat
TEA triethylamine
Temp. temperature
tert. tertiary
TFA trifluoroacetic acid
THE tetrahydrofuran
wt weight
X-Phos G1 Chloro-(2-dicyclohexylphosphino-2',4',6'-triisopropyl-1,1'-biphenyl)[2-(2-aminoethyl)-phenyl)]-palladium(II)

Methods

HPLC-MS Methods:
Method A

| Method Name: | Z003_S05 |
|---|---|
| Device description: | Agilent 1200 with DA- and MS-Detector |
| Column: | XBridge C18_3.0 × 30 mm_2.5 μm |

| | |
|---|---|
| Column producer: | Waters |
| Description: | |

| Gradient/Solvent Time [min] | % Sol [Water 0.1% NH$_3$] | % Sol [Acetonitrile] | Flow [ml/min] | Temp [° C.] | Back pressure [PSI] |
|---|---|---|---|---|---|
| 0.0 | 95.0 | 5.0 | 2.2 | 60.0 | |
| 0.2 | 95.0 | 5.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Method B

| | |
|---|---|
| Method Name: | Z011_S03 |
| Device description: | Agilent 1200 with DA- and MS-Detector |
| Column: | XBridge C18_3.0 × 30 mm_2.5 μm |
| Column producer: | Waters |
| Description: | |

| Gradient/Solvent Time [min] | % Sol [Water 0.1% NH$_3$] | % Sol [Acetonitrile] | Flow [ml/min] | Temp [° C.] | Back pressure [PSI] |
|---|---|---|---|---|---|
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 13.0 | 60.0 | |

Method C

| | |
|---|---|
| Method Name: | Z018_S04 |
| Device description: | Agilent 1200 with DA- and MS-Detector |
| Column: | Sunfire C18_3.0 × 30 mm_2.5 μm |
| Column producer: | Waters |
| Description: | |

| Gradient/Solvent Time [min] | % Sol [Water 0.1% TFA] | % Sol [Acetonitrile] | Flow [ml/min] | Temp [° C.] | Back pressure [PSI] |
|---|---|---|---|---|---|
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Chiral SFC Analytical Methods:
Method 1:

| | |
|---|---|
| Method Name: | G_IG_IPA_NH3_002 |
| Device description: | Agilent 1260 Infinity II SFC with DAD |
| Column: | Chiralpak ® IG_3 × 100 mm_3 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 95.0 | 5.0 | 2.0 | 40.0 | 2175.0 |
| 3.6 | 40.0 | 60.0 | 2.0 | 40.0 | 2175.0 |
| 4.0 | 40.0 | 60.0 | 2.0 | 40.0 | 2175.0 |

Method 2:

| | |
|---|---|
| Method Name: | G_SB_IPA_NH3_001 |
| Device description: | Agilent 1260 SFC with DAD and MS |

-continued

| Column: | CHIRAL ART ® Cellulose SB_4.6 × 250 mm_5 μm |
| --- | --- |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 95.0 | 5.0 | 4.0 | 40.0 | 2175.0 |
| 9.0 | 40.0 | 60.0 | 4.0 | 40.0 | 2175.0 |
| 10.0 | 40.0 | 60.0 | 4.0 | 40.0 | 2175.0 |

Method 3:

| Method Name: | G_SC_MEOH_NH3_001 |
| --- | --- |
| Device description: | Agilent 1260 SFC with DAD and MS |
| Column: | CHIRAL ART ® Cellulose SC_4.6 × 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
| --- | --- | --- | --- | --- | --- |
| 0.0 | 95.0 | 5.0 | 4.0 | 40.0 | 2175.0 |
| 9.0 | 40.0 | 60.0 | 4.0 | 40.0 | 2175.0 |
| 10.0 | 40.0 | 60.0 | 4.0 | 40.0 | 2175.0 |

Method 4:

| Method Name: | I_AC_10_IPA_NH3_002 |
| --- | --- |
| Device description: | Agilent 1260 Infinity II SFC with DAD |
| Column: | CHIRAL ART ® Amylose-C Neo_3 × 100 mm_3 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 90.0 | 10.0 | 2.0 | 40.0 | 2175.0 |
| 4.0 | 90.0 | 10.0 | 2.0 | 40.0 | 2175.0 |

Method 5:

| Method Name: | I_AC_15_IPA_NH3_002 |
| --- | --- |
| Device description: | Agilent 1260 Infinity II SFC with DAD |
| Column: | CHIRAL ART ® Amylose-C Neo_3 × 100 mm_3 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 85.0 | 15.0 | 2.0 | 40.0 | 2175.0 |
| 4.0 | 85.0 | 15.0 | 2.0 | 40.0 | 2175.0 |

Method 6:

| Method Name: | I_AC_20_IPA_NH3_002 |
| --- | --- |
| Device description: | Agilent 1260 Infinity II SFC with DAD |
| Column: | CHIRAL ART ® Amylose-C Neo_3 × 100 mm_3 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 80.0 | 20.0 | 2.0 | 40.0 | 2175.0 |

| | | | | | |
|---|---|---|---|---|---|
| 4.0 | 80.0 | 20.0 | 2.0 | 40.0 | 2175.0 |

Method 7:

| | |
|---|---|
| Method Name: | I_ADH_15_IPA_NH3_001 |
| Device description: | Agilent 1260 SFC with DAD and ELSD |
| Column: | Chiralpak ® AD-H_4.6 × 250 mm_5 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 8:

| | |
|---|---|
| Method Name: | I_C2_10_MEOH_NH3_002 |
| Device description: | Agilent 1260 Infinity II SFC with DAD |
| Column: | Lux(R) Cellulose-2_3 × 100 mm_3 μm |
| Column producer: | Phenomenex |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

Method 9:

| | |
|---|---|
| Method Name: | I_C2_15_IPA_NH3_001 |
| Device description: | Agilent 1260 SFC with DAD and ELSD |
| Column: | Lux ® Cellulose-2_4.6 × 250 mm_5 μm |
| Column producer: | Phenomenex |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 10:

| | |
|---|---|
| Method Name: | I_C2_15_MEOH_NH3_001 |
| Device description: | Agilent 1260 SFC with DAD and ELSD |
| Column: | Lux ® Cellulose-2_4.6 × 250 mm_5 μm |
| Column producer: | Phenomenex |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 11:

| | |
|---|---|
| Method Name: | I_C2_15_MEOH_NH3_002 |
| Device description: | Agilent 1260 Infinity II SFC with DAD |
| Column: | Lux(R) Cellulose-2_3 × 100 mm_3 μm |

Method 12:

| Method Name: | I_C2_20_IPA_NH3_001 |
|---|---|
| Device description: | Agilent 1260 SFC with DAD and ELSD |
| Column: | Lux ® Cellulose-2_4.6 × 250 mm_5 μm |
| Column producer: | Phenomenex |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 13:

| Method Name: | I_C2_20_IPA_NH3_002 |
|---|---|
| Device description: | Agilent 1260 Infinity II SFC with DAD |
| Column: | Lux(R) Cellulose-2_3 × 100 mm_3 μm |
| Column producer: | Phenomenex |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 80.0 | 20.0 | 2.0 | 40.0 | 2175.0 |
| 4.0 | 80.0 | 20.0 | 2.0 | 40.0 | 2175.0 |

Method 14:

| Method Name: | I_C2_20_MEOH_NH3_002 |
|---|---|
| Device description: | Agilent 1260 Infinity II SFC with DAD |
| Column: | Lux(R) Cellulose-2_3 × 100 mm_3 μm |
| Column producer: | Phenomenex |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 80.0 | 20.0 | 2.0 | 40.0 | 2175.0 |
| 4.0 | 80.0 | 20.0 | 2.0 | 40.0 | 2175.0 |

Method 15:

| Method Name: | I_C4_10_MEOH_NH3_002 |
|---|---|
| Device description: | Agilent 1260 Infinity II SFC with DAD |
| Column: | Lux(R) Cellulose-4_3 × 100 mm_3 μm |
| Column producer: | Phenomenex |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

Method 16:

-continued

| Column producer: | Phenomenex |
|---|---|
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 2.0 | 40.0 | 2175.0 |
| 4.0 | 85.0 | 15.0 | 2.0 | 40.0 | 2175.0 |

| Method Name: | I_IA_10_ETOH_NH3_001 |
| --- | --- |
| Device description: | Agilent 1260 SFC with DAD and MS |
| Column: | Chiralpak ® IA_4.6 × 250 mm_5 μm |
| Column producer: | Daicel |
| Description: | |

| Gradient/Solvent Time [min] | % Sol [scCO2] | % Sol [ETOH 20 mM NH3] | Flow [ml/min] | Temp [° C.] | Back pressure [PSI] |
| --- | --- | --- | --- | --- | --- |
| 0.0 | 90.0 | 10.0 | 4.0 | 40.0 | 2175.0 |
| 10.0 | 90.0 | 10.0 | 4.0 | 40.0 | 2175.0 |

Method 17:

| Method Name: | I_IA_10_MEOH_NH3_001 |
| --- | --- |
| Device description: | Agilent 1260 SFC with DAD and MS |
| Column: | Chiralpak ® IA_4.6 × 250 mm_5 μm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
| --- | --- | --- | --- | --- | --- |
| 0.0 | 90.0 | 10.0 | 4.0 | 40.0 | 2175.0 |
| 10.0 | 90.0 | 10.0 | 4.0 | 40.0 | 2175.0 |

Method 18:

| Method Name: | I_IA_15_MEOH_NH3_001 |
| --- | --- |
| Device description: | Agilent 1260 SFC with DAD and MS |
| Column: | Chiralpak ® IA_4.6 × 250 mm_5 μm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
| --- | --- | --- | --- | --- | --- |
| 0.0 | 85.0 | 15.0 | 4.0 | 40.0 | 2175.0 |
| 10.0 | 85.0 | 15.0 | 4.0 | 40.0 | 2175.0 |

Method 19:

| Method Name: | I_IA_25_MEOH_NH3_001 |
| --- | --- |
| Device description: | Agilent 1260 SFC with DAD and MS |
| Column: | Chiralpak ® IA_4.6 × 250 mm_5 μm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
| --- | --- | --- | --- | --- | --- |
| 0.0 | 75.0 | 25.0 | 4.0 | 40.0 | 2175.0 |
| 10.0 | 75.0 | 25.0 | 4.0 | 40.0 | 2175.0 |

Method 20:

| Method Name: | I_IA_30_IPA_NH3_001 |
| --- | --- |
| Device description: | Agilent 1260 SFC with DAD and MS |
| Column: | Chiralpak ® IA_4.6 × 250 mm_5 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 70.0 | 30.0 | 4.0 | 40.0 | 2175.0 |
| 10.0 | 70.0 | 30.0 | 4.0 | 40.0 | 2175.0 |

Method 21:

Method 22:

| Method Name: | I_IBN_15_IPA_NH3 | | | | |
|---|---|---|---|---|---|
| Device description: | Agilent 1260 SFC with DAD and MS | | | | |
| Column: | Chiralpak ® IB N_4.6 × 250 mm_5 µm | | | | |
| Column producer: | Daicel | | | | |
| Description: | | | | | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 22:

| Method Name: | I_IC_20_MEOH_NH3_001 | | | | |
|---|---|---|---|---|---|
| Device description: | Agilent 1260 SFC with DAD and MS | | | | |
| Column: | Chiralpak ® IC_4.6 × 250 mm_5 µm | | | | |
| Column producer: | Daicel | | | | |
| Description: | | | | | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 23:

| Method Name: | I_IG_10_IPA_NH3_002 | | | | |
|---|---|---|---|---|---|
| Device description: | Agilent 1260 Infinity II SFC with DAD | | | | |
| Column: | Chiralpak ® IG_3 × 100 mm_3 µm | | | | |
| Column producer: | Daicel | | | | |
| Description: | | | | | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

Method 24:

| Method Name: | I_IG_10_MEOH_NH3_002 | | | | |
|---|---|---|---|---|---|
| Device description: | Agilent 1260 Infinity II SFC with DAD | | | | |
| Column: | Chiralpak ® IG_3 × 100 mm_3 µm | | | | |
| Column producer: | Daicel | | | | |
| Description: | | | | | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

Method 25:

| Method Name: | I_IG_15_IPA_NH3_001 | | | | |
|---|---|---|---|---|---|
| Device description: | Agilent 1260 SFC with DAD and MS | | | | |
| Column: | Chiralpak ® IG_4.6 × 250 mm_5 µm | | | | |
| Column producer: | Daicel | | | | |
| Description: | | | | | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 26:

| | | | | | |
|---|---|---|---|---|---|
| Method Name: | | I_IG_15_IPA_NH3_002 | | | |
| Device description: | | Agilent 1260 Infinity II SFC with DAD | | | |
| Column: | | Chiralpak ® IG_3 × 100 mm_3 μm | | | |
| Column producer: | | Daicel | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 85.0 | 15.0 | 2.0 | 40.0 | 2175.0 |
| 4.0 | 85.0 | 15.0 | 2.0 | 40.0 | 2175.0 |

Method 27:

| | | | | | |
|---|---|---|---|---|---|
| Method Name: | | I_IG_15_MEOH_NH3_001 | | | |
| Device description: | | Agilent 1260 SFC with DAD and MS | | | |
| Column: | | Chiralpak ® IG_4.6 × 250 mm_5 μm | | | |
| Column producer: | | Daicel | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 85.0 | 15.0 | 4.0 | 40.0 | 2175.0 |
| 10.0 | 85.0 | 15.0 | 4.0 | 40.0 | 2175.0 |

Method 28:

| | | | | | |
|---|---|---|---|---|---|
| Method Name: | | I_IG_20_IPA_NH3_001 | | | |
| Device description: | | Agilent 1260 SFC with DAD and MS | | | |
| Column: | | Chiralpak ® IG_4.6 × 250 mm_5 μm | | | |
| Column producer: | | Daicel | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 4.0 | 40.0 | 2175.0 |
| 10.0 | 80.0 | 20.0 | 4.0 | 40.0 | 2175.0 |

Method 29:

| | | | | | |
|---|---|---|---|---|---|
| Method Name: | | I_IG_20_MEOH_NH3_001 | | | |
| Device description: | | Agilent 1260 SFC with DAD and MS | | | |
| Column: | | Chiralpak ® IG_4.6 × 250 mm_5 μm | | | |
| Column producer: | | Daicel | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 80.0 | 20.0 | 4.0 | 40.0 | 2175.0 |
| 10.0 | 80.0 | 20.0 | 4.0 | 40.0 | 2175.0 |

Method 30:

| | | | | | |
|---|---|---|---|---|---|
| Method Name: | | I_IG_25_MEOH_NH3_001 | | | |
| Device description: | | Agilent 1260 SFC with DAD and MS | | | |
| Column: | | Chiralpak ® IG_4.6 × 250 mm_5 μm | | | |
| Column producer: | | Daicel | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 75.0 | 25.0 | 4.0 | 40.0 | 2175.0 |
| 10.0 | 75.0 | 25.0 | 4.0 | 40.0 | 2175.0 |

Method 31:

| Method Name: | I_IG_30_IPA_NH3_001 |
|---|---|
| Device description: | Agilent 1260 SFC with DAD and MS |
| Column: | Chiralpak ® IG_4.6 × 250 mm_5 µm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 70.0 | 30.0 | 4.0 | 40.0 | 2175.0 |

Method 32:

| Method Name: | I_IG_35_MEOH_NH3_001 |
|---|---|
| Device description: | Agilent 1260 SFC with DAD and MS |
| Column: | Chiralpak ® IG_4.6 × 250 mm_5 µm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 65.0 | 35.0 | 4.0 | 40.0 | 2175.0 |
| 10.0 | 65.0 | 35.0 | 4.0 | 40.0 | 2175.0 |

Method 33:

| Method Name: | I_SA_05_IPA_NH3_001 |
|---|---|
| Device description: | Agilent 1260 SFC with DAD and MS |
| Column: | CHIRAL ART ® Amylose SA_4.6 × 250 mm_5 µm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 95.0 | 5.0 | 4.0 | 40.0 | 2175.0 |
| 10.0 | 95.0 | 5.0 | 4.0 | 40.0 | 2175.0 |

Method 34:

| Method Name: | I_SA_10_IPA_NH3_001 |
|---|---|
| Device description: | Agilent 1260 SFC with DAD and MS |
| Column: | CHIRAL ART ® Amylose SA_4.6 × 250 mm_5 µm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

Method 35:

| Method Name: | I_SA_10_MEOH_NH3_001 |
|---|---|
| Device description: | Agilent 1260 SFC with DAD and MS |
| Column: | CHIRAL ART@ Amylose SA_4.6 × 250 mm_5 µm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

Method 36:

| Method Name: | I_SA_15_IPA_NH3_001 |
|---|---|
| Device description: | Agilent 1260 SFC with DAD and MS |
| Column: | CHIRAL ART ® Amylose SA_4.6 × 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 37:

| Method Name: | I_SA_15_MEOH_NH3_001 |
|---|---|
| Device description: | Agilent 1260 SFC with DAD and MS |
| Column: | CHIRAL ART ® Amylose SA_4.6 × 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 38:

| Method Name: | I_SA_20_IPA_NH3_001 |
|---|---|
| Device description: | Agilent 1260 SFC with DAD and MS |
| Column: | CHIRAL ART ® Amylose SA_4.6 × 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 39:

| Method Name: | I_SA_20_MEOH_NH3_001 |
|---|---|
| Device description: | Agilent 1260 SFC with DAD and MS |
| Column: | CHIRAL ART ® Amylose SA_4.6 × 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 40:

| Method Name: | I_SA_25_IPA_NH3_001 |
|---|---|
| Device description: | Agilent 1260 SFC with DAD and MS |
| Column: | CHIRAL ART ® Amylose SA_4.6 × 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Method 41:

| | | | | | |
|---|---|---|---|---|---|
| Method Name: | | I_SA_25_MEOH_NH3_001 | | | |
| Device description: | | Agilent 1260 SFC with DAD and MS | | | |
| Column: | | CHIRAL ART ® Amylose SA_4.6 × 250 mm_5 μm | | | |
| Column producer: | | YMC | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 75.0 | 25.0 | 4.0 | 40.0 | 2175.0 |
| 10.0 | 75.0 | 25.0 | 4.0 | 40.0 | 2175.0 |

Method 42:

| | | | | | |
|---|---|---|---|---|---|
| Method Name: | | I_SA_35_MEOH_NH3_001 | | | |
| Device description: | | Agilent 1260 SFC with DAD and MS | | | |
| Column: | | CHIRAL ART ® Amylose SA_4.6 × 250 mm_5 μm | | | |
| Column producer: | | YMC | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 65.0 | 35.0 | 4.0 | 40.0 | 2175.0 |
| 10.0 | 65.0 | 35.0 | 4.0 | 40.0 | 2175.0 |

Method 43

| | | | | | |
|---|---|---|---|---|---|
| Method Name: | | I_SB_10_IPA_NH3_001 | | | |
| Device description: | | Agilent 1260 SFC with DAD and MS | | | |
| Column: | | CHIRAL ART ® Cellulose SB_4.6 × 250 mm_5 μm | | | |
| Column producer: | | YMC | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 4.0 | 40.0 | 2175.0 |
| 10.0 | 90.0 | 10.0 | 4.0 | 40.0 | 2175.0 |

Method 44:

| | | | | | |
|---|---|---|---|---|---|
| Method Name: | | I_SB_10_MEOH_NH3_001 | | | |
| Device description: | | Agilent 1260 SFC with DAD and MS | | | |
| Column: | | CHIRAL ART ® Cellulose SB_4.6 × 250 mm_5 μm | | | |
| Column producer: | | YMC | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 90.0 | 10.0 | 4.0 | 40.0 | 2175.0 |
| 10.0 | 90.0 | 10.0 | 4.0 | 40.0 | 2175.0 |

Method 45:

| | | | | | |
|---|---|---|---|---|---|
| Method Name: | | I_SB_15_IPA_NH3_001 | | | |
| Device description: | | Agilent 1260 SFC with DAD and MS | | | |
| Column: | | CHIRAL ART ® Cellulose SB_4.6 × 250 mm_5 μm | | | |
| Column producer: | | YMC | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 85.0 | 15.0 | 4.0 | 40.0 | 2175.0 |
| 10.0 | 85.0 | 15.0 | 4.0 | 40.0 | 2175.0 |

Method 46:

| Method Name: | I_SB_15_MEOH_NH3_001 |
|---|---|
| Device description: | Agilent 1260 SFC with DAD and MS |
| Column: | CHIRAL ART ® Cellulose SB_4.6 × 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 47:

| Method Name: | I_SB_20_MEOH_NH3_001 |
|---|---|
| Device description: | Agilent 1260 SFC with DAD and MS |
| Column: | CHIRAL ART ® Cellulose SB_4.6 x 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 48:

| Method Name: | I_SB_25_IPA_NH3_001 |
|---|---|
| Device description: | Agilent 1260 SFC with DAD and MS |
| Column: | CHIRAL ART ® Cellulose SB_4.6 x 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Method 49:

| Method Name: | I_SC_05_IPA_NH3_001 |
|---|---|
| Device description: | Agilent 1260 SFC with DAD and MS |
| Column: | CHIRAL ART ® Cellulose SC_4.6 x 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 95.0 | 5.0 | 4.0 | 40.0 | 2175.0 |
| 10.0 | 95.0 | 5.0 | 4.0 | 40.0 | 2175.0 |

Method 50:

| Method Name: | I_SC_10_IPA_NH3_001 |
|---|---|
| Device description: | Agilent 1260 SFC with DAD and MS |
| Column: | CHIRAL ART ® Cellulose SC_4.6 x 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

Method 51:

| Method Name: | I_SC_10_IPA_NH3_002 |
|---|---|
| Device description: | Agilent 1260 Infinity II SFC with DAD |
| Column: | CHIRAL ART ® Cellulose-SC_3 x 100 mm_3 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

Method 52:

| Method Name: | I_SC_10_MEOH_NH3_001 |
|---|---|
| Device description: | Agilent 1260 SFC with DAD and MS |
| Column: | CHIRAL ART ® Cellulose SC_4.6 x 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

Method 53:

| Method Name: | I_SC_10_MEOH_NH3_002 |
|---|---|
| Device description: | Agilent 1260 Infinity II SFC with DAD |
| Column: | CHIRAL ART ® Cellulose-SC_3 x 100 mm_3 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 90.0 | 10.0 | 2.0 | 40.0 | 2175.0 |
| 4.0 | 90.0 | 10.0 | 2.0 | 40.0 | 2175.0 |

Method 54:

| Method Name: | I_SC_15_IPA_NH3_001 |
|---|---|
| Device description: | Agilent 1260 SFC with DAD and MS |
| Column: | CHIRAL ART ® Cellulose SC_4.6 x 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 55:

| Method Name: | I_SC_15_MEOH_NH3_001 |
|---|---|
| Device description: | Agilent 1260 SFC with DAD and MS |
| Column: | CHIRAL ART ® Cellulose SC_4.6 x 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Method 56:

| Method Name: | I_SC_20_IPA_NH3_001 |
|---|---|
| Device description: | Agilent 1260 SFC with DAD and MS |
| Column: | CHIRAL ART ® Cellulose SC_4.6 x 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 57:

| Method Name: | I_SC_20_MEOH_NH3_001 |
|---|---|
| Device description: | Agilent 1260 SFC with DAD and MS |
| Column: | CHIRAL ART ® Cellulose SC_4.6 x 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 58:

| Method Name: | I_SC_25_IPA_NH3_001 |
|---|---|
| Device description: | Agilent 1260 SFC with DAD and MS |
| Column: | CHIRAL ART ® Cellulose SC_4.6 x 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Method 59:

| Method Name: | I_SC_25_MEOH_NH3_001 |
|---|---|
| Device description: | Agilent 1260 SFC with DAD and MS |
| Column: | CHIRAL ART ® Cellulose SC_4.6 x 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Method 60:

| Method Name: | I_SC_30_IPA_NH3_001 |
|---|---|
| Device description: | Agilent 1260 SFC with DAD and MS |
| Column: | CHIRAL ART ® Cellulose SC_4.6 x 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 70.0 | 30.0 | 4.0 | 40.0 | 2175.0 |

Method 61:

| Method Name: | I_SJ_10_IPA_NH3_001 |
| --- | --- |
| Device description: | Agilent 1260 SFC with DAD and MS |
| Column: | CHIRAL ART ® Cellulose SJ_4.6 x 250 mm_5 µm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 90.0 | 10.0 | 2.0 | 40.0 | 2175.0 |
| 10.0 | 90.0 | 10.0 | 2.0 | 40.0 | 2175.0 |

Method 62:

| Method Name: | I_SZ_10_MEOH_NH3_003 |
| --- | --- |
| Device description: | Agilent 1260 Infinity II SFC with DAD and MS |
| Column: | CHIRAL ART ® Cellulose SZ_4.6 × 250 mm_5 µm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
| --- | --- | --- | --- | --- | --- |
| 0.0 | 90.0 | 10.0 | 4.0 | 40.0 | 2175.0 |
| 10.0 | 90.0 | 10.0 | 4.0 | 40.0 | 2175.0 |

Method 63:

| Method Name: | I_SC_15_MEOH_NH3_003 |
| --- | --- |
| Device description: | Agilent 1260 Infinity II SFC with DAD and MS |
| Column: | CHIRAL ART ® Cellulose SC_4.6 × 250 mm_5 µm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
| --- | --- | --- | --- | --- | --- |
| 0.0 | 85.0 | 15.0 | 4.0 | 40.0 | 2175.0 |
| 10.0 | 85.0 | 15.0 | 4.0 | 40.0 | 2175.0 |

Method 64:

| Method Name: | I_SC_10_IPA_NH3_003 |
| --- | --- |
| Device description: | Agilent 1260 Infinity II SFC with DAD and MS |
| Column: | CHIRAL ART ® Cellulose SC_4.6 × 250 mm_5 µm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 90.0 | 10.0 | 4.0 | 40.0 | 2175.0 |
| 10.0 | 90.0 | 10.0 | 4.0 | 40.0 | 2175.0 |

Method 65:

| Method Name: | I_IG_30_MEOH_NH3_002 |
| --- | --- |
| Device description: | Agilent 1260 Infinity II SFC with DAD and MS |
| Column: | CHIRAL ART ® Cellulose SC_4.6 × 250 mm_5 µm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
| --- | --- | --- | --- | --- | --- |
| 0.0 | 70.0 | 30.0 | 2.0 | 40.0 | 2175.0 |
| 4.0 | 70.0 | 30.0 | 2.0 | 40.0 | 2175.0 |

Method 64:

| Method Name: | I_IG_35_IPA_NH3_003 |
|---|---|
| Device description: | Agilent 1260 Infinity II SFC with DAD |
| Column: | Chiralpak ® IG_4.6 × 250 mm_5 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 65.0 | 35.0 | 4.0 | 40.0 | 2175.0 |
| 10.0 | 65.0 | 35.0 | 4.0 | 40.0 | 2175.0 |

Method 65:

| Method Name: | I_IG_20_IPA_NH3_003 |
|---|---|
| Device description: | Agilent 1260 Infinity II SFC with DAD |
| Column: | Chiralpak ® IG_4.6 × 250 mm_5 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Method 66:

| Method Name: | I_IH_05_MEOH_NH3_003 |
|---|---|
| Device description: | Agilent 1260 Infinity II SFC with DAD |
| Column: | Chiralpak ® IG_4.6 × 250 mm_5 μm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 95.0 | 5.0 | 4.0 | 40.0 | 2175.0 |
| 10.0 | 95.0 | 5.0 | 4.0 | 40.0 | 2175.0 |

Method 67:

| Method Name: | I_IH_10_IPA_NH3_003 |
|---|---|
| Device description: | Agilent 1260 Infinity II SFC with DAD |
| Column: | Chiralpak ® IG_4.6 × 250 mm_5 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

Method 68:

| Method Name: | I_IG_15_MEOH_NH3_003 |
|---|---|
| Device description: | Agilent 1260 Infinity II SFC with DAD |
| Column: | Chiralpak ® IG_4.6 × 250 mm_5 μm |
| Column producer: | Daicel |
| Description: | |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

| | | | | | |
|---|---|---|---|---|---|
| Method Name: | | I_IG_15_IPA_NH3_003 | | | |
| Device description: | | Agilent 1260 Infinity II SFC with DAD | | | |
| Column: | | Chiralpak ® IG_4.6 × 250 mm_5 μm | | | |
| Column producer: | | Daicel | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 85.0 | 15.0 | 4.0 | 40.0 | 2175.0 |
| 10.0 | 85.0 | 15.0 | 4.0 | 40.0 | 2175.0 |

Method 69:

| | | | | | |
|---|---|---|---|---|---|
| Method Name: | | I_IG_20_MEOH_NH3_002 | | | |
| Device description: | | Agilent 1260 Infinity II SFC with DAD | | | |
| Column: | | Chiralpak ® IG_3 × 100 mm_3 μm | | | |
| Column producer: | | Daicel | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 80 | 20 | 2.0 | 40.0 | 2175.0 |
| 4.0 | 80 | 20 | 2.0 | 40.0 | 2175.0 |

Method 70:

| | | | | | |
|---|---|---|---|---|---|
| Method Name: | | I_SB_10_IPA_NH3_003 | | | |
| Device description: | | Agilent 1260 Infinity II SFC with DAD | | | |
| Column: | | CHIRAL ART ® Cellulose SB_4.6 × 250 mm_5 μm | | | |
| Column producer: | | YMC | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90 | 10 | 4.0 | 40.0 | 2175.0 |
| 10.0 | 90 | 10 | 4.0 | 40.0 | 2175.0 |

Method 71

| | | | | | |
|---|---|---|---|---|---|
| Method Name: | | I_SC_15_IPA_NH3_003 | | | |
| Device description: | | Agilent 1260 Infinity II SFC with DAD | | | |
| Column: | | CHIRAL ART ® Cellulose SB_4.6 × 250 mm_5 μm | | | |
| Column producer: | | YMC | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 85 | 15 | 4.0 | 40.0 | 2175.0 |
| 10.0 | 85 | 15 | 4.0 | 40.0 | 2175.0 |

Method 72

| | | | | | |
|---|---|---|---|---|---|
| Method Name: | | I_SZ_20_MEOH_NH3_003 | | | |
| Device description: | | Agilent 1260 Infinity II SFC with DAD | | | |
| Column: | | CHIRAL ART ® Cellulose SB_4.6 × 250 mm_5 μm | | | |
| Column producer: | | YMC | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 80 | 20 | 4.0 | 40.0 | 2175.0 |
| 10.0 | 80 | 15 | 4.0 | 40.0 | 2175.0 |

Method 73

| Method Name: | I_C4_20_MEOH_NH3_002 |
| --- | --- |
| Device description: | Agilent 1260 Infinity II SFC with DAD |
| Column: | Lux(R) Cellulose-4_3 × 100 mm_3 μm |
| Column producer: | Phenomenex |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 80 | 20 | 2.0 | 40.0 | 2175.0 |
| 10.0 | 80 | 20 | 2.0 | 40.0 | 2175.0 |

Method 74

| Method Name: | I_SC_20_IPA_NH3_003 |
| --- | --- |
| Device description: | Agilent 1260 Infinity II SFC with DAD and MS |
| Column: | CHIRAL ART ® Cellulose SC_4.6 × 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 80 | 20 | 4.0 | 40.0 | 2175.0 |
| 10.0 | 80 | 20 | 4.0 | 40.0 | 2175.0 |

Method 75

| Method Name: | I_SC_20_IPA_NH3_003 |
| --- | --- |
| Device description: | Agilent 1260 Infinity II SFC with DAD and MS |
| Column: | CHIRAL ART ® Cellulose SC_4.6 × 250 mm_5 μm |
| Column producer: | YMC |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 80 | 20 | 4.0 | 40.0 | 2175.0 |
| 10.0 | 80 | 20 | 4.0 | 40.0 | 2175.0 |

Method 76

| Method Name: | I_SB10_20_MEOH_NH3_003 |
| --- | --- |
| Device description: | Agilent 1260 Infinity II SFC with DAD and MS |
| Column: | CHIRAL ART ® Cellulose SC_4.6 × 250 mm_5 μm |
| Column producer: | YMC |
| Description: | |

| Gradient/Solvent Time [min] | % Sol [scCO2] | % Sol [MEOH 20 mM NH3] | Flow [ml/min] | Temp [° C.] | Back pressure [PSI] |
| --- | --- | --- | --- | --- | --- |
| 0.0 | 90 | 10 | 4.0 | 40.0 | 2175.0 |
| 10.0 | 90 | 10 | 4.0 | 40.0 | 2175.0 |

Method 77

| Method Name: | I_C4_25_IPA_NH3_002 |
| --- | --- |
| Device description: | Agilent 1260 Infinity II SFC with DAD |
| Column: | Lux(R) Cellulose-4_3 × 100 mm_3 μm |
| Column producer: | Phenomenex |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 75 | 25 | 2.0 | 40.0 | 2175.0 |
| 4.0 | 75 | 25 | 2.0 | 40.0 | 2175.0 |

Method 78

| Method Name: | I_IG_25_IPA_NH3_002 |
| --- | --- |
| Device description: | Agilent 1260 Infinity II SFC with DAD |
| Column: | Chiralpak ® IG_3 × 100 mm_3 μm |
| Column producer: | Daicel |
| Description: | |

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 75 | 25 | 2.0 | 40.0 | 2175.0 |
| 4.0 | 75 | 25 | 2.0 | 40.0 | 2175.0 |

| | | | | | |
|---|---|---|---|---|---|
| Method Name: | | I_SB_15_MEOH_NH3_002 | | | |
| Device description: | | Agilent 1260 Infinity II SFC with DAD | | | |
| Column: | | CHIRAL ART ® Cellulose SC_3 × 100 mm_3 μm | | | |
| Column producer: | | YMC | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 85.0 | 15.0 | 2.0 | 40.0 | 2175.0 |
| 4.0 | 85.0 | 15.0 | 2.0 | 40.0 | 2175.0 |

Method 79

| | | | | | |
|---|---|---|---|---|---|
| Method Name: | | I_AC_10_IPA_NH3_002 | | | |
| Device description: | | Agilent 1260 Infinity II SFC with DAD | | | |
| Column: | | CHIRAL ART ® Amylose-C Neo_3 × 100 mm_3 μm | | | |
| Column producer: | | YMC | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

Method 80

| | | | | | |
|---|---|---|---|---|---|
| Method Name: | | I_IA_10_ETOH_NH3_001 | | | |
| Device description: | | Agilent 1260 SFC with DAD and MS | | | |
| Column: | | Chiralpak ® IA_4.6 × 250 mm_5 μm | | | |
| Column producer: | | Daicel | | | |
| Description: | | | | | |
| Gradient/Solvent Time [min] | % Sol [scCO2] | % Sol [ETOH 20 mM NH3] | Flow [ml/min] | Temp [° C.] | Back pressure [PSI] |
| 0.0 | 90.0 | 10.0 | 4.0 | 40.0 | 2175.0 |
| 10.0 | 90.0 | 10.0 | 4.0 | 40.0 | 2175.0 |

Method 81

| | | | | | |
|---|---|---|---|---|---|
| Method Name: | | I_C4_10_MEOH_NH3_002 | | | |
| Device description: | | Agilent 1260 Infinity II SFC with DAD | | | |
| Column: | | Lux(R) Cellulose-4_3 × 100 mm_3 μm | | | |
| Column producer: | | Phenomenex | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

Method 82

| | | | | | |
|---|---|---|---|---|---|
| Method Name: | | I_SA_10_MEOH_NH3_001 | | | |
| Device description: | | Agilent 1260 SFC with DAD and MS | | | |
| Column: | | CHIRAL ART ® Amylose SA_4.6 × 250 mm_5 μm | | | |
| Column producer: | | YMC | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 90.0 | 10.0 | 4.0 | 40.0 | 2175.0 |
| 10.0 | 90.0 | 10.0 | 4.0 | 40.0 | 2175.0 |

Method 83

| Method Name: | I_IA_10_ETOH_NH3_001 | | | | |
|---|---|---|---|---|---|
| Device description: | Agilent 1260 SFC with DAD and MS | | | | |
| Column: | Chiralpak ® IA_4.6 × 250 mm_5 μm | | | | |
| Column producer: | Daicel | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 2.0 | 40.0 | 2175.0 |
| 4.0 | 80.0 | 20.0 | 2.0 | 40.0 | 2175.0 |

Method 84

| Method Name: | I_AC_20_IPA_NH3_002 | | | | |
|---|---|---|---|---|---|
| Device description: | Agilent 1260 Infinity II SFC with DAD | | | | |
| Column: | CHIRAL ART ® Amylose-C Neo_3 × 100 mm_3 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 80.0 | 20.0 | 2.0 | 40.0 | 2175.0 |
| 4.0 | 80.0 | 20.0 | 2.0 | 40.0 | 2175.0 |

Method 85

| Method Name: | I_C4_10_MEOH_NH3_002 | | | | |
|---|---|---|---|---|---|
| Device description: | Agilent 1260 Infinity II SFC with DAD | | | | |
| Column: | Lux(R) Cellulose-4_3 × 100 mm_3 μm | | | | |
| Column producer: | Phenomenex | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

Method 86

| Method Name: | I_SZ_10_IPA_NH3_003 | | | | |
|---|---|---|---|---|---|
| Device description: | Agilent 1260 Infinity II SFC with DAD and MS | | | | |
| Column: | CHIRAL ART ® Cellulose SZ_4.6 × 250 mm_5 μm | | | | |
| Column producer: | YMC | | | | |
| Description: | | | | | |
| Gradient/Solvent Time [min] | % Sol [scCO2] | % Sol [IPA 20 mM NH3] | Flow [ml/min] | Temp [° C.] | Back pressure [PSI] |
| 0.0 | 90.0 | 10.0 | 4.0 | 40.0 | 2175.0 |
| 10.0 | 90.0 | 10.0 | 4.0 | 40.0 | 2175.0 |

Method 87

| Method Name: | I_C2_10_MEOH_NH3_002 | | | | |
|---|---|---|---|---|---|
| Device description: | Agilent 1260 Infinity II SFC with DAD | | | | |
| Column: | Lux(R) Cellulose-2_3 × 100 mm_3 μm | | | | |
| Column producer: | Phenomenex | | | | |
| Description: | | | | | |
| Gradient/Solvent Time [min] | % Sol [scCO2] | % Sol [MEOH 20 mM NH3] | Flow [ml/min] | Temp [° C.] | Back pressure [PSI] |
| 0.0 | 90.0 | 10.0 | 2.0 | 40.0 | 2175.0 |
| 4.0 | 90.0 | 10.0 | 2.0 | 40.0 | 2175.0 |

Method 88

| Method Name: | I_SA_15_MEOH_NH3_001 |
|---|---|
| Device description: | Agilent 1260 SFC with DAD and MS |
| Column: | CHIRAL ART ® Amylose SA_4.6 × 250 mm_5 μm |
| Column producer: | CHIRAL ART ® Amylose SA_4.6 × 250 mm_5 μm |
| Description: | YMC |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

NMR method: NMR spectra were recorded on a Bruker AVANCE IIIHD 400 MHz instrument using TopSpin 3.2 pl6 software. Chemical shifts are given in parts per million (ppm) downfield from an internal reference like trimethylsilane and/or water and/or solvent (eg. d6-DMSO) in δ units. Selected data are reported in the following manner: chemical shift (multiplicity, coupling constants (J), number of hydrogens). Abbreviations are as follows: s (singlet), d (doublet), t (triplet), q (quartet), spt (septet), m (multiplet), br (broad).

EXAMPLES

Example 1

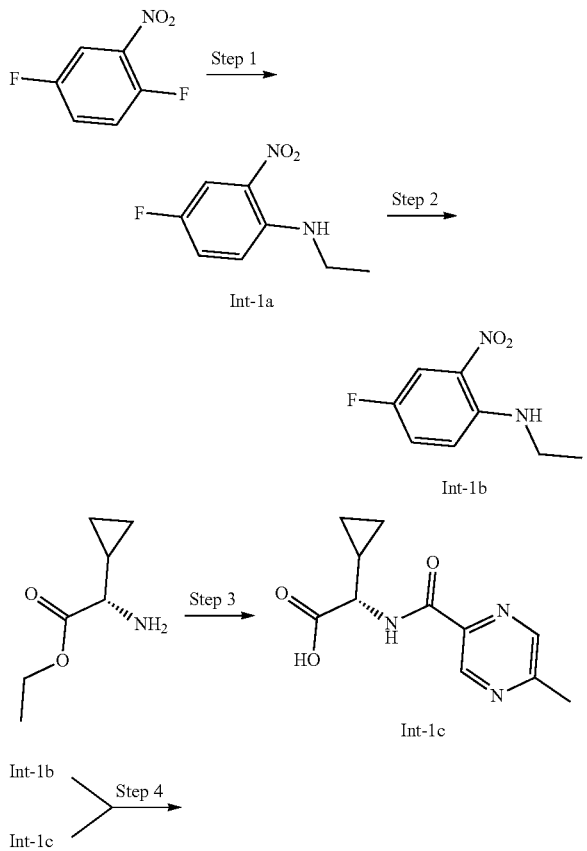

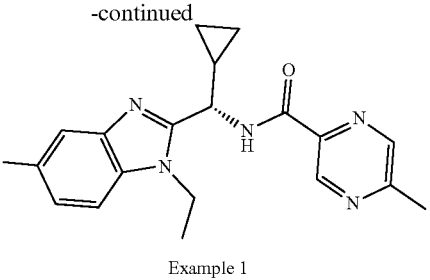

Example 1

Step 1

1,4-Difluoro-2-nitro-benzene (1 g, 6.3 mmol) is mixed with 2N ethyl-amine solution in THF (15 mL, 30 mmol) and stirred at ambient temperature for 16 h. The mixture is filtered, and the filtrate is concentrated in vacuo. The residue is washed with water and filtered, washed with water and dried at ambient temperature.

Yield: 1.13 g (6.1 mmol; 98%) Int-1a

MS (ESI$^+$): (M+H)$^+$ 185; HPLC: RT=1.05 min, Method: Z018_S04

Step 2:

Int-1a (100 mg, 0.54 mmol) is mixed with 50 mg Raney nickel in 10 mL THF and hydrogenated at 50 psi for 2 h. The mixture is filtered, and the filtrate concentrated in vacuo.

Yield: 80 mg (0.52 mmol; 96%) Int-1b

MS (ESI$^+$): (M+H)$^+$ 155; HPLC: RT=0.55 min, Method: Z018_S04

Step 3:

(2S)-2-Amino-2-cyclopropyl-acetic acid ethyl ester hydrochloride (2.9 g, 18 mmol) is mixed with 5-methyl-pyrazine-2-carboxylic acid (3.0 g, 22 mmol) and TEA (10 mL, 72 mmol) in 100 mL THF at 0° C. and CIP (5.2 g, 19 mmol) is added. After stirring for 30 min at 0° C., the mixture is filtered, and the filtrate concentrated i. vac. The residue is washed with aq. Na$_2$CO$_3$ solution (0.5N) and extracted with DCM, dried over magnesiumsulfate and concentrated i. vac. The residue is taken up with 40 mL MeOH, mixed with aq. NaOH solution (4N, 6.0 mL, 24 mmol) and stirred for 1 h at ambient temperature. Afterwards, the mixture is acidified by addition of AcOH, filtered, and the filtrate purified by preparative HPLC (gradient (H$_2$O+0.15% TFA)/ACN: 9:1→7:3, C-18 Sunfire, 50° C.). The fractions containing product are unified and freezedried.

Yield: 3.0 g (13 mmol; 73%) Int-1c

MS (ESI$^+$): (M+H)$^+$ 236; HPLC: RT=0.73 min, Method: Z018_S04

Step 4:

To a mixture of Int-1b (80 mg, 0.52 mmol) and Int-1c (100 mg, 0.43 mmol) with NMM (160 μL, 1.5 mmol) in 5 mL DCM at 0° C. is added PPA (50%, 280 μL, 0.48 mmol). The cooling is removed, and the mixture is stirred for 45 min. 100 μL water is added and stirred for 30 min at ambient temperature. Afterwards, 5 mL AcOH is added and stirred at ambient temperature for 16 h. The mixture is concentrated i. vac. and the residue purified by preparative HPLC (gradient (H$_2$O+0.15% TFA)/ACN: 88:12→68:32, C-18 Sunfire, 50° C.). The fractions containing product are unified, and freeze-dried. The residue is taken up in MeOH and sent through a cartridge equipped with ion exchange resin (Agilent PL-HCO3 MP SPE) and concentrated i. vac.

Yield: 110 mg (0.31 mmol; 73%) example 1

Example 1: N-[(S)-cyclopropyl(1-ethyl-5-fluoro-1H-1,3-benzodiazol-2-yl)methyl]-5-methylpyrazine-2-carboxamide

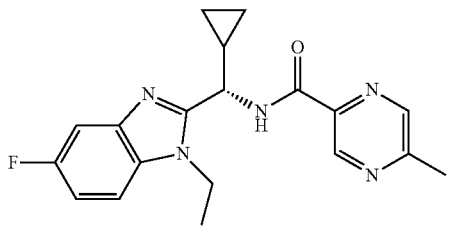 [SMILES: CCn1c([C@@H](NC(=O)c2cnc(C)cn2)C2CC2)nc2cc(F)ccc21]

HPLC-MS; Method: Z018_S04; R$_t$ [min] : 0.75     MS: 354 (M + H)$^+$
Chiral SFC Rt Method I_SC_20_IPA_NH3_001     Rt [min]: 3.07
$^1$H NMR (400 MHz, DMSO-d$_6$) δ ppm 0.37-0.61 (m, 4 H) 1.28 (t, J = 7.16 Hz, 3 H) 1.68-1.77 (m, 1 H) 2.58-2.62 (m, 3 H) 4.26-4.43 (m, 2 H) 4.95 (t, J = 8.55 Hz, 1 H) 7.11 (td, J = 9.28, 2.47 Hz, 1 H) 7.45 (dd, J = 9.76, 2.41 Hz, 1 H) 7.59 (dd, J = 8.81, 4.75 Hz, 1 H) 8.64 (s, 1 H) 9.05 (d, J = 1.27 Hz, 1 H) 9.12 (d, J = 8.24 Hz, 1 H)

In analogy to example 1, the following products are obtained:

Example 2: N-[(1R,2R)-2-methoxy-1-[1-(2-methoxyethyl)-5-(trifluoromethoxy)-1H-1,3-benzodiazol-2-yl]propyl]-5-methylpyrazine-2-carboxamide

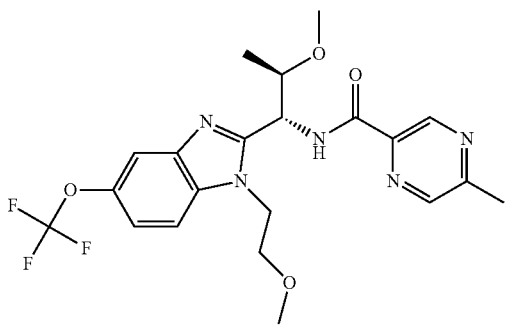 [SMILES: COCCn1c([C@@H](NC(=O)c2cnc(C)cn2)[C@@H](C)OC)nc2cc(OC(F)(F)F)ccc21]

HPLC-MS; Method: Z018_S04; R$_t$ [min] : 0.97     MS: 468 (M + H)$^+$
Chiral SFC Rt Method: I_SA_10_IPA_NH3_001.M     Rt [min]: 2.64
$^1$H NMR (400 MHz, DMSO-d$_6$) δ ppm 1.26 (d, J = 6.08 Hz, 3 H) 2.58-2.61 (m, 3 H) 3.16 (d, J = 3.93 Hz, 6 H) 3.62-3.74 (m, 2 H) 3.97-4.04 (m, 1 H) 4.49-4.64 (m, 2 H) 5.52 (dd, J = 9.06, 7.79 Hz, 1 H) 7.24 (dd, J = 8.81, 1.33 Hz, 1 H) 7.64 (s, 1 H) 7.70 (d, J = 8.87 Hz, 1 H) 8.65 (d, J = 1.14 Hz, 1 H) 8.99 (d, J = 9.13 Hz, 1 H) 9.06 (d, J = 1.39 Hz, 1 H)

Example 3: N-[(S)-cyclopropyl(1-ethyl-5-fluoro-1H-1,3-benzodiazol-2-yl)methyl]-5-(difluoromethyl)pyrazine-2-carboxamide

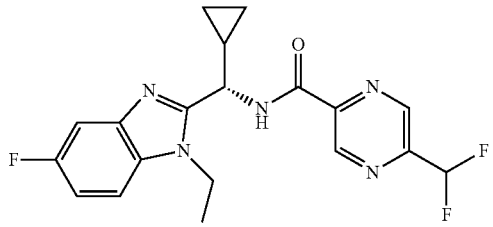 [SMILES: CCn1c([C@@H](NC(=O)c2cnc(C(F)F)cn2)C2CC2)nc2cc(F)ccc21]

HPLC-MS; Method: Z011_S03; R$_t$ [min] : 0.99    MS: 390 (M + H)$^+$
Chiral SFC Rt Method: I_SC_10_IPA_NH3_001.M    Rt [min]: 2.52
$^1$H NMR (400 MHz, DMSO-d$_6$) δ ppm 0.35-0.65 (m, 4 H) 1.25-1.35 (m, 3 H) 1.71-1.81 (m, 1 H) 4.08-4.47 (m, 2 H) 4.96 (br t, J = 7.98 Hz, 1 H) 7.07-7.14 (m, 1 H) 7.21 (m, 1H) 7.45 (dd, J = 9.82, 2.47 Hz, 1 H) 7.60 (dd, J = 8.87, 4.82 Hz, 1 H) 9.06 (s, 1 H) 9.28 (s, 1 H) 9.37 (br d, J = 7.48 Hz, 1 H)

Example 5: N-[(S)-cyclopropyl[5-fluoro-1-(2-methoxyethyl)-1H-1,3-benzodiazol-2-yl]methyl]-5-(difluoromethyl)pyrazine-2-carboxamide

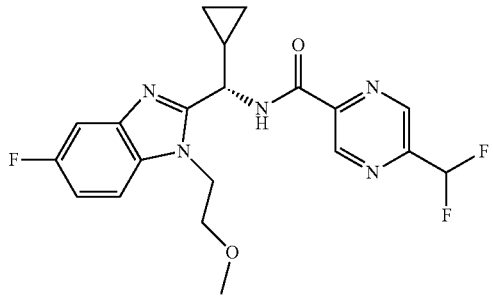 [SMILES: COCCn1c([C@@H](NC(=O)c2cnc(C(F)F)cn2)C2CC2)nc2cc(F)ccc21]

HPLC-MS; Method: Z011_S03; R$_t$ [min] : 0.99    MS: 420 (M + H)$^+$
Chiral SFC Rt Method: I_IG_25_MEOH_NH3_001.M    Rt [min]: 4.06
$^1$H NMR (400 MHz, DMSO-d$_6$) δ ppm 0.37-0.65 (m, 4 H) 1.71-1.92 (m, 1 H) 3.13 (s, 3 H) 3.55-3.68 (m, 2 H) 4.39-4.65 (m, 2 H) 5.02 (t, J = 8.55 Hz, 1 H) 7.06-7.14 (m, 1 H) 7.21 (m, 1 H) 7.45 (dd, J = 9.76, 2.53 Hz, 1 H) 7.60 (dd, J = 8.87, 4.69 Hz, 1 H) 9.04 (s, 1 H) 9.24-9.32 (m, 2 H)

Example 6: N-[(S)-cyclopropyl[5-fluoro-1-(2-methoxyethyl)-1H-1,3-benzodiazol-2-yl]methyl]-5-methylpyrazine-2-carboxamide

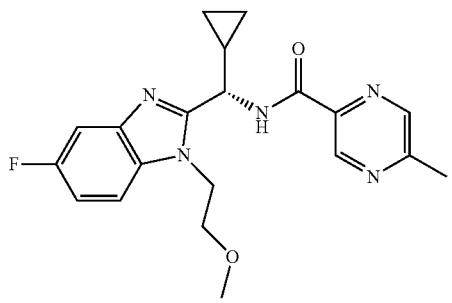 [SMILES: COCCn1c([C@@H](NC(=O)c2cnc(C)cn2)C2CC2)nc2cc(F)ccc21]

HPLC-MS; Method: Z011_S03; R$_t$ [min] : 0.90    MS: 384 (M + H)$^+$
$^1$H NMR (400 MHz, DMSO-d$_6$) δ ppm 0.37-0.61 (m, 4 H) 1.73-1.83 (m, 1 H) 2.59 (s, 3 H) 3.14 (s, 3 H) 3.55-3.67 (m, 2 H) 4.40-4.63 (m, 2 H) 5.01 (t, J = 8.62 Hz, 1 H) 7.10 (td, J = 9.31, 2.53 Hz, 1 H) 7.45 (dd, J = 9.76, 2.53 Hz, 1 H) 7.59 (dd, J = 8.87, 4.82 Hz, 1 H) 8.63 (s, 1 H) 9.02 (d, J = 8.49 Hz, 1 H) 9.05 (d, J = 1.27 Hz, 1 H)

Example 12: N-[(S)-cyclopropyl[1-(2-methoxyethyl)-5-(trifluoromethoxy)-1H-1,3-benzodiazol-2-yl]methyl]-5-methylpyrazine-2-carboxamide -continued

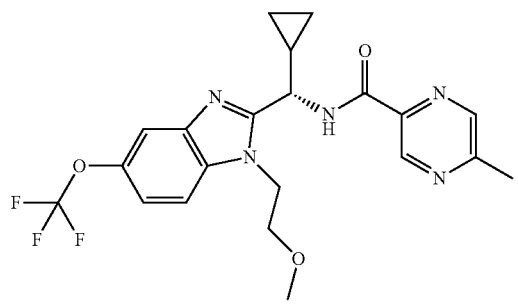 [SMILES: COCCn1c([C@@H](NC(=O)c2cnc(C)cn2)C2CC2)nc2cc(OC(F)(F)F)ccc21]

HPLC-MS; Method: Z018_S04; R$_t$ [min] : 0.96  MS: 450 (M + H)$^+$
Chiral SFC Rt Method: I_IG_20_IPA_NH3_001.M  Rt [min]: 2.80
$^1$H NMR (400 MHz, DMSO-d$_6$) δ ppm 0.37-0.62 (m, 4 H) 1.75-1.84 (m, 1 H) 2.59 (s, 3 H) 3.14 (s, 3 H) 3.59-3.67 (m, 2 H) 4.44-4.67 (m, 2 H) 5.02 (t, J = 8.62 Hz, 1 H) 7.24 (dd, J = 8.81, 1.33 Hz, 1 H) 7.65 (s, 1 H) 7.69 (d, J = 8.87 Hz, 1 H) 8.63 (d, J-1.01 Hz, 1 H) 9.02-9.09 (m, 2 H)

Example 13: N-[(S)-cyclopropyl[5-(difluoromethoxy)-1-(2-methoxyethyl)-1H-1,3-benzodiazol-2-yl]methyl]-5-methylpyrazine-2-carboxamide

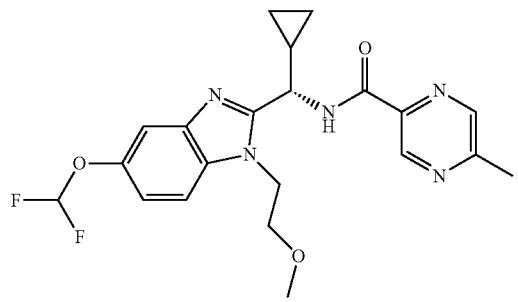 [SMILES: COCCn1c([C@@H](NC(=O)c2cnc(C)cn2)C2CC2)nc2cc(OC(F)F)ccc21]

HPLC-MS; Method: Z018_S04; R$_t$ [min] : 0.83  MS: 432 (M + H)$^+$
Chiral SFC Rt Method: I_IG_35_MEOH_NH3_001.M  Rt [min]: 4.00
$^1$H NMR (400 MHz, DMS-D$_6$) δ ppm 0.37-0.61 (m, 4 h) 1.74-1.83 (m, 1 H) 2.57-2.61 (m, 3 H) 3.12-3.15 (m, 3 H), 3.58-3.65 (m, 2H) 4.45 (dt, J = 15.46, 4.56 Hz, 1H) 4.56-4.64 (m, 1 H) 5.01 (t, J = 8.55 Hz, 1 H) 7.09 (dd, J = 8.74, 2.28 Hz, 1 h) 7.16 (m, 1 H) 7.46 (d, J = 2.15 Hz, 1 H) 7.62 (d, J = 8.74 Hz, 1 H) 8.63 (d, J = 1.01 Hz, 1 H) 9.01-9.07 (m, 2 H)

Example 15: N-[(S)-cyclopropyl[1-(2,2-difluoroethyl)-6-fluoro-5-methyl-1H-1,3-benzodiazol-2-yl]methyl]-5-methylpyrazine-2-carboxamide

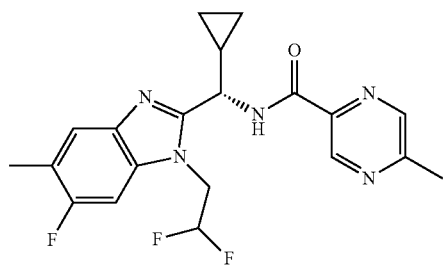

MS: 404 (M + H)$^+$
Chiral SFC Rt Method: I_SA_15_IPA_NH3_001.M  Rt [min]: 1.88
$^1$H NMR (400 MHz, DMSO-d$_6$) δ ppm 0.36-0.62 (m, 4 H) 1.77-1.86 (m, 1 H) 2.32 (d, J = 1.77 Hz, 3 H) 2.52-2.66 (m, 3 H) 4.75-4.98 (m, 3 H) 6.26-6.57 (m, 1 H) 7.45 (d, J = 10.01 Hz, 1 H) 7.55 (d, J = 6.97 Hz, 1 H) 8.63 (d, J = 0.89 Hz, 1 H) 9.04 (d, J = 1.39 Hz, 1 H) 9.13 (d, J = 8.24 Hz, 1 H)

Example 17: N-[(1S)-1-(1-ethyl-5-fluoro-1H-1,3-benzodiazol-2-yl)-2-methylpropyl]-5-methylpyrazine-2-carboxamide

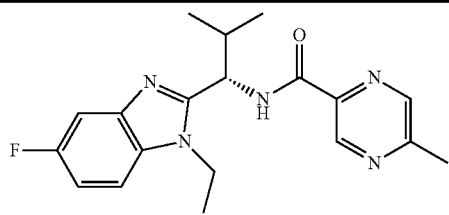

HPLC-MS; Method: Z003_S05; R$_t$ [min] : 1.15  MS: 356 (M + H)$^+$
Chiral SFC Rt Method: I_SB_10_MEOH_NH3_001  Rt [min]: 1.79
$^1$H NMR (400 MHz, DMSO-d$_6$) δ ppm 0.89 (m, 3H) 1.03 (m, 3H) 1.32 (m, 3 H) 2.52-
2.61 (m, 4 H) 4.42 (qq, J = 14.74, 7.23 Hz, 2 H) 5.21 (t, J = 8.81 Hz, 1 H) 7.11 (td,
J = 9.28, 2.47 Hz, 1 H) 7.44 (dd, J = 9.89, 2.41 Hz, 1 H) 7.60 (dd, J = 8.87, 4.82 Hz, 1 H)
8.63 (s, 1 H) 8.85 (d, J = 9.13 Hz, 1 H) 9.05 (d, J = 1.14 Hz, 1 H)

In analogy to example 1 the following compounds have been obtained. The product is a mixture of four stereoisomers which are separated by chiral SFC: examples 19, 19-1, 19-2, 19-3

Example 19: N-[(R)-[1-(2-methoxyethyl)-5-(trifluoromethyl)-1H-1,3-benzodiazol-2-yl][(2R)-oxolan-2-yl]methyl]-5-methylpyrazine-2-carboxamide

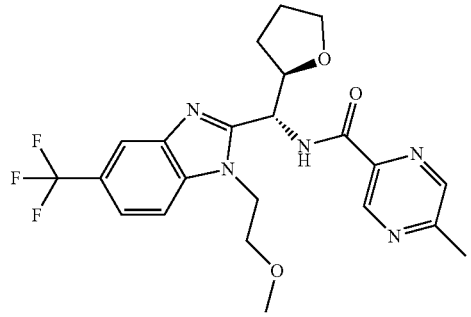 [SMILES: COCCn1c([C@@H](NC(=O)c2cnc(C)cn2)[C@H]2CCCO2)nc2cc(C(F)(F)F)ccc21]

HPLC-MS; Method: Z018_S04; R$_t$ [min] : 1.00  MS: 464 (M + H)$^+$
Chiral SFC Rt Method: I_C2_15_IPA_NH3_001  Rt [min]: 4.89

Example 19-1: N-{[1-(2-methoxyethyl)-5-(trifluoromethyl)-1H-1,3-benzodiazol-2-yl](oxolan-2-yl)methyl}-5-methylpyrazine-2-carboxamide

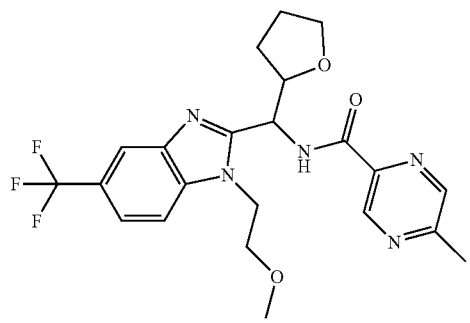 [SMILES: COCCn1c(C(NC(=O)c2cnc(C)cn2)C2CCCO2)nc2cc(C(F)(F)F)ccc21]

HPLC-MS; Method: Z018_S04; R$_t$ [min] : 1.00  MS: 464 (M + H)$^+$
Chiral SFC Rt Method: I_C2_15_IPA_NH3_001  Rt [min]: 2.83

Example 19-2: N-{[1-(2-methoxyethyl)-5-(trifluoromethyl)-1H-1,3-benzodiazol-2-yl](oxolan-2-yl)methyl}-5-methylpyrazine-2-carboxamide -continued
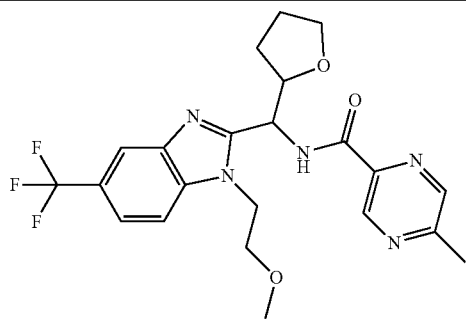
HPLC-MS; Method: Z018_S04; R$_t$ [min] : 1.00  
Chiral SFC Rt Method: I_C2_15_IPA_NH3_001
MS: 464 (M + H)$^+$  
Rt [min]: 5.78
Example 19-3: N-{[1-(2-methoxyethyl)-5-(trifluoromethyl)-1H-1,3-benzodiazol-2-yl](oxolan-2-yl)methyl}-5-methylpyrazine-2-carboxamide
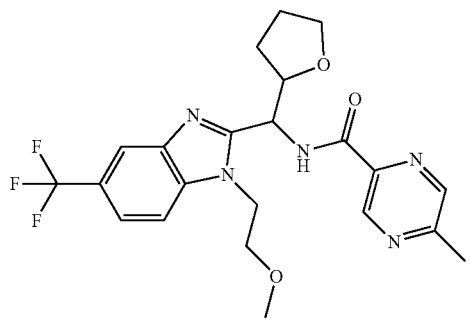 [SMILES: COCCn1c(C(NC(=O)c2cnc(C)cn2)C2CCCO2)nc2cc(C(F)(F)F)ccc21]
HPLC-MS; Method: Z018_S04; R$_t$ [min] : 1.00  
Chiral SFC Rt Method: I_C2_15_IPA_NH3_001
MS: 464 (M + H)$^+$  
Rt [min]: 3.54
In analogy to example 1, the following products are obtained:

Example 22: N-[(1R,2R)-2-methoxy-1-[1-methyl-5-(trifluoromethyl)-1H-1,3-benzodiazol-2-yl]propyl]-5-methylpyrazine-2-carboxamide

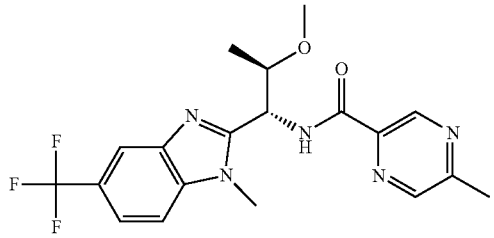 [SMILES: CO[C@H](C)[C@H](NC(=O)c1cnc(C)cn1)c1nc2cc(C(F)(F)F)ccc2n1C]

HPLC-MS; Method: Z018_S04; R$_t$ [min] : 0.95      MS: 408 (M + H)$^+$
$^1$H NMR (400 MHz, DMSO-d$_6$) δ ppm 1.08 (d, J = 6.21 Hz, 3 H) 2.61 (s, 3 H) 3.97 (s, 3 H) 4.03-4.14 (m, 1 H) 5.54 (dd, J = 7.98, 5.32 Hz, 1 H) 7.59 (dd, J = 8.55, 1.33 Hz, 1 H) 7.81 (d, J = 8.49 Hz, 1 H) 8.02 (s, 1 H) 8.69 (d, J = 0.89 Hz, 1 H) 8.95 (d, J = 7.98 Hz, 1 H) 9.07 (d, J = 1.27 Hz, 1 H)

Example 24: N-[(1S)-2-cyclopropyl-1-[5-fluoro-1-(2-methoxyethyl)-1H-1,3-benzodiazol-2-yl]ethyl]-5-methylpyrazine-2-carboxamide

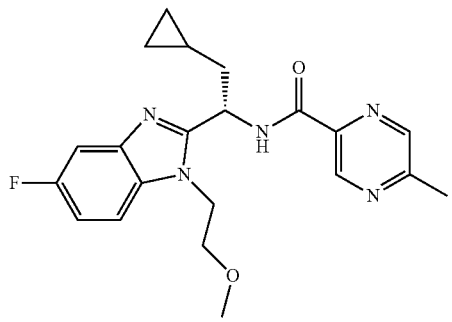 [SMILES: COCCn1c([C@H](CC2CC2)NC(=O)c2cnc(C)cn2)nc2cc(F)ccc21]

HPLC-MS; Method: Z018_S04; R$_t$ [min] : 0.85      MS: 398 (M + H)$^+$
Chiral SFC Rt Method: I_C2_20_IPA_NH3_002      Rt [min]: 1.23
$^1$H NMR (400 MHz, DMSO-d$_6$) δ ppm −0.02-0.15 (m, 2 H) 0.30-0.40 (m, 2 H) 0.71-0.81 (m, 1 H) 2.00 (ddt, J = 50.17, 13.96, 6.97, 6.97 Hz, 2 H) 2.55-2.65 (m, 3 H) 3.14-3.16 (m, 3 H) 3.60-3.69 (m, 3 H) 4.47 (dt, J = 15.33, 4.63 Hz, 1 H) 4.64 (dt, J = 15.37, 5.69 Hz, 1 H) 5.53-5.60 (m, 1 H) 7.10 (td, J = 9.28, 2.47 Hz, 1 H) 7.42 (dd, J = 9.76, 2.41 Hz, 1 H) 7.59 (dd, J = 8.93, 4.75 Hz, 1 H) 8.63 (d, J = 0.89 Hz, 1 H) 8.99 (d, J = 8.49 Hz, 1 H) 9.05 (d, J = 1.27 Hz, 1 H)

Example 27: N-[(S)-cyclopropyl[5-fluoro-1-(2,2,2-trifluoroethyl)-1H-1,3-benzodiazol-2-yl]methyl]-5-methylpyrazine-2-carboxamide

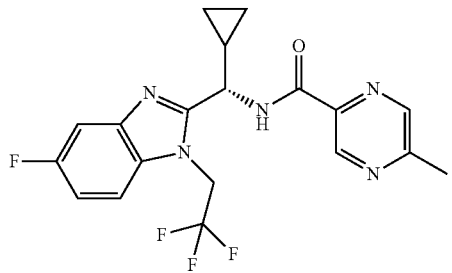 [SMILES: Cc1cnc(C(=O)N[C@H](c2nc3cc(F)ccc3n2CC(F)(F)F)C2CC2)cn1]

MS: 408 (M + H)$^+$
Chiral SFC Rt Method: I_SB_10_IPA_NH3_001      Rt [min]: 2.27
$^1$H NMR (400 MHz, DMSO-d$_6$) δ ppm 0.39-0.65 (m, 4 H) 1.84-1.93 (m, 1 H) 2.57-2.61 (m, 3 H) 4.89 (t, J = 8.55 Hz, 1 H) 5.37-5.56 (m, 2 H) 7.20 (td, J = 9.32, 2.53 Hz, 1 H) 7.53 (dd, J = 9.51, 2.41 Hz, 1 H) 7.69 (dd, J = 8.87, 4.69 Hz, 1 H) 8.63 (s, 1 H) 9.04 (d, J = 1.14 Hz, 1 H) 9.20 (d, J = 8.11 Hz, 1 H)

Example 30: N-[(S)-cyclopropyl(5-fluoro-1-methyl-1H-1,3-benzodiazol-2-yl)methyl]-5-(difluoromethyl)pyrazine-2-carboxamide

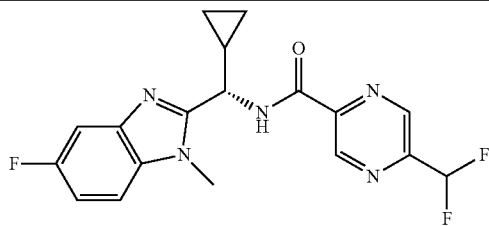

HPLC-MS; Method: Z011_S03; R$_t$ [min] : 0.96  MS: 376 (M + H)⁺
Chiral SFC Rt Method: I_SC_10_IPA_NH3_001.M  Rt [min]: 3.35
¹H NMR (400 MHz, DMSO-d$_6$) δ ppm 0.38-0.61 (m, 4 H) 1.65-1.81 (m, 1 H) 3.84
(s, 3 H) 4.98 (br t, J = 7.86 Hz, 1 H) 7.07-7.16 (m, 1 H) 7.21 (m, 1 H) 7.45 (dd, J = 9.82,
2.47 Hz, 1 H) 7.57 (dd, J = 8.87, 4.69 Hz, 1 H) 9.06 (s, 1 H) 9.28 (s, 1 H) 9.37 (br d,
J = 7.35 Hz, 1 H)

Example 31: N-[(S)-cyclopropyl[1-methyl-5-(trifluoromethyl)-1H-1,3-benzodiazol-2-
yl]methyl]-5-methylpyrazine-2-carboxamide

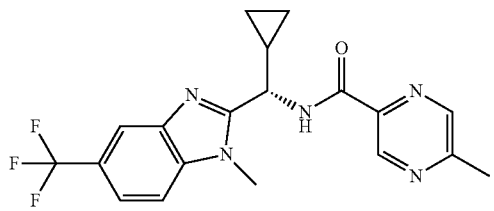 [SMILES: Cc1cnc(C(=O)N[C@H](c2nc3cc(C(F)(F)F)ccc3n2C)C2CC2)cn1]

HPLC-MS; Method: Z011_S03; R$_t$ [min] : 1.00  MS: 390 (M + H)⁺
Chiral SFC Rt Method: I_SA_15_IPA_NH3_001.M  Rt [min]: 2.84
¹H NMR (400 MHz, DMSO-d$_6$) δ ppm 0.39-0.62 (m, 4 H) 1.66-1.79 (m, 1 H) 2.57-
2.63 (m, 3 H) 3.89 (s, 3 H) 5.01 (t, J = 8.30 Hz, 1 H) 7.58 (dd, J = 8.55, 1.46 Hz, 1 H) 7.78
(d, J = 8.62 Hz, 1 H) 8.02 (s, 1 H) 8.65 (d, J = 1.01 Hz, 1 H) 9.05 (d, J = 1.39 Hz, 1 H) 9.21
(d, J = 7.98 Hz, 1 H)

Example 32: N-[(R)-[(3R)-3-hydroxyoxaN-3-yl][1-methyl-5-(trifluoromethyl)-1H-1,3-
benzodiazol-2-yl]methyl]-5-methylpyrazine-2-carboxamide

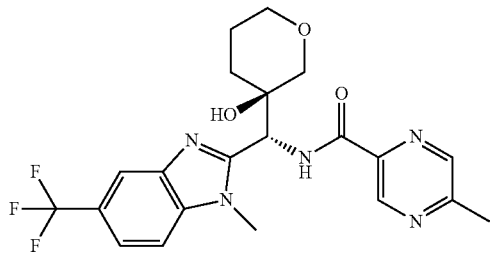 [SMILES: Cc1cnc(C(=O)N[C@H](c2nc3cc(C(F)(F)F)ccc3n2C)[C@]2(O)CCCOC2)cn1]

MS: 450 (M + H)⁺;
Chiral SFC Rt Method: I_C2_20_MEOH_NH3_002  Rt [min]: 1.15
¹H NMR (400 MHz, DMSO-d$_6$) δ ppm 1.55-1.92 (m, 4 H) 2.59-2.62 (m, 3 H) 3.32-
3.80 (m, 4 H) 3.98 (s, 3 H) 5.47 (s, 1 H) 5.66 (d, J = 9.13 Hz, 1 H) 7.60 (dd, J = 8.62, 1.39
Hz, 1 H) 7.81 (d, J = 8.49 Hz, 1 H) 8.04 (s, 1 H) 8.68 (d, J = 1.01 Hz, 1 H) 8.87 (d, J = 9.13
Hz, 1 H) 9.07 (d, J = 1.39 Hz, 1 H)

Example 34: N-[(S)-(5-bromo-1-methyl-1H-1,3-benzodiazol-2-yl)(cyclopropyl)methyl]-
5-methylpyrazine-2-carboxamide

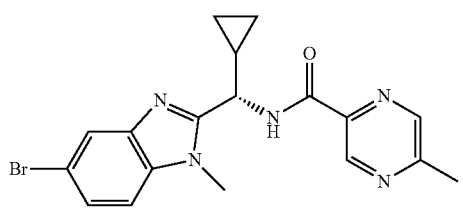

HPLC-MS; Method: Z018_S04; R$_t$ [min] : 0.79  MS: 400 (M + H)⁺
Chiral SFC Rt Method: I_SB_20_MEOH_NH3_001  Rt [min]: 3.19
¹H NMR (400 MHz, DMSO-d$_6$) δ ppm 0.38-0.61 (m, 4 H) 1.65-1.75 (m, 1 H) 2.60 (s,
3 H) 3.83 (s, 3 H) 4.98 (t, J = 8.30 Hz, 1 H) 7.39 (dd, J = 8.62, 1.77 Hz, 1 H) 7.54 (d, J = 8.62 Hz, 1 H) 7.84 (d, J = 1.77 Hz, 1 H) 8.64 (s, 1 H) 9.05 (d, J = 1.27 Hz, 1 H) 9.14 (d, J = 7.98 Hz, 1 H)

Example 35: N-[(S)-cyclopropyl[1-(2-methoxyethyl)-5-(trifluoromethyl)-1H-1,3-benzodiazol-2-yl]methyl]-5-methylpyrazine-2-carboxamide

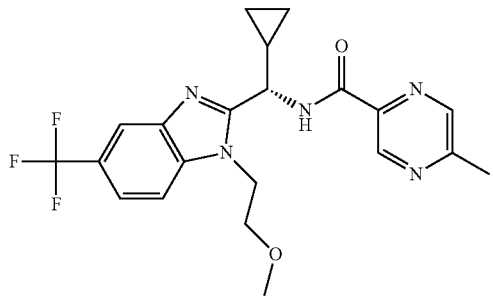 [SMILES: COCCn1c([C@@H](NC(=O)c2cnc(C)cn2)C2CC2)nc2cc(C(F)(F)F)ccc21]

HPLC-MS; Method: Z018_S04; R$_t$ [min] : 0.99  
Chiral SFC Rt Method: I_IG_25_MEOH_NH3_001  
MS: 434 (M + H)$^+$  
Rt [min]: 3.99  
$^1$H NMR (400 MHz, DMSO-d$_6$) δ ppm 0.37-0.63 (m, 4 H) 1.77-1.87 (m, 1 H) 2.59 (s, 3 H) 3.13 (s, 3 H) 3.60-3.68 (m, 2 H) 4.48-4.56 (m, 1 H) 4.62-4.70 (m, 1 H) 5.05 (t, J = 8.62 Hz, 1 H) 7.57 (dd, J = 8.49, 1.39 Hz, 1 H) 7.81 (d, J = 8.49 Hz, 1 H) 8.02 (s, 1 H) 8.63 (d, J = 1.01 Hz, 1 H) 9.05 (d, J = 1.39 Hz, 1 H) 9.10 (d, J = 8.36 Hz, 1 H)

Example 37: N-[(1S)-1-[1-(2,2-difluoroethyl)-5-fluoro-1H-1,3-benzodiazol-2-yl]-2-methylpropyl]-5-methylpyrazine-2-carboxamide

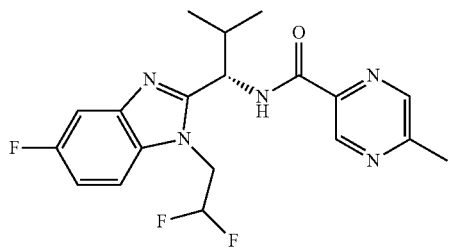

HPLC-MS; Method: Z011_S03; R$_t$ [min] : 0.98  
Chiral SFC Rt Method: I_SA_10_IPA_NH3_001  
MS: 392 (M + H)$^+$  
Rt [min]: 2.36  
$^1$H NMR (400 MHz, DMSO-d$_6$) δ ppm 0.82-1.11 (m, 6 H) 2.58 (s, 3 H) 2.59-2.70 (m, 1 H) 4.80-5.15 (m, 2 H) 5.17-5.25 (m, 2H) 6.31-6.67 (m, 1 H) 7.15 (td, J = 9.31, 2.41 Hz, 1 H) 7.48 (dd, J = 9.63, 2.41 Hz, 1 H) 7.63 (dd, J = 8.87, 4.69 Hz, 1 H) 8.62 (s, 1 H) 8.94 (d, J = 9.00 Hz, 1 H) 9.04 (d, J = 1.27 Hz, 1 H)

Example 45: N-[(S)-(5-cyano-1,4-dimethyl-1H-1,3-benzodiazol-2-yl)(cyclopropyl)methyl]-5-methylpyrazine-2-carboxamide

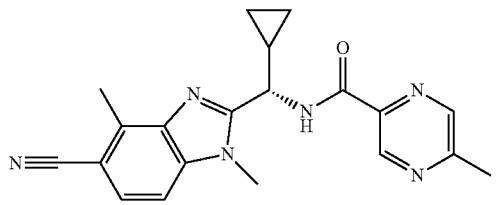 [SMILES: Cc1cnc(C(=O)N[C@H](c2nc3c(C)c(C#N)ccc3n2C)C2CC2)cn1]

HPLC-MS; Method: Z018_S04; R$_t$ [min] : 0.86  
Chiral SFC Rt Method: I_IA_25_MEOH_NH3_001  
MS: 361 (M + H)$^+$  
Rt [min]: 2.28  
$^1$H NMR (400 MHz, DMSO-d$_6$) δ ppm 0.39-0.68 (m, 4 H) 1.72-1.82 (m, 1 H) 2.59 (s, 3 H) 2.72 (s, 3 H) 3.87 (s, 3 H) 4.90-4.96 (m, 1 H) 7.58 (s, 2 H) 8.65 (d, J = 0.89 Hz, 1 H) 9.04 (d, J = 1.27 Hz, 1 H) 9.25 (d, J = 7.86 Hz, 1 H)

In analogy to example 1 the following compounds have been obtained. The product is a mixture of four stereoisomers which are separated by chiral SFC: examples 48, 48-1, 48-2, 48-3

Example 48: 5-(difluoromethyl)-N-[(S)-[5-fluoro-1-(2-methoxyethyl)-1H-1,3-benzodiazol-2-yl][(3R)-oxolaN-3-yl]methyl]pyrazine-2-carboxamide

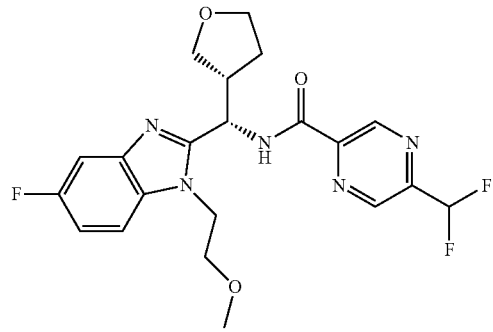 [SMILES: COCCn1c([C@@H](NC(=O)c2cnc(C(F)F)cn2)[C@H]2CCOC2)nc2cc(F)ccc21]

HPLC-MS; Method: Z011_S03; R$_t$ [min] : 0.94   MS: 450 (M + H)$^+$
Chiral SFC Rt Method: I_ADH_15_IPA_NH3_001   Rt [min]: 1.79
$^1$H NMR (400 MHz, DMSO-d$_6$) δ ppm 1.51-1.61 (m, 1 H) 1.89-2.01 (m, 1 H) 3.14 (s, 3 H) 3.35-3.45 (m, 1 H) 3.57-3.84 (m, 6 H) 4.41-4.51 (m, 1 H) 4.68-4.77 (m, 1 H) 5.51 (t, J = 9.31 Hz, 1 H) 7.11 (m, 1 H) 7.19 (m, 1 H) 7.46 (dd, J = 9.76, 2.41 Hz, 1 H) 7.60 (dd, J = 8.87, 4.82 Hz, 1 H) 9.00 (s, 1 H) 9.28 (s, 1 H) 9.33 (d, J = 9.00 Hz, 1 H)

Example 48-1: 5-(difluoromethyl)-N-{[5-fluoro-1-(2-methoxyethyl)-1H-1,3-benzodiazol-2-yl](oxolan-3-yl)methyl}pyrazine-2-carboxamide

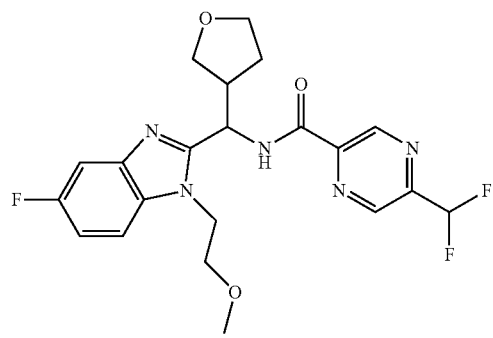 [SMILES: COCCn1c(C(NC(=O)c2cnc(C(F)F)cn2)C2CCOC2)nc2cc(F)ccc21]

HPLC-MS; Method: Z011_S03; R$_t$ [min] : 0.94   MS: 450 (M + H)$^+$
Chiral SFC Rt Method: I_ADH_15_IPA_NH3_001   Rt [min]: 2.76

Example 48-2: 5-(difluoromethyl)-N-{[5-fluoro-1-(2-methoxyethyl)-1H-1,3-benzodiazol-2-yl](oxolan-3-yl)methyl}pyrazine-2-carboxamide

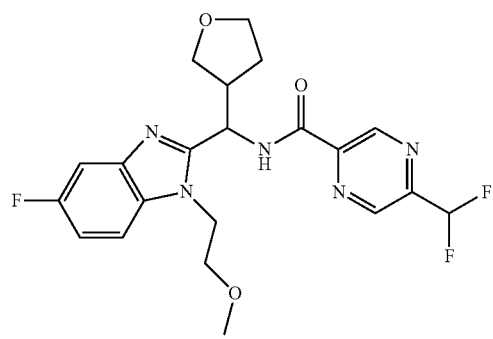 [SMILES: COCCn1c(C(NC(=O)c2cnc(C(F)F)cn2)C2CCOC2)nc2cc(F)ccc21]

HPLC-MS; Method: Z011_S03; R$_t$ [min] : 0.94   MS: 450 (M + H)$^+$
Chiral SFC Rt Method: I_ADH_15_IPA_NH3_001   Rt [min]: 2.01

Example 48-3: 5-(difluoromethyl)-N-{ [5-fluoro-1-(2-methoxyethyl)-1H-1,3-benzodiazol-2-yl](oxolan-3-yl)methyl}pyrazine-2-carboxamide

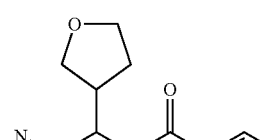

The following compounds are obtained in analogy to example 1.

Example 49: N-[(S)-cyclopropyl[5-(difluoromethoxy)-1-ethyl-1H-1,3-benzodiazol-2-yl]methyl]-5-methylpyrazine-2-carboxamide

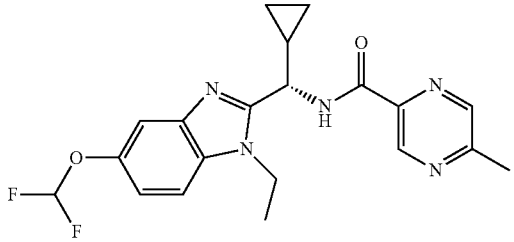 [SMILES: CCn1c([C@@H](NC(=O)c2cnc(C)cn2)C2CC2)nc2cc(OC(F)F)ccc21]

HPLC-MS; Method: Z018_S04; R$_t$ [min] : 0.81   MS: 402 (M + H)$^+$
Chiral SFC Rt Method: I_SC_15_IPA_NH3_001   Rt [min]: 3.41
$^1$H NMR (400 MHz, DMSO-d$_6$) δ ppm 0.37-0.63 (m, 4 H) 1.29 (m, 3H) 1.67-1.77 (m, 1 H) 2.58-2.61 (m, 3 H) 4.35 (m, 2 H) 4.96 (t, J = 8.43 Hz, 1 H) 7.10 (dd, J = 8.74, 2.28 Hz, 1 H) 7.15 (m, 1 H) 7.46 (d, J = 2.15 Hz, 1 H) 7.61 (d, J = 8.74 Hz, 1 H) 8.64 (d, J = 1.01 Hz, 1 H) 9.05 (d, J = 1.39 Hz, 1 H) 9.12 (d, J = 8.24 Hz, 1 H)

Example 52: N-[(S)-(5-bromo-6-fluoro-1-methyl-1H-1,3-benzodiazol-2-yl)(cyclopropyl)methyl]-5-methylpyrazine-2-carboxamide

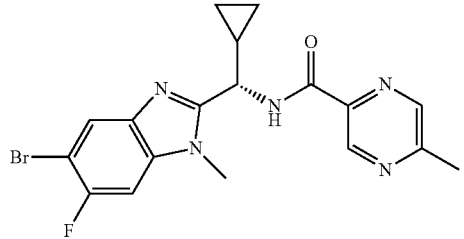 [SMILES: Cc1cnc(C(=O)N[C@H](c2nc3cc(Br)c(F)cc3n2C)C2CC2)cn1]

HPLC-MS; Method: Z018_S04; R$_t$ [min] : 0.88   MS: 418 (M + H)$^+$
Chiral SFC Rt Method: I_SA_35_MEOH_NH3_001   Rt [min]: 4.56
$^1$H NMR (400 MHz, DMSO-d$_6$) δ ppm 0.39-0.61 (m, 4 H) 1.66-1.75 (m, 1 H) 2.60 (s, 3 H) 3.81 (s, 3 H) 4.96 (t, J = 8.36 Hz, 1 H) 7.71 (d, J = 9.12 Hz, 1 H) 7.97 (d, J = 6.34 Hz, 1 H) 8.64 (s, 1 H) 9.04 (d, J = 1.14 Hz, 1 H) 9.15 (d, J = 8.11 Hz, 1 H)

Example 59: 5-(difluoromethyl)-N-[(1S)-1-(1-ethyl-5-fluoro-1H-1,3-benzodiazol-2-yl)-2-methylpropyl]pyrazine-2-carboxamide

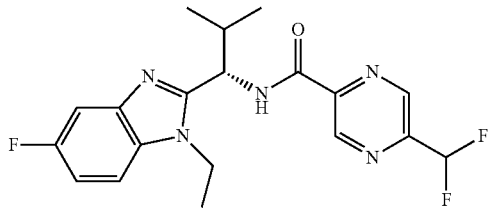

MS: 392 (M + H)$^+$
Chiral SFC Rt Method: I_SA_05_IPA_NH3_001   Rt [min]: 7.64
$^1$H NMR (400 MHz, DMSO-d$_6$) δ ppm 0.88-1.06 (m, 6 H) 1.33 (m, 3 H) 2.52-2.60 (m, 1 H) 4.43 (m, 2 H) 5.23 (t, J = 8.87 Hz, 1 H) 7.06-7.14 (m, 1 H) 7.20 (m, 1 H) 7.44 (dd, J = 9.82, 2.47 Hz, 1 H) 7.61 (dd, J = 8.87, 4.69 Hz, 1 H) 9.05 (s, 1 H) 9.08 (d, J = 9.00 Hz, 1 H) 9.28 (d, J = 1.27 Hz, 1 H)

Example 64: N-[(1S)-1-(5-fluoro-1-methyl-1H-1,3-benzodiazol-2-yl)-2-methylpropyl]-5-methylpyrazine-2-carboxamide

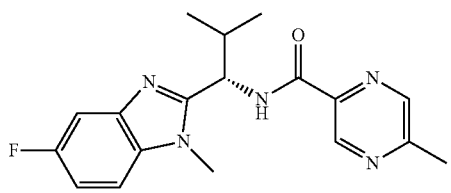 [SMILES: Cc1cnc(C(=O)N[C@H](c2nc3cc(F)ccc3n2C)C(C)C)cn1]

HPLC-MS; Method: Z018_S04; R$_t$ [min] : 0.76  MS: 342 (M + H)$^+$
Chiral SFC Rt Method: I_IG_30_IPA_NH3_001  Rt [min]: 3.61
$^1$H NMR (400 MHz, DMSO-d$_6$) δ ppm 0.86-1.05 (m, 6 H) 0.95 (d, J = 46.89 Hz, 3 H)
2.43-2.52 (m, 1 H) 2.58-2.61 (m, 3 H) 3.89 (s, 3 H) 5.24 (t, J = 8.36 Hz, 1 H) 7.11
(ddd, J = 9.70, 8.87, 2.47 Hz, 1 H) 7.44 (m, 1 H) 7.57 (m, 1 H) 8.65 (m, 1 H) 8.89 (m, 1
H) 9.05 (m, 1 H)

Example 67: N-[(S)-cyclopropyl[5-(difluoromethoxy)-6-fluoro-1-(2-methoxyethyl)-1H-
1,3-benzodiazol-2-yl]methyl]-5-methylpyrazine-2-carboxamide

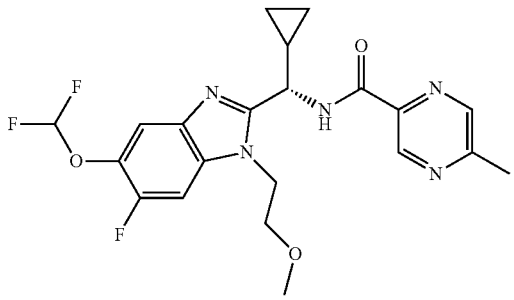 [SMILES: COCCn1c([C@@H](NC(=O)c2cnc(C)cn2)C2CC2)nc2cc(OC(F)F)c(F)cc21]

HPLC-MS; Method: Z018_S04; R$_t$ [min] : 0.92  MS: 450 (M + H)$^+$
Chiral SFC Rt Method: I_SC_15_IPA_NH3_001  Rt [min]: 2.51
$^1$H NMR (400 MHz, DMSO-d$_6$) δ ppm 0.37-0.61 (m, 4 H) 1.73-1.82 (m, 1 H) 2.59 (s,
3 H) 3.14 (s, 3 H) 3.57-3.65 (m, 2 H) 4.39-4.63 (m, 2 H) 5.00 (t, J = 8.62 Hz, 1 H) 7.18
(m, 1 H) 7.63 (d, J = 7.22 Hz, 1 H) 7.69-7.75 (s, 1 H) 8.63 (s, 1 H) 9.01-9.07 (m, 2 H)

In analogy to example 1 the following compounds have been obtained. The product is a mixture of four stereoisomers which are separated by chiral SFC: examples 70, 70-1, 70-2, 70-3

Example 70: N-[(S)-[1-ethyl-5-(trifluoromethoxy)-1H-1,3-benzodiazol-2-yl][(3R)-
oxolan-3-yl]methyl]-5-methylpyrazine-2-carboxamide

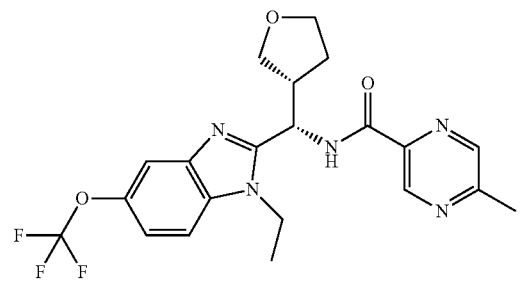 [SMILES: CCn1c([C@@H](NC(=O)c2cnc(C)cn2)[C@H]2CCOC2)nc2cc(OC(F)(F)F)ccc21]

HPLC-MS; Method: Z018_S04; R$_t$ [min] : 0.97  MS: 450 (M + H)$^+$
Chiral SFC Rt Method: I_IA_10_ETOH_NH3_001  Rt [min]: 3.67
$^1$H NMR (400 MHz, DMSO-d$_6$) δ ppm 1.18-1.32 (m, 3 H) 1.50-1.60 (m, 1 H) 1.99
(m, 1 H) 2.57-2.60 (m, 3 H) 3.57-3.84 (m, 4 H) 4.33-4.50 (m, 2 H) 5.46 (t, J = 9.00
Hz, 1 H) 7.25 (dd, J = 8.81, 1.33 Hz, 1 H) 7.66 (d, J = 1.01 Hz, 1 H) 7.69 (d, J = 8.87 Hz, 1
H) 8.61 (d, J = 1.01 Hz, 1 H) 9.05 (d, J = 1.39 Hz, 1 H) 9.24 (d, J = 9.00 Hz, 1 H)

Example 70-1: N-{[1-ethyl-5-(trifluoromethoxy)-1H-1,3-benzodiazol-2-yl](oxolan-3-
yl)methyl}-5-methylpyrazine-2-carboxamide

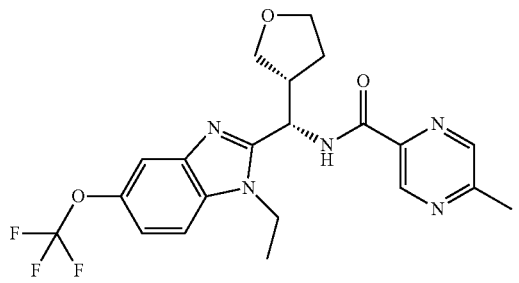 [SMILES: CCn1c([C@@H](NC(=O)c2cnc(C)cn2)[C@H]2CCOC2)nc2cc(OC(F)(F)F)ccc21]

HPLC-MS; Method: Z018_S04; $R_t$ [min] : 0.97  MS: 450 (M + H)⁺
Chiral SFC Rt Method: I_C4_10_MEOH_NH3_002  Rt [min]: 0.79

Example 70-2: N-{[1-ethyl-5-(trifluoromethoxy)-1H-1,3-benzodiazol-2-yl](oxolan-3-yl)methyl}-5-methylpyrazine-2-carboxamide

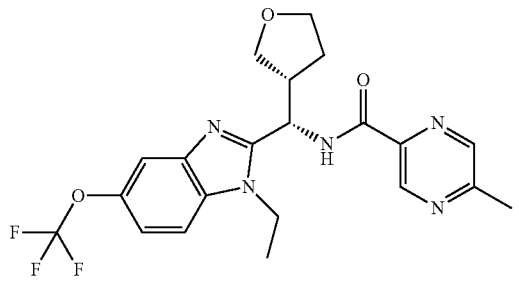 [SMILES: CCn1c([C@@H](NC(=O)c2cnc(C)cn2)[C@H]2CCOC2)nc2cc(OC(F)(F)F)ccc21]

HPLC-MS; Method Z018_S04; $R_t$ [min] : 0.97  MS: 450 (M + H)⁺
Chiral SFC Rt Method: I_C4_10_MEOH_NH3_002  Rt [min]: 1.33
¹H NMR (400 MHz, DMSO-d₆) δ ppm 1.23 (t, J = 7.10 Hz, 3 H) 1.76-1.94 (m, 1 H) 1.94-2.06 (m, 1 H) 2.52-2.61 (m, 3 H) 3.33-3.49 (m, 2 H) 3.60-3.73 (m, 1 H) 3.73-3.93 (m, 2 H) 4.25-4.43 (m, 2 H) 5.37-5.53 (m, 1 H) 7.25 (d, J = 8.90 Hz, 1 H) 7.65-7.69 (m, 2 H) 8.61 (d, J = 1.01 Hz, 1 H) 9.08 (d, J = 1.39 Hz, 1 H) 9.32 (d, J = 8.27 Hz, 1 H)

Example 70-3: N-{[1-ethyl-5-(trifluoromethoxy)-1H-1,3-benzodiazol-2-yl](oxolan-3-yl)methyl}-5-methylpyrazine-2-carboxamide

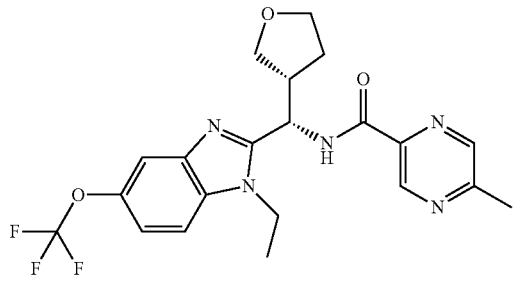 [SMILES: CCn1c([C@@H](NC(=O)c2cnc(C)cn2)[C@H]2CCOC2)nc2cc(OC(F)(F)F)ccc21]

HPLC-MS; Method: Z018_S04; $R_t$ [min] : 0.97  MS: 450 (M + H)⁺
Chiral SFC Rt Method: I_IA_10_ETOH_NH3_001  Rt [min]: 4.34

The following compounds are obtained in analogy to example 1

Example 72: N-[(1S)-1-(5-chloro-1-methyl-1H-1,3-benzodiazol-2-yl)-2-methylpropyl]-5-methylpyrazine-2-carboxamide

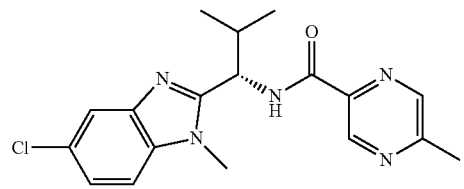 [SMILES: Cc1cnc(C(=O)N[C@H](c2nc3cc(Cl)ccc3n2C)C(C)C)cn1]

HPLC-MS; Method: Z018_S04; R_t [min] : 0.84   MS: 358 (M + H)⁺
Chiral SFC Rt Method: I_SC_25_IPA_NH3_001   Rt [min]: 2.38
   ¹H NMR (400 MHz, DMSO-d₆) δ ppm 0.85-1.05 (m, 6 H) 2.59 (s, 3 H) 3.89 (s, 3 H)
5.25 (t, J = 8.36 Hz, 1 H) 7.27 (dd, J = 8.62, 1.90 Hz, 1 H) 7.60 (d, J = 8.62 Hz, 1 H) 7.70
   (d, J = 1.65 Hz, 1 H) 8.65 (s, 1 H) 8.91 (d, J = 8.87 Hz, 1 H) 9.05 (d, J = 1.01 Hz, 1 H)

Example 73: N-[(S)-cyclopropyl(1-cyclopropyl-5-fluoro-1H-1,3-benzodiazol-2-yl)methyl]-5-methylpyrazine-2-carboxamide

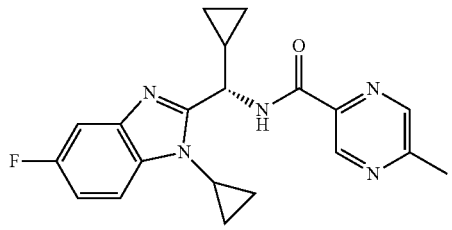 [SMILES: Cc1cnc(C(=O)N[C@H](c2nc3cc(F)ccc3n2C2CC2)C2CC2)cn1]

HPLC-MS; Method: Z018_S04; R_t [min] : 0.80   MS: 366 (M + H)⁺
Chiral SFC Rt Method: I_SC_20_IPA_NH3_001   Rt [min]: 3.85
   ¹H NMR (400 MHz, DMSO-d₆) δ ppm 0.39-0.65 (m, 4 H) 1.00-1.32 (m, 4 H) 1.56-
1.66 (m, 1 H) 2.58-2.62 (m, 3 H) 3.35-3.42 (m, 1 H) 5.23 (t, J = 8.24 Hz, 1 H) 7.12 (td,
J = 9.31, 2.53 Hz, 1 H) 7.45 (dd, J = 9.70, 2.47 Hz, 1 H) 7.59 (dd, J = 8.81, 4.75 Hz, 1 H)
   8.65 (d, J = 0.89 Hz, 1 H) 8.97 (d, J = 8.11 Hz, 1 H) 9.05 (d, J = 1.39 Hz, 1 H)

Example 80: N-[(1R,2R)-1-[5-(difluoromethoxy)-1-methyl-1H-1,3-benzodiazol-2-yl]-2-methoxypropyl]-5-(difluoromethyl)pyrazine-2-carboxamide

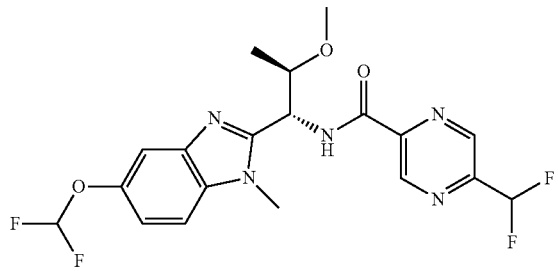

HPLC-MS; Method: Z011_S03; R_t [min] : 0.99   MS: 442 (M + H)⁺
   ¹H NMR (400 MHz, DMSO-d₆) δ ppm 1.04-1.12 (m, 3 H) 2.50 (s, 3 H) 3.32 (s, 3 H)
3.92 (s, 3 H) 4.04-4.13 (m, 1H) 5.47-5.54 (m, 1 H) 7.17 (m, 1 H) 7.22 (m, 1 H) 7.38
(m, 1 H) 7.44-7.46 (m, 1 H) 7.61-7.65 (m, 1 H) 9.06-9.13 (m, 1 H) 9.27-9.31 (m, 1
H)

In analogy to example 1 the following compounds are obtained. The product is a mixture of four stereoisomers. Two stereoisomers are obtained by chiral SFC separation: examples 84, 84-1

Example 84: N-[(S)-[5-fluoro-1-(propan-2-yl)-1H-1,3-benzodiazol-2-yl][(3R)-oxolan-3-yl]methyl]-5-methylpyrazine-2-carboxamide

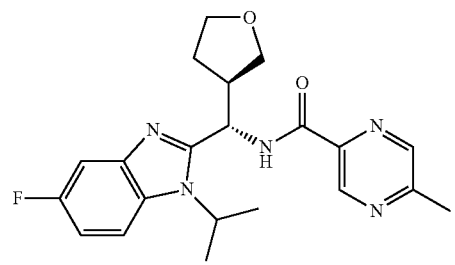 [SMILES: Cc1cnc(C(=O)N[C@H](c2nc3cc(F)ccc3n2C(C)C)[C@H]2CCOC2)cn1]

HPLC-MS; Method: Z003_S05; $R_t$ [min] : 1.11    MS: 398 (M + H)$^+$
Chiral SFC Rt Method: I_IG_25_MEOH_NH3_001    Rt [min]: 4.36
$^1$H NMR (400 MHz, DMSO-d$_6$) δ ppm 1.40-1.65 (m, 7 H) 1.95-2.05 (m, 1 H) 2.58 (s, 3 H) 3.21-3.28 (m, 1 H) 3.59-3.83 (m, 4 H) 5.00 (spt, J = 6.80 Hz, 1 H) 5.49 (t, J = 8.93 Hz, 1 H) 7.05 (m, 1 H) 7.45 (m, 1 H) 7.74 (m, 1 H) 8.60 (s, 1 H) 9.05 (s, 1 H) 9.21 (m, 1 H)

Example 84-1: N-{ [5-fluoro-1-(propan-2-yl)-1H-1,3-benzodiazol-2-yl](oxolan-3-yl)methyl }-5-methylpyrazine-2-carboxamide

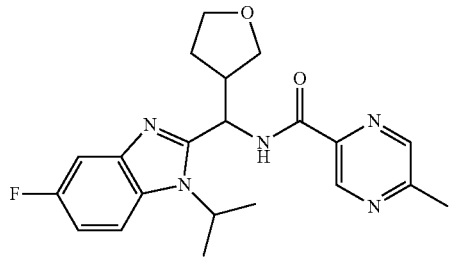 [SMILES: Cc1cnc(C(=O)NC(c2nc3cc(F)ccc3n2C(C)C)C2CCOC2)cn1]

HPLC-MS; Method: Z003_S05; $R_t$ [min] : 1.11    MS: 398 (M + H)$^+$
Chiral SFC Rt Method: I_IG_25_MEOH_NH3_001    Rt [min]: 5.07

In analogy to example 1 the following compounds are obtained. The product is a mixture of four stereoisomers which are separated by chiral SFC: example 91, 91-1, 91-2, 91-3

Example 91: N-[(S)-[5-chloro-1-(2-methoxyethyl)-1H-1,3-benzodiazol-2-yl][(3S)-oxolan-3-yl]methyl]-5-methylpyrazine-2-carboxamide

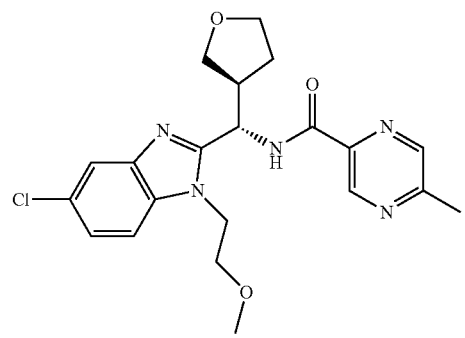 [SMILES: COCCn1c([C@@H](NC(=O)c2cnc(C)cn2)[C@@H]2CCOC2)nc2cc(Cl)ccc21]

HPLC-MS; Method: Z011_S03; $R_t$ [min]: 0.94    MS: 430 (M + H)$^+$
Chiral SFC Rt Method: I_AC_20_IPA_NH3_002    Rt [min]: 1.36
$^1$H NMR (400 MHz, DMSO-d$_6$) δ ppm 1.51-1.61 (m, 1H) 1.88-1.99 (m, 1H) 2.57 (s, 3H) 3.13 (s, 3H) 3.33-3.41 (m, 1H) 3.55-3.81 (m, 6H) 4.42-4.76 (m, 2H) 5.50 (t, J = 9.31 Hz, 1H) 7.27 (dd, J = 8.62, 2.03 Hz, 1H) 7.61 (d, J = 8.62 Hz, 1H) 7.71 (d, J = 1.90 Hz, 1H) 8.59 (s, 1H) 9.05 (d, J = 1.14 Hz, 1H) 9.10 (d, J = 9.12 Hz, 1H)

Example 91-1: N-{[5-chloro-1-(2-methoxyethyl)-1H-1,3-benzodiazol-2-yl](oxolan-3-yl)methyl}-5-methylpyrazine-2-carboxamide -continued

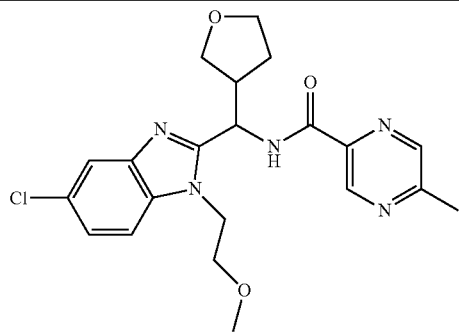

HPLC-MS; Method: Z011_S03; $R_t$ [min]: 0.94  MS: 430 (M + H)$^+$
Chiral SFC Rt Method: I_AC_20_IPA_NH3_002  Rt [min]: 0.85
Example 91-2: N-{[5-chloro-1-(2-methoxyethyl)-1H-1,3-benzodiazol-2-yl](oxolan-3-yl)methyl}-5-methylpyrazine-2-carboxamide

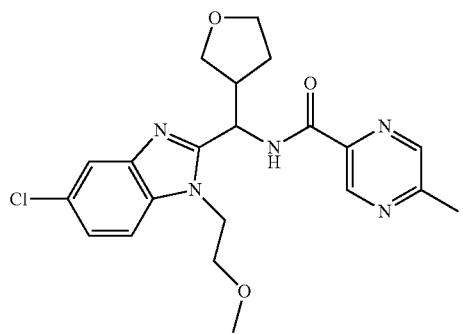 [SMILES: COCCn1c(C(NC(=O)c2cnc(C)cn2)C2CCOC2)nc2cc(Cl)ccc21]

HPLC-MS; Method: Z011_S03; $R_t$ [min]: 0.94  MS: 430 (M + H)$^+$
Chiral SFC Rt Method: I_AC_20_IPA_NH3_002  Rt [min]: 1.26
Example 91-3: N-{[5-chloro-1-(2-methoxyethyl)-1H-1,3-benzodiazol-2-yl](oxolan-3-yl)methyl}-5-methylpyrazine-2-carboxamide

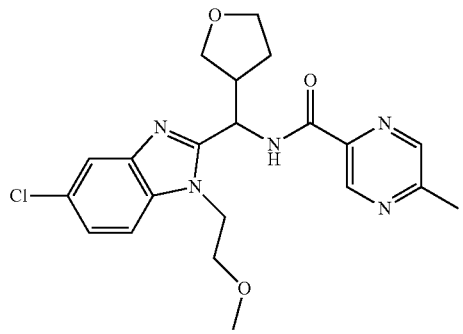 [SMILES: COCCn1c(C(NC(=O)c2cnc(C)cn2)C2CCOC2)nc2cc(Cl)ccc21]

HPLC-MS; Method: Z011_S03; $R_t$ [min]: 0.94  MS: 430 (M + H)$^+$
Chiral SFC Rt Method: I_AC_20_IPA_NH3_002  Rt [min]: 1.61

In analogy to example 1 the following compounds are obtained:

Example 93: N-[(R)-(1-hydroxycyclobutyl)[1-methyl-5-(trifluoromethyl)-1H-1,3-benzodiazol-2-yl]methyl]-5-methylpyrazine-2-carboxamide

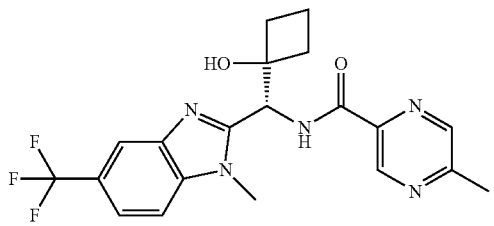 [SMILES: Cc1cnc(C(=O)N[C@H](c2nc3cc(C(F)(F)F)ccc3n2C)C2(O)CCC2)cn1]

HPLC-MS; Method: Z011_S03; R$_t$ [min]: 1.04  MS: 420 (M + H)$^+$
Chiral SFC Rt Method: I_SC_10_MEOH_NH3_002  Rt [min]: 0.81
$^1$H NMR (400 MHz, DMSO-d$_6$) δ ppm 1.57-1.70 (m, 1H) 1.71-1.86 (m, 1H) 1.91-2.10 (m, 2H) 2.20-2.40 (m, 2H) 2.45 (m, 6H) 2.61 (s, 3H) 3.96 (s, 3H) 5.60 (d, J = 8.87 Hz, 1H) 5.86 (s, 1H) 7.59 (dd, J = 8.62, 1.39 Hz, 1H) 7.79 (d, J = 8.49 Hz, 1H) 8.03 (s, 1H) 8.68 (d, J = 0.89 Hz, 1H) 8.83 (d, J = 8.87 Hz, 1H) 9.09 (d, J = 1.39 Hz, 1H)
Example 95: N-[(1S)-2-cyclopropyl-1-{1-[2-(difluoromethoxy)ethyl]-5-fluoro-1H-1,3-benzodiazol-2-yl}ethyl]-5-methylpyrazine-2-carboxamide

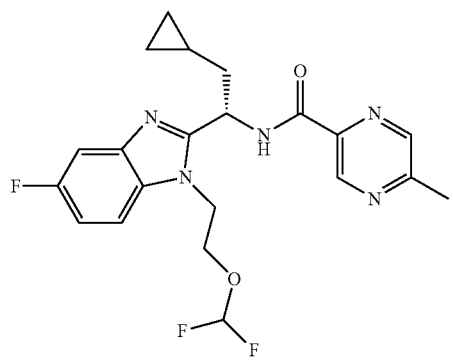

HPLC-MS; Method: Z018_S04; R$_t$ [min]: 0.91  MS: 434 (M + H)$^+$
Chiral SFC Rt Method: G_SC_MEOH_NH3_001  Rt [min]: 2.46
$^1$H NMR (400 MHz, DMSO-d$_6$) δ ppm −0.04-0.05 (m, 1H) 0.06-0.18 (m, 1H) 0.27-0.38 (m, 2H) 0.70-0.81 (m, 1H) 1.86-2.18 (m, 2H) 2.59 (s, 3H) 4.18 (t, J = 5.20 Hz, 2H) 4.57-4.83 (m, 2H) 5.54 (m, 1H) 6.57 (m, 1H) 7.12 (m, 1H) 7.44 (m, 1H) 7.62 (m, 1H) 8.62 (m, 1H) 9.00-9.09 (m, 2H)
Example 96: N-[(S)-cyclopropyl (6-fluoro-1,5-dimethyl-1H-1,3-benzodiazol-2-yl)methyl]-5-methylpyrazine-2-carboxamide

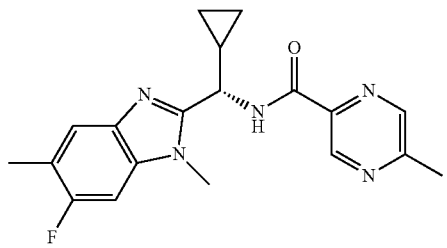

HPLC-MS; Method: Z018_S04; R$_t$ [min]: 0.75  MS: 354 (M + H)$^+$
Chiral SFC Rt Method: I_SA_25_MEOH_NH3_001  Rt [min]: 2.77
$^1$H NMR (400 MHz, DMSO-d$_6$) δ ppm 0.35-0.59 (m, 4H) 1.63-1.72 (m, 1H) 2.31 (d, J = 1.90 Hz, 3H) 2.60 (s, 3H) 3.78 (s, 3H) 4.98 (t, J = 8.36 Hz, 1H) 7.40 (d, J = 10.01 Hz, 1H) 7.51 (d, J = 6.97 Hz, 1H) 8.64 (s, 1H) 9.05 (d, J = 1.27 Hz, 1H) 9.08 (d, J = 8.11 Hz, 1H)

In analogy to example 1 the following compounds are obtained. The product is a mixture of four stereoisomers which are separated by chiral SFC: example 97, 97-1, 97-2, 97-3

Example 97: N-[(S)-[1-ethyl-5-(trifluoromethoxy)-1H-1,3-benodiazol-2-yl][(3S)-oxolan-3-yl]methyl]-5-methylpyrazine-2-carboxamide -continued

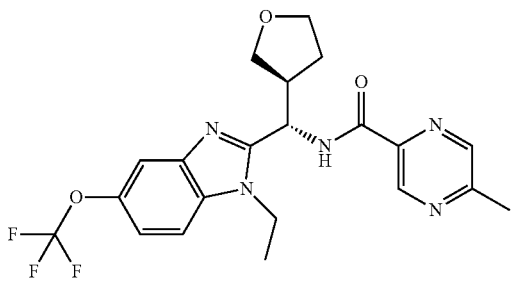 [SMILES: CCn1c([C@@H](NC(=O)c2cnc(C)cn2)[C@@H]2CCOC2)nc2cc(OC(F)(F)F)ccc21]

HPLC-MS; Method: Z018_S04; R$_t$ [min]: 0.97  MS: 448 (M + H)$^+$
Chiral SFC Rt Method: I_C4_10_MEOH_NH3_002  Rt [min]: 1.33
$^1$H NMR (400 MHz, DMSO-d$_6$) δ ppm 1.20-1.30 (m, 3H) 1.72-188 (m, 1H) 1.95-2.09 (m, 1H) 2.57-2.61
(m, 3H) 3.33-3.44 (m, 2H) 3.61-3.71 (m, 1H) 3.73-3.88 (m, 2H) 4.25-4.43 (m, 2H) 5.42 (t, J = 9.25 Hz, 1H)
7.25 (d, J = 8.85 Hz, 1H) 7.65-7.70 (m, 2H) 8.61 (d, J = 1.01 Hz, 1H) 9.08 (d, J = 1.39 Hz, 1H) 9.34 (d,
J = 9.34 (d, J = 9.12 Hz, 1H)
Example 97-1: N-{[1-ethyl-5-(trifluoromethoxy)-1H-1,3-benzodiazol-2-yl])oxolan-3-yl)methyl}-5-
methylpyrazine-2-carboxamide

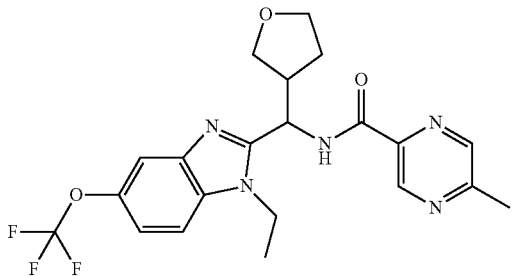

HPLC-MS; Method: Z018_S018_S04; R$_t$ [min]: 0.97  MS: 448 (M + H)$^+$
Chiral SFC Rt Method: I_IA_10_ETOH_NH3_001  Rt [min]: 3.67
$^1$H NMR (400 MHz, DMSO-d$_6$) δ ppm 1.28 (t, J = 7.16 Hz, 3H) 1.49-1.60 (m, 1H) 1.94-2.03 (m, 1H)
2.56-2.60 (m, 3H) 3.26-3.35 (m, 1H) 3.63 (q, J = 7.56 Hz, 1H) 3.69-3.84 (m, 3H) 4.33-4.50 (m, 2H) 5.46 (t,
J = 9.06 Hz, 1H) 7.25 (dd, J = 8.74, 1.39 Hz, 1H) 7.66 (d, J = 1.14 Hz, 1H) 7.69 (d, J = 8.87 Hz, 1H) 8.61
(d, J = 1.01 Hz, 1H) 9.05 (d, J = 1.39 Hz, 1H) 9.24 (d, J = 8.87 Hz, 1H)
Example 97-2: N-{[1-ethyl-5-(trifluoromethoxy)-1H-1,3-benzodiazol-2-yl](oxolan-3-yl)methyl}-5-
methylpyrazine-2-carboxamide

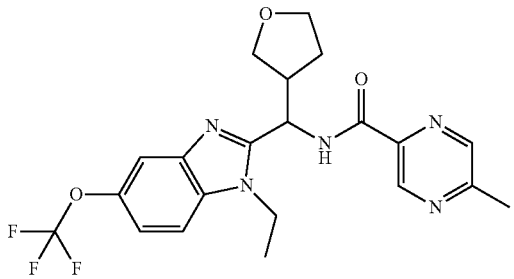 [SMILES: CCn1c(C(NC(=O)c2cnc(C)cn2)C2CCOC2)nc2cc(OC(F)(F)F)ccc21]

HPLC-MS; Method: Z018_S04; R$_t$ [min]: 0.97  MS: 448 (M + H)$^+$
Chiral SFC Rt Method: I_IA_10_ETOH_NH3_001  Rt [min]: 4.35
Example 97-3: N-{[1-ethyl-5-(trifluoromethoxy)-1H-1,3-benzodiazol-2-yl](oxolan-3-yl)methyl}-5-
methylpyrazine-2-carboxamide

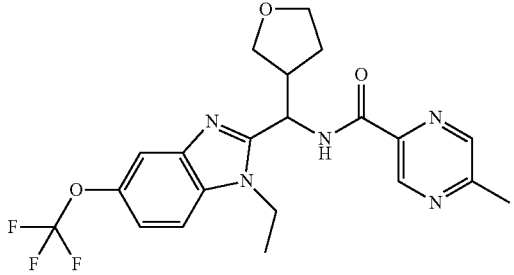 [SMILES: CCn1c(C(NC(=O)c2cnc(C)cn2)C2CCOC2)nc2cc(OC(F)(F)F)ccc21]

HPLC-MS; Method: Z018_S04; R$_t$ [min]: 0.97  MS: 448 (M + H)$^+$

The following compounds are obtained in analogy to example 1.

Example 98: N-[(1R)-1-[1-ethyl-5-(trifluoromethoxy)-1H-1,3-benzodiazol-2-yl]-2-hydroxy-2-methylpropyl]-5-methylpyrazine-2-carboxamide

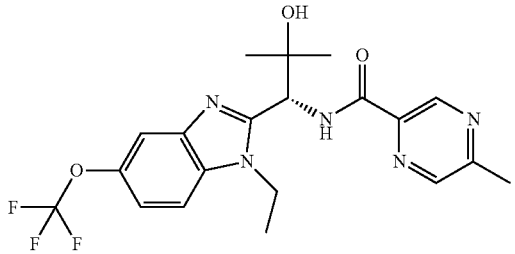 [SMILES: CCn1c([C@@H](NC(=O)c2cnc(C)cn2)C(C)(C)O)nc2cc(OC(F)(F)F)ccc21]

HPLC-MS; Method: Z011_S03; $R_t$ [min]: 1.07    MS: 438 (M + H)$^+$
Chiral SFC Rt Method: I_SA_10_IPA_NH3_001    Rt [min]: 1.98

$^1$H NMR (400 MHz, DMSO-d$_6$) δ ppm 1.21-1.29 (m, 6H) 1.32-1.41 (m, 3H) 2.60 (s, 3H) 4.42-4.61 (m, 2H) 5.43 (d, J = 9.25 Hz, 1H) 7.25 (d, J = 8.90 Hz, 1H) 7.67 (s, 1H) 7.73 (d, J = 8.74 Hz, 1H) 8.71 (d, J = 9.25 Hz, 1H) 9.06 (s, 1H)

Example 99: N-[(1S)-2-cyclopropyl-1-{1-[2-(difluoromethoxy)ethyl]-5-fluoro-1H-1,3-benzodiazol-2-yl}-5-(difluoromethyl)pyrazine-2-carboxamide

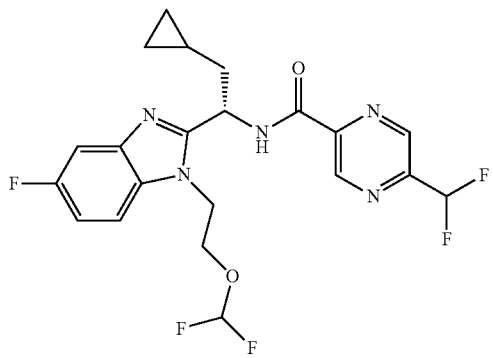

HPLC-MS; Method: Z018_S04; $R_t$ [min]: 0.97    MS: 470 (M + H)$^+$
Chiral SFC Rt Method: G_SC_MEOH_NH3_001    Rt [min]: 1.52

$^1$H NMR(400 MHz, DMSO-d$_6$) δ ppm 0.00-0.08 (m, 1H) 0.13-0.22 (m, 1H) 0.32-0.45 (m, 2H) 0.76-0.86 (m, 1H) 1.96-2.06 (m, 1H) 2.16-2.27 (m, 1H) 4.21-4.27 (m, 2H) 4.71-4.80 (m, 1H) 4.82-4.93 (m, 1H) 5.61-5.69 (m, 1H) 657 (m, 1H) 7.22 (m, 1H) 7.28-7.37 (m, 1H) 7.57 (dd, J = 9.12, 2.41 Hz, 1H) 7.83 (dd, J = 9.00, 4.56 Hz, 1H) 9.06 (s, 1H) 9.29 (d, J = 1.14 Hz, 1H) 9.52 (br d, J = 7.73 Hz, 1H)

Example 105: N-[(1S)-2-cyclopropyl-1-[1-methyl-5-(trifluoromethoxy)-1H-1,3-benzodizaol-2-yl]ethyl]-5-methylpyrazine-2-carboxamide

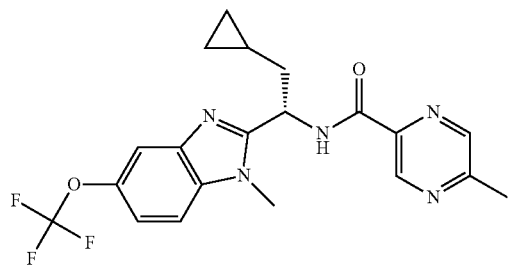 [SMILES: Cc1cnc(C(=O)N[C@@H](CC2CC2)c2nc3cc(OC(F)(F)F)ccc3n2C)cn1]

HPLC-MS; Method: Z018_S04; $R_t$ [min]: 0.94    MS: 420 (M + H)$^+$
Chiral SFC Rt Method: I_SC_10_IPA_NH3_001    Rt [min]: 3.03

$^1$H NMR (400 MHz, DMSO-d$_6$) δ ppm −0.01 (m, 1H) 0.01-0.15 (m, 1H) 0.29-0.39 (m, 2H) 0.68-0.87 (m, 1H) 2.01 (t, J = 6.97 Hz, 2H) 2.58-2.61 (m, 3H) 3.89 (s, 3H) 5.50-5.57 (m, 1H) 7.25 (d, J = 8.81 Hz, 1H) 7.63 (d, J = 1.01 Hz, 1H) 7.67 (d, J = 8.74 Hz, 1H) 8.64 (d, J = 1.01 Hz, 1H) 9.05 (d, J = 1.39 Hz, 1H) 9.11 (d, J = 8.11 Hz, 1H)

Example 108: N-[(1S)-1-{5-chloro-1-[2-(difluoromethoxy)ethyl]-1H-1,3-benzodiazol-2-yl}-2-cyclopropylethyl]-5-(difluoromethyl)pyrazine-2-carboxamide

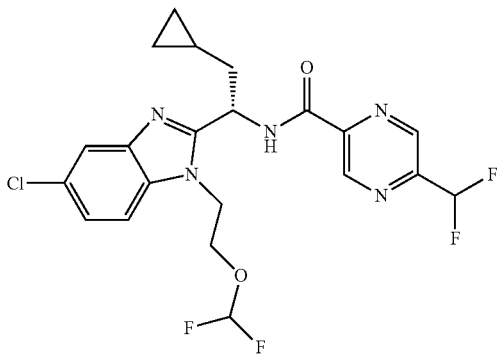 [SMILES: O=C(N[C@@H](CC1CC1)c1nc2cc(Cl)ccc2n1CCOC(F)F)c1cnc(C(F)F)cn1]

HPLC-MS; Method: Z018_S04; R$_t$ [min]: 1.05      MS: 486 (M + H)$^+$
Chiral SFC Rt Method: G_SB_IPA_NH3_001      Rt [min]: 3.45
$^1$H NMR (400 MHz. DMSO-d$_6$) δ ppm 0.01-0.19 (m, 2H) 0.31-0.44 (m, 2H) 0.75-0.85 (m, 1H) 1.96-2.04 (m, 1H) 2.14-2.23 (m, 1H) 4.18-4.26 (m, 2H) 4.66-4.91 (m, 2H) 5.59-5.66 (m, 1H) 6.56 (m, 1H) 6.56 (m, 1H) 7.21 (m, 1H) 7.41 (dd, J = 8.74, 1.90 Hz, 1H) 7.78 (m, 2H) 9.04-9.07 (m, 1H) 9.28 (d, J = 1.27 Hz, 1H) 9.47 (d, J = 8.11 Hz, 1H)

Example 110: N-[(S)-(6-bromo-5-fluoro-1-methyl-1H-1,3-benzodiazol-2-yl)(cycloprophly)methyl]-5-methylpyrazine-2-carboxamide

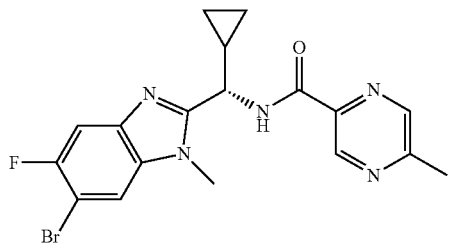 [SMILES: Cc1cnc(C(=O)N[C@H](c2nc3cc(F)c(Br)cc3n2C)C2CC2)cn1]

HPLC-MS; Method: Z018_S04; R$_t$ [min]: 0.87      MS: 418 (M + H)$^+$
$^1$H NMR (400 MHz, DMSO-d$_6$) δ ppm 0.37-0.60 (m, 4H) 1.65-1.74 (m, 1H) 2.60 (s, 3H) 3.83 (s, 3H) 4.96 (t, J = 8.36 Hz, 1H) 7.67 (d, J = 9.51 Hz, 1H) 7.99 (d, J = 6.21 Hz, 1H) 8.64 (s, 1H) 9.04 (d, J = 1.27 Hz, 1H) 9.15 (d, J = 7.98 Hz, 1H)

Example 117: N-[(1S)-1-(5-chloro-1-cyclopropyl-1H-1,3-benzodiazol-2-yl)-2-cyclopropylethyl]-5-(difluoromethyl)pyrazine-2-carboxamide

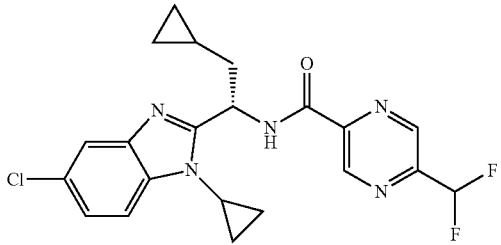 [SMILES: O=C(N[C@@H](CC1CC1)c1nc2cc(Cl)ccc2n1C1CC1)c1cnc(C(F)F)cn1]

HPLC-MS; Method:Z011_S03; R$_t$ [min]: 1.11      MS: 432 (M + H)$^+$
Chiral SFC Rt Method: I_SC_15_MEOH_NH3_001      Rt [min]: 2.34
$^1$H NMR (400 MHz, DMSO-d$_6$) δ ppm −0.05--−0.01 (m, 1H) 0.10-0.17 (m, 1H) 0.32-0.43 (m, 2H) 0.73-0.82 (m, 1H) 1.03-1.13 (m, 1H) 1.23-1.36 (m, 3H) 2.01 (m, 2H) 3.35-3.46 (m, 1H) 5.76 (m, 1H) 7.21 (s, 1H) 7.28 (dd, J = 8.59, 2.02 Hz, 1H) 7.61 (d, J = 8.59 Hz 1H) 7.67 (d, J = 2.02 Hz, 1H) 9.07 (s, 1H) 9.22-9.29 (m, 2H)

Example 118: N-[(1S)-2-cyclopropyl-1-(1-cyclopropyl-5,6-difluoro-1H-1,3-benzodiazol-2-yl)ethyl]-5-(difluoromethyl)pyrazine-2-carboxamide

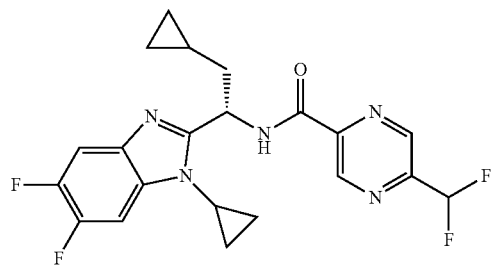 [SMILES: O=C(N[C@@H](CC1CC1)c1nc2cc(F)c(F)cc2n1C1CC1)c1cnc(C(F)F)cn1]

HPLC-MS; Method: Z011_S03: R$_t$ [min]: 1.09      MS: 434 (M + H)$^+$
Chiral SFC Rt Method: I_SC_15_MEOH_NH3_001      Rt [min]: 1.51
$^1$H NMR (400 MHz, DMSO-d$_6$) δ ppm −0.05−−0.01 (m, 1H) 0.04-0.17 (m, 1H) 0.32-0.44 (m, 2H) 0.72-0.83 (m, 2H) 0.72-0.83 (m, 1H) 1.03-1.13 (m, 1H) 1.19-1.32 (m, 3H) 2.00 (m, 2H) 3.37-3.43 (m, 1H) 5.71-5.77 (m, 1H) 7.21 (m, 1H) 7.63-7.71 (m, 2H) 9.06 (s, 1H) 9.23-9.30 (m, 2H)
Example 119: N-[(1R,2R)-1-[1-(2-cyclopropoxyethyl)-5-(trifluoromethoxy)-1H-1,3-benzodiazol-2-yl]-2-methoxypropyl]-5-methylpyrazine-2-carboxamide

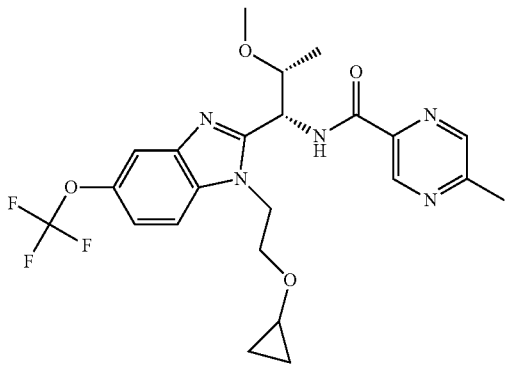 [SMILES: CO[C@H](C)[C@H](NC(=O)c1cnc(C)cn1)c1nc2cc(OC(F)(F)F)ccc2n1CCOC1CC1]

HPLC-MS: Method: Z018_S04: R$_t$ [min]: 1.14      MS: 494 (M + H)$^+$
Chiral SFC Rt Method: I_IG_15_IPA_NH3_002      Rt [min]: 1.37
$^1$H NMR (400 MHz, DMSO-d$_6$) δ ppm 0.07-0.35 (m, 4H) 1.07 (d, J = 6.21 Hz, 3H) 2.59-2.62 (m, 3H) 3.13-3.26 (m, 1H) 3.31 (s, 3H) 3.70-3.85 (m, 2H) 4.02-4.11 (m, 1H) 4.46-4.69 (m, 2H) 5.25-5.59 (m, 1H) 7.26 (3, J = 8.19 Hz, 1H) 7.67 (d, J = 1.27 Hz, 1H) 7.72 (d, J = 8.87 Hz, 1H) 8.65-8.68 (m, 1H) 8.87 (d, J = 8.36 Hz, 1H) 9.06-9.09 (m, 1H)
Example 120: N-[(1R,2R)-1-[1-(2-cyclobutoxyethyl)-5-(trifluoromethoxy)-1H-1,3-benzodiazol-2-yl]-2-methoxypropyl]-5-methylpyrazine-2-carboxamide

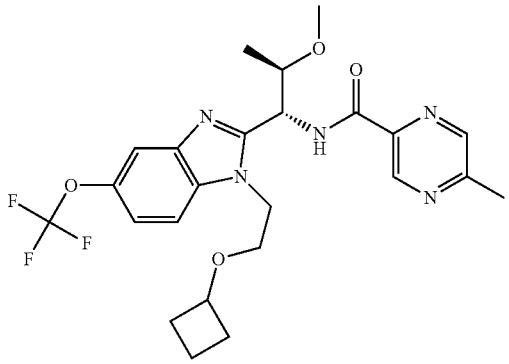 [SMILES: CO[C@H](C)[C@H](NC(=O)c1cnc(C)cn1)c1nc2cc(OC(F)(F)F)ccc2n1CCOC1CCC1]

HPLC-MS; Method: Z011_S03; R$_t$ [min]: 1.17      MS: 308 (M + H)$^+$
Chiral SFC Rt Method: I_IG_15_IPA_NH3_002      Rt [min]: 157
Example 123: N-[(1R,2R)-2-meethoxy-1-[1-(propan-2-yl)-5-(trifluoromethoxy)-1H-1,3-benzodiazol-2-yl]propyl]-5-methylpyrazine-2-carboxamide

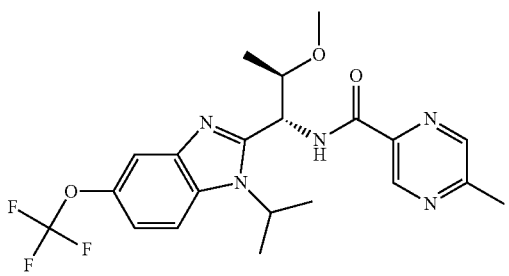 [SMILES: CO[C@H](C)[C@H](NC(=O)c1cnc(C)cn1)c1nc2cc(OC(F)(F)F)ccc2n1C(C)C]

HPLC-MS; Method: Z011_S03; R$_t$ [min]: 1.13      MS: 452 (M + H)$^+$
Chiral SFC Rt Method: G_IG_IPA_NH3_002      Rt [min]: 1.34
$^1$H NMR (400 HHz, DMSO-d$_6$) δ ppm 1.05-1.14 (m, 3H) 1.51-1.69 (m, 6H) 2.61 (s, 3H) 3.31 (s, 3H) 4.03 (m, 1H) 5.07-5.16 (m, 1H) 5.55-5.62 (m, 1H) 7.24 (dd, J = 8.93, 1.46 Hz, 1H) 7.69 (s, 1H) 7.94 (d, J = 9.00 Hz, 1H) 8.69 (d, J = 0.89 Hz, 1H) 8.96 (d, J = 7.86 Hz, 1H) 9.07 (d, J = 1.27 Hz 1H)
Example 125: N-[(1S)-1-{5-chloro-1-[2-(difluoromethoxy)ethyl]-1H-1,3-benzodiazol-2-yl}-2-cyclopropylethyl]-5-methylpyrazine-2-carboxamide -continued

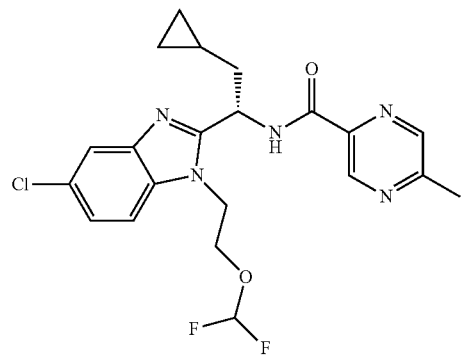 [SMILES: Cc1cnc(C(=O)N[C@@H](CC2CC2)c2nc3cc(Cl)ccc3n2CCOC(F)F)cn1]

MS: 450 (M + H)+
Chiral SFC Rt Method: I_C2_15_MEOH_NH3_001     Rt [min]: 2.99
¹H NMR (400 MHz, DMSO-d₆) δ ppm −0.04-0.05 (m, 1H) 0.09-0.17 (m, 1H) 0.29-0.40 (m, 2H) 0.70-0.85 (m, 1H) 1.18-1.37 (m, 1H) 1.90-2.15 (m, 2H) 2.59 (s, 3H) 4.18 (m, 2H) 4.58-4.82 (m, 2H) 5.55 (m, 1H) 6.56 (m, 1H) 7.28 (dd, J = 8.62, 2.03 Hz, 1H) 7.64 (d, J = 8.62 Hz, 1H) 7.70 (d, J = 1.90 Hz, 1H) 8.62 (d, J = 0.89 Hz, 1H) 9.03-9.07 (m, 2H)

Example 129: N-[(1R,2R)-2-methoxy-1-{ 1-[(2R)-1-methoxypropan-2-yl]-5-(trifluoromethoxy)-1H-1,3-benzodiazol-2-yl}propyl]-5-methylpyrazine-2-carboxamide

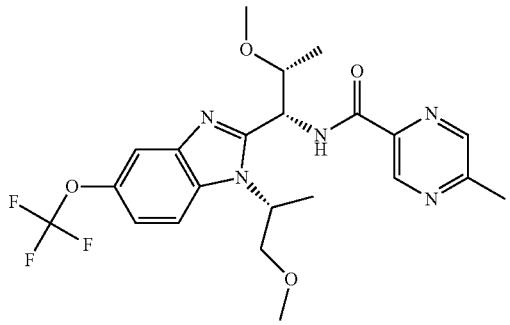 [SMILES: COC[C@@H](C)n1c([C@@H](NC(=O)c2cnc(C)cn2)[C@@H](C)OC)nc2cc(OC(F)(F)F)ccc21]

HPLC-MS; Method: Z011_S03; R$_t$ [min]: 1.09     MS: 482 (M + H)+
¹H NMR (400 MHz, DMSO-d₆) δ ppm 1.15 (d, J = 6.21 Hz, 3H) 1.52 (d, J = 6.97 Hz, 3H) 2.61 (s, 3H) 3.21 (s, 3H) 3.25 (s, 3H) 3.71-3.80 (m, 1H) 3.92-4.01 (m, 1H) 4.19 (m, 1H) 5.05-5.22 (m, 2H) 5.46-5.55 (m, 1H) 7.23 (br d, J = 9.00 Hz, 1H) 7.66 (s, 1H) 7.92 (d, J = 8.87 Hz, 1H) 8.67 (s, 1H) 8.92 (d, J = 8.49 Hz, 1H) 9.06 (s, 1H)

Example 4

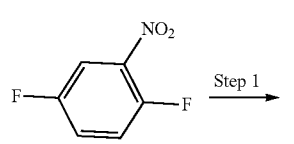

Step 1

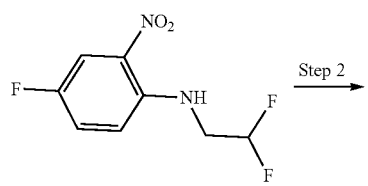

Int-4a

Step 2

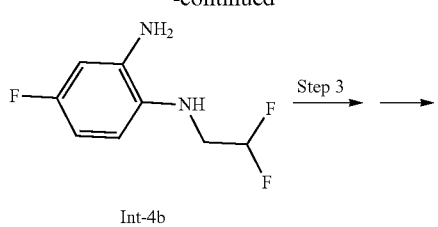

Int-4b

Step 3

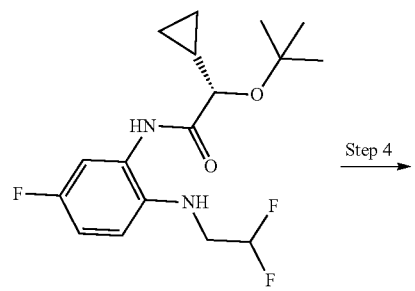

Int-4c

Step 4

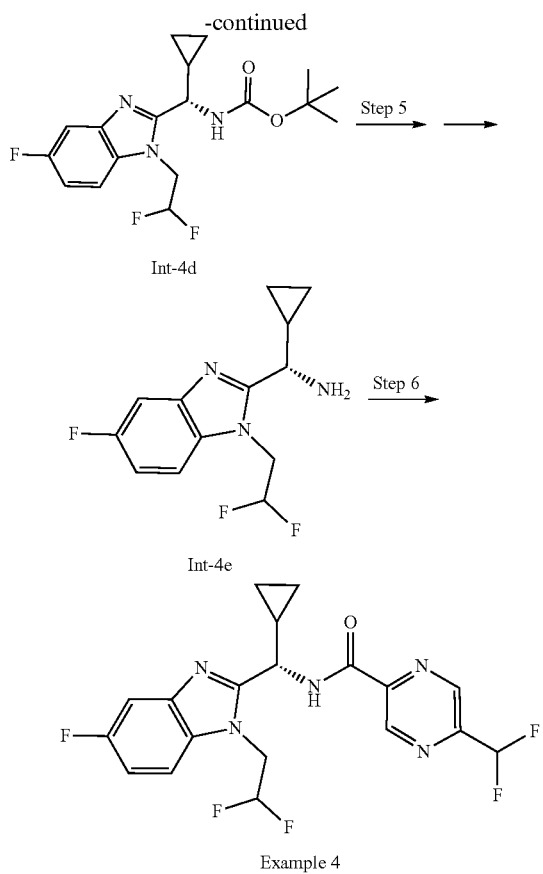

Example 4

Step 1:
A mixture of 1,4-difluoro-2-nitro-benzene (100 g; 0.63 mol) and 2,2-difluoroethylamine (266 mL; 3.8 mol) in 800 mL ACN with $K_2CO_3$ (400 g; 1.3 mol) is stirred at 80° C. for 2 d. The mixture is filtered, and the filtrate is concentrated i. vac. The residue is used without further purification.

$R_f$: 0.4 (PE/EtOAc 85:15)
Yield: 105 g (0.48 mol; 76%) Int-4a
MS (ESI$^+$): (M+H)$^+$ 221; HPLC: RT=1.00 min, Method: Z018_S04

Step 2:
A mixture of Int-4a (50 g, 0.23 mol) with 10 g Raney-nickel in 500 mL MeOH is hydrogenated at ambient temperature at 50 psi (hydrogen gas) for 4 h. Afterwards, the mixture is filtered, washed with EtOAc and concentrated i. vac. The residue is used without further purification.

$R_f$: 0.4 (PE/EtOAc 85:15)
Yield: 45 g (0.22 mol; 98%) Int-4b
MS (ESI$^+$): (M+H)$^+$ 191; HPLC: RT=0.71 min, Method: Z018_S04

Step 3:
To a mixture of Int-4b (91 g, 0.48 mol) and (S)-Boc-amino-cyclopropyl-acetic acid (103 g, 0.48 mol) in 300 mL pyridine is added PPA (50 wt % in EtOAc, 609 g, 0.96 mol) at 0° C. The mixture is then stirred at ambient temperature for 16 h. 600 mL of water is added and the mixture extracted with EtOAc. The combined organic layers are dried over $Na_2SO_4$, filtered and concentrated. The residue is used without further purification.

Yield: 125 g (0.32 mol; 67%) Int-4c
MS (ESI$^+$): (M+H)$^+$ 388; HPLC: RT=1.02 min, Method: Z011_S03

Step 4:
Int-4c (100 g, 0.26 mol) is stirred at 40° C. for 2 days in 300 mL acetic acid. Afterwards, the mixture is concentrated, 600 mL water added and extracted with EtOAc. The combined organic layers are washed with aq. $NaHCO_3$ solution, dried over $Na_2SO_4$, filtered, and the filtrate concentrated. The residue is purified by column chromatography (100-200 mesh silica gel, PE/EtOAc 7:3), the product containing fractions combined and all solvent removed i. vac. The residue is taken up in diethyl ether and the solvent evaporated. Yield: 70 g (0.19 mol; 73%) Int-4d MS (ESI$^+$): (M+H)$^+$ 370; HPLC: RT=1.17 min, Method: Z003_S05

Step 5:
To Int-4d (80 g, 0.22 mol) in 50 mL dioxane is added HCl in dioxane (4M, 100 mL) and the mixture stirred at ambient temperature for 4 h. The mixture is then filtered and the solid washed with diethyl ether and dried. Yield: 67 g (0.22 mol; quant.) Int-4e
MS (ESI$^+$): (M+H)$^+$ 270; HPLC: RT=0.83 min, Method: Z011_S03

Step 6:
To 5-(difluoromethyl)-pyrazine-carboxylic acid (4.4 g, 25 mmol) in 70 mL EtOAc is added Int-4e (7.0 g, 23 mmol) and 12.7 mL TEA (92 mmol). At 0° C., PPA solution (50 wt % in EtOAc, 17.7 mL, 30 mmol) is added over a period of 4 min to avoid heating above 5° C. After further 15 min, cooling is removed and the mixture stirred for 1.5 h at ambient temperature. 70 mL EtOAc are added followed by aq. $NH_3$ solution to adjust pH to basic and the organic phase collected. The organic phase is washed with half-conc. NaCl (aq.), dried over $MgSO_4$ and concentrated i. vac. The residue is purified by column chromatography (XBridge C18, 10 μm, eluent gradient: ($H_2O$+0.1% $NH_3$):ACN 61:39→41:59). Product containing fractions are combined and concentrated i. vac. The suspension is filtered, the solid washed with water and dried at 50° C.

Yield: 5.8 g (13.7 mmol; 60%)

Example 4: N-[(S)-cyclopropyl[1-(2,2-difluoroethyl)-5-fluoro-1H-1,3-benzodiazol-2-yl]methyl]-5-(difluoromethyl)pyrazine-2-carboxamide -continued
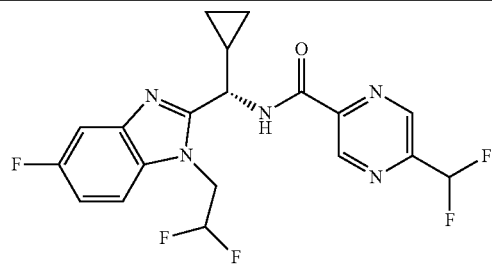
HPLC-MS; Method: Z011_S03; R$_t$ [min]: 0.99  MS: 426 (M + H)$^+$
Chiral SFC Rt Method: Method I_IG_25_MEOH_NH3_001  Rt [min]: 3.07
$^1$H NMR (400 MHz, DMSO-d$_6$) δ ppm 0.39-0.64 (m, 4H) 1.83-1.93 (m, 1H) 4.74-5.11 (m, 3H) 6.45 (m, 1H) 7.13-7.20 (m, 1H) 7.21 (m, 1H) 7.50 (m, 1H) 7.64 (m, 1H) 9.04 (s, 1H) 9.28 (s, 1H) 9.44 (m, 4 H)
In analogy to example 4, the following products are obtained:

Example 7: N-[(S)-cyclopropyl[5-fluoro-1-(propan-2-yl)-1H-1,3-benzodiazol-2-yl]methyl]-5-methylpyrazine-2-carboxamide

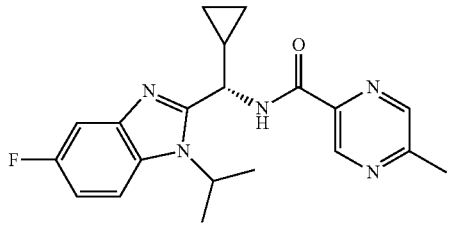 [SMILES: Cc1cnc(C(=O)N[C@H](c2nc3cc(F)ccc3n2C(C)C)C2CC2)cn1]

HPLC-MS; Method: Z011_S03; R$_t$ [min]: 0.98  MS: 368 (M + H)$^+$
Chiral SFC Rt Method: I_IG_20_IPA_NH3_001  Rt [min]: 3.81
$^1$H NMR (400 MHz, DMSO-d$_6$) δ ppm 0.35-0.69 (m, 4H) 1.41-1.61 (m, 6H) 1.61-1.78 (m, 1H) 2.58-2.61 (m, 3H) 4.87-5.03 (m, 2H) 7.05 (m, 1H) 7.46 (m, 1H) 7.75 (m, 1H) 8.64 (m, 1H) 9.05 (m, 1H) 9.16 (m, 1H)

Example 8: N-[(S)-[5-chloro-1-(2-methoxyethyl)-1H-1,3-benzodiazol-2-yl](cyclopropyl)methyl]-5-methylpyrazine-2-carboxamide

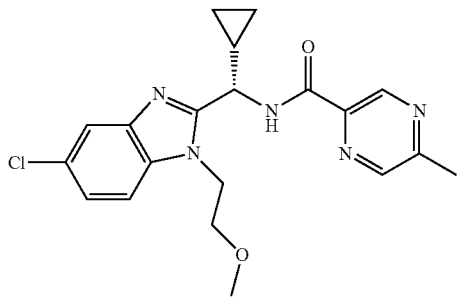 [SMILES: COCCn1c([C@@H](NC(=O)c2cnc(C)cn2)C2CC2)nc2cc(Cl)ccc21]

HPLC-MS; Method: Z011_S03; R$_t$ [min]: 0.99  MS: 400 (M + H)$^+$
Chiral SFC Rt Method: I_C2_20_IPA_NH3_002  Rt [min]: 1.37
$^1$H NMR (400 MHz, DMSO-d$_6$) δ ppm 0.36-0.61 (m, 4H) 1.74-1.84 (m, 1H) 2.59 (s, 3H) 3.13 (s, 3H) 3.56-3.65 (m, 2H) 4.40-4.63 (m, 2H) 5.01 (t, J = 8.62 Hz, 1H) 7.27 (dd, J = 8.68, 1.96 Hz, 1H) 7.61 (d, J = 8.62 Hz, 1H) 7.71 (d, J = 1.90 Hz, 1H) 8.63 (d, J = 1.01 Hz, 1H) 9.05 (d, J = 6.96 Hz, 2H) 9.05 (s, 1H)

Example 9: N-[(S)-cyclopropyl[1-(2,2-difluoroethyl)-4-fluoro-5-methyl-1H-1,3-benzodiazol-2-yl]methyl]-5-methylpyrazine-2-carboxamide

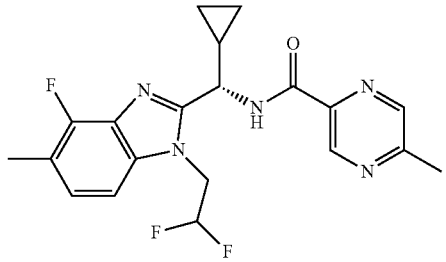

MS: 404 (M + H)$^+$
Chiral SFC Rt Method: I_SC_15_IPA_NH3_001  Rt [min]: 2.94
$^1$H NMR (400 MHz, DMSO-d$_6$) δ ppm 0.38-0.69 (m, 4H) 1.75-1.92 (m, 1H) 2.33 (d, J = 1.65 Hz, 3H) 2.55-2.63 (m, 3H) 4.78-5.03 (m, 3H) 6.43 (m, 1H) 7.15 (t, J = 7.54 Hz, 1H) 7.34 (d, J = 8.24 Hz, 1H) 8.63 (s, 1H) 9.04 (d, J = 1.39 Hz, 1H) 9.23 (d, J = 8.11 Hz, 1H)

Example 10: N-[(S)-cyclopropyl[1-(2,2-difluoroethyl)-5-fluoro-1H-1,3-benzodiazol-2-yl]methyl]-5-methylpyrazine-2-carboxamide

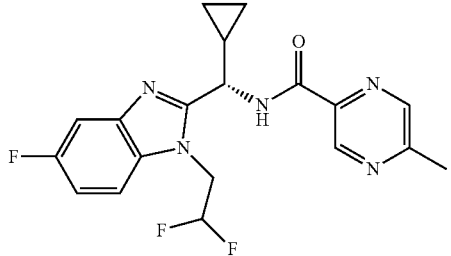 [SMILES: Cc1cnc(C(=O)N[C@H](c2nc3cc(F)ccc3n2CC(F)F)C2CC2)cn1]

HPLC-MS; Method: Z003_S05; R$_t$ [min]: 1.09     MS: 390 (M + H)$^+$
Chiral SFC Rt Method: I_SA_15_IPA_NH3_001     Rt [min]: 2.43
$^1$H NMR (400 MHz, DMSO-d$_6$) δ ppm 0.37-0.63 (m, 4H) 1.79-1.89 (m, 1H) 2.59 (s, 3H) 4.81-5.08 (m, 3H) 6.44 (m, 1H) 7.16 (td, J = 9.28, 2.47 Hz, 1H) 7.49 (dd, J = 9.63, 2.41 Hz, 1H) 7.63 (dd, J = 8.93, 4.75 Hz, 1H) 8.63 (d, J = 0.89 Hz, 1H) 9.04 (d, J = 1.39 Hz, 1H) 9.18 (d, J = 8.24 Hz, 1H)

Example 11: N-[(S)-[5-chloro-1-(2-methoxyethyl)-1H-1,3-benzodiazol-2-yl](cyclopropyl)methyl]-5-(difluoromethyl)pyrazine-2-carboxamide

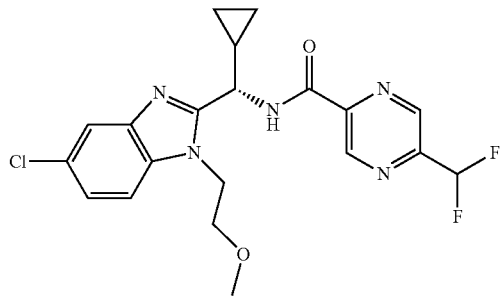 [SMILES: COCCn1c([C@@H](NC(=O)c2cnc(C(F)F)cn2)C2CC2)nc2cc(Cl)ccc21]

HPLC-MS; Method: Z011_S03; R$_t$ [min]: 1.03     MS: 436 (M + H)$^+$
Chiral SFC Rt Method: I_IBN_15_IPA_NH3     Rt [min]: 3.21
$^1$H NMR (400 MHz, DMSO-d$_6$) δ ppm 0.38-0.63 (m, 4H) 1.78-1.87 (m, 1H) 3.08-3.20 (m, 3H) 3.62 (t, J = 5.13 Hz, 2H) 4.42-4.70 (m, 2H) 4.93-5.05 (m, 6H) 7.21 (m, 1H) 7.27 (dd, J = 8.62, 2.03 Hz, 1H) 7.62 (d, J = 8.62 Hz, 1H) 7.71 (d, J = 1.90 Hz, 1H) 9.04 (s, 1H) 9.26-9.32 (m, 2H)

Example 16: N-[(S)-cyclopropyl[5,6-difluoro-1-(2-methoxyethyl)-1H-1,3-benzodiazol-2-yl]methyl]-5-methylpyrazine-2-carboxamide

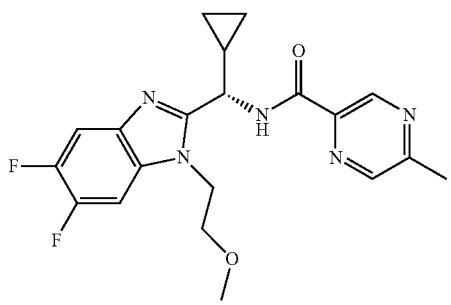 [SMILES: COCCn1c([C@@H](NC(=O)c2cnc(C)cn2)C2CC2)nc2cc(F)c(F)cc21]

HPLC-MS; Method: Z011_S03; R$_t$ [min]: 0.96     MS: 402 (M + H)$^+$
$^1$H NMR (400 MHz, DMSO-d$_6$) δ ppm 0.33-0.60 (m, 4H) 1.74-1.83 (m, 1H) 2.59 (s, 3H) 3.13 (s, 3H) 3.51-3.69 (m, 2H) 4.37-4.63 (m, 2H) 5.00 (t, J = 8.62 Hz, 1H) 7.68-7.61 (m, 2H) 8.62 (s, 1H) 9.00-9.09 (m, 2H)

Example 25: N-[(S)-(5-chloro-1-ethyl-1H-1,3-benzodiazol-2-yl) (cyclopropyl)methyl]-5-methylpyrazine-2-carboxamide

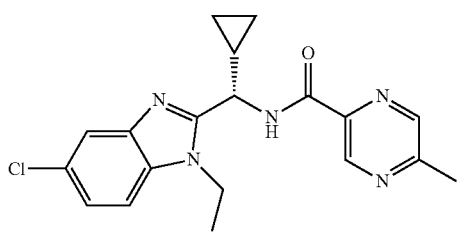 [SMILES: CCn1c([C@@H](NC(=O)c2cnc(C)cn2)C2CC2)nc2cc(Cl)ccc21]

MS: 370 (M + H)$^+$
Chiral SFC Rt Method: I_SB_15_MEOH_NH3_001     Rt [min]: 2.70
$^1$H NMR (400 MHz, DMSO-d$_6$) δ ppm 0.37-0.67 (m, 4H) 1.24-1.30 (m, 3H) 1.69-1.78 (m, 1H) 2.58-2.61 (m, 3H) 4.34 (m, 2H) 4.95 (m, 1H) 7.27 (dd, J = 8.55, 1.96 Hz, 1H) 7.61 (d, J = 8.62 Hz, 1H) 7.71 (d, J = 1.90 Hz, 1H) 8.64 (s, 1H) 9.05 (d, J = 1.14 Hz, 1H) 9.15 (d, J = 8.24 Hz, 1H)

Example 26: N-[(1R,2R)-1-(5-bromo-6-fluoro-1-methyl-1H-1,3-benzodiazol-2-yl)-2-methoxypropyl]-5-methylpyrazine-2-carboxamide

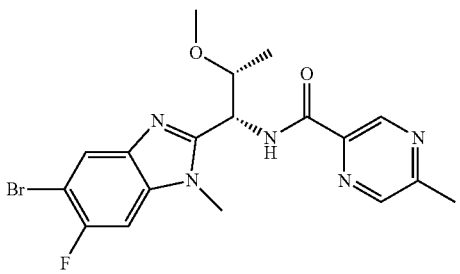 [SMILES: CO[C@H](C)[C@H](NC(=O)c1cnc(C)cn1)c1nc2cc(Br)c(F)cc2n1C]

HPLC-MS; Method: Z011_S03; R$_t$ [min]: 0.99      MS: 436 (M + H)⁺
Chiral SFC Rt Method: I_SB_15_IPA_NH3_001      Rt [min]: 3.68
¹H NMR (400 MHz, DMSO-d$_6$) δ ppm 1.06 (d, J = 6.21 Hz, 3H) 2.61 (s, 3H) 3.30 (s, 3H) 3.89 (s, 3H)
4.00-4.08 (m, 1H) 5.49 (m, 1H) 7.75 (d, J = 9.13 Hz, 1H) 7.98 (d, J = 6.34 Hz, 1H) 8.68 (d, J = 1.01
Hz, 1H) 8.90 (d, J = 7.98 Hz, 1H) 9.07 (d, J = 1.27 Hz, 1H)

Example 28: N-[(1R,2R)-1-[5,6-difluoro-1-(2-methoxyethyl)-1H-1,3-benzodiazol-2-yl]-2-
(difluoromethoxy)propyl]-5-methylpyrazine-2-carboxamide

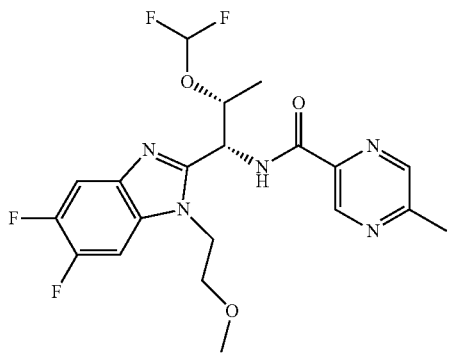 [SMILES: COCCn1c([C@@H](NC(=O)c2cnc(C)cn2)[C@@H](C)OC(F)F)nc2cc(F)c(F)cc21]

HPLC-MS; Method: Z011_S03; R$_t$ [min]: 1.01      MS: 456 (M + H)⁺
Chiral SFC Rt Method: I_SA_10_IPA_NH3_001      Rt [min]: 2.33
¹H NMR (400 MHz, DMSO-d$_6$) δ ppm 1.25 (d, J = 6.21 Hz, 3H) 2.57-2.61 (m, 3H) 3.16 (s, 3H)
3.58-3.67 (m, 2H) 4.47-4.75 (m, 2H) 5.04 (m, 1H) 5.68 (m, 1H) 6.55-7.00 (m, 2H) 7.74 (m, 1H) 7.81
(m, 1H) 8.64 (d, J = 1.01 Hz, 1H) 9.02 (d, J = 9.13 Hz, 1H) 9.07 (d, J = 1.39 Hz, 1H)

Example 29: N-[(1R,2R)-1-(5-chloro-1-methyl-1H-1,3-benzodiazol-2-yl)-2-methoxypropyl]-5-
methylpyrazine-2-carboxamide

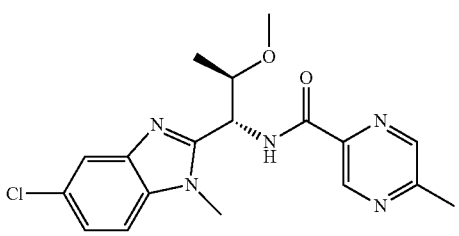 [SMILES: CO[C@H](C)[C@H](NC(=O)c1cnc(C)cn1)c1nc2cc(Cl)ccc2n1C]

HPLC-MS; Method: Z018_S04; R$_t$ [min]: 0.83      MS: 374 (M + H)⁺
Chiral SFC Rt Method: I_SA_15_MEOH_NH3_001      Rt [min]: 3.52
¹H NMR (400 MHz, DMSO-d$_6$) δ ppm 1.06 (d, J = 6.21 Hz, 3H) 2.61 (s, 3H) 3.31 (s, 3H) 3.87-3.95
(m, 3H) 4.01-4.10 (m, 1H) 5.50 (dd, J = 7.98, 5.32 Hz, 1H) 7.29 (dd, J = 8.68, 1.96 Hz, 1H) 7.62 (d,
J = 8.49 Hz, 1H) 7.71 (d, J = 1.65 Hz, 1H) 8.69 (d, J = 0.89 Hz, 1H) 8.92 (d, J = 7.98 Hz, 1H) 9.07
(d, J = 1.39 Hz, 1H)

Example 36: N-[(S)-cyclopropyl[1-ethyl-5-(trifluoromethyl)-1H-1,3-benzodiazol-2-yl]methyl]-5-
methylpyrazine-2-carboxamide

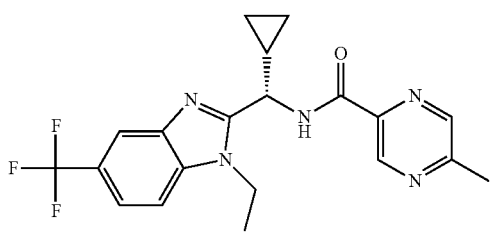 [SMILES: CCn1c([C@@H](NC(=O)c2cnc(C)cn2)C2CC2)nc2cc(C(F)(F)F)ccc21]

| | MS: 404 (M + H)+ |
|---|---|
| Chiral SFC Rt Method: I_IA_15_MEOH_NH3_001 | Rt [min]: 2.53 |

¹H NMR (400 MHz, DMSO-$d_6$) δ ppm 0.39-0.68 (m, 4H) 1.30 (t, J = 7.16 Hz, 3H) 1.72-1.81 (m, 1H) 2.58-2.62 (m, 3H) 4.31-4.50 (m, 2H) 4.99 (t, J = 8.49 Hz, 1H) 7.57 (dd, J = 8.55, 1.46 Hz, 1H) 7.80 (d, J = 8.49 Hz, 1H) 8.02 (s, 1H) 8.64 (d, J = 1.01 Hz, 1H) 9.05 (d, J = 1.39 Hz, 1H) 9.22 (d, J = 8.11 Hz, 1H)

Example 39: N-[(1R)-1-(1-ethyl-5-fluoro-1H-1,3-benzodiazol-2-yl)-2-hydroxy-2-methylpropyl]-5-methylpyrazine-2-carboxamide

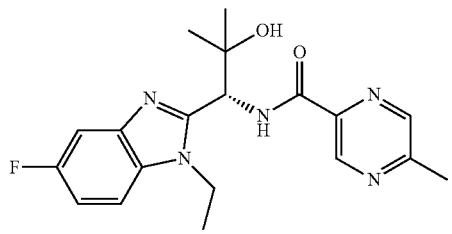

| HPLC-MS; Method: Z011_S03; $R_t$ [min]: 0.94 | MS: 372 (M + H)+ |
|---|---|
| Chiral SFC Rt Method: I_SA_15_IPA_NH3_001 | Rt [min]: 1.90 |

¹H NMR (400 MHz, DMSO-$d_6$) δ ppm 1.20-1.27 (m, 6H) 1.31-1.38 (m, 3H) 2.60 (s, 3H) 4.40-4.57 (m, 2H) 5.24 (s, 1H) 5.41 (m, 1H) 7.12 (m, 1H) 7.46 (dd, J = 9.76, 2.28 Hz, 1H) 7.63 (m, 1H) 8.66 (s, 1H) 8.69 (d, J = 9.38 Hz, 1H) 9.06 (s, 1H)

In analogy to example 4 the following compounds have been obtained as a mixture of four stereoisomers which are separated by chiral SFC: examples 40, 40-1, 40-2, 53

Example 40: 5-(difluoromethyl)-N-[(R)-[1-(2-methoxyethyl)-5-(trifluoromethoxy)-1H-1,3-benzodiazol-2-yl][(2S)-oxolan-2-yl]methyl]pyrazine-2-carboxamide

| HPLC-MS; Method: Z011_S03; $R_t$ [min]: 1.09 | MS: 516 (M + H)+ |
|---|---|
| Chiral SFC Rt Method: I_ADH_15_IPA_NH3_001 | Rt [min]: 1.68 |

¹H NMR (400 MHz, DMSO-$d_6$) δ ppm 1.80-2.19 (m, 4H) 3.17 (s, 3H) 3.60-3.87 (m, 4H) 4.48-4.66 (m, 3H) 5.45 (m, 1H) 7.21 (m, 1H) 7.22-7.26 (m, 1H) 7.62 (s, 1H) 7.70 (d, J = 8.87 Hz, 1H) 9.07 (s, 1H) 9.26 (d, J = 8.87 Hz, 1H) 9.29 (s, 1H)

Example 40-1: 5-(difluoromethyl)-N-{[1-(2-methoxyethyl)-5-(trifluoromethoxy)-1H-1,3-benzodiazol-2-yl](oxolan-2-yl)methyl}pyrazine-2-carboxamide HPLC-MS; Method: Z011_S03; R_t [min]: 1.09    MS: 516 (M + H)+
Chiral SFC Rt Method: I_ADH_15_IPA_NH3_001    Rt [min]: 1.39
$^1$H NMR (400 MHz, DMSO-d$_6$) δ ppm 1.80-2.19 (m, 4H) 3.17 (s, 3H) 3.60-3.87 (m, 4H) 4.48-4.66 (m, 3H) 5.45 (m, 1H) 7.21 (m, 1H) 7.22-7.26 (m, 1H) 7.62 (s, 1H) 7.70 (d, J = 8.87 Hz, 1H) 9.07 (s, 1H) 9.26 (d, J = 8.87 Hz, 1H) 9.29 (s, 1H)

Example 40-2: 5-(difluoromethyl)-N-{ [1-(2-methoxyethyl)-5-(trifluoromethoxy)-1H-1,3-benzodiazol-2-yl](oxolan-2-yl)methyl}pyrazine-2-carboxamide

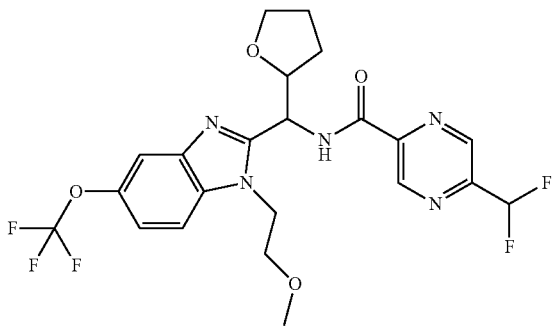 [SMILES: COCCn1c(C(NC(=O)c2cnc(C(F)F)cn2)C2CCCO2)nc2cc(OC(F)(F)F)ccc21]

HPLC-MS; Method: Z011_S03; R_t [min]: 1.09    MS: 516 (M + H)+
Chiral SFC Rt Method: I_C2_10_MEOH_NH3_002    Rt [min]: 0.82

Example 53: 5-(difluoromethyl)-N-[(R)-[1-(2-methoxyethyl)-5-(trifluoromethoxy)-1H-1,3-benzodiazol-2-yl][(2R)-oxolaN-2-yl]methyl]pyrazine-2-carboxamide

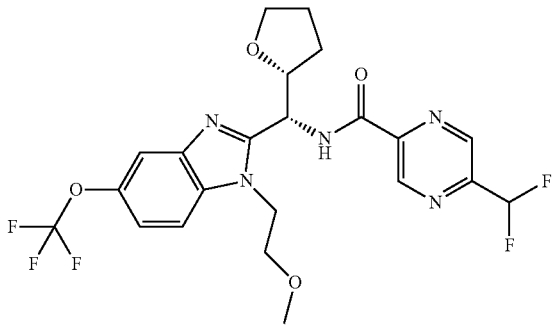 [SMILES: COCCn1c([C@@H](NC(=O)c2cnc(C(F)F)cn2)[C@H]2CCCO2)nc2cc(OC(F)(F)F)ccc21]

HPLC-MS; Method: Z011_S03; R_t [min]: 1.09    MS: 305 (M + H)+; 249 (M + H − Isobutene)+
Chiral SFC Rt Method: I_C2_10_MEOH_NH3_002    Rt [min]: 0.59
$^1$H NMR (400 MHz, DMSO-d$_6$) δ ppm 1.61-2.00 (m, 4H) 3.16-3.18 (m, 3H) 3.62-3.78 (m, 4H) 4.54-4.77 (m, 3H) 5.60 (dd, J = 8.43, 7.16 Hz, 1H) 7.21 (m, 1H) 7.26 (d, J = 8.70 Hz, 1H) 7.65-7.68 (m, 1H) 7.72 (d, J = 8.87 Hz, 1H) 9.04-9.10 (m, 2H) 9.30 (d, J = 1.14 Hz, 1H)

In analogy to example 4 the following compounds are obtained.

Example 42: N-[(S)-(5-bromo-4-chloro-1-methyl-1H-1,3-benzodiazol-2-yl) (cyclopropyl)methyl]-5-methylpyrazine-2-carboxamide

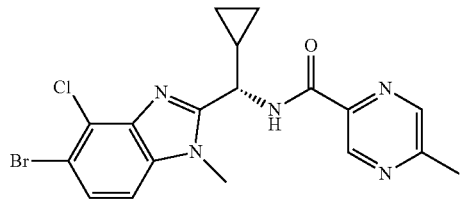 [SMILES: Cc1cnc(C(=O)N[C@H](c2nc3c(Cl)c(Br)ccc3n2C)C2CC2)cn1]

HPLC-MS; Method: Z018_S04; R$_t$ [min]: 1.03      MS: 434 (M + H)$^+$
Chiral SFC Rt Method: I_SB_25_IPA_NH3_001      Rt [min]: 3.68
$^1$H NMR (400 MHz, DMSO-d$_6$) δ ppm 0.40-0.63 (m, 4H) 1.72-1.85 (m, 1H) 2.58-2.61 (m, 3H) 3.86 (s, 3H) 4.87-4.93 (m, 1H) 7.53-7.60 (m, 2H) 8.65 (d, J = 1.01 Hz, 1H) 9.03 (d, J = 1.39 Hz, 1H) 9.26 (d, J = 7.86 Hz, 1H)

Example 43: N-[(1R,2R)-2-methoxy-1-[1-methyl-5-(trifluoromethoxy)-1H-1,3-benzodiazol-2-yl]propyl]-5-methylpyrazine-2-carboxamide

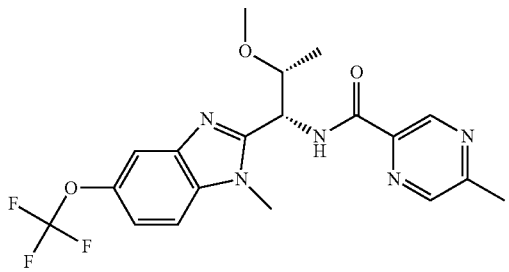 [SMILES: CO[C@H](C)[C@H](NC(=O)c1cnc(C)cn1)c1nc2cc(OC(F)(F)F)ccc2n1C]

HPLC-MS; Method: Z011_S03; R$_t$ [min]: 1.03      MS: 424 (M + H)$^+$
Chiral SFC Rt Method: I_IG_20_IPA_NH3_001      Rt [min]: 3.79
$^1$H NMR (400 MHz, DMSO-d$_6$) δ ppm 1.08 (d, J = 6.21 Hz, 3H) 2.56-2.66 (m, 3H) 3.32 (s, 3H) 3.91-3.98 (s, 3H) 4.02-4.11 (m, 1H) 5.51 (dd, J = 7.98, 5.32 Hz, 1H) 7.28 (d, J = 8.78 Hz, 1H) 7.66 (d, J = 1.01 Hz, 1H) 7.70 (d, J = 8.74 Hz, 1H) 8.69 (d, J = 1.01 Hz, 1H) 8.93 (d, J = 7.86 Hz, 1H) 9.07 (d, J = 1.39 Hz, 1H)

Example 46: N-[(S)-cyclopropyl[1-ethyl-5-(trifluoromethoxy)-1H-1,3-benzodiazol-2-yl]methyl]-5-methylpyrazine-2-carboxamide

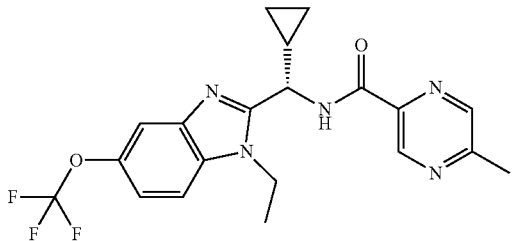 [SMILES: CCn1c([C@@H](NC(=O)c2cnc(C)cn2)C2CC2)nc2cc(OC(F)(F)F)ccc21]

HPLC-MS; Method: Z011_S03; R$_t$ [min]: 1.06      MS: 420 (M + H)$^+$
Chiral SFC Rt Method: I_SA_10_IPA_NH3_001      Rt [min]: 2.67
$^1$H NMR (400 MHz, DMSO-d$_6$) δ ppm 0.39-0.62 (m, 4H) 1.30 (t, J = 7.10 Hz, 3H) 1.70-1.79 (m, 1H) 2.58-2.61 (m, 3H) 3.57 (s, 3H) 4.37 (m, 2H) 4.96 (t, J = 8.55 Hz, 1H) 7.25 (dd, J = 8.81, 1.33 Hz, 1H) 7.66 (d, J = 1.14 Hz, 1H) 7.69 (d, J = 8.87 Hz, 1H) 8.64 (d, J = 1.01 Hz, 1H) 9.05 (d, J = 1.39 Hz, 1H) 9.17 (d, J = 8.24 Hz, 1H)

Example 47: N-[(S)-(5-chloro-1-methyl-1H-1,3-benzodiazol-2-yl) (cyclopropyl)methyl]-5-methylpyrazine-2-carboxamide

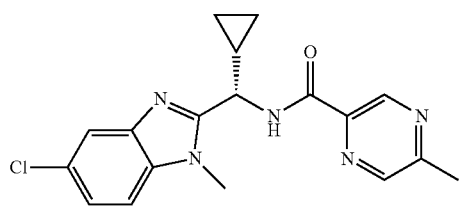 [SMILES: Cc1cnc(C(=O)N[C@H](c2nc3cc(Cl)ccc3n2C)C2CC2)cn1]

HPLC-MS; Method: Z018_S04; R$_t$ [min]: 0.78      MS: 356 (M + H)$^+$
Chiral SFC Rt Method: I_SC_20_MEOH_NH3_001      Rt [min]: 3.76
$^1$H NMR (400 MHz, DMSO-d$_6$) δ ppm 0.38-0.60 (m, 4H) 1.66-1.75 (m, 1H) 2.60 (s, 3H) 3.83 (s, 3H) 4.98 (t, J = 8.36 Hz, 1H) 7.28 (dd, J = 8.62, 2.03 Hz, 1H) 7.59 (d, J = 8.49 Hz, 1H) 7.71 (d, J = 1.77 Hz, 1H) 8.65 (d, J = 0.89 Hz, 1H) 9.05 (d, J = 1.27 Hz, 1H) 9.14 (d, J = 7.98 Hz, 1H)

Example 50: N-[(1R)-1-(1-ethyl-5,6-difluoro-1H-1,3-benzodiazol-2-yl)-2-hydroxy-2-methylpropyl]-5-

-continued methylpyrazine-2-carboxamide

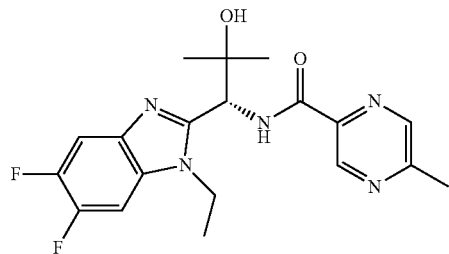 [SMILES: CCn1c([C@@H](NC(=O)c2cnc(C)cn2)C(C)(C)O)nc2cc(F)c(F)cc21]

HPLC-MS; Method: Z018_S04; $R_t$ [min]: 0.86  MS: 390 (M + H)⁺
Chiral SFC Rt Method: I_IG_20_IPA_NH3_001  Rt [min]: 2.22
¹H NMR (400 MHz, DMSO-d₆) δ ppm 1.19-1.27 (m, 6H) 1.30-1.36 (m, 3H) 2.58-2.62 (m, 3H) 4.35-4.59 (m, 2H) 5.20 (s, 1H) 5.36-5.41 (m, 1H) 7.72 (dd, J = 11.15, 7.48 Hz, 1H) 7.82 (dd, J = 10.77, 7.35 Hz, 1H) 8.64-8.70 (m, 2H) 9.06 (d, J = 1.39 Hz, 1H)

Example 51: N-[(S)-cyclopropyl (5-fluoro-1-methyl-1H-1,3-benzodiazol-2-yl)methyl]-5-methylpyrazine-2-carboxamide

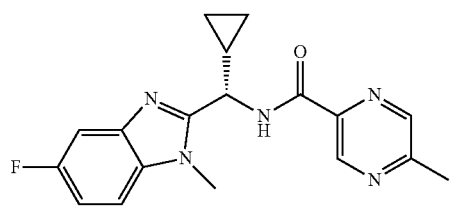 [SMILES: Cc1cnc(C(=O)N[C@H](c2nc3cc(F)ccc3n2C)C2CC2)cn1]

MS: 340 (M + H)⁺
Chiral SFC Rt Method: I_SC_20_MEOH_NH3_001  Rt [min]: 2.72
¹H NMR (400 MHz, DMSO-d₆) δ ppm 0.36-0.60 (m, 4H) 1.65-1.75 (m, 1H) 2.60 (s, 3H) 3.83 (s, 3H) 4.98 (t, J = 8.30 Hz, 1H) 7.12 (m, 1H) 7.45 (dd, J = 9.82, 2.47 Hz, 1H) 7.56 (dd, J = 8.81, 4.75 Hz, 1H) 8.65 (s, 1H) 9.05 (d, J = 1.27 Hz, 1H) 9.12 (d, J = 8.11 Hz, 1H)

Example 55: N-[(S)-(5-chloro-1-methyl-1H-1,3-benzodiazol-2-yl) (cyclopropyl)methyl]-5-(difluoromethyl)pyrazine-2-carboxamide

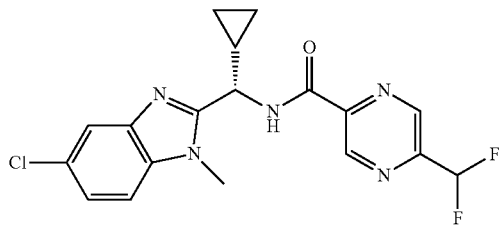 [SMILES: Cn1c([C@@H](NC(=O)c2cnc(C(F)F)cn2)C2CC2)nc2cc(Cl)ccc21]

HPLC-MS; Method: Z018_S04; $R_t$ [min]: 0.85  MS: 392 (M + H)⁺
Chiral SFC Rt Method: I_SC_15_IPA_NH3_001  Rt [min]: 2.85
¹H NMR (400 MHz, DMSO-d₆) δ ppm 0.38-0.60 (m, 4H) 1.69-1.78 (m, 1H) 3.83 (s, 3H) 4.98 (t, J = 8.43 Hz, 1H) 7.21 (m, 1H) 7.28 (dd, J = 8.62, 2.03 Hz, 1H) 7.59 (d, J = 8.74 Hz, 1H) 7.71 (d, J = 1.90 Hz, 1H) 9.06 (s, 1H) 9.28 (s, 1H) 9.39 (d, J = 7.98 Hz, 1H)

In analogy to example 4 the following compounds have been obtained. The product is a mixture of four stereoisomers which are separated by chiral SFC: examples 58, 58-1, 58-2, 89

Example 58: N-[(R)-[1-(2-methoxyethyl)-5-(trifluoromethoxy)-1H-1,3-benzodiazol-2-yl][(2S)-oxolan-2-yl]methyl]-5-methylpyrazine-2-carboxamide -continued

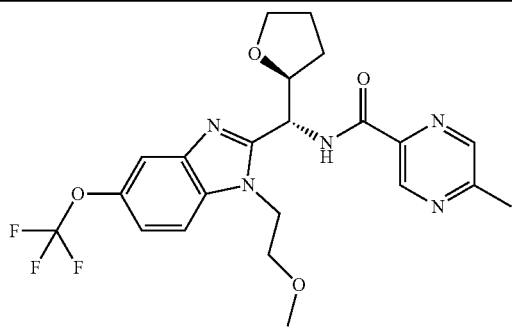

HPLC-MS; Method: Z011_S03; R$_t$ [min]: 1.04     MS: 480 (M + H)$^+$
Chiral SFC Rt Method: I_C2_15_IPA_NH3_002     Rt [min]: 1.48
$^1$H NMR (400 MHz, DMSO-d$_6$) δ ppm 1.60-1.84 (m, 3 H) 1.89-1.99 (m, 1 H) 2.59 (s,
3 H) 3.17 (s, 3 H) 3.57 (s, 3 H) 3.62-3.80 (m, 4 H) 4.54-4.74 (m, 3 H) 5.59 (dd,
J = 8.36, 6.97 Hz, 1 H) 7.26 (d, J = 8.93 Hz, 1 H) 7.66 (s, 1 H) 7.71 (d, J = 8.87 Hz, 1 H)
8.64 (s, 1 H) 8.87 (d, J = 8.49 Hz, 1 H) 9.07 (d, J = 1.14 Hz, 1 H)
Example 58-1: N-{[1-(2-methoxyethyl)-5-(trifluoromethoxy)-1H-1,3-
benzodiazol-2-yl](oxolan-2-yl)methyl}-5-
methylpyrazine-2-carboxamide

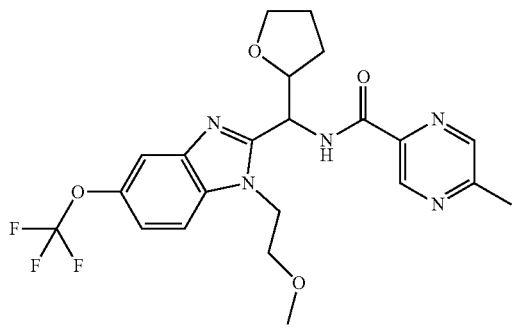 [SMILES: COCCn1c(C(NC(=O)c2cnc(C)cn2)C2CCCO2)nc2cc(OC(F)(F)F)ccc21]

HPLC-MS; Method: Z011_S03; R$_t$ [min]: 1.04     MS: 480 (M + H)$^+$
Chiral SFC Rt Method: I_C2_15_IPA_NH3_002     Rt [min]: 1.06
$^1$H NMR (400 MHz, DMSO-d$_6$) δ ppm 1.80-2.02 (m, 3 H) 2.02-2.14 (m, 1 H) 2.59 (s,
3 H) 3.16 (s, 3 H) 3.59-3.78 (m, 3 H) 3.78-3.86 (m, 1 H) 4.44-4.65 (m, 3 H) 5.44 (t,
J = 8.74 Hz, 1 H) 7.24 (d, J = 8.93 Hz, 1 H) 7.62 (s, 1 H) 7.69 (d, J = 8.87 Hz, 1 H) 8.65
(s, 1 H) 9.03 (d, J = 8.87 Hz, 1 H) 9.05 (d, J = 1.27 Hz, 1 H)
Example 58-2: N-{[1-(2-methoxyethyl)-5-(trifluoromethoxy)-1H-1,3-
benzodiazol-2-yl](oxolan-2-yl)methyl}-5-
methylpyrazine-2-carboxamide

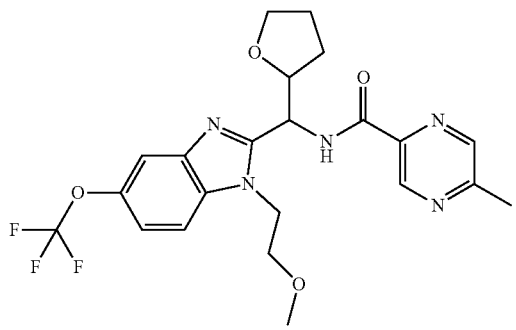

HPLC-MS; Method: Z011_S03; R$_t$ [min]: 1.04     MS: 480 (M + H)$^+$
Chiral SFC Rt Method: I_C2_15_IPA_NH3_002     Rt [min]: 1.76
$^1$H NMR (400 MHz, DMSO-d$_6$) δ ppm 1.60-1.99 (m, 4 H) 2.59 (s, 3 H) 3.17 (s, 3 H)
3.62-3.75 (m, 4 H) 4.53-4.79 (m, 3 H) 5.59 (dd, J = 8.49, 6.84 Hz, 1 H) 7.26 (dd,
J = 8.81, 1.33 Hz, 1 H) 7.66 (s, 1 H) 7.71 (d, J = 8.87 Hz, 1 H) 8.64 (d, J = 1.01 Hz, 1 H)
8.87 (d, J = 8.49 Hz, 1 H) 9.07 (d, J = 1.39 Hz, 1 H)

In analogy to example 4 the following compounds are obtained:

Example 65: 5-(difluoromethyl)-N-[(1R)-1-(1-ethyl-5-fluoro-1H-1,3-benzodiazol-2-yl)-2-hydroxy-2-methylpropyl]pyrazine-2-carboxamide

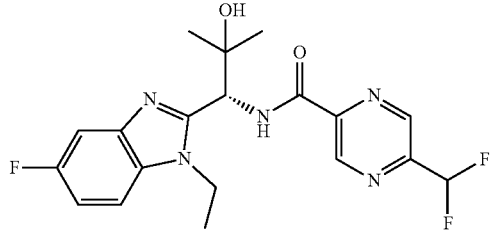 [SMILES: CCn1c([C@@H](NC(=O)c2cnc(C(F)F)cn2)C(C)(C)O)nc2cc(F)ccc21]

HPLC-MS; Method: Z018_S04; R$_t$ [min]: 0.82    MS: 408 (M + H)$^+$
Chiral SFC Rt Method: I_SA_15_IPA_NH3_001    Rt [min]: 1.32
$^1$H NMR (400 MHz, DMSO-d$_6$) δ ppm 1.22-1.30 (m, 6 H) 1.32-1.40 (m, 3 H) 4.40-4.59 (m, 2 H) 5.26 (s, 1 H) 5.44 (d, J = 9.25 Hz, 1 H) 7.09-7.16 (m, 1 H) 7.21 (m, 1 H) 7.47 (dd, J = 9.76, 2.41 Hz, 1 H) 7.64 (dd, J = 1 H) 8.80 (d, J = 9.38 Hz, 1 H) 9.10 (s, 1 H) 9.30 8.87, 4.82 Hz, (d, J = 1.27 Hz, 1 H)

Example 68: N-[(R)-(5-chloro-1-methyl-1H-1,3-benzodiazol-2-yl)[(2S)-oxolan-2-yl]methyl]-5-methylpyrazine-2-carboxamide

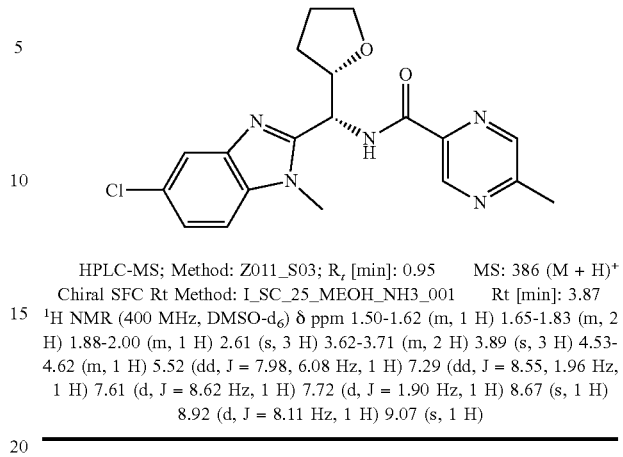

HPLC-MS; Method: Z011_S03; R$_t$ [min]: 0.95    MS: 386 (M + H)$^+$
Chiral SFC Rt Method: I_SC_25_MEOH_NH3_001    Rt [min]: 3.87
$^1$H NMR (400 MHz, DMSO-d$_6$) δ ppm 1.50-1.62 (m, 1 H) 1.65-1.83 (m, 2 H) 1.88-2.00 (m, 1 H) 2.61 (s, 3 H) 3.62-3.71 (m, 2 H) 3.89 (s, 3 H) 4.53-4.62 (m, 1 H) 5.52 (dd, J = 7.98, 6.08 Hz, 1 H) 7.29 (dd, J = 8.55, 1.96 Hz, 1 H) 7.61 (d, J = 8.62 Hz, 1 H) 7.72 (d, J = 1.90 Hz, 1 H) 8.67 (s, 1 H) 8.92 (d, J = 8.11 Hz, 1 H) 9.07 (s, 1 H)

In analogy to example 4 the following compounds are obtained. The product is as a mixture of four stereoisomers which are separated by chiral SFC: example 71, 71-1, 71-2, 71-3

Example 71: N-[(R)-[1-(2-methoxyethyl)-5-(trifluoromethyl)-1H-1,3-benzodiazol-2-yl](oxolan-2-yl)methyl]-5-methylpyrazine-2-carboxamide

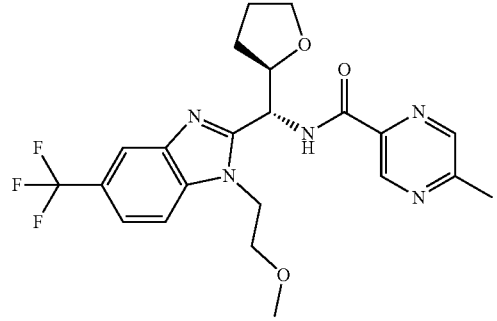 [SMILES: COCCn1c([C@@H](NC(=O)c2cnc(C)cn2)[C@H]2CCCO2)nc2cc(C(F)(F)F)ccc21]

HPLC-MS; Method: Z018_S04; R$_t$ [min]: 1.00    MS: 464 (M + H)$^+$
Chiral SFC Rt Method: I_C2_15_IPA_NH3_001    Rt [min]: 2.83
$^1$H NMR (400 MHz, DMSO-d$_6$) δ ppm 1.79-2.00 (m, 3 H) 2.04-2.15 (m, 1 H) 2.59 (s, 3 H) 3.16 (s, 3 H) 3.61-3.76 (m, 3 H) 3.81-3.87 (m, 1 H) 4.47-4.69 (m, 3 H) 5.46 (t, J = 8.74 Hz, 1 H) 7.56 (d, J = 7.48 Hz, 1 H) 7.81 (d, J = 8.62 Hz, 1 H) 7.98 (s, 1 H) 8.65 (s, 1 H) 9.05 (d, J = 1.14 Hz, 1 H) 9.08 (d, J = 8.74 Hz, 1 H)

Example 71-1: N-{[1-(2-methoxyethyl)-5-(trifluoromethyl)-1H-1,3-benzodiazol-2-yl](oxolan-2-yl)methyl}-5-methylpyrazine-2-carboxamide

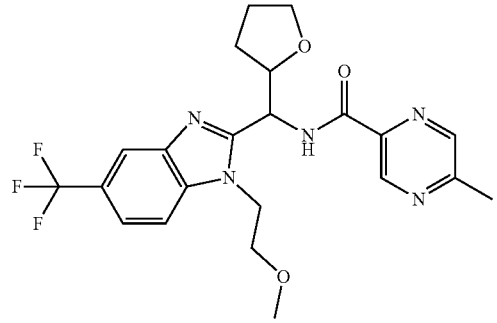 [SMILES: COCCn1c(C(NC(=O)c2cnc(C)cn2)C2CCCO2)nc2cc(C(F)(F)F)ccc21]

HPLC-MS; Method: Z018_S04; R$_t$ [min]: 1.00    MS: 464 (M + H)$^+$
Chiral SFC Rt Method: I_C2_15_IPA_NH3_001    Rt [min]: 3.54

Example 71-2: N-{[1-(2-methoxyethyl)-5-(trifluoromethyl)-1H-1,3-benzodiazol-2-yl](oxolan-2-yl)methyl}-5-methylpyrazine-2-carboxamide

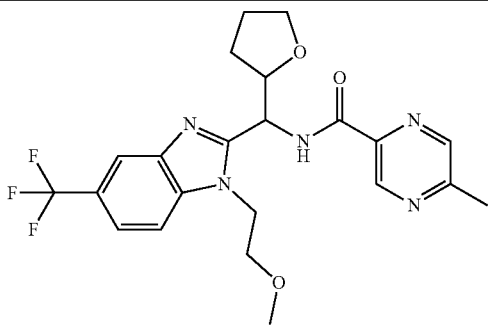

HPLC-MS; Method: Z018_S04; R, [min]: 1.00     MS: 464 (M + H)+
Chiral SFC Rt Method: I_C2_15_IPA_NH3_001     Rt [min]: 4.89
Example 71-3: N-{[1-(2-methoxyethyl)-5-(trifluoromethyl)-1H-1,3-benzodiazol-2-yl](oxolan-2-yl)methyl}-5-methylpyrazine-2-carboxamide

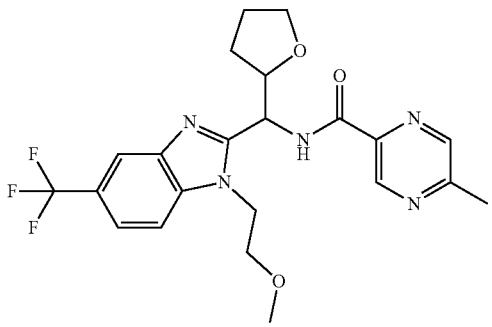 [SMILES: COCCn1c(C(NC(=O)c2cnc(C)cn2)C2CCCO2)nc2cc(C(F)(F)F)ccc21]

HPLC-MS; Method: Z018_S04; R, [min]: 1.00     MS: 464 (M + H)+
Chiral SFC Rt Method: I_C2_15_IPA_NH3_001     Rt [min]: 5.78
Example 74: N-[(S)-cyclopropyl[1-methyl-5-(trifluoromethoxy)-1H-1,3-benzodiazol-2-yl]methyl]-5-methylpyrazine-2-carboxamide

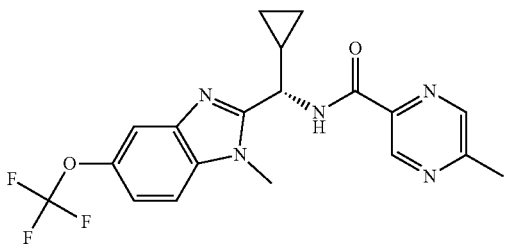 [SMILES: Cc1cnc(C(=O)N[C@H](c2nc3cc(OC(F)(F)F)ccc3n2C)C2CC2)cn1]

HPLC-MS; Method: Z018_S04; R, [min]: 0.88     MS: 406 (M + H)+
Chiral SFC Rt Method: I_SA_10_MEOH_NH3_001     Rt [min]: 2.73
$^{1}$H NMR (400 MHz, DMSO-$d_6$) δ ppm 0.39-0.65 (m, 4 H) 1.65-1.77 (m, 1 H) 2.60 (s, 3 H) 3.57 (s, 3 H) 3.86 (s, 6 H) 4.98 (t, J = 8.36 Hz, 1 H) 7.26 (dd, J = 8.68, 1.33 Hz, 1 H) 7.65 (s, 1 H) 7.66 (d, J = 9.13 Hz, 2 H) 8.65 (s, 1 H) 9.05 (d, J = 1.27 Hz, 1 H) 9.16 (d, J = 7.98 Hz, 1 H)

Out of the four stereoisomers, two stereoisomers are isolated after separation by chiral SFC: example 76, 76-1

Example 76: N-[(S)-(5-chloro-1-methyl-1H-1,3-benzodiazol-2-yl)[(1S)-2,2-difluorocyclopropyl]methyl]-5-methylpyrazine-2-carboxamide

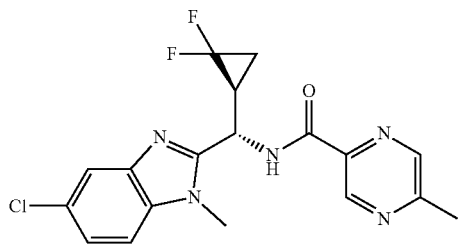 [SMILES: Cc1cnc(C(=O)N[C@H](c2nc3cc(Cl)ccc3n2C)[C@@H]2CC2(F)F)cn1]

HPLC-MS; Method: Z018_S04; R$_t$ [min]: 0.93    MS: 392 (M + H)$^+$
Chiral SFC Rt Method: I_AC_15_IPA_NH3_002    Rt [min]: 1.27
$^1$H NMR (400 MHz, DMSO-d$_6$) δ ppm 1.50-1.62 (m, 1 H) 1.70 1.83 (m, 1 H) 2.56-2.63 (m, 3 H) 2.80-2.96 (m, 1 H) 3.75 (s, 3 H) 5.26 (t, J = 9.19 Hz, 1 H) 7.30 (dd, J = 8.62, 2.03 Hz, 1 H) 7.59 (d, J = 8.62 Hz, 1 H) 7.76 (d, J = 1.77 Hz, 1 H) 8.63 (s, 1 H) 9.07 (s, 1 H) 9.73 (d, J = 8.49 Hz, 1 H)

Example 76-1: N-[(5-chloro-1-methyl-1H-1,3-benzodiazol-2-yl)(2,2-difluorocyclopropyl)methyl]-5-methylpyrazine-2-carboxamide

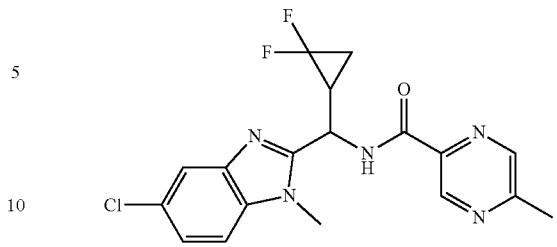

HPLC-MS; Method: Z018_S04; R$_t$ [min]: 0.93    MS: 392 (M + H)$^+$
Chiral SFC Rt Method: I_AC_15_IPA_NH3_002    Rt [min]: 0.78

In analogy to example 4 the following compounds are obtained. The product is a mixture of four stereoisomers which are separated by chiral SFC: examples 78, 78-1, 78-2, 78-3

Example 78: 5-methyl-N-[(S)-[1-methyl-5-(trifluoromethoxy)-1H-1,3-benzodiazol-2-yl][(3S)-oxan-3-yl]methyl}pyrazine-2-carboxamide

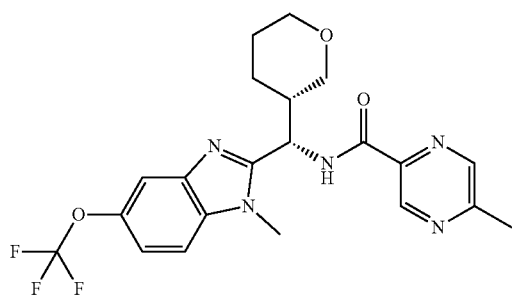 [SMILES: Cc1cnc(C(=O)NC(c2nc3cc(OC(F)(F)F)ccc3n2C)C2CCCOC2)cn1]

HPLC-MS; Method: Z018_S04; R$_t$ [min]: 0.96    MS: 450 (M + H)$^+$
Chiral SFC Rt Method: I_SA_10_MEOH_NH3_001    Rt [min]: 3.27
$^1$H NMR (400 MHz, DMSO-d$_6$) δ ppm 1.38-1.56 (m, 2 H) 1.62-1.75 (m, 1 H) 1.71-1.93 (m, 1 H) 2.52-2.58 (m, 1 H) 2.59 (s, 3 H) 3.15-3.24 (m, 1 H) 3.35-3.45 (m, 1 H) 3.62-3.73 (m, 2 H) 3.88 (s, 3 H) 5.46 (t, J = 8.93 Hz, 1 H) 7.26 (dd, J = 8.68, 1.33 Hz, 1 H) 7.65 (s, 1 H) 7.66 (d, J = 8.99 Hz, 2 H) 8.63 (s, 1 H) 9.05 (d, J = 1.27 Hz, 1 H) 9.08 (d, J = 8.87 Hz, 1 H)

Example 78-1: 5-methyl-N-{[1-methyl-5-(trifluoromethoxy)-1H-1,3-benzodiazol-2-yl](oxan-3-yl)methyl}pyrazine-2-carboxamide

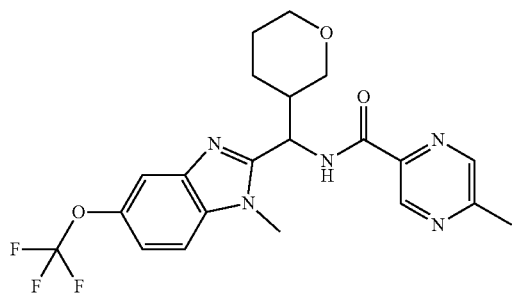 [SMILES: Cc1cnc(C(=O)NC(c2nc3cc(OC(F)(F)F)ccc3n2C)C2CCCOC2)cn1]

HPLC-MS; Method: Z018_S04; R$_t$ [min]: 0.96    MS: 450 (M + H)$^+$
Chiral SFC Rt Method: I_SA_15_MEOH_NH3_001    Rt [min]: 2.02

Example 78-2: 5-methyl-N-{[1-methyl-5-(trifluoromethoxy)-1H-1,3-benzodiazol-2-yl](oxan-3-yl)methyl}pyrazine-2-carboxamide

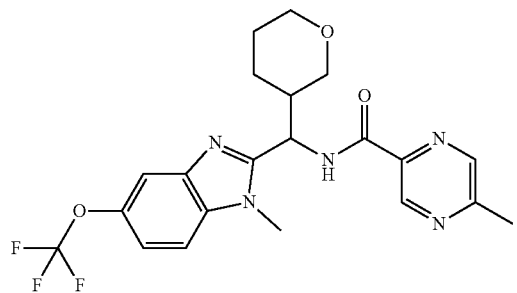 [SMILES: Cc1cnc(C(=O)NC(c2nc3cc(OC(F)(F)F)ccc3n2C)C2CCCOC2)cn1]

HPLC-MS; Method: Z018_S04; R$_t$ [min]: 0.96 MS: 450 (M + H)$^+$
Chiral SFC Rt Method: I_SA_15_MEOH_NH3_001 Rt [min]: 3.49
$^1$H NMR (400 MHz, DMSO-d$_6$) δ ppm 0.84-1.59 (m, 5 H) 2.58 (s, 3 H) 3.33-3.43 (m, 2 H) 3.73 (br d, J = 11.28 Hz, 1 H) 3.92 (s, 3 H) 3.95-4.10 (m, 1 H) 5.34 (t, J = 9.00 Hz, 1 H) 7.26 (d, J = 8.82 Hz, 1 H) 7.62-7.69 (m, 2 H) 8.63 (s, 1 H) 9.01 (d, J = 1.27 Hz, 1 H) 9.14 (d, J = 8.49 Hz, 1 H)

Example 78-3: 5-methyl-N-{[1-methyl-5-(trifluoromethoxy)-1H-1,3-benzodiazol-2-yl](oxan-3-yl)methyl}pyrazine-2-carboxamide

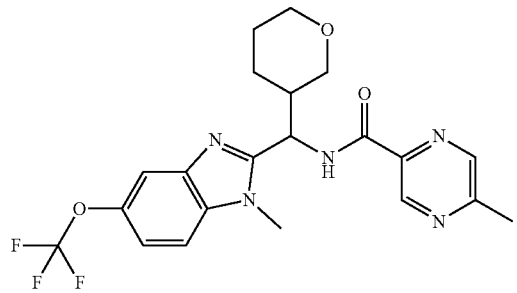

HPLC-MS; Method: Z018_S04; R$_t$ [min]: 0.96 MS: 450 (M + H)$^+$
Chiral SFC Rt Method: I_SA_10_MEOH_NH3_001 Rt [min]: 1.94

In analogy to example 4 the following compounds are obtained.

Example 81: N-[(1R)-1-(5-chloro-1-ethyl-1H-1,3-benzodiazol-2-yl)-2-hydroxy-2-methylpropyl]-5-methylpyrazine-2-carboxamide

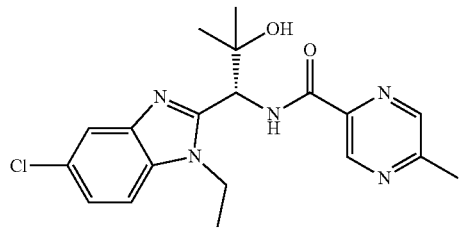 [SMILES: CCn1c([C@@H](NC(=O)c2cnc(C)cn2)C(C)(C)O)nc2cc(Cl)ccc21]

HPLC-MS; Method: Z018_S04; $R_t$ [min]: 0.83  MS: 388 (M + H)⁺
Chiral SFC Rt Method: I_SA_15_IPA_NH3_001  Rt [min]: 2.72
¹H NMR (400 MHz, DMSO-d₆) δ ppm 1.20-1.27 (m, 6 H) 1.31-1.38 (m, 3 H) 2.60 (s, 3 H) 4.40-4.60 (m, 2 H) 5.23 (s, 1 H) 5.42 (d, J = 9.38 Hz, 1 H) 7.28 (dd, J = 8.62, 2.03 Hz, 1 H) 7.65 (d, J = 8.62 Hz, 1 H) 7.73 (d, J = 1.90 Hz, 1 H) 8.67 (d, J = 1.01 Hz, 1 H) 8.71 (d, J = 9.25 Hz, 1 H) 9.07 (d, J = 1.27 Hz, 1 H)

Example 83: N-[(1R)-1-[1-(2,2-difluoroethyl)-5-fluoro-1H-1,3-benzodiazol-2-yl]-2-hydroxy-2-methylpropyl]-5-(difluoromethyl)pyrazine-2-carboxamide

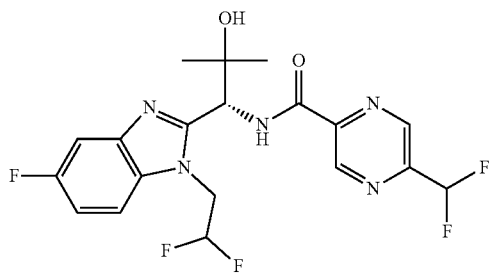 [SMILES: CC(C)(O)[C@H](NC(=O)c1cnc(C(F)F)cn1)c1nc2cc(F)ccc2n1CC(F)F]

HPLC-MS; Method: Z018_S04; $R_t$ [min]: 1.00  MS: 444 (M + H)⁺
Chiral SFC Rt Method: I_SA_10_IPA_NH3_001  Rt [min]: 1.62
¹H NMR (400 MHz, DMSO-d₆) δ ppm 1.22 (s, 3 H) 1.28 (s, 3 H) 4.93-5.26 (m, 2 H) 5.32 (s, 1 H) 5.49 (d, J = 9.25 Hz, 1 H) 6.50 (m, 1 H) 7.15-7.20 (m, 1 H) 7.22 (m, 1 H) 7.52 (dd, J = 9.57, 2.47 Hz, 1 H) 7.67 (dd, J = 8.87, 4.69 Hz, 1 H) 8.84 (d, J = 9.12 Hz, 1 H) 9.11 (s, 1 H) 9.31 (d, J = 1.27 Hz, 1 H)

Example 86: N-[(1S)-1-(5-chloro-1-methyl-1H-1,3-benzodiazol-2-yl)-2-cyclopropylethyl]-5-methylpyrazine-2-carboxamide

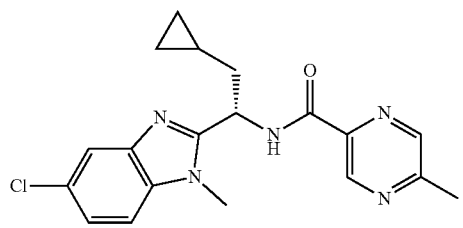 [SMILES: Cc1cnc(C(=O)N[C@@H](CC2CC2)c2nc3cc(Cl)ccc3n2C)cn1]

HPLC-MS; Method: Z011_S03; $R_t$ [min]: 1.01  MS: 370 (M + H)⁺
Chiral SFC Rt Method: I_SC_25_MEOH_NH3_001  Rt [min]: 3.23
¹H NMR (400 MHz, DMSO-d₆) δ ppm –0.07--0.01 (m, 1 H) 0.05-0.15 (m, 1 H) 0.28-0.38 (m, 2 H) 0.67-0.77 (m, 1 H) 2.00 (t, J = 6.95 Hz, 2 H) 2.60 (s, 3 H) 3.86 (s, 3 H) 5.49-5.56 (m, 1 H) 7.27 (dd, J = 8.59, 1.77 Hz, 1 H) 7.59 (d, J = 8.59 Hz, 1 H) 7.69 (d, J = 2.02 Hz, 1 H) 8.65 (s, 1 H) 9.05 (d, J = 1.26 Hz, 1 H) 9.11 (d, J = 8.08 Hz, 1 H)

Example 88: N-[(1R,2R)-1-(5-bromo-1,4-dimethyl-1H-1,3-benzodiazol-2-yl)-2-methoxypropyl]-5-methylpyrazine-2-carboxamide

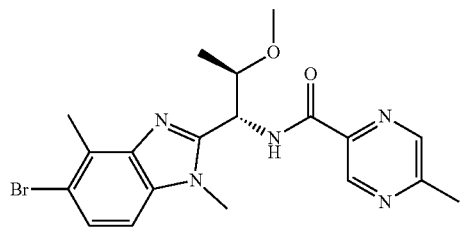

HPLC-MS; Method: Z018_S04; $R_t$ [min]: 0.90  MS: 432 (M + H)⁺
¹H NMR (400 MHz, DMSO-d₆) δ ppm 1.03-1.10 (m, 3 H) 2.57 (s, 3 H) 2.60 (s, 3 H) 3.33 (s, 3 H) 3.89 (s, 3 H) 4.09 (quin, J = 6.11 Hz, 1 H) 5.46 (dd, J = 7.92, 5.77 Hz, 1 H)

7.37-7.44 (m, 2 H) 8.68 (d, J = 1.01 Hz, 1 H) 8.95 (d, J = 7.86 Hz, 1 H) 9.06 (d, J = 1.39 Hz, 1 H)

Example 100: N-[(S)-(5-chloro-6-fluoro-1-methyl-1H-1,3-benzodiazol-2-yl)(cyclopropyl)methyl]-5-methylpyrazine-2-carboxamide

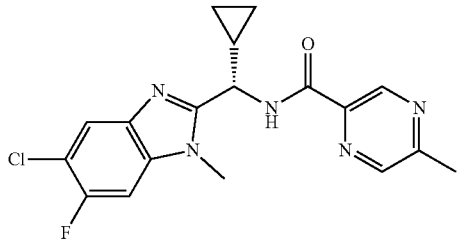 [SMILES: Cc1cnc(C(=O)N[C@H](c2nc3cc(Cl)c(F)cc3n2C)C2CC2)cn1]

HPLC-MS; Method: Z011_S03; R$_t$ [min]: 0.98  MS: 374 (M + H)$^+$
Chiral SFC Rt Method: I_IA_30_IPA_NH3_001  Rt [min]: 2.78

1H NMR (400 MHz, DMSO-d$_6$) δ ppm 0.38-0.46 (m, 1 H) 0.48-0.61 (m, 3 H) 1.66-1.76 (m, 1 H) 2.60 (s, 3 H) 3.81 (s, 3 H) 4.96 (t, J = 8.36 Hz, 1 H) 7.73 (d, J = 9.63 Hz, 1 H) 7.86 (d, J = 6.84 Hz, 1 H) 8.64 (d, J = 1.01 Hz, 1 H) 9.05 (d, J = 1.39 Hz, 1 H) 9.15 (d, J = 7.98 Hz, 1 H)

Example 101: N-[(S)-(5-chloro-1-cyclopropyl-1H-1,3-benzodiazol-2-yl)(cyclopropyl)methyl]-5-methylpyrazine-2-carboxamide

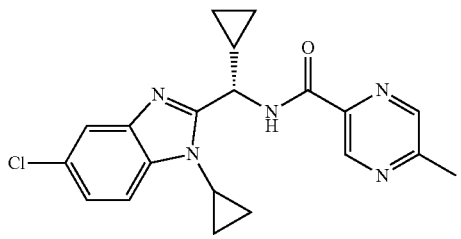 [SMILES: Cc1cnc(C(=O)N[C@H](c2nc3cc(Cl)ccc3n2C2CC2)C2CC2)cn1]

MS: 382 (M + H)$^+$
Chiral SFC Rt Method: I_SC_20_MEOH_NH3_001  Rt [min]: 3.55

$^1$H NMR (400 MHz, DMSO-d$_6$) δ ppm 0.39-0.65 (m, 4 H) 1.01-1.30 (m, 4 H) 1.57-1.67 (m, 1 H) 2.58-2.62 (m, 3 H) 3.35-3.42 (m, 1 H) 5.22 (t, J = 8.30 Hz, 1 H) 7.28 (dd, J = 8.62, 1.90 Hz, 1 H) 7.60 (d, J = 8.62 Hz, 1 H) 7.70 (d, J = 2.03 Hz, 1 H) 8.65 (d, J = 1.14 Hz, 1 H) 8.99 (d, J = 8.11 Hz, 1 H) 9.04 (d, J = 1.27 Hz, 1 H)

Example 104: N-[(1R)-1-[1-ethyl-5-(trifluoromethyl)-1H-1,3-benzodiazol-2-yl]-2-hydroxy-2-methylpropyl]-5-methylpyrazine-2-carboxamide

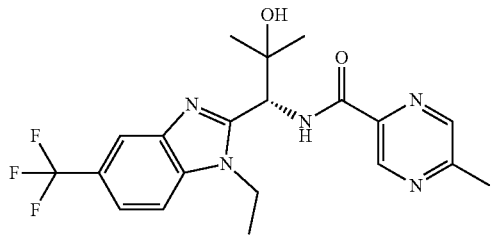 [SMILES: CCn1c([C@@H](NC(=O)c2cnc(C)cn2)C(C)(C)O)nc2cc(C(F)(F)F)ccc21]

HPLC-MS; Method: Z011_S03; R$_t$ [min]: 1.05  MS: 406 (M + H)$^+$
Chiral SFC Rt Method: I_IA_10_MEOH_NH3_001  Rt [min]: 1.57

$^1$H NMR (400 MHz, DMSO-d$_6$) δ ppm 1.22-1.30 (m, 6 H) 1.33-1.38 (m, 3 H) 2.60 (s, 3 H) 4.47-4.65 (m, 2 H) 5.22 (s, 1 H) 5.46 (d, J = 9.38 Hz, 1 H) 7.58 (dd, J = 8.55, 1.46 Hz, 1 H) 7.84 (d, J = 8.49 Hz, 1 H) 8.04 (s, 1 H) 8.68 (d, J = 1.01 Hz, 1 H) 8.74 (d, J = 9.25 Hz, 1 H) 9.06 (d, J = 1.39 Hz, 1 H)

Example 106: N-[(1S)-1-(5-chloro-1-methyl-1H-1,3-benzodiazol-2-yl)-2-cyclopropylethyl]-5-(difluoromethyl)pyrazine-2-carboxamide

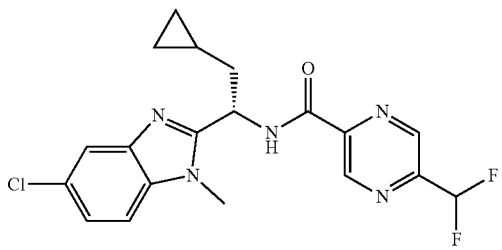 [SMILES: Cn1c([C@H](CC2CC2)NC(=O)c2cnc(C(F)F)cn2)nc2cc(Cl)ccc21]

HPLC-MS; Method: Z011_S03; R$_t$ [min]: 1.05  MS: 406 (M + H)$^+$
Chiral SFC Rt Method: I_SC_25_MEOH_NH3_001  Rt [min]: 1.64
$^1$H NMR (400 MHz, DMSO-d$_6$) δ ppm −0.04-0.03 (m, 1 H) 0.07-0.16 (m, 1 H) 0.28-
0.42 (m, 2 H) 0.70-0.80 (m, 1 H) 2.03 (t, J = 7.07 Hz, 2 H) 3.87 (s, 3 H) 5.55 (q, J = 7.07
Hz, 1 H) 7.21 (m, 1 H) 7.28 (dd, J = 8.59, 2.02 Hz, 1 H) 7.60 (d, J = 8.59 Hz, 1 H) 7.69 (d,
J = 2.02 Hz, 1 H) 9.06 (s, 1 H) 9.29 (s, 1 H) 9.33 (d, J = 8.08 Hz, 1 H)
Example 107: N-[(S)-(4-chloro-5-fluoro-1-methyl-1H-1,3-benzodiazol-2-
yl)(cyclopropyl)methyl]-5-methylpyrazine-2-carboxamide

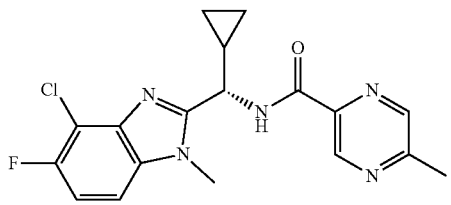 [SMILES: Cc1cnc(C(=O)N[C@H](c2nc3c(Cl)c(F)ccc3n2C)C2CC2)cn1]

HPLC-MS; Method: Z011_S03; R$_t$ [min]: 0.96  MS: 374 (M + H)$^+$
Chiral SFC Rt Method: I_SB_15_MEOH_NH3_001  Rt [min]: 3.04
$^1$H NMR (400 MHz, DMSO-d$_6$) δ ppm 0.39-0.65 (m, 4 H) 1.72-1.82 (m, 1 H) 2.58-
2.61 (m, 3 H) 3.87 (s, 3 H) 4.89 (dd, J = 8.81, 8.05 Hz, 1 H) 7.31 (dd, J = 10.14, 8.87 Hz,
1 H) 7.58 (dd, J = 8.87, 4.18 Hz, 1 H) 8.65 (d, J = 1.01 Hz, 1 H) 9.03 (d, J = 1.27 Hz, 1 H)
9.26 (d, J = 7.86 Hz, 1 H)
Example 109: N-[(1R)-1-(5-bromo-4-ethyl-1-methyl-1H-1,3-benzodiazol-2-yl)-2-
hydroxy-2-methylpropyl]-5-methylpyrazine-2-carboxamide

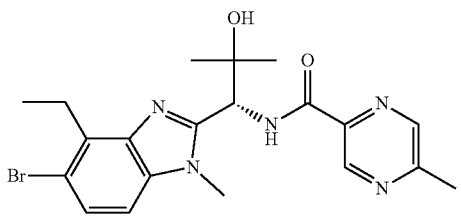 [SMILES: CCc1c(Br)ccc2c1nc([C@@H](NC(=O)c1cnc(C)cn1)C(C)(C)O)n2C]

HPLC-MS; Method: Z018_S04; R$_t$ [min]: 0.92  MS: 446 (M + H)$^+$
Chiral SFC Rt Method: I_SJ_10_IPA_NH3_001  Rt [min]: 3.28
$^1$H NMR (400 MHz, DMSO-d$_6$) δ ppm 1.15-1.22 (m, 3 H) 1.22-1.28 (m, 6 H) 2.58-
2.61 (m, 3 H) 3.01-3.15 (m, 2 H) 3.90 (s, 3 H) 5.27 (s, 1 H) 5.37-5.43 (m, 2 H) 7.36-
7.43 (m, 2 H) 8.67 (d, J = 1.01 Hz, 1 H) 8.75 (d, J = 9.13 Hz, 1 H) 9.07 (d, J = 1.39 Hz, 1
H)
Example 112: N-[(S)-(5-chloro-4-methoxy-1-methyl-1H-1,3-benzodiazol-2-
yl)(cyclopropyl)methyl]-5-methylpyrazine-2-carboxamide

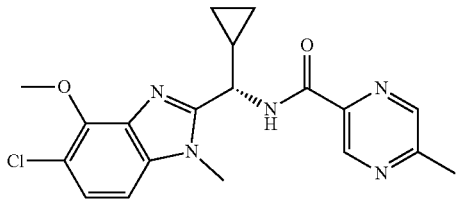 [SMILES: COc1c(Cl)ccc2c1nc([C@@H](NC(=O)c1cnc(C)cn1)C1CC1)n2C]

HPLC-MS; Method: Z018_S04; R$_t$ [min]: 1.00  MS: 369 (M + H)$^+$
Chiral SFC Rt Method: I_SA_20_IPA_NH3_001  Rt [min]: 3.68
$^1$H NMR (400 MHz, DMSO-d$_6$) δ ppm 0.37-0.62 (m, 4 H) 1.68-1.80 (m, 1 H) 2.60 (s,
3 H) 3.81 (s, 3 H) 4.31 (s, 3 H) 4.96 (t, J = 8.36 Hz, 1 H) 7.20-7.29 (m, 2 H) 8.65 (d,
J = 1.01 Hz, 1 H) 9.06 (d, J = 1.27 Hz, 1 H) 9.19 (d, J = 7.98 Hz, 1 H)
Example 114: N-[(1S)-2-cyclopropyl-1-(1-cyclopropyl-5-fluoro-1H-1,3-benzodiazol-2-
yl)ethyl]-5-(difluoromethyl)pyrazine-2-carboxamide

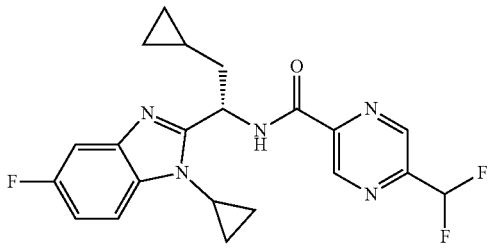 [SMILES: O=C(N[C@@H](CC1CC1)c1nc2cc(F)ccc2n1C1CC1)c1cnc(C(F)F)cn1]

HPLC-MS; Method: Z011_S03; R$_t$ [min]: 1.07  MS: 416 (M + H)$^+$
Chiral SFC Rt Method: I_SC_10_MEOH_NH3_001  Rt [min]: 2.19
$^1$H NMR (400 MHz, DMSO-d$_6$) δ ppm −0.05-0.04 (m, 1 H) 0.10-0.17 (m, 1 H) 0.32-
0.44 (m, 2 H) 0.72-0.83 (m, 1 H) 1.03-1.13 (m, 1 H) 1.20-1.34 (m, 3 H) 2.00 (ddt,
J = 43.63, 13.91, 6.97, 6.97 Hz, 2 H) 3.36-3.47 (m, 1 H) 5.75 (q, J = 7.27 Hz, 1 H) 7.06-
7.15 (m, 1 H) 7.21 (m, 1 H) 7.41 (dd, J = 9.70, 2.47 Hz, 1 H) 7.59 (dd, J = 8.87, 4.82 Hz,
1 H) 9.07 (s, 1 H) 9.21 (d, J = 8.11 Hz, 1 H) 9.28 (s, 1 H)

Example 115: N-[(S)-cyclopropyl[1-cyclopropyl-5-(trifluoromethoxy)-1H-1,3-benzodiazol-2-yl]methyl]-5-methylpyrazine-2-carboxamide

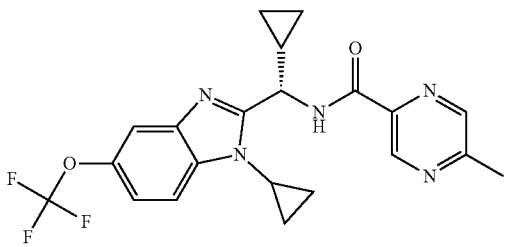 [SMILES: Cc1cnc(C(=O)N[C@H](c2nc3cc(OC(F)(F)F)ccc3n2C2CC2)C2CC2)cn1]

MS: 432 (M + H)$^+$
Chiral SFC Rt Method: I_IG_25_MEOH_NH3_001  Rt [min]: 3.51
$^1$H NMR (400 MHz, DMSO-d$_6$) δ ppm 0.38-0.49 (m, 1 H) 0.52-0.65 (m, 3 H) 1.02-
1.13 (m, 1 H) 1.18-1.31 (m, 3 H) 1.57-1.67 (m, 1 H) 2.58-2.62 (m, 3 H) 3.37-3.44
(m, 1 H) 5.22 (t, J = 8.24 Hz, 1 H) 7.26 (m, 1 H) 7.64 (s, 1 H) 7.68 (d, J = 8.74 Hz, 1 H)
8.65 (d, J = 1.01 Hz, 1 H) 9.01 (d, J = 7.98 Hz, 1 H) 9.04 (d, J = 1.27 Hz, 1 H)

Example 116: N-[(S)-cyclopropyl[1-cyclopropyl-5-(trifluoromethyl)-1H-1,3-benzodiazol-2-yl]methyl]-5-methylpyrazine-2-carboxamide

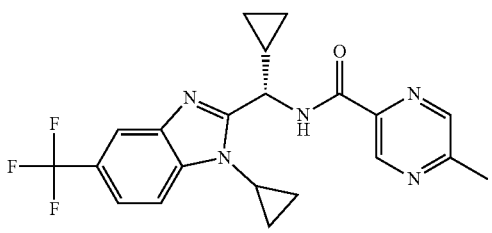 [SMILES: Cc1cnc(C(=O)N[C@H](c2nc3cc(C(F)(F)F)ccc3n2C2CC2)C2CC2)cn1]

MS: 416 (M + H)$^+$
Chiral SFC Rt Method: I_IC_20_MEOH_NH3_001  Rt [min]: 2.12
$^1$H NMR (400 MHz, DMSO-d$_6$) δ ppm 0.38-0.49 (m, 1 H) 0.54-0.66 (m, 3 H) 1.05-
1.14 (m, 1 H) 1.20-1.26 (m, 3 H) 1.59-1.69 (m, 1 H) 2.60 (s, 3 H) 3.40-3.47 (m, 1
H) 5.24 (t, J = 8.24 Hz, 1 H) 7.59 (dd, J = 8.55, 1.46 Hz, 1 H) 7.80 (d, J = 8.49 Hz, 1 H)
8.00 (s, 1 H) 8.65 (d, J = 1.01 Hz, 1 H) 9.02-9.07 (m, 2 H)

Example 121: 5-(difluoromethyl)-N-[(1R,2R)-2-methoxy-1-[1-(2-methoxyethyl)-5-(trifluoromethoxy)-1H-1,3-benzodiazol-2-yl]propyl]pyrazine-2-carboxamide

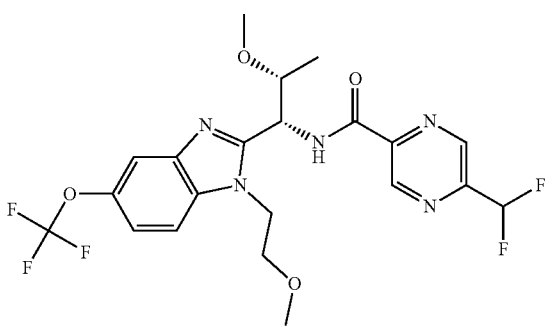 [SMILES: COCCn1c([C@@H](NC(=O)c2cnc(C(F)F)cn2)[C@@H](C)OC)nc2cc(OC(F)(F)F)ccc21]

MS: 504 (M + H)$^+$
Chiral SFC Rt Method: I_IG_10_IPA_NH3_002  Rt [min]: 1.02
$^1$H NMR (400 MHz, DMSO-d$_6$) δ ppm 1.09 (d, J = 6.21 Hz, 3 H) 3.18 (s, 3 H) 3.32 (s, 3
H) 3.65-3.73 (m, 2 H) 4.15 (quin, J = 6.15 Hz, 1 H) 4.56-4.75 (m, 2 H) 5.59 (dd,
J = 8.24, 6.08 Hz, 1 H) 7.21 (m, 1 H) 7.26 (dd, J = 8.87, 1.27 Hz, 1 H) 7.64-7.67 (m, 1
H) 7.73 (d, J = 8.87 Hz, 1 H) 9.04-9.10 (m, 2 H) 9.30 (s, 1 H)

Example 122: N-[(S)-(5-bromo-4-cyclopropyl-1-methyl-1H-1,3-benzodiazol-2-yl)(cyclopropyl)methyl]-5-methylpyrazine-2-carboxamide -continued

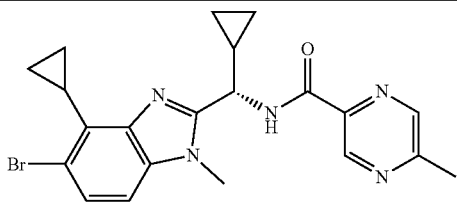

HPLC-MS; Method: Z018_S04; $R_t$ [min]: 0.93  MS: 440 (M + H)$^+$
Chiral SFC Rt Method: I_SC_30_IPA_NH3_001  Rt [min]: 3.25
$^1$H NMR (400 MHz, DMSO-$d_6$) δ ppm 0.35-0.43 (m, 1 H) 0.46-0.61 (m, 3 H) 0.96-
1.09 (m, 2 H) 1.61-1.76 (m, 3 H) 2.24-2.31 (m, 1 H) 2.60 (s, 3 H) 3.77 (s, 3 H) 4.96
(t, J = 8.30 Hz, 1 H) 7.28 (d, J = 8.62 Hz, 1 H) 7.40 (d, J = 8.62 Hz, 1 H) 8.65 (d, J = 1.01
Hz, 1 H) 9.05 (d, J = 1.27 Hz, 1 H) 9.13 (d, J = 7.98 Hz, 1 H)

Example 124: N-[(1R,2R)-2-methoxy-1-[1-(2-methoxyethyl)-5-(trifluoromethoxy)-1H-
1,3-benzodiazol-2-yl]propyl]-5-(trifluoromethyl)pyrazine-2-carboxamide

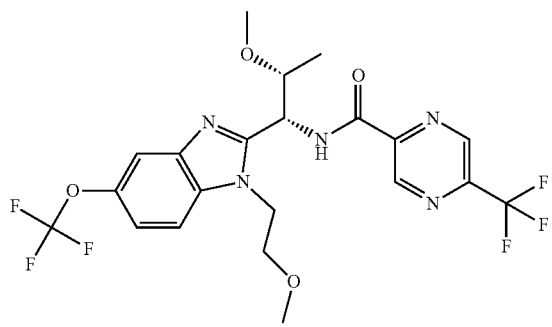 [SMILES: COCCn1c([C@@H](NC(=O)c2cnc(C(F)(F)F)cn2)[C@@H](C)OC)nc2cc(OC(F)(F)F)ccc21]

HPLC-MS; Method: Z011_S03; $R_t$ [min]: 1.16  MS: 522 (M + H)$^+$
Chiral SFC Rt Method: I_IG_10_IPA_NH3_002  Rt [min]: 0.89
$^1$H NMR (400 MHz, DMSO-$d_6$) δ ppm 1.10 (d, J = 6.21 Hz, 3 H) 3.18 (s, 3 H) 3.32 (s, 3
H) 3.64-3.74 (m, 2 H) 4.15 (quin, J = 6.15 Hz, 1 H) 4.56-4.76 (m, 2 H) 5.60 (dd,
J = 8.30, 6.15 Hz, 1 H) 7.26 (dd, J = 8.81, 1.33 Hz, 1 H) 7.65 (s, 1 H) 7.73 (d, J = 8.74 Hz,
1 H) 9.11 (d, J = 8.36 Hz, 1 H) 9.32 (s, 1 H) 9.36 (s, 1 H)

Example 127: N-[(S)-(3,3-difluorocyclobutyl)(1-ethyl-5-fluoro-1H-1,3-benzodiazol-2-
yl)methyl]-5-methylpyrazine-2-carboxamide

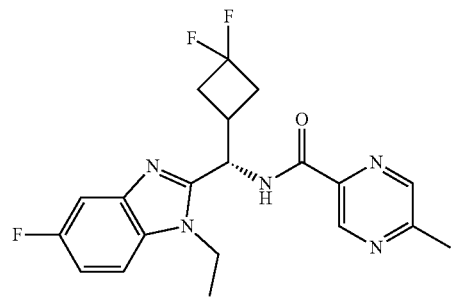 [SMILES: CCn1c([C@@H](NC(=O)c2cnc(C)cn2)C2CC(F)(F)C2)nc2cc(F)ccc21]

HPLC-MS; Method: Z011_S03; $R_t$ [min]: 0.99  MS: 404 (M + H)$^+$
Chiral SFC Rt Method: I_C2_10_MEOH_NH3_002  Rt [min]: 1.22
$^1$H NMR (400 MHz, DMSO-$d_6$) δ ppm 1.22 (m, 3 H) 2.38-2.79 (m, 7 H) 3.18-3.28
(m, 1 H) 4.25-4.35 (m, 2 H) 5.02-5.15 (m, 1 H) 5.60-5.71 (m, 1 H) 7.12 (ddd,
J = 9.70, 8.93, 2.53 Hz, 1 H) 7.47 (dd, J = 9.76, 2.41 Hz, 1 H) 7.58 (dd, J = 8.81, 4.75 Hz,
1 H) 8.61 (d, J = 0.89 Hz, 1 H) 9.10 (d, J = 1.39 Hz, 1 H) 9.36 (d, J = 9.00 Hz, 1 H)

Example 14

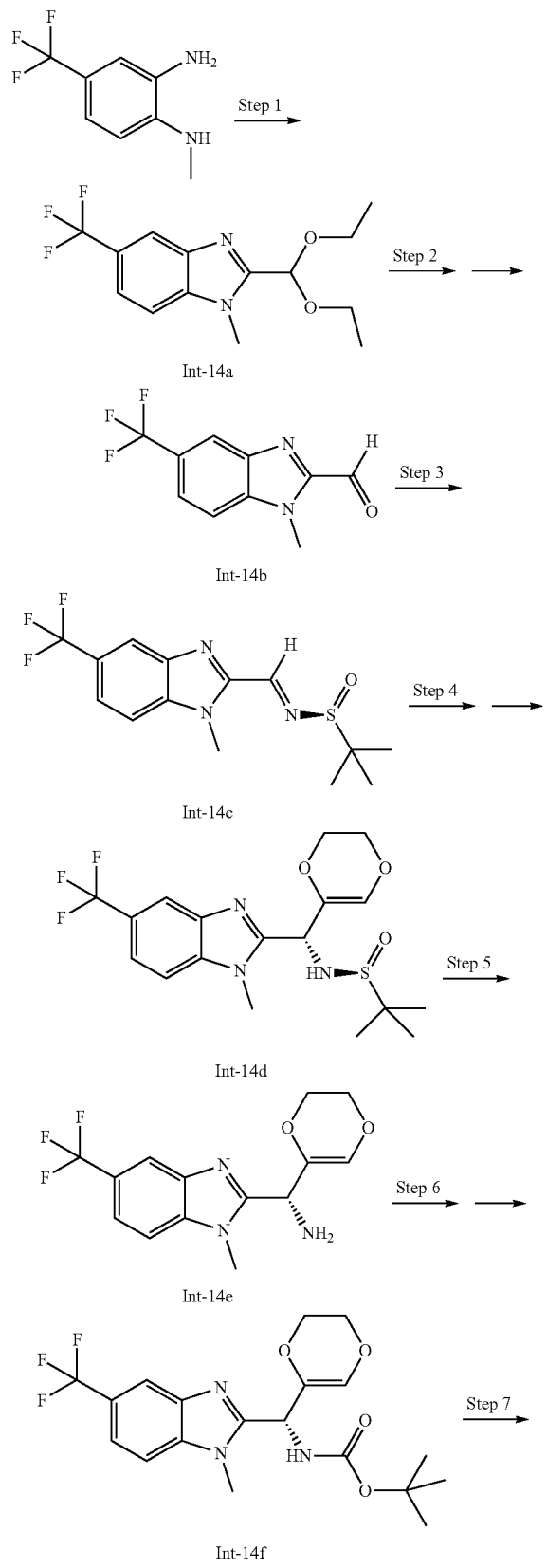

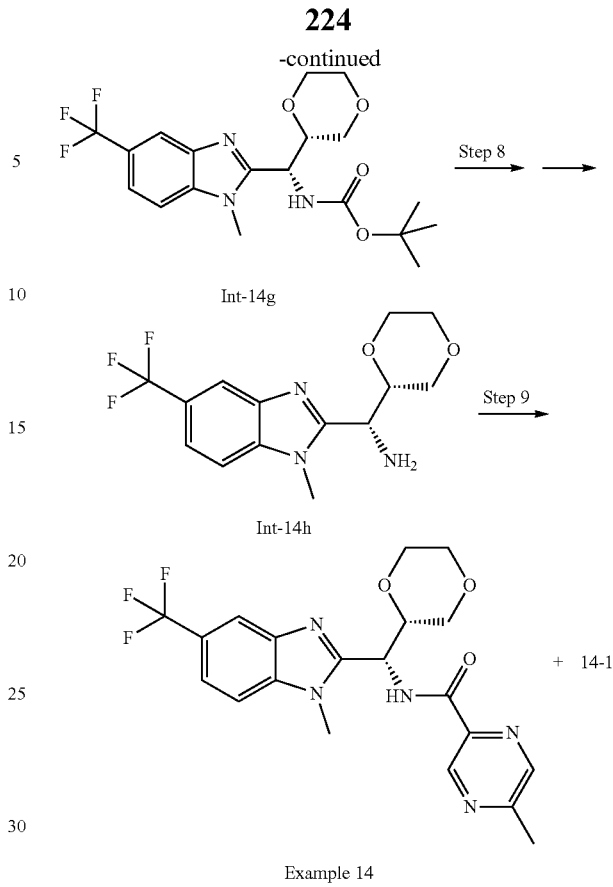

Example 14

Step 1:

Sodium (0.95 g, 41.2 mmol) is given into 80 mL EtOH and the mixture cooled to not exceed 35° C. and stirred for 45 min. N1-methyl-4-(trifluoromethyl)-benzene-1,2-diamine (2.50 g, 12.9 mmol) and ethyl diethoxy acetate (4.15 mL, 23.2 mmik) in 20 mL EtOH are added, and the mixture heated to reflux for 20 h. Then, 200 mL sat. aq. NH$_4$CL are added, the mixture is concentrated i. vac., the residue diluted with 250 mL water and extracted with ethyl acetate. The combined organic layers are dried over MgSO$_4$ and concentrated i. vac. The residue is taken up in THF/MeOH and purified by column chromatography (XBridge C18, 10 µm, eluent gradient: (H$_2$O+0.15% NH$_3$) ACN: 56:44→36:64). Product containing fractions are combined and freeze-dried. The solid was taken up in DCM and concentrated i. vac. Yield: 1.78 g (5.89 mmol; 46%) Int-14a MS (ESI$^+$): (M+H)$^+$ 303; HPLC: RT=1.05 min, Method: Z011_S03

Step 2:

A mixture from Int-14a (12.8 g, 42.3 mmol) and hydrochloric acid in dioxane (4N; 128 mL, 512 mmol) is stirred and heated to reflux for 1.5 h. Heating was removed and the mixture poured into a mixture of 800 mL water with 500 mL sat. aq. NaHCO$_3$ solution. The mixture is stirred for 5 min and filtered. The solid is washed with water and dried i. vac., the residue is taken up in n-butyl acetate and concentrated i. vac. Yield: 9.33 g (40.1 mmol; 95%) Int-14b MS (ESI$^+$): (M+H)$^+$ 229; HPLC: RT=0.88 min, Method: Z011_S03

Step 3:

Int-14b (23.2 g, 99.6 mmol), (S)-(−)-2-methyl-2-propanesulfinamide (13.3 g, 105 mmol) and Cs$_2$CO$_3$ (42.2 g, 130 mmol) in 370 mL DCM are stirred under heating and reflux for 1.25 h. Then heating is removed, MgSO$_4$ is added, the mixture filtrated and the filtrate concentrated i. vac.

The residue is taken up in DCM and di-isopropyl ether and concentrated i. vac. The forming solid is filtrated and collected. The filtrate is further concentrated i. vac. and the residue purified via column chromatography (silica gel; eluent gradient: petroleum ether:EtOAc: 80:20→45:55). The product containing fractions are combined and concentrated i. vac. The residue is combined with the collected solid. Yield: 31.6 g (95.4 mmol; 96%) Int-14c MS (ESI$^+$): (M+H)$^+$ 332; HPLC: RT=1.07 min, Method: Z018_S04 Chiral SFC Rt 4.27 min (Method: I_SA_10_IPA_NH3_003)

Step 4:

Under argon atmosphere and in extra dried glassware, 1-4 dioxene (17.18 mL, 211.25 mmol) in 150 mL THF is cooled to −35° C. and n-hexyl lithium (2.45N in hexane; 76.98 mL, 188.52 mmol) is added with the temperature staying below −30° C. Then cooling is removed, and the mixture warmed to 20° C. The mixture is cooled immediately to 0° C. and stirred at this temperature for 30 min. Then the mixture is cooled to −65° C. and added to a mixture of Int-14c (50 g, 150.89 mmol) in 500 mL THF at −75° C. under argon in extra dried glassware in a way to keep the temperature of the mixture below −70° C. Afterwards the mixture is stirred at −70° C. for 20 min. Then the mixture is poured into 650 mL sat. aq. NH$_4$Cl solution. tert.butyl methyl ether (650 ml) is added and the mixture warmed to room temperature under stirring. The aq. layer is extracted with tert. butyl methyl ether, the combined organic layers washed with brine, dried over MgSO$_4$ and concentrated i. vac. To the residue EtOAc (70 ml) is added. The mixture is filtrated and washed with EtOAc, the solid is collected. The obtained product contained only one stereoisomer. Yield: 38.5 g (92 mmol; 61%) Int-14d Chiral SFC Rt 5.38 min (Method: I_IH_15_IPA_NH3_003)

Step 5:

To Int-14d (15.4 g, ~90%, 33.2 mmol) in 347 mL MeOH at 10° C. is added hydrogen chloride in dioxane (4N, 18.3 mL, 73.0 mmil). The cooling is removed after 5 min and the mixture stirred for 22 h at ambient temperature. Then conc. aq. NH$_3$ solution is added to adjust the pH to 7.5 and the mixture concentrated i. vac. The residue is adjusted to pH 8 by addition of conc. aq. NH$_3$ solution, 300 mL water are added and the mixture is extracted with DCM. The aq. layer is adjusted to pH 10 by addition of Na$_2$CO$_3$ solution (aq., 2N) and extracted with EtOAc. The organic layers are washed with water, combined, dried over MgSO$_4$ and concentrated i. vac.

Yield: 12.4 g (content~75%; 29.8 mmol; 90%) Int-14e

MS (ESI$^+$): (M+H)$^+$ 314; HPLC: RT=0.87 min, Method: Z011_S03

Chiral SFC Rt 3.51 min (Method: I_IG_20_IPA_NH3_003)

Step 6:

To Int-14e (12.4 g, ~75%, 29.8 mmol) in 250 mL DCM with TEA (8.8 mL, 63.3 mmol) is added Boc$_2$O (8.3 g, 38.0 mmol) and the mixture stirred at ambient temperature for 15.5 h. The organic layer is washed with water, dried over MgSO$_4$ and concentrated i. vac. Then it is purified via chromatography (silica gel, eluent gradient: petroleum ether: EtOAc 75:25→45:55). The product containing fractions are combined and concentrated i. vac.

Yield: 9.82 g (23.7 mmol; 75%) Int-14f

MS (ESI$^+$): (M+H)$^+$ 414

Chiral SFC Rt 4.64 min (Method: I_IG_10_IPA_NH3_003)

Step 7:

Int-14f (8.8 g, 21.3 mmol) in 300 mL THF is mixed with palladium on charcoal (10%, 1.3 g) and the mixture hydrogenated under a hydrogen atmosphere at 60 psi for 22 h, then further palladium on charcoal is added (10%, 1 g), hydrogenation is continued for 5 h, then additional palladium on charcoal is added (10%, 0.5 g) and hydrogenation is continued for 3 h. The mixture is allowed to stay overnight, then it is filtered and concentrated i. vac. The product is obtained as a mixture of stereoisomers, which is used further without separation. Only the major isomer is depicted in the synthesis scheme.

Yield: 8.76 g (21.1 mmol; 99%) Int-14 g

MS (ESI$^+$): (M+H)$^+$ 416; HPLC: RT=1.04 min, Method: Z011_S03

Stereoisomer 1: Chiral SFC Rt 2.69 min (Method: I_IG_10_IPA_NH3_003)

Stereoisomer 2: Chiral SFC Rt 3.33 min (Method: I_IG_10_IPA_NH3_003)

Step 8:

TFA (14.3 mL, 186 mmol) is added to Int-14 g (7.7 g, 18.7 mmol) in 65 mL DCM at 5° C. Cooling is removed and the mixture stirred for 3.8 h at ambient temperature. 150 g ice is added and the mixture adjusted to pH ~10 by addition of conc. aq. NH$_3$ solution. The aqueous layer is extracted with DCM, the combined organic layers dried over MgSO$_4$ and concentrated i. vac.

Yield: 5.92 g (18.7 mmol; quant.) Int-14 h

Chiral SFC Rt 2.57 min (Method: I_SA_10_MEOH_NH3_003)

Step 9:

To a mixture of Int-14 h (5.9 g, 18.7 mmol) with NMM (5.1 mL, 46.8 mmol) in 59 mL EtOAc is added 5-methylpyraine-2-carboxylic acid (3.2 g, 22.6 mmol) and the mixture cooled to 0° C. under stirring. Then PPA (50% in EtOAc; 14.5 mL, 24.3 mmol) is added dropwise while keeping the temperature below 10° C. Cooling is removed after 5 min and the mixture stirred at ambient temperature for 75 min. Water is added and the mixture adjusted to pH 9 by adding NMM. The aq. layer is extracted with EtOAc, the combined organic layers washed with half-conc. brine, charcoal added, stirred and dried over MgSO$_4$. After filtration the mixture is concentrated i. vac., the residue taken up in EtOAc and purified via chromatography (silica gel, eluent: EtOAc:EtOH 97:3). The product containing fractions are combined and concentrated i. vac. The product is obtained as a mixture of two stereoisomers, which is purified by chiral SFC.

Yield: 4.05 g (9.30 mmol) example 14 and 0.71 g (1.63 mmol) example 14-1

---

Example 14: N-[(R)-[(2S)-1,4-dioxan-2-yl][1-methyl-5-(trifluoromethyl)-1H-1,3-benzodiazol-2-yl]methyl]-5-methylpyrazine-2-carboxamide

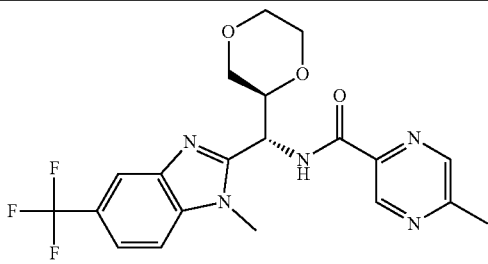

HPLC-MS; Method: Z018_S04; R, [min]: 0.94  MS: 436 (M + H)+
Chiral SFC Rt Method: I_C2_20_MEOH_NH3_002  Rt [min]: 1.37
$^1$H NMR (400 MHz, DMSO-d$_6$) δ ppm 2.61 (s, 3 H) 3.31-3.39 (m, 1 H) 3.41-3.50 (m,
1 H) 3.58-3.68 (m, 2 H) 3.76-3.85 (m, 2 H) 3.95 (s, 3 H) 4.30-4.37 (m, 1 H) 5.62
(dd, J = 8.11, 6.59 Hz, 1 H) 7.60 (dd, J = 8.49, 1.39 Hz, 1 H) 7.80 (d, J = 8.62 Hz, 1 H)
8.00-8.04 (m, 1 H) 8.67 (d, J = 0.89 Hz, 1 H) 9.05-9.09 (m, 2 H)
Example 14-1: N-[(1,4-dioxan-2-yl)[1-methyl-5-(trifluoromethyl)-
1H-1,3-benzodiazol-2-yl]methyl]-5-methylpyrazine-2-
carboxamide

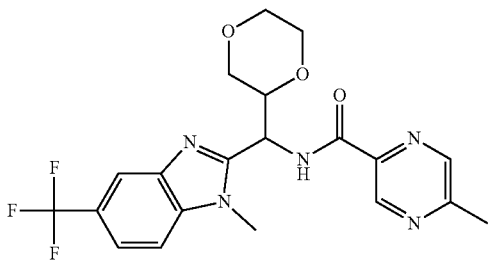 [SMILES: Cc1cnc(C(=O)NC(c2nc3cc(C(F)(F)F)ccc3n2C)C2COCCO2)cn1]

HPLC-MS; Method: Z018_S04; R, [min]: 0.94  MS: 436 (M + H)+
Chiral SFC Rt Method: I_C2_20_MEOH_NH3_002  Rt [min]: 0.99
$^1$H NMR (400 MHz, DMSO-d$_6$) δ ppm 2.55-2.63 (m, 3 H) 3.45-3.58 (m, 3 H) 3.58-
3.76 (m, 2 H) 3.93 (s, 3 H) 4.02 (dd, J = 11.34, 2.34 Hz, 1 H) 4.26 (td, J = 9.28, 2.47 Hz,
1 H) 5.48 (t, J = 8.74 Hz, 1 H) 7.58 (dd, J = 8.62, 1.39 Hz, 1 H) 7.79 (d, J = 8.49 Hz, 1 H)
8.01 (s, 1 H) 8.66 (d, J = 1.01 Hz, 1 H) 9.02 (d, J = 1.39 Hz, 1 H) 9.32 (d, J = 8.49
Hz, 1 H)

Examples 18 and 54

Step 1:

To a mixture of 1,2-diamino-4-bromo-3-methyl-benzene (110 mg, 0.55 mmol), Int-1c (120 mg, 0.51 mmol) and NMM (190 µL, 1.7 mmol) in 5 mL DCM is added PPA (50% in EtOAc; 330 µL, 0.56 mmol) at 0° C. After 45 min stirring at 0° C., 200 µL water is added and the mixture stirred at ambient temperature for 30 min. Then 5 mL acetic acid is added and the mixture stirred at ambient temperature for 16 h. The mixture is concentrated i. vac. and purified via prep. HPLC (C-18 Sunfire at 50° C., eluent gradient (water+ 0.15% TFA):ACN 83:17→63:37). The product containing fractions are combined, set basic with aq. NH₃ solution and concentrated i. vac. The aq. phase is extracted with DCM, the combined organic layers dried over MgSO₄ and concentrated i. vac. Yield: 200 mg (0.50 mol; 98%) Int-18a MS (ESI⁺): (M+H)⁺ 400; HPLC: RT=0.79 min, Method: Z018_S04

Step 2:

Int-18a (200 mg, 0.5 mmol) together with 1-bromo-2-methoxy-ethane (50 µL, 0.53 mmol) and Cs₂CO₃ (300 mg, 0.92 mmol) in 3 mL DMF is stirred at ambient temperature for 16 h. Then it is stirred at 50° C. for 30 min, followed by addition of Cs₂CO₃ (300 mg, 0.92 mmol) and 1-bromo-2-methoxy-ethane (50 µL, 0.53 mmol) and stirring for 20 h at ambient temperature. DCM and water are added and the aq. phase is extracted with DCM. The organic layers are combined, dried over MgSO₄ and concentrated i. vac. The residue is purified via prep. HPLC (C-18 X-Bridge at 50° C., eluent gradient (water+0.15% NH₃):ACN 54:46→34:66). The product containing fractions are combined and freeze-dried. Yield: 170 mg (0.37 mol; 74%) example 54

Example 54: N-[(S)-[5-bromo-1-(2-methoxyethyl)-4-methyl-1H-1,3-benzodiazol-2-yl](cyclopropyl)methyl]-5-methylpyrazine-2-carboxamide

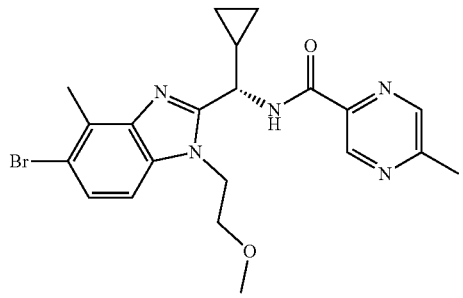 [SMILES: COCCn1c([C@@H](NC(=O)c2cnc(C)cn2)C2CC2)nc2c(C)c(Br)ccc21]

HPLC-MS; Method: Z018_S04; $R_t$ [min]: 0.93  MS: 458 (M + H)⁺
Chiral SFC Rt Method: Method  Rt [min]: 2.28
I_SA_20_MEOH_NH3_001
¹H NMR (400 MHz, DMSO-d₆) δ ppm 0.40-0.62 (m, 4 H) 1.79-1.87 (m, 1 H) 2.57-2.61 (m, 6 H) 3.13 (m, 3 H) 3.60 (t, J = 5.07 Hz, 2 H) 4.42 (dt, J = 15.37, 4.48 Hz, 1 H) 4.61 (dt, J = 15.30, 5.78 Hz, 1 H) 4.97 (t, J = 8.68 Hz, 1 H) 7.36-7.42 (m, 2 H) 8.63 (s, 1 H) 9.00-9.08 (m, 2 H)

Step 3:

Example 54 (155 mg, 0.34 mmol) together with Zn(CN)₂ (80 mg, 0.68 mmol) and X-Phos G1 (15 mg, 0.02 mmol) in 750 µL NMP are stirred under argon at 100° C. for 30 min. Afterwards, water is added and the mixture sonicated. 10 mL of ACN/THF 1:1 mixture is added, the mixture is filtered and the filtrate is purified via prep. HPLC (C-18 X-Bridge at 50° C., eluent gradient (water+0.15% NH₃):ACN 65:35→45:55). The product containing fractions are combined and freeze-dried. The residue is further purified by chiral SFC.

Yield: 90 mg (0.27 mmol; 66%) Example 18

Example 18: N-[(S)-[5-cyano-1-(2-methoxyethyl)-4-methyl-1H-1,3-benzodiazol-2-yl](cyclopropyl)methyl]-5-methylpyrazine-2-carboxamide

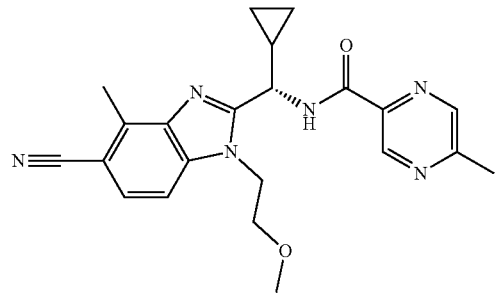 [SMILES: COCCn1c([C@@H](NC(=O)c2cnc(C)cn2)C2CC2)nc2c(C)c(C#N)ccc21]

HPLC-MS; Method: Z018_S04; $R_t$ [min]: 0.94  MS: 405 (M + H)⁺
Chiral SFC Rt Method: Method  Rt [min]: 1.66
I_SA_20_MEOH_NH3_001
¹H NMR (400 MHz, DMSO-d₆) δ ppm 0.39-1.24 (m, 4 H) 1.81-1.90 (m, 1 H) 2.59 (s, 3 H) 2.73 (s, 3 H) 3.13 (s, 3 H) 3.62 (t, J = 5.07 Hz, 2 H) 4.43-4.70 (m, 2 H) 4.98 (t, J = 8.62 Hz, 1 H) 7.54-7.62 (m, 2 H) 8.63 (s, 1 H) 9.04 (d, J = 1.14 Hz, 1 H) 9.12 (d, J = 8.24 Hz, 1 H)

Example 20

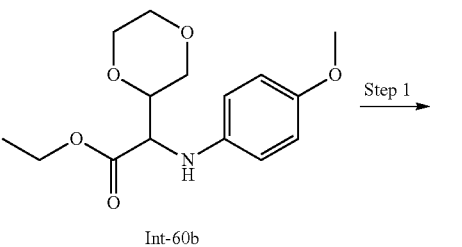

Int-60b

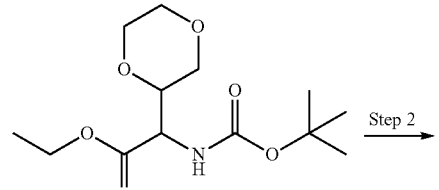

Int-20a

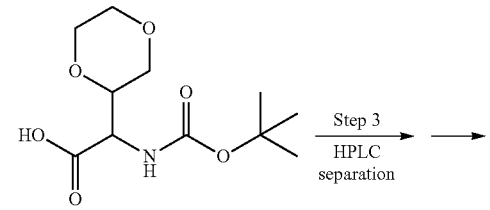

Int-20b

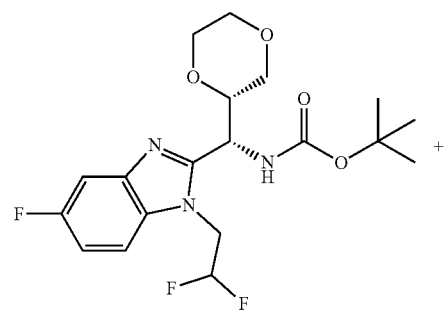

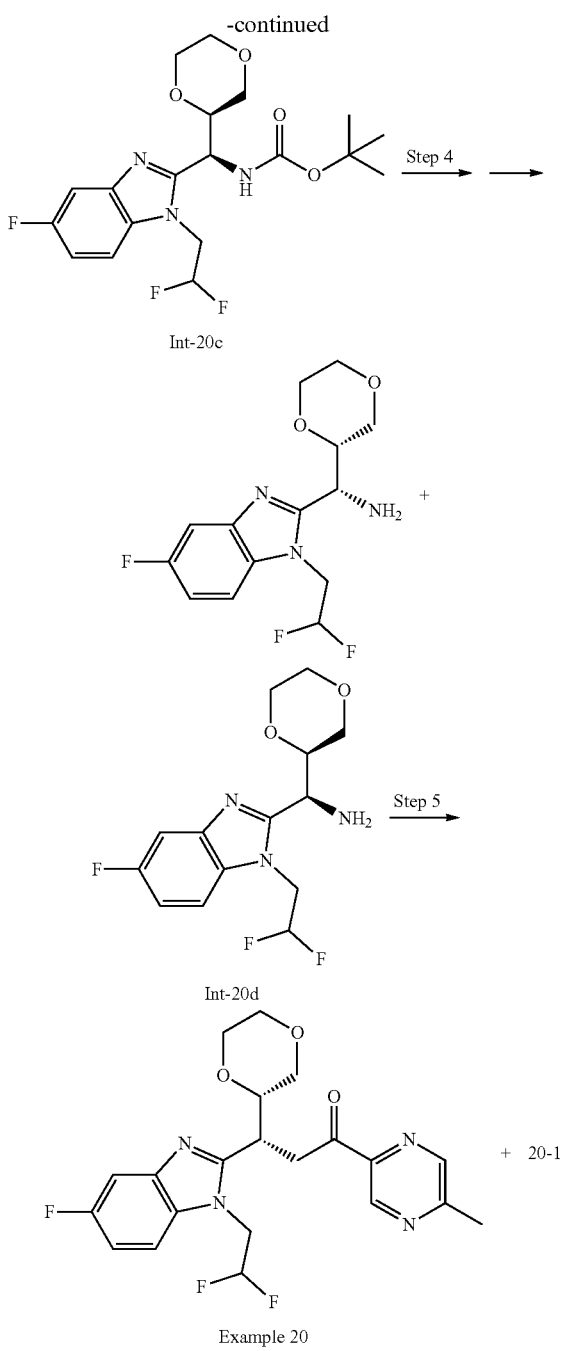

Int-20c

Int-20d

Example 20

Step 1:

To Int-60b (1.30 g, 4.4 mmol) in 30 mL ACN and 10 mL water is added cer(IV)-ammonium nitrate (3.62 g, 6.6 mmol) and the mixture stirred at ambient temperature for 3 h. Then, the mixture is concentrated i. vac., the residue taken up with water and extracted with EtOAc. The combined organic layers are dried over $Na_2SO_4$ and concentrated i. vac. The residue is taken up in 3 mL THF and 10 mL TEA, $Boc_2O$ (3.48 g, 6.4 mmol) is added and the mixture stirred at ambient temperature for 3 h. Afterwards, the mixture is concentrated i. vac.

Yield: 0.80 g (2.8 mmol; 63%) Int-20a

MS (ESI$^+$): (M+H)$^+$ 290

Step 2:

LiOH (0.10 g, 4.2 mmol) is added to Int-20a (0.80 g, 2.8 mmol) in 10 mL MeOH and 3 mL water and the mixture stirred at ambient temperature for 3 h. Then the mixture is concentrated i. vac. and purified by prep. HPLC.

Yield: 0.60 g (2.3 mmol, 82%) Int-20b as mixture of stereoisomers

MS (ESI$^+$): (M+H)$^+$ 262

Step 3:

To a mixture of int-4b (280 mg, 1.4 mmol), int-20b (380 mg, 1.4 mmol) and NMM (0.95 mL, 8.7 mmol) in 3 mL DCM is added PPA (50% in EtOAc; 1.3 mL, 2.2 mmol) at 0° C. After 2 h stirring at 0° C., the mixture is concentrated i. vac. Then 2.1 g acetic acid is added and the mixture stirred at 50° C. for 8 d. The mixture is concentrated i. vac. The mixture contains four stereoisomers, which can be separated into two pairs of enantiomers via prep. HPLC (C-18 Sunfire 10 μm, eluent gradient (water+0.15% TFA):ACN 64:36→44:56). The product containing fractions are combined and freeze-dried. Only one pair of enantiomers (Int-20c) is used in step 4 which is depicted in the reaction scheme.

Stereoisomer pair 1: Int-20c as a mixture of enantiomers: Yield: 119 mg (0.29 mmol; 20%). MS (ESI$^+$): (M+H)$^+$ 416; HPLC: RT=0.98 min, Method: Z018_S04

Stereoisomer pair 2 as a mixture of enantiomers: Yield: 104 mg (0.25 mmol; 17%)

MS (ESI$^+$): (M+H)$^+$ 416; HPLC: RT=0.97 min, Method: Z018_S04

Step 4:

Int-20c (119 mg, 0.29 mmol) is stirred at ambient temperature for 2 h in HCl in dioxane (4N; 3.0 mL, 12 mmol). The mixture is concentrated i. vac.

Yield: 111 mg (0.29 mmol; quant.) Int-20d as mixture of enantiomers

MS (ESI$^+$): (M+H)$^+$ 316

Step 5:

A mixture of Int-20d (111 mg, 0.29 mmol), 5-methyl-pyrazine-2-carboxylic acid (39 mg, 0.29 mmol) and NMM (189 μL, 1.7 mmol) in 3.5 mL DCM is stirred at 0° C., PPA (50% in EtOAc; 0.3 mL, 0.5 mmol) is added and the mixtures stirred for 1 h at 0° C. The mixture is concentrated i. vac., taken up in ACN, filtered and the filtrate purified by prep. HPLC (C-18 X-Bridge 10 μm, eluent gradient (water+ 0.15% NH$_3$):ACN 71:29→51:49). The product containing fractions are combined and freeze-dried. Afterwards chiral SFC is performed to get the desired enantiomers (example 20 and 20-1).

Yield: 28 mg (64 μmol; 45%) example 20

Example 20: N-[(R)-[1-(2,2-difluoroethyl)-5-fluoro-1H-1,3-benzodiazol-2-yl][(2S)-1,4-dioxan-2-yl]methyl]-5-methylpyrazine-2-carboxamide -continued

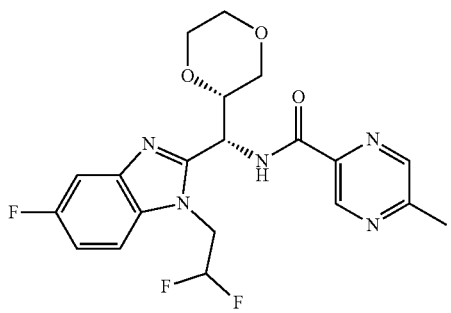 [SMILES: Cc1cnc(C(=O)N[C@H](c2nc3cc(F)ccc3n2CC(F)F)[C@H]2COCCO2)cn1]

HPLC-MS; Method: Z011_S03; $R_t$ [min]: 0.90  MS: 436 (M + H)$^+$
Chiral SFC Rt Method: I_IG_25_MEOH_NH3_001  Rt [min]: 4.14
$^1$H NMR (400 MHz, DMSO-d$_6$) δ ppm 2.60 (s, 3 H) 3.37-3.49 (m, 1 H) 3.57-3.68 (m, 2 H) 3.70-3.77 (m, 1 H) 3.78-3.85 (m, 1 H) 4.36-4.43 (m, 1 H) 4.89-5.14 (m, 2 H) 5.54 (t, J = 7.73 Hz, 1 H) 6.47 (m, 1 H) 7.18 (m, 1 H) 7.50 (dd, J = 9.57, 2.47 Hz, 1 H) 7.65 (dd, J = 8.93, 4.75 Hz, 1 H) 8.65 (d, J = 1.01 Hz, 1 H) 9.05 (d, J = 1.39 Hz, 1 H) 9.10 (d, J = 8.24 Hz, 1 H)

Example 20-1: N-[(S)-[1-(2,2-difluoroethyl)-6-(trifluoromethyl)-1H-1,3-benzodiazol-2-yl][(2R)-1,4-dioxan-2-yl]methyl]-5-methylpyrazine-2-carboxamide:

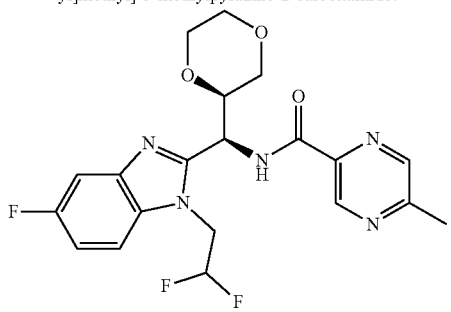

HPLC-MS; Method: Z011_S03; $R_t$ [min]: 0.90  MS: 436 (M + H)$^+$
Chiral SFC Rt Method: I_IG_25_MEOH_NH3_001  Rt [min]: 2.5
$^1$H NMR (400 MHz, DMSO-d$_6$) δ ppm 2.58-2.61 (m, 3 H) 3.23-3.28 (m, 1 H) 3.38-3.55 (m, 1 H) 3.55-3.69 (m, 2 H) 3.73 (dd, J = 11.41, 2.41 Hz, 1 H) 3.81 (br d, J = 11.28 Hz, 1 H) 4.37-4.43 (m, 1 H) 4.89-5.13 (m, 2 H) 5.54 (t, J = 7.73 Hz, 1 H) 6.28-6.65 (m, 1 H) 7.18 (td, J = 9.31, 2.41 Hz, 1 H) 7.51 (dd, J = 9.57, 2.47 Hz, 1 H) 7.65 (dd, J = 8.93, 4.75 Hz, 1 H) 8.65 (d, J = 1.14 Hz, 1 H) 9.05 (d, J = 1.39 Hz, 1 H) 9.11 (d, J = 8.24 Hz, 1 H)

Example 23 and Example 77

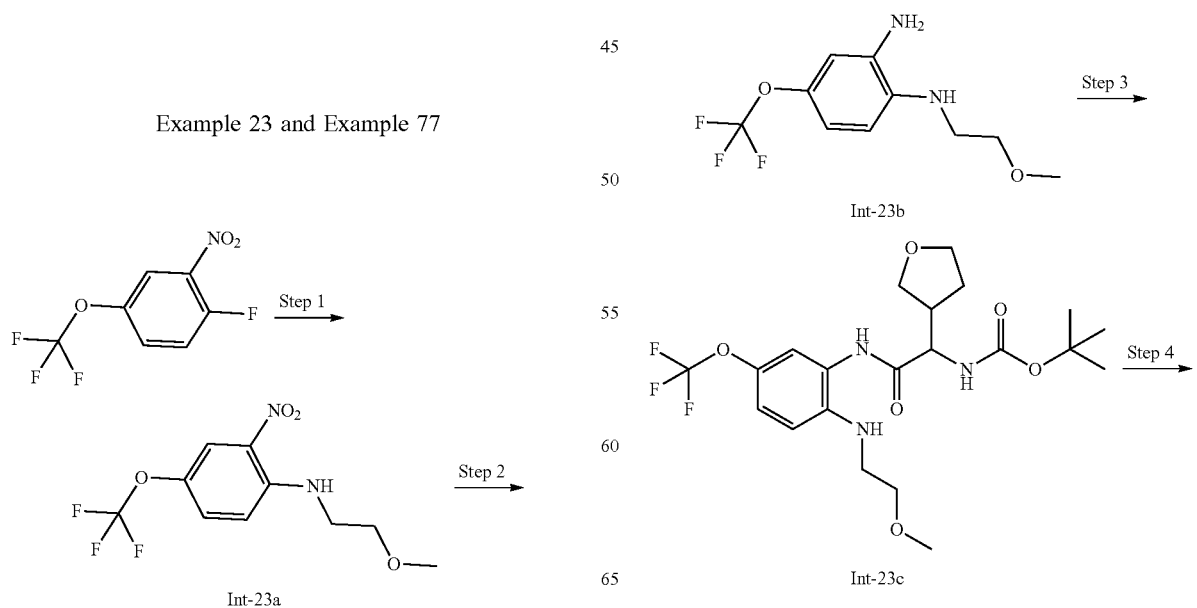

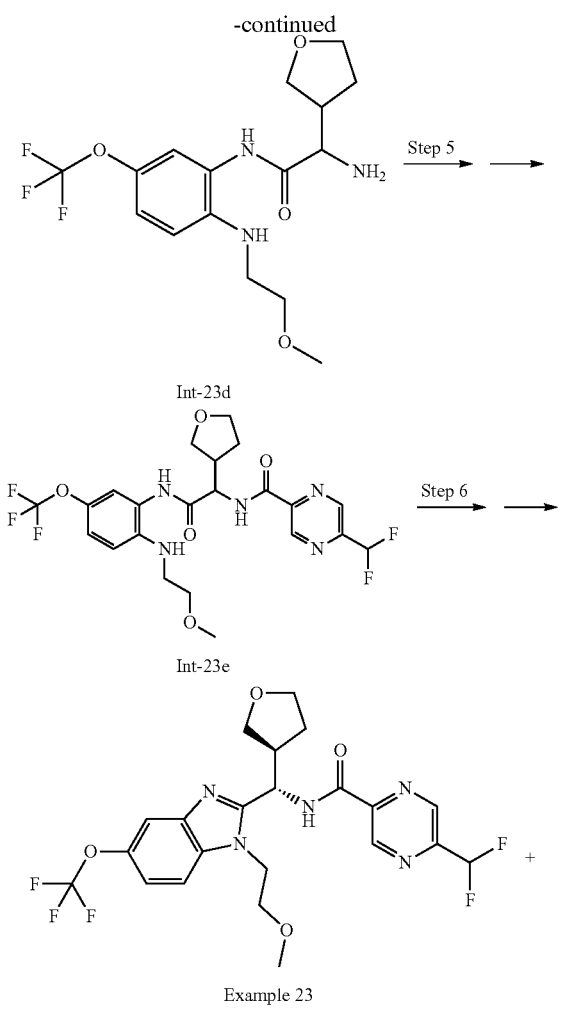

Step 1:

1-fluoro-2-nitro-4-(trifluoromethoxy)-benzene (50 g, 0.22 mol) is mixed with 2-methoxy-ethylamine (33.4 g, 0.44 mol) in 250 mL THF, TEA (31 mL, 0.22 mol) is added and the mixture stirred at 50° C. for 2 h. Afterwards, EtOAc and water are added, and the organic layer washed with brine and concentrated.

Yield: 62 g (0.22 mol; quant.) Int-23a

MS (ESI$^+$): (M+H)$^+$ 281; HPLC: RT=1.07 min, Method: Z011_S03

Step 2:

Int-23a (62 g, 0.22 mol) with 7.5 g Raney-nickel in 600 mL THF is hydrogenated for 16 h at ambient temperature with 50 psi hydrogen gas. The mixture is filtered and the filtrate concentrated i. vac. The residue is used without further purification.

Yield: 55.8 g (0.22 mol; quant.) Int-23b

MS (ESI$^+$): (M+H)$^+$ 251; HPLC: RT=0.96 min, Method: Z011_S03

Step 3:

PPA (50% in EtOAc, 14.4 mL, 24 mmol) is added to a mixture of Int-23b (3.7 g, 15 mmol) with 2-(Boc-amino)-2-(tetrahydrofuran-3-yl)-acetic acid (3.0 g, 12.2 mmol) and NMM (8.1 mL, 73 mmol) in 60 mL DCM at 0° C. and then stirred for 2 h at ambient temperature. The mixture is concentrated i. vac., EtOAc and water are added and the organic layer washed with aq. NaHCO$_3$ solution, dried over Na$_2$SO$_4$ and concentrated i. vac. The residue is purified by prep. HPLC.

Yield: 5.1 g (11 mmol; 87%) Int-23c

MS (ESI$^+$): (M+H)$^+$ 478; HPLC: RT=1.05 min, Method: Z011_S03

Step 4:

Int-23c (5.1 g, 11 mmol) is stirred with HCl in dioxane (4N, 20 mL, 80 mmol) for 2 h at ambient temperature. Afterwards, the mixture is concentrated i. vac. The residue is used without further purification.

Yield: 4.5 g (11 mmol; quant.) Int-23d

MS (ESI$^+$): (M+H)$^+$ 378; HPLC: RT=0.90 min, Method: Z011_S03

Step 5:

Int-23d (2.3 g, 5.6 mmol) is added to a mixture of 5-(difluoromethyl)-pyrazine-2-carboxylic acid (0.97 g, 5.6 mmol), TBTU (1.96 g, 6.1 mmol) and TEA (3.9 mL, 28 mmol) in 20 mL DMF and the mixture stirred for 3 h at ambient temperature. Water is then added and the mixture purified by prep. HPLC.

Yield: 1.4 g (2.6 mmol; 47%) Int-23e

MS (ESI$^+$): (M+H)$^+$ 534; HPLC: RT=1.02 min, Method: Z011_S03

Step 6:

Int-23e (1.4 g, 2.6 mmol) is mixed with 10 mL acetic acid and stirred at 95° C. for 2 h. The mixture is concentrated i. vac. and the residue taken up in THF and water. The mixture is set basic with aq. NH$_3$ solution and purified by prep. HPLC. The mixture of four stereoisomers is separated by chiral SFC. Biological potency is described for example 23 and 77.

Yield: 107 mg (0.21 mmol; 35%) example 23

The following compounds are obtained: examples 23, 77, 23-1, 23-2

Example 23: 5-(difluoromethyl)-N-[(S)-[1-(2-methoxyethyl)-5-(trifluoromethoxy)-1H-1,3-benzodiazol-2-yl][(3S)-oxolan-3-yl]methyl]pyrazine-2-carboxamide -continued

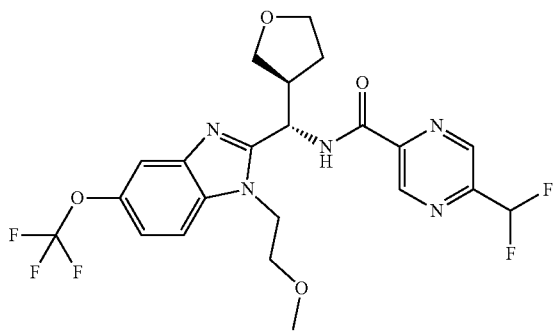 [SMILES: COCCn1c([C@@H](NC(=O)c2cnc(C(F)F)cn2)[C@@H]2CCOC2)nc2cc(OC(F)(F)F)ccc21]

HPLC-MS; Method: Z011_S03; $R_t$ [min]: 1.05   MS: 516 (M + H)$^+$
Chiral SFC Rt Method: Method I_AC_10_IPA_NH3_002   Rt [min]: 1.31
$^1$H NMR (400 MHz, DMSO-d$_6$) δ ppm 1.50-1.63 (m, 1 H) 1.89-2.01 (m, 1 H) 3.15 (s,
  3 H) 3.35-3.46 (m, 1 H) 3.59-3.83 (m, 6 H) 4.47-4.55 (m, 1 H) 4.71-4.80 (m, 1 H)
  5.53 (br t, J = 8.93 Hz, 1 H) 7.20 (m, 1 H) 7.25 (dd, J = 8.74, 1.27 Hz, 1 H) 7.65-7.68 (m,
  1 H) 7.71 (d, J = 8.87 Hz, 1 H) 9.00 (s, 1 H) 9.26-9.30 (m, 1 H) 9.37 (br d, J = 8.24 Hz, 1 H)
    Example 77: 5-(difluoromethyl)-N-[(S)-[1-(2-methoxyethyl)-5-(trifluoromethoxy)-1H-
      1,3-benzodiazol-2-yl][(3R)-oxolan-3-yl]methyl]pyrazine-2-carboxamide

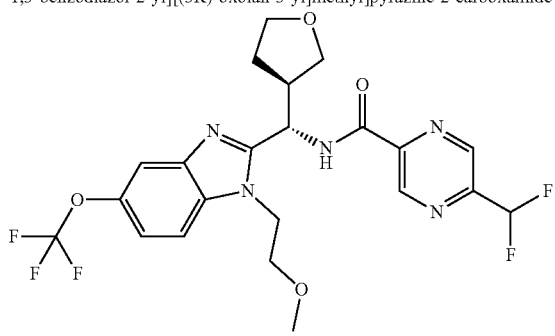

HPLC-MS; Method: Z011_S03; $R_t$ [min]: 1.05   MS: 516 (M + H)$^+$
Chiral SFC Rt Method: Method I_AC_10_IPA_NH3_002   Rt [min]: 2.30
$^1$H NMR (400 MHz, DMSO-d$_6$) δ ppm 1.75-1.84 (m, 1 H) 1.98-2.08 (m, 1 H) 3.12 (s,
  3 H) 3.33-3.49 (m, 2 H) 3.58-3.84 (m, 5 H) 4.43-4.51 (m, 1 H) 4.62-4.72 (m, 1 H)
  5.52 (t, J = 9.57 Hz, 1 H) 7.20 (m, 1 H) 7.23-7.27 (m, 1 H) 7.65-7.71 (m, 2 H) 9.01 (s,
    1 H) 9.29 (s, 1 H) 9.44 (d, J = 9.12 Hz, 1 H)
    Example 23-1: 5-(difluoromethyl)-N-[1-(2-methoxyethyl)-5-(trifluoromethoxy)-1H-1,3-
      benzodiazol-2-yl](oxolan-3-yl)methyl]pyrazine-2-carboxamide

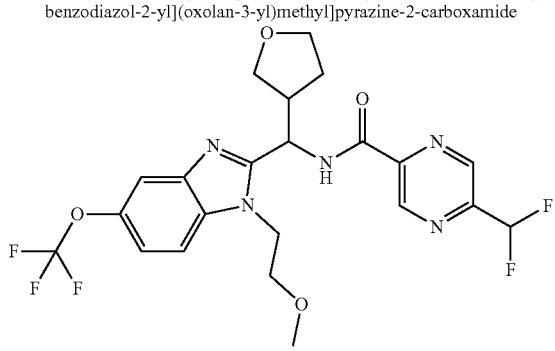

HPLC-MS; Method: Z011_S03; $R_t$ [min]: 1.05   MS: 516 (M + H)$^+$
Chiral SFC Rt Method: Method I_AC_10_IPA_NH3_002   Rt [min]: 1.014
    Example 23-2: 5-(difluoromethyl)-N)-[1-(2-methoxyethyl)-5-(trifluoromethoxy)-1H-
      1,3-benzodiazol-2-yl](oxolan-3-yl)methyl]pyrazine-2-carboxamide

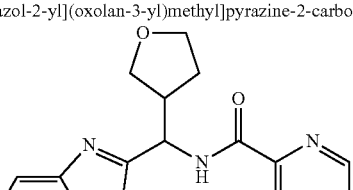

In analogy to example 23 the following compounds are obtained. The product is a mixture of four stereoisomers which are separated by chiral SFC: examples 56, 56-1, 56-2, 75

Example 56: 5-methyl-N-[(R)-[1-methyl-5-(trifluoromethyl)-1H-1,3-benzodiazol-2-yl][(2R)-oxolan-2-yl]methyl]pyrazine-2-carboxamide

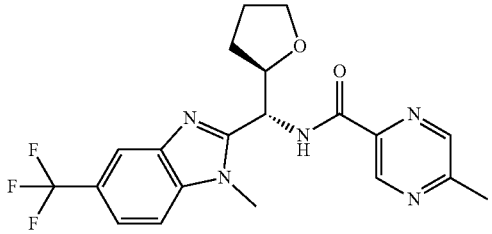

MS: 420 (M + H)⁺
Chiral SFC Rt Method: I_IC_15_MEOH_NH3_002      Rt [min]: 2.02
¹H NMR (400 MHz, DMSO-d₆) δ ppm 1.56-1.82 (m, 3 H) 1.91-2.02 (m, 1 H) 2.61 (s, 3 H) 3.63-3.75 (m, 2 H) 3.95 (s, 3 H) 4.60 (q, J = 6.42 Hz, 1 H) 5.57 (dd, J = 7.98, 6.08 Hz, 1 H) 7.60 (dd, J = 8.62, 1.39 Hz, 1 H) 7.81 (d, J = 8.62 Hz, 1 H) 8.03 (s, 1 H) 8.67 (s, 1 H) 8.96 (d, J = 7.98 Hz, 1 H) 9.07 (d, J = 1.27 Hz, 1 H)

Example 56-1: 5-methyl-N-{[1-methyl-5-(trifluoromethyl)-1H-1,3-benzodiazol-2-yl](oxolan-2-yl)methyl}pyrazine-2-carboxamide

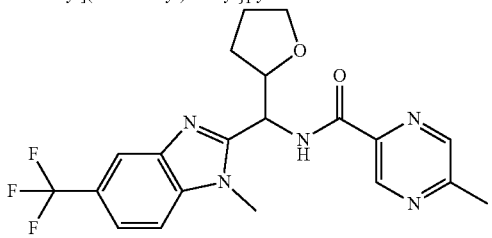

MS: 420 (M + H)⁺
Chiral SFC Rt Method: I_AC_20_IPA_NH3_002       Rt [min]: 0.62

Example 56-2: 5-methyl-N-{[1-methyl-5-(trifluoromethyl)-1H-1,3-benzodiazol-2-yl](oxolan-2-yl)methyl}pyrazine-2-carboxamide

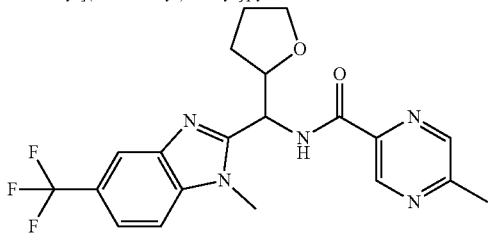

MS: 420 (M + H)⁺
Chiral SFC Rt Method: I_C2_15_MEOH_NH3_002      Rt [min]: 1.48

Example 75: 5-methyl-N-[(R)-[1-methyl-5-(trifluoromethyl)-1H-1,3-benzodiazol-2-yl][(2R)-oxolan-2-yl]methyl]pyrazine-2-carboxamide

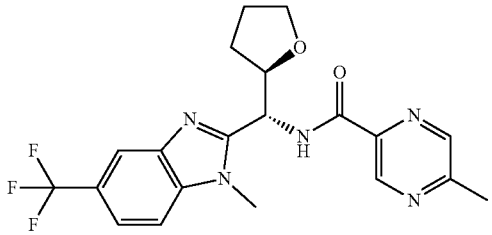

MS: 420 (M + H)⁺
Chiral SFC Rt Method: I_AC_20_IPA_NH3_002       Rt [min]: 0.86
¹H NMR (400 MHz, DMSO-d₆) δ ppm 1.81-2.00 (m, 3 H) 2.06-2.17 (m, 1 H) 2.60 (s, 3 H) 3.62-3.70 (m, 1 H) 3.82-3.90 (m, 1 H) 3.95 (s, 3 H) 4.46-4.55 (m, 1 H) 5.41 (t, J = 8.49 Hz, 1 H) 7.62 (dd, J = 8.62, 1.27 Hz, 1 H) 7.83 (d, J = 8.49 Hz, 1 H) 8.00 (s, 1 H) 8.67 (s, 1 H) 9.04 (d, J = 1.27 Hz, 1 H) 9.24 (d, J = 8.36 Hz, 1 H)

In analogy to example 23 the following compounds are obtained. The product is a mixture of four stereoisomers which are separated by chiral SFC: examples 62, 62-1, 62-2, 62-3

Example 62: N-[(S)-[1-(2-methoxyethyl)-5-(trifluoromethoxy)-1H-1,3-benzodiazol-2-yl][(3R)-oxolan-3-yl]methyl]-5-methylpyrazine-2-carboxamide

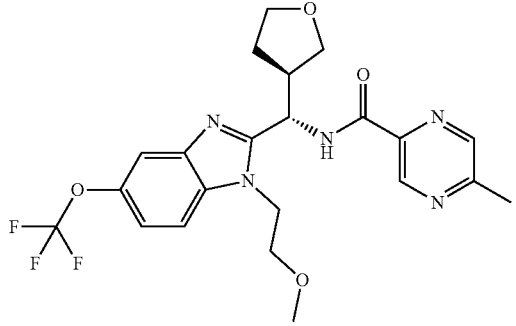 [SMILES: COCCn1c([C@@H](NC(=O)c2cnc(C)cn2)[C@H]2CCOC2)nc2cc(OC(F)(F)F)ccc21]

HPLC-MS; Method: Z011_S03; R$_t$ [min]: 1.00     MS: 480 (M + H)$^+$
Chiral SFC Rt Method: I_SC_10_IPA_NH3_002     Rt [min]: 1.67
$^1$H NMR (400 MHz, DMSO-d$_6$) δ ppm 1.50-1.63 (m, 1 H) 1.88-2.01 (m, 1 H) 2.57 (s, 3 H) 3.10-3.18 (s, 3 H) 3.33-3.44 (m, 1 H) 3.58-3.82 (m, 6 H) 4.41-4.54 (m, 1 H) 4.69-4.83 (m, 1 H) 5.51 (t, J = 9.25 Hz, 1 H) 7.25 (d, J = 8.84 Hz, 1 H) 7.66 (d, J = 0.76 Hz, 1 H) 7.69 (d, J = 8.87 Hz, 1 H) 8.59 (s, 1 H) 9.05 (d, J = 1.14 Hz, 1 H) 9.12 (d, J = 9.00 Hz, 1 H)

Example 62-1: N-{[1-(2-methoxyethyl)-5-(trifluoromethoxy)-1H-1,3-benzodiazol-2-yl](oxolan-3-yl)methyl}-5-methylpyrazine-2-carboxamide

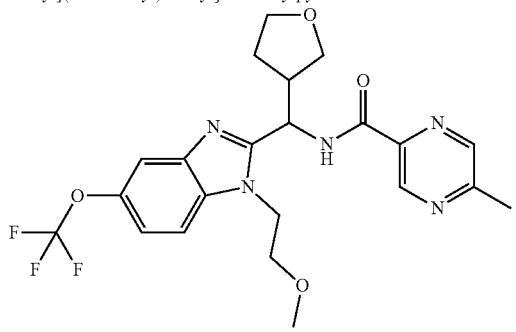

HPLC-MS; Method: Z011_S03; R$_t$ [min]: 1.00     MS: 480 (M + H)$^+$
Chiral SFC Rt Method: I_SC_10_IPA_NH3_002     Rt [min]: 1.20

Example 62-2: N-{[1-(2-methoxyethyl)-5-(trifluoromethoxy)-1H-1,3-benzodiazol-2-yl](oxolan-3-yl)methyl}-5-methylpyrazine-2-carboxamide

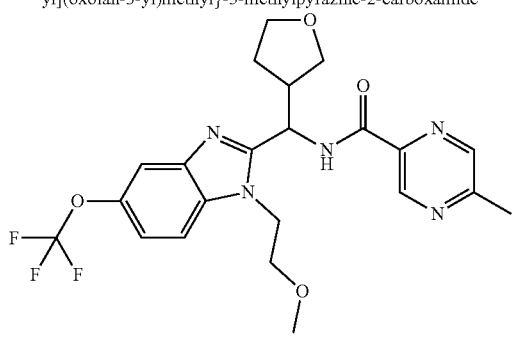

HPLC-MS; Method: Z011_S03; R$_t$ [min]: 1.00     MS: 480 (M + H)$^+$
Chiral SFC Rt Method: I_SC_10_IPA_NH3_002     Rt [min]: 1.12

Example 62-3: N-{[1-(2-methoxyethyl)-5-(trifluoromethoxy)-1H-1,3-benzodiazol-2-yl](oxolan-3-yl)methyl}-5-methylpyrazine-2-carboxamide

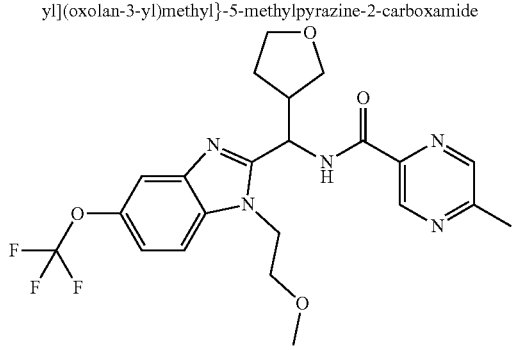

HPLC-MS; Method: Z011_S03; R$_t$ [min]: 1.00     MS: 480 (M + H)$^+$
Chiral SFC Rt Method: I_SC_10_IPA_NH3_002     Rt [min]: 1.92

In analogy to example 23 the following compounds are obtained. The product is a mixture of four stereoisomers which are separated by chiral SFC: examples 82, 82-1, 82-2, 82-3

Example 82: 5-methyl-N-[(S)-[1-methyl-5-(trifluoromethyl)-1H-1,3-benzodiazol-2-yl][(3R)-oxan-3-yl]methyl]pyrazine-2-carboxamide

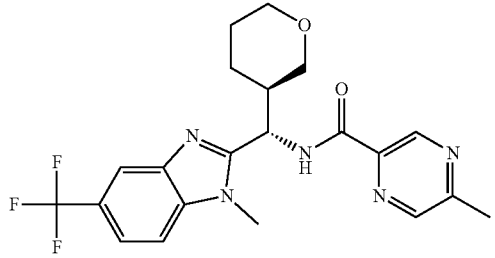 [SMILES: Cc1cnc(C(=O)N[C@H](c2nc3cc(C(F)(F)F)ccc3n2C)[C@H]2CCCOC2)cn1]

HPLC-MS; Method: Z011_S03; $R_t$ [min]: 0.98   MS: 434 (M + H)$^+$
Chiral SFC Rt Method: I_AC_15_IPA_NH3_002   Rt [min]: 1.03
$^1$H NMR (400 MHz, DMSO-d$_6$) δ ppm 1.41-1.57 (m, 2 H) 1.62-1.73 (m, 1 H) 1.82-1.95 (m, 1 H) 2.59 (s, 3 H) 3.16-3.24 (m, 1 H) 3.36-3.47 (m, 2 H) 3.62-3.47 (m, 2 H) 3.91 (s, 3 H) 5.49 (t, J = 9.00 Hz, 1 H) 7.58 (d, J = 7.92 Hz, 1 H) 7.78 (d, J = 8.49 Hz, 1 H) 8.02 (s, 1 H) 8.60-8.67 (m, 1 H) 9.05 (d, J = 1.27 Hz, 1 H) 9.12 (d, J = 8.87 Hz, 1 H)

Example 82-1: 5-methyl-N-{[1-methyl-5-(trifluoromethyl)-1H-1,3-benzodiazol-2-yl](oxan-3-yl)methyl}pyrazine-2-carboxamide

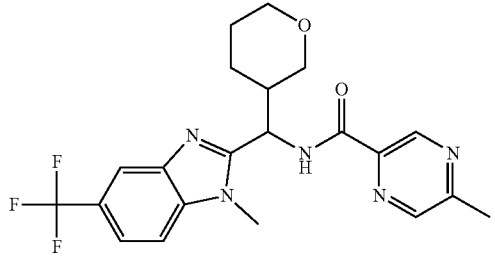 [SMILES: Cc1cnc(C(=O)NC(c2nc3cc(C(F)(F)F)ccc3n2C)C2CCCOC2)cn1]

HPLC-MS; Method: Z011_S03; $R_t$ [min]: 0.98   MS: 434 (M + H)$^+$
Chiral SFC Rt Method: I_AC_15_IPA_NH3_002   Rt [min]: 1.36

Example 82-2: 5-methyl-N-{[1-methyl-5-(trifluoromethyl)-1H-1,3-benzodiazol-2-yl](oxan-3-yl)methyl}pyrazine-2-carboxamide

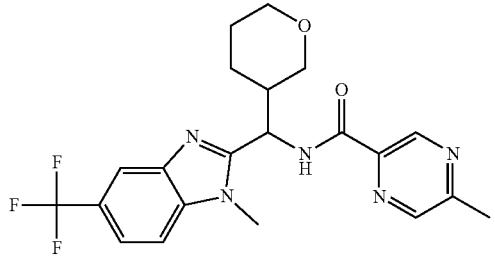 [SMILES: Cc1cnc(C(=O)NC(c2nc3cc(C(F)(F)F)ccc3n2C)C2CCCOC2)cn1]

HPLC-MS; Method: Z011_S03; $R_t$ [min]: 0.98   MS: 434 (M + H)$^+$
Chiral SFC Rt Method: I_AC_15_IPA_NH3_002   Rt [min]: 1.96

Example 82-3: 5-methyl-N-{[1-methyl-5-(trifluoromethyl)-1H-1,3-benzodiazol-2-yl](oxan-3-yl)methyl}pyrazine-2-carboxamide

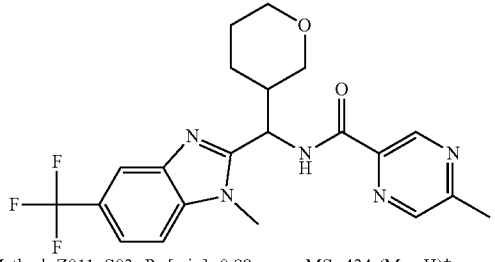

HPLC-MS; Method: Z011_S03; $R_t$ [min]: 0.98   MS: 434 (M + H)$^+$
Chiral SFC Rt Method: I_AC_15_IPA_NH3_002   Rt [min]: 0.7

In analogy to example 23 the following compounds are obtained. The product is a mixture of four stereoisomers which are separated by chiral SFC: 87, 87-1, 87-2, 87-3

Example 87: N-[(S)-[1-(2-methoxyethyl)-5-(trifluoromethyl)-1H-1,3-benzodiazol-2-yl][(3R)-oxolan-3-yl]methyl]-5-methylpyrazine-2-carboxamide

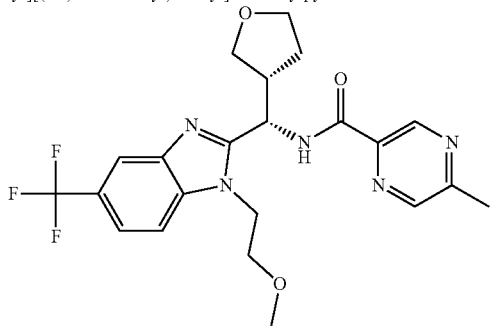

HPLC-MS; Method: Z011_S03; R$_t$ [min]: 0.99     MS: 464 (M + H)$^+$
Chiral SFC Rt Method: I_SC_15_IPA_NH3_001     Rt [min]: 2.76
$^1$H NMR (400 MHz, DMSO-d$_6$) δ ppm 1.51-1.63 (m, 1 H) 1.90-2.00 (m, 1 H) 2.54-2.61 (m, 3 H) 3.13 (s, 3 H) 3.33-3.45 (m, 1 H) 3.60-3.85 (m, 6 H) 4.53 (dt, J = 15.24, 3.91 Hz, 1 H) 4.78 (ddd, J = 15.21, 7.54, 4.63 Hz, 1 H) 5.54 (t, J = 9.25 Hz, 1 H) 7.57 (d, J = 8.62 Hz, 1 H) 7.81 (d, J = 8.49 Hz, 1 H) 8.02 (s, 1 H) 8.60 (s, 1 H) 9.05 (s, 1 H) 9.17 (d, J = 9.12 Hz, 1 H)

Example 87-1: N-{[1-(2-methoxyethyl)-5-(trifluoromethyl)-1H-1,3-benzodiazol-2-yl](oxolan-3-yl)methyl}-5-methylpyrazine-2-carboxamide

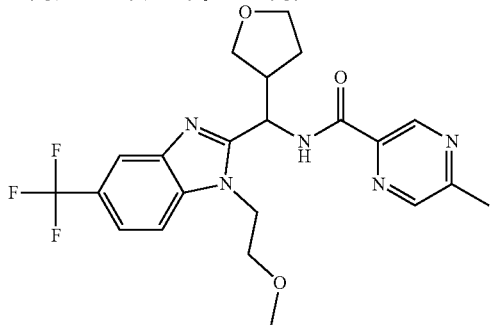

HPLC-MS; Method: Z011_S03; R$_t$ [min]: 0.99     MS: 464 (M + H)$^+$
Chiral SFC Rt Method: I_SC_15_IPA_NH3_001     Rt [min]: 2.04
$^1$H NMR (400 MHz, DMSO-d$_6$) δ ppm 1.74-1.83 (m, 1 H) 1.97-2.07 (m, 1 H) 2.58 (s, 3 H) 3.11 (s, 3 H) 3.33-3.40 (m, 1 H) 3.40-3.54 (m, 1 H) 3.58-3.71 (m, 3 H) 3.71-3.93 (m, 2 H) 4.50 (dt, J = 15.27, 4.21 Hz, 1 H) 4.70 (ddd, J = 15.18, 7.64, 4.44 Hz, 1 H) 5.53 (t, J = 9.57 Hz, 1 H) 7.57 (dd, J = 8.55, 1.33 Hz, 1 H) 7.80 (d, J = 8.62 Hz, 1 H) 8.02 (s, 1 H) 8.58-8.63 (m, 1 H) 9.07 (d, J = 1.27 Hz, 1 H) 9.24 (d, J = 9.12 Hz, 1 H)

Example 87-2: N-{[1-(2-methoxyethyl)-5-(trifluoromethyl)-1H-1,3-benzodiazol-2-yl](oxolan-3-yl)methyl}-5-methylpyrazine-2-carboxamide

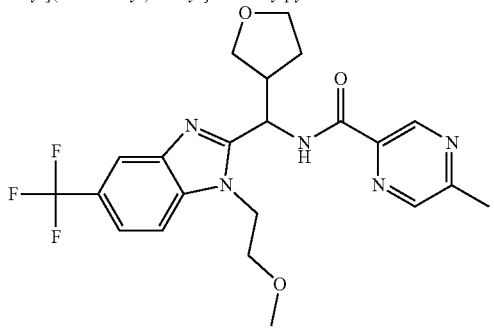

HPLC-MS; Method: Z011_S03; R$_t$ [min]: 0.99     MS: 464 (M + H)$^+$
Chiral SFC Rt Method: I_SC_15_IPA_NH3_001     Rt [min]: 2.04

Example 87-3: N-{[1-(2-methoxyethyl)-5-(trifluoromethyl)-1H-1,3-benzodiazol-2-yl](oxolan-3-yl)methyl}-5-methylpyrazine-2-carboxamide

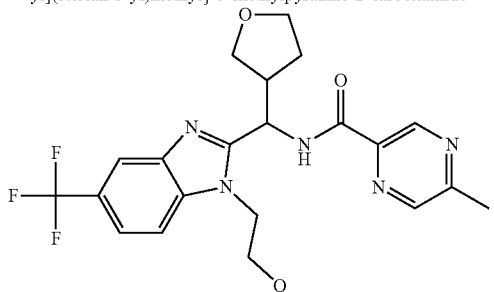

In analogy to example 23 the following compounds are obtained. The product is a mixture of four stereoisomers which are separated by chiral SFC: examples 90, 90-1, 90-2, 102

Example 90: 5-(difluoromethyl)-N-[(S)-[1-(2-methoxyethyl)-5-(trifluoromethyl)-1H-1,3-benzodiazol-2-yl][(3S)-oxolan-3-yl]methyl]pyrazine-2-carboxamide

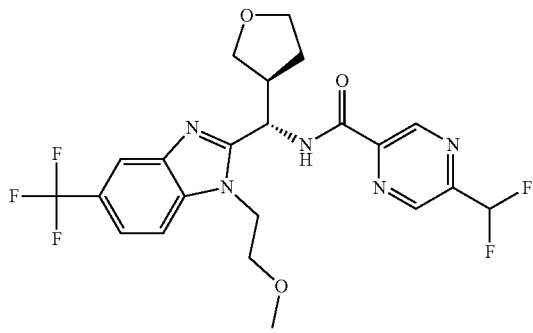 [SMILES: COCCn1c([C@@H](NC(=O)c2cnc(C(F)F)cn2)[C@@H]2CCOC2)nc2cc(C(F)(F)F)ccc21]

HPLC-MS; Method: Z011_S03; R$_t$ [min]: 1.03     MS: 500 (M + H)$^+$
Chiral SFC Rt Method: I_AC_10_IPA_NH3_002     Rt [min]: 1.68
$^1$H NMR (400 MHz, DMSO-d$_6$) δ ppm 1.51-1.65 (m, 1 H) 1.88-2.02 (m, 1 H) 3.14 (s, 3 H) 3.38-3.48 (m, 1 H) 3.60-3.74 (m, 4 H) 3.74-3.85 (m, 2 H) 4.49-4.58 (m, 1 H) 4.73-4.85 (m, 1 H) 5.49-5.62 (m, 1 H) 7.19 (m, 1 H) 7.55-7.60 (m, 1 H) 7.82 (d, J = 8.62 Hz, 1 H) 8.03 (s, 1 H) 9.00 (s, 1 H) 9.28 (s, 1 H) 9.43 (br s, 1 H)

Example 90-1: 5-(difluoromethyl)-N-{[1-(2-methoxyethyl)-5-(trifluoromethyl)-1H-1,3-benzodiazol-2-yl](oxolan-3-yl)methyl}pyrazine-2-carboxamide

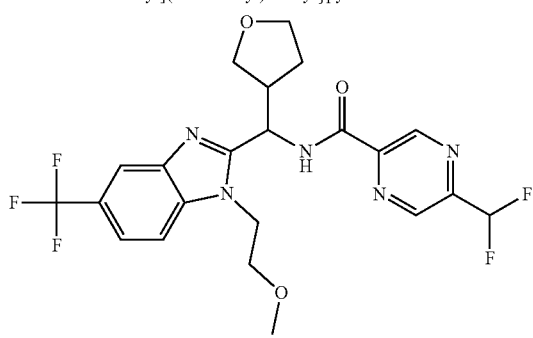

HPLC-MS; Method: Z011_S03; R$_t$ [min]: 1.03     MS: 500 (M + H)$^+$
Chiral SFC Rt Method: I_AC_10_IPA_NH3_002     Rt [min]: 0.71

Example 90-2: 5-(difluoromethyl)-N-{[1-(2-methoxyethyl)-5-(trifluoromethyl)-1H-1,3-benzodiazol-2-yl](oxolan-3-yl)methyl}pyrazine-2-carboxamide

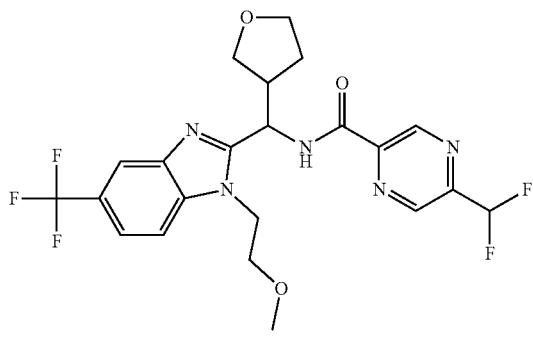 [SMILES: COCCn1c(C(NC(=O)c2cnc(C(F)F)cn2)C2CCOC2)nc2cc(C(F)(F)F)ccc21]

HPLC-MS; Method: Z011_S03; R$_t$ [min]: 1.03     MS: 500 (M + H)$^+$
Chiral SFC Rt Method: I_AC_10_IPA_NH3_002     Rt [min]: 1.32

Example 102: 5-(difluoromethyl)-N-[(S)-[1-(2-methoxyethyl)-5-(trifluoromethyl)-1H-1,3-benzodiazol-2-yl][(3R)-oxolan-3-yl]methyl]pyrazine-2-carboxamide

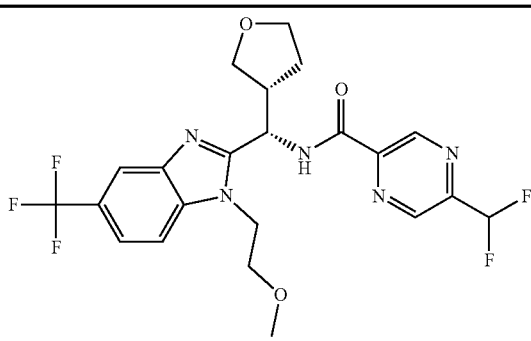

HPLC-MS; Method: Z011_S03; R$_t$ [min]: 1.03    MS: 500 (M + H)$^+$
Chiral SFC Rt Method: I_AC_10_IPA_NH3_002    Rt [min]: 1.02
$^1$H NMR (400 MHz, DMSO-d$_6$) δ ppm 1.76-1.86 (m, 1 H) 1.99-2.09 (m, 1 H) 3.11 (s, 3 H) 3.33-3.39 (m, 1 H) 3.41-3.53 (m, 1 H) 3.59-3.72 (m, 3 H) 3.72-3.87 (m, 2 H) 4.45-4.56 (m, 1 H) 4.65-4.75 (m, 1 H) 5.51-5.60 (m, 1 H) 7.20 (m, 1 H) 7.54-7.61 (m, 1 H) 7.81 (d, J = 8.49 Hz, 1 H) 8.02 (s, 1 H) 9.01 (s, 1 H) 9.30 (s, 1 H) 9.51 (d, J = 9.00 Hz, 1 H)

In analogy to example 23 the following compounds are obtained.

Example 92: N-[(1S)-1-(5-chloro-1-cyclopropyl-1H-1,3-benzodiazol-2-yl)-2-cyclopropylethyl]-5-methylpyrazine-2-carboxamide

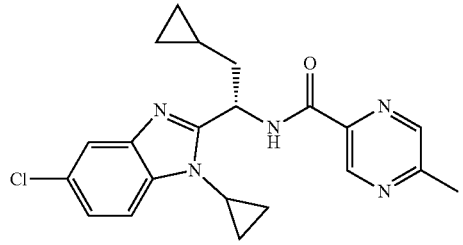 [SMILES: Cc1cnc(C(=O)N[C@@H](CC2CC2)c2nc3cc(Cl)ccc3n2C2CC2)cn1]

HPLC-MS; Method: Z011_S03; R$_t$ [min]: 1.07    MS: 396 (M + H)$^+$
Chiral SFC Rt Method: I_SC_25_MEOH_NH3_001    Rt [min]: 3.26
$^1$H NMR (400 MHz, DMSO-d$_6$) δ ppm −0.07−−0.01 (m, 1 H) 0.08-0.16 (m, 1 H) 0.29-0.44 (m, 2 H) 0.69-0.81 (m, 1 H) 1.02-1.14 (m, 1 H) 1.20-1.36 (m, 3 H) 1.98 (ddt, J = 49.85, 13.89, 6.97, 6.97 Hz, 2 H) 2.57-2.62 (m, 3 H) 3.36-3.47 (m, 1 H) 5.73 (q, J = 7.10 Hz, 1 H) 7.28 (dd, J = 8.62, 2.03 Hz, 1 H) 7.60 (d, J = 8.62 Hz, 1 H) 7.67 (d, J = 1.90 Hz, 1 H) 8.65 (d, J = 1.01 Hz, 1 H) 9.01 (d, J = 8.11 Hz, 1 H) 9.04 (d, J = 1.39 Hz, 1 H)

In analogy to example 23 the following compounds are obtained. The product is a mixture of four stereoisomers which are separated by chiral SFC: examples 103, 103-1, 103-2, 103-3

Example 103: N-[(S)-[1-(2-methoxyethyl)-5-(trifluoromethyl)-1H-1,3-benzodiazol-2-yl][(3R)-oxan-3-yl]methyl]-5-methylpyrazine-2-carboxamide -continued

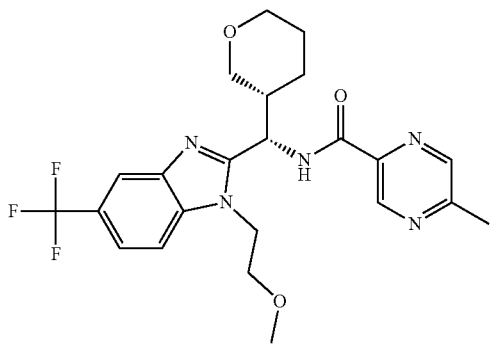 [SMILES: COCCn1c([C@@H](NC(=O)c2cnc(C)cn2)[C@H]2CCCOC2)nc2cc(C(F)(F)F)ccc21]

HPLC-MS; Method: Z011_S03; R$_t$ [min]: 1.02    MS: 478 (M + H)$^+$
Chiral SFC Rt Method: I_IG_20_MEOH_NH3_001    Rt [min]: 4.12
$^1$H NMR (400 MHz, DMSO-d$_6$) δ ppm 1.40-1.54 (m, 2 H) 1.61-1.75 (m, 1 H) 1.85-1.98 (m, 1 H) 2.58 (s, 3 H) 3.12-3.22 (m, 4 H) 3.37-3.50 (m, 2 H) 3.60-3.75 (m, 4 H) 4.49-4.74 (m, 2 H) 5.53 (t, J = 9.38 Hz, 1 H) 7.57 (d, J = 7.60 Hz, 1 H) 7.81 (d, J = 8.49 Hz, 1 H) 8.02 (s, 1 H) 8.61 (s, 1 H) 8.99 (d, J = 9.25 Hz, 1 H) 9.06 (s, 1 H)
Example 103-1: N-{[1-(2-methoxyethyl)-5-(trifluoromethyl)-1H-1,3-benzodiazol-2-yl](oxan-3-yl)methyl}-5-methylpyrazine-2-carboxamide

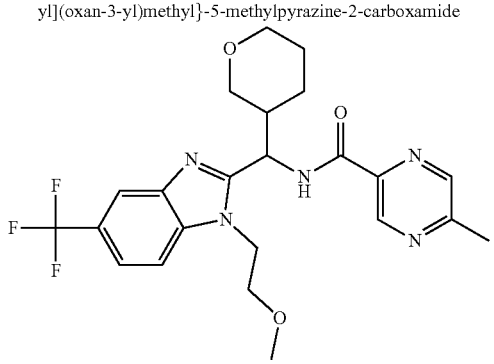

HPLC-MS; Method: Z011_S03; R$_t$ [min]: 1.02    MS: 478 (M + H)$^+$
Chiral SFC Rt Method: I_SA_10_MEOH_NH3_001    Rt [min]: 2.23
Example 103-2: N-{[1-(2-methoxyethyl)-5-(trifluoromethyl)-1H-1,3-benzodiazol-2-yl](oxan-3-yl)methyl}-5-methylpyrazine-2-carboxamide

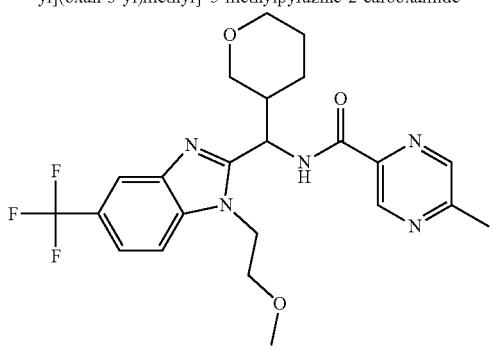

HPLC-MS; Method: Z011_S03; R$_t$ [min]: 1.02    MS: 478 (M + H)$^+$
Chiral SFC Rt Method: I_SA_10_MEOH_NH3_001    Rt [min]: 2.94
Example 103-3: N-{[1-(2-methoxyethyl)-5-(trifluoromethyl)-1H-1,3-benzodiazol-2-yl](oxan-3-yl)methyl}-5-methylpyrazine-2-carboxamide

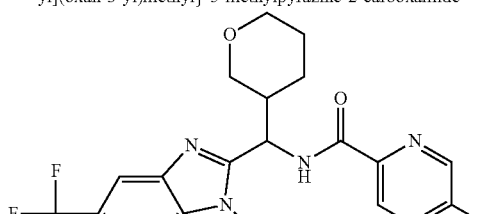

In analogy to example 23 the following compounds are obtained. The product is a mixture of four stereoisomers which are separated with RP-HPLC (SF, TFA, narrow, ACN/H2O) into two pairs of enantiomers: examples 113, 113-1. For example 113 the absolute stereochemistry is only randomly assigned Example 113: 5-(difluoromethyl)-N-[(R)-[1-methyl-5-(trifluoromethoxy)-1H-1,3-benzodiazol-2-yl][(2R)-oxolan-2-yl]methyl]pyrazine-2-carboxamide

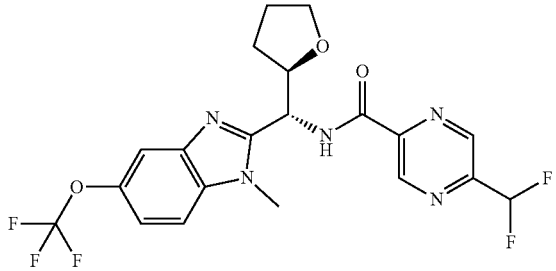 [SMILES: Cn1c([C@@H](NC(=O)c2cnc(C(F)F)cn2)[C@H]2CCCO2)nc2cc(OC(F)(F)F)ccc21]

MS: 472 (M + H)$^+$
$^1$H NMR (400 MHz, DMSO-d$_6$) δ ppm 1.61-2.03 (m, 4 H) 3.56-3.74 (m, 2 H) 3.93 (s, 3 H) 4.57-4.68 (m, 1 H) 5.56 (dd, J = 8.05, 6.40 Hz, 1 H) 7.22 (m, 1 H) 7.30 (dd, J = 8.87, 1.27 Hz, 1 H) 7.66-7.69 (m, 1 H) 7.72 (d, J = 8.74 Hz, 1 H) 9.09 (s, 1 H) 9.14 (d, J = 7.98 Hz, 1 H) 9.29-9.32 (m, 1 H)

Example 113-1: 5-(difluoromethyl)-N-{[1-methyl-5-(trifluoromethoxy)-1H-1,3-benzodiazol-2-yl](oxolan-2-yl)methyl}pyrazine-2-carboxamide

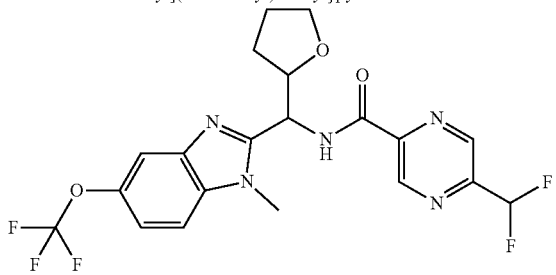

MS: 472 (M + H)$^+$
$^1$H NMR (400 MHz, DMSO-d$_6$) δ ppm 1.61-1.83 (m, 3 H) 1.93-2.03 (m, 1 H) 3.68-3.96 (m, 5 H) 4.62 (q, J = 6.38 Hz, 1 H) 5.56 (dd, J = 8.05, 6.40 Hz, 1 H) 7.08-7.35 (m, 2 H) 7.66-7.69 (m, 1 H) 7.72 (d, J = 8.74 Hz, 1 H) 9.09 (s, 1 H) 9.14 (d, J = 7.98 Hz, 1 H) 9.29-9.32 (m, 1 H)

The following compounds are obtained in analogy to example 23

Example 126: N-[(1R)-2-hydroxy-1-[1-(2-methoxyethyl)-5-(trifluoromethyl)-1H-1,3-benzodiazol-2-yl]-2-methylpropyl]-5-methylpyrazine-2-carboxamide

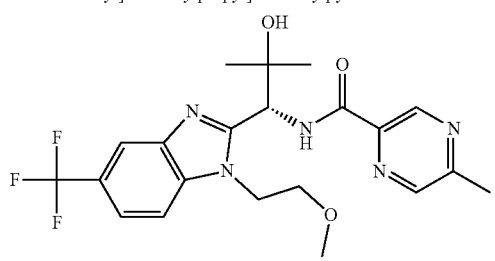

MS: 452 (M + H)$^+$
Chiral SFC Rt Method: I_IG_10_MEOH_NH3_002    Rt [min]: 1.09
$^1$H NMR (400 MHz, DMSO-d$_6$) δ ppm 1.22 (s, 3 H) 1.26 (s, 3 H) 2.60 (s, 3 H) 3.16 (s, 3 H) 3.67-3.75 (m, 2 H) 4.63-4.82 (m, 2 H) 5.27 (s, 1 H) 5.55 (d, J = 9.38 Hz, 1 H) 7.58 (dd, J = 8.62, 1.39 Hz, 1 H) 7.84 (d, J = 8.49 Hz, 1 H) 8.05 (s, 1 H) 8.67 (s, 1 H) 8.71 (d, J = 9.38 Hz, 1 H) 9.08 (d, J = 1.27 Hz, 1 H)

Example 130: N-[(1R,2R)-2-methoxy-1-[1-(3-methoxypropyl)-5-(trifluoromethoxy)-1H-1,3-benzodiazol-2-yl]propyl]-5-methylpyrazine-2-carboxamide

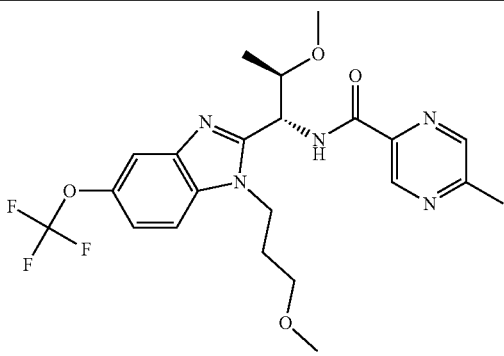

HPLC-MS; Method: Z011_S03; R_t [min]: 1.10    MS: 482 (M + H)+
Chiral SFC Rt Method: I_IG_10_IPA_NH3_002    Rt [min]: 2.10
$^1$H NMR (400 MHz, DMSO-$d_6$) δ ppm 1.00-1.15 (m, 3 H) 1.91-2.12 (m, 2 H) 2.59-
2.62 (m, 3 H) 3.19-3.25 (m, 3 H) 3.25-3.37 (m, 5 H) 3.97-4.09 (m, 1 H) 4.35-4.53
(m, 2 H) 5.47-5.53 (m, 1 H) 7.27 (d, J = 8.85 Hz, 1 H) 7.68 (s, 1 H) 7.69 (d, J = 9.51 Hz,
2 H) 8.65-8.69 (m, 1 H) 8.90 (d, J = 8.11 Hz, 1 H) 9.04-9.09 (m, 1 H)
Example 131: N-[(1R,2R)-1-[1-cyclopropyl-5-(trifluoromethoxy)-1H-1,3-benzodiazol-
2-yl]-2-methoxypropyl]-5-methylpyrazine-2-carboxamide

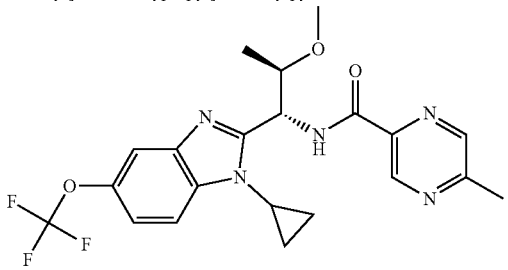

HPLC-MS; Method: Z011_S03; R_t [min]: 1.09    MS: 450 (M + H)+
Chiral SFC Rt Method: I_IG_15_IPA_NH3_002    Rt [min]: 1.29
$^1$H NMR (400 MHz, DMSO-$d_6$) δ ppm 1.07-1.17 (m, 3 H) 1.21-1.36 (m, 4 H) 2.57-
2.62 (m, 3 H) 3.31 (s, 3 H) 3.44-3.52 (m, 1 H) 3.99-4.11 (m, 1 H) 5.68-5.75 (m, 1 H)
7.27 (d, J = 8.61 Hz, 1 H) 7.64 (s, 1 H) 7.70 (d, J = 8.31 Hz, 1 H) 8.66-8.70 (m, 1 H)
8.80 (d, J = 8.36 Hz, 1 H) 9.04-9.07 (m, 1 H)

Example 33

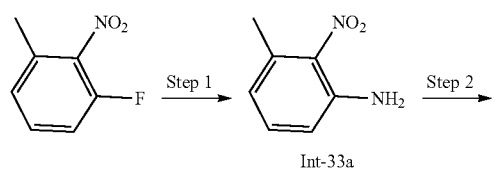

Int-33a

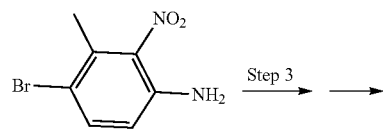

Int-33b

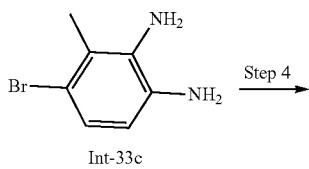

Int-33c

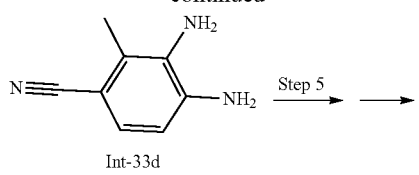

Int-33d

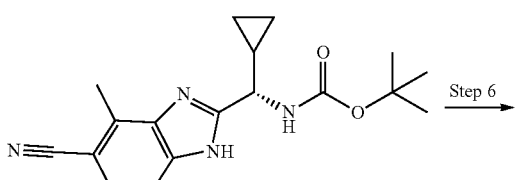

Int-33e

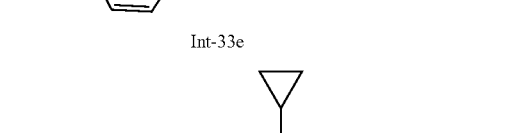

Int-33f

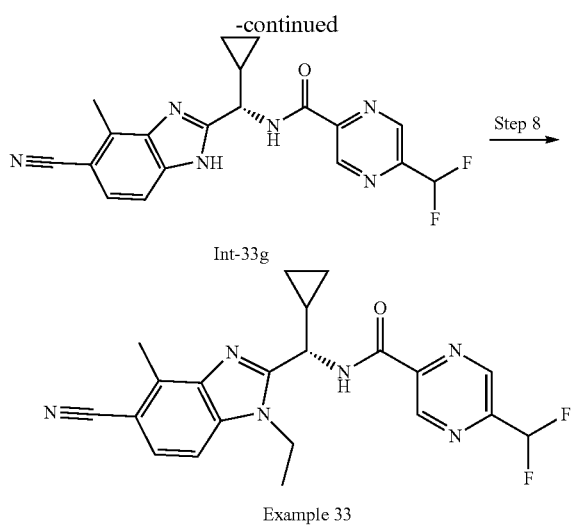

Int-33g

Example 33

Step 1:

A mixture with 1-fluoro-3-methyl-2-nitro-benzene (5.0 g, 32 mmol) and aq. NH$_3$ solution (32%, 15 mL, 248 mmol) in 30 mL ACN is stirred for 4 d at 100° C. in an autoclave. Afterwards, water is added and the mixture is concentrated i. vac. The formed solid is filtered off and washed with water and dried. The product is used without further purification.

Yield: 4.0 g (26 mmol; 81%) Int-33a

MS (ESI$^+$): (M+H)$^+$ 153; HPLC: RT=0.87 min, Method: Z018_S04

Step 2:

Int-33a (4.0 g, 26 mmol) in 40 mL ACN is mixed with NBS (4.7 g, 26 mmol) and the mixture stirred at ambient temperature for 30 min. Water is added and the mixture is concentrated i. vac. The formed solid is filtered off, washed with water and dried. The product is used without further purification.

Yield: 6.0 g (26 mmol; quant.) Int-33b

MS (ESI$^+$): (M+H)$^+$ 231/233 (Br); HPLC: RT=1.01 min, Method: Z018_S04

Step 3:

A mixture of Int-33b (6.0 g, 26 mmol) with Raney-nickel (600 mg) in 60 mL THF is hydrogenated at ambient temperature at 50 psi hydrogen pressure. The mixture is filtered and the filtrate is concentrated i. vac. The residue is used without further purification.

Yield: 5.2 g (25.6 mmol; 98%) Int-33c

MS (ESI$^+$): (M+H)$^+$ 201/203 (Br); HPLC: RT=0.79 min, Method: Z018_S04

Step 4:

A mixture of Int-33c (3.0 g, 14.9 mmol) with Zn(CN)$_2$ (2.5 g, 21.3 mmol) and XPhos-G1 (500 mg, 0.68 mmol) in 10 mL NMP is stirred at 100° C. for 1 h. After cooling, the mixture is poured into 150 mL water, 10 mL DCM added, stirred vigorously and filtered. The aq. phase is separated and extracted with DCM, the combined organic layers are dried over MgSO$_4$ and concentrated i. vac. The solid from the filtration is washed with MeOH, the extracts combined with the residue from the extraction and concentrated i. vac. The residue is purified via prep. HPLC (X-Bridge C-18, eluent-gradient (H$_2$O+0.15% NH$_3$):ACN 95:5→75:25. The product containing fractions are combined and concentrated i. vac. Yield: 1.74 g (11.8 mmol; 79%) Int-33 d MS (ESI$^+$): (M+H)$^+$ 148; HPLC: RT=0.55 min, Method: Z011_S03

Step 5:

A mixture of Int-33d (500 mg, 3.4 mmol) and (2S)-2-Boc-amino-2-cyclopropyl-acetic acid (750 mg, 3.5 mmol) in 6.0 mL pyridine is stirred at 0° C. and PPA (50% in EtOAc, 3.0 mL, 5.1 mmol) is added. After 15 min at 0° C., the mixture is stirred at ambient temperature for 30 min. Water and DCM are added, the aq. phase extracted with DCM and the combined organic layers dried over MgSO$_4$ and concentrated i. vac. The residue is taken up with dioxane and freeze-dried. The residue is taken up in 10 mL AcOH and stirred at ambient temperature for 4 d. The mixture is purified via prep. HPLC (Sunfire C-18 at 50° C., eluent gradient (H$_2$O+0.15% TFA):ACN 80:20→60:40). The product containing fractions are combined and freeze-dried.

Yield: 1.3 g (3.0 mmol, 88%) Int-33e

MS (ESI$^+$): (M+H)$^+$ 327; HPLC: RT=0.83 min, Method: Z018_S04

Step 6:

Int-33e (1.3 g, 3 mmol) is stirred in a HCl in dioxane (4N, 10 mL, 40 mmol) at ambient temperature for 1 h. The mixture is concentrated i. vac. and the residue used without further purification.

Yield: 900 mg (3 mmol, quant.) Int-33f. MS (ESI$^+$): (M+H)$^+$ 227; HPLC: RT=0.66 min, Method: Z018_S04

Step 7:

To a mixture of Int-33f (225 mg, 0.75 mmol) with 5-(difluoromethyl)-pyrazine-2-carboxylic acid (160 mg, 0.92 mmol) and TEA (550 µL, 4.0 mmol) in 3 mL DMF is added TBTU (260 mg, 0.81 mmol) and the mixture stirred at ambient temperature for 15 min. Water is added and the mixture purified by prep. HPLC (X-Bridge C-18 at 50° C., eluent-gradient (H$_2$O+0.15% NH$_3$):ACN 73:27→53:47). The product containing fractions are combined and freez-edried.

Yield: 220 mg (0.58 mmol, 77%) Int-33 g

MS (ESI$^+$): (M+H)$^+$ 383; HPLC: RT=0.85 min, Method: Z018_S04

Step 8:

Int-33f (100 mg, 0.26 mmol) is stirred together with ethyl 4-methylbenzene-1-sulfonate (55 mg, 0.28 mmol) and Cs$_2$CO$_3$ (200 mg, 0.61 mmol) in 2 mL DMF at ambient temperature for 40 h. Then, ethyl 4-methylbenzene-1-sulfonate (50 mg, 0.25 mmol) is added and stirred at ambient temperature for 24 h. Then, THF is added to the mixture and the resulting mixture filtered and the filtrate purified via prep. HPLC (X-Bridge C-18 at 50° C., eluent-gradient (H$_2$O+0.15% NH$_3$):ACN 6:4→4:6). The product containing fractions are combined and concentrated i. vac. The residue is further purified by chiral SFC. Yield: 52 mg (0.10 mmol, 42%) example 33

Example 33: N-[(S)-(5-cyano-1-ethyl-4-methyl-1H-1,3-benzodiazol-2-yl)(cyclopropyl)methyl]-5-(difluoromethyl)pyrazine-2-carboxamide -continued

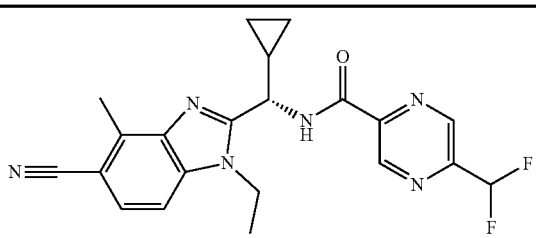

HPLC-MS; Method: Z018_S04; R$_t$ [min]: 0.98  MS: 411 (M + H)$^+$
Chiral SFC Rt Method: Method I_SC_20_IPA_NH3_001  Rt [min]: 2.97
$^1$H NMR (400 MHz, DMSO-d$_6$) δ ppm 0.44-0.66 (m, 4 H) 1.25-1.35 (m, 3 H) 1.74-1.90 (m, 1 H) 2.72 (s, 3 H) 4.31-4.48 (m, 2 H) 4.94 (t, J = 8.55 Hz, 1 H) 7.21 (m, 1 H) 7.56-7.62 (m, 2 H) 9.06 (s, 1 H) 9.27 (s, 1 H) 9.51 (d, J = 7.98 Hz, 1 H)

In analogy to example 33, the following products are obtained:

Example 38: N-[(S)-(5-cyano-1-ethyl-4-methyl-1H-1,3-benzodiazol-2-yl)(cyclopropyl)methyl]-5-methylpyrazine-2-carboxamide

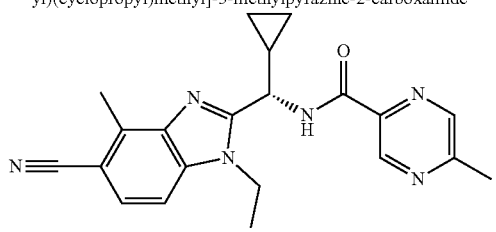

HPLC-MS; Method: Z018_S04; R$_t$ [min]: 0.91  MS: 375 (M + H)$^+$
Chiral SFC Rt Method: I_SA_20_MEOH_NH3_001  Rt [min]: 1.65
$^1$H NMR (400 MHz, DMSO-d$_6$) δ ppm 0.41-0.64 (m, 4 H) 1.28 (t, J = 7.16 Hz, 3 H) 1.75-1.84 (m, 1 H) 2.59 (s, 3 H) 2.72 (s, 3 H) 4.30-4.47 (m, 2 H) 4.92 (t, J = 8.55 Hz, 1 H) 7.55-7.62 (m, 2 H) 8.65 (s, 1 H) 9.04 (d, J = 1.39 Hz, 1 H) 9.25 (d, J = 7.98 Hz, 1 H)

Example 44

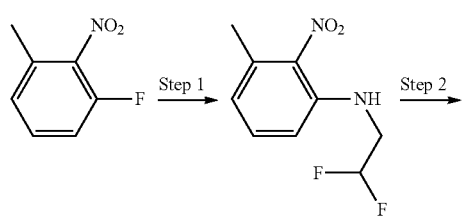

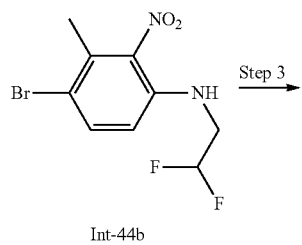

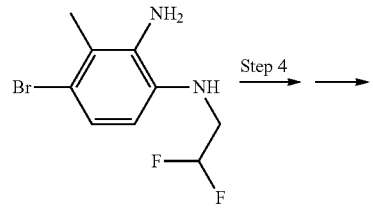

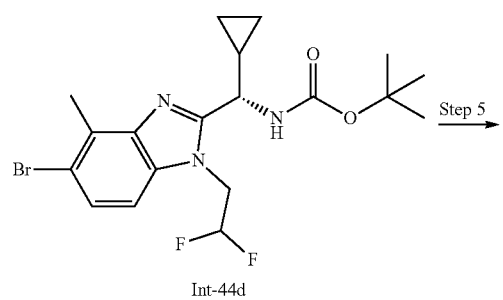

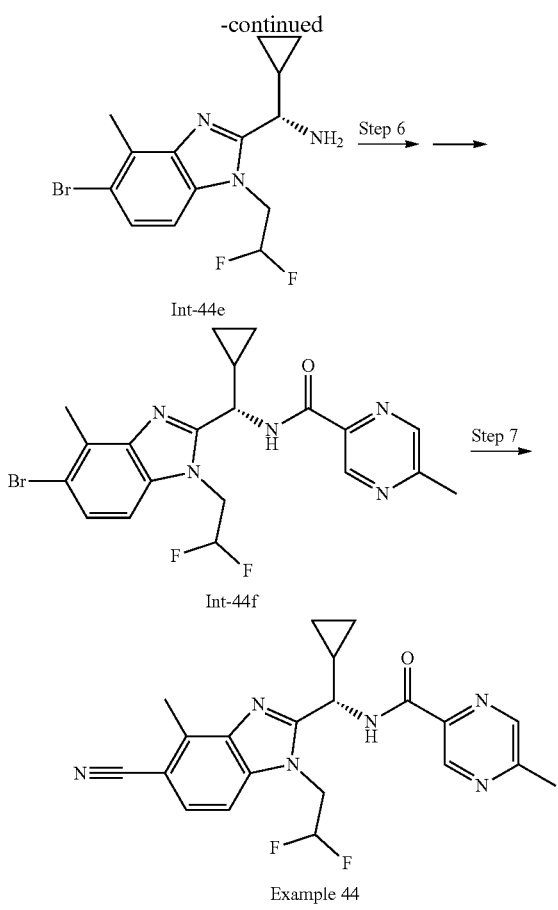

Int-44e

Int-44f

Example 44

Step 1:

A mixture with 1-fluoro-3-methyl-2-nitro-benzene (2.0 g, 13.3 mmol) and difluoroethylamine (4.0 g, 49 mmol) in 10 mL ACN is stirred for 35 h at 140° C. in a microwave oven. Afterwards, the mixture is filtered and the filtrate concentrated i. vac. The residue is taken up with water and DCM, the aq. phase extracted with DCM, the organic layers combined, dried over $MgSO_4$ and concentrated i. vac. Yield: 2.8 g (~90%; 12 mmol; 90%) Int-44a MS (ESI$^+$): (M+H)$^+$ 217; HPLC: RT=1.03 min, Method: Z018_S04

Step 2:

Int-44a (2.8 g, 12 mmol) in 30 mL ACN is mixed with NBS (2.1 g, 12 mmol) and the mixture stirred at ambient temperature for 30 min. Water is added and the mixture purified via prep. HPLC (X-Bridge C-18 at 50° C., eluent-gradient ($H_2O$+0.15% $NH_3$):ACN 5:5→3:7). The product containing fractions are combined and concentrated i. vac., sonicated to form a solid and filtered. The solid is washed with water and dried i. vac. Yield: 2.7 g (9.2 mmol; 78%) Int-44b MS (ESI$^+$): (M+H)$^+$ 295/297 (Br); HPLC: RT=1.12 min, Method: Z018_S04

Step 3:

A mixture of Int-44b (750 mg, 2.5 mmol) with Raney-nickel (100 mg) in 20 mL THF is hydrogenated at ambient temperature at 50 psi hydrogen pressure. Then the mixture is filtered and the filtrate purified via prep. HPLC (X-Bridge C-18 at 50° C., eluent-gradient ($H_2O$+0.15% $NH_3$):ACN 62:38→42:58). The product containing fractions are combined and freezedried. Yield: 540 mg (2.0 mmol; 80%) Int-44c MS (ESI$^+$): (M+H)$^+$ 265/267 (Br); HPLC: RT=0.97 min, Method: Z018_S04

Step 4:

A mixture of Int-44c (150 mg, 0.57 mmol) and (2S)-2-Boc-amino-2-cyclopropyl-acetic acid (125 mg, 0.58 mmol) in 4.0 mL pyridine is stirred at 0° C. and PPA (50% in EtOAc, 600 µL, 1.0 mmol) is added. After 1 h at 0° C., water is added and a precipitate is filtered off, washed with water and taken up with 5 mL AcOH. The mixture is stirred at ambient temperature for 40 h. Then the mixture is stirred at 60° C. for 48 h. The residue is concentrated i. vac., taken up with THF/MeOH, set to basic conditions with TEA and purified via prep. HPLC (X-Bridge C-18, 10 µm, eluent-gradient ($H_2O$+0.1% $NH_3$):ACN 46:54→26:74). The product containing fractions are combined and freeze-dried. Yield: 141 mg (0.32 mmol, 56%) Int-44d MS (ESI$^+$): (M+H)$^+$ 444/446 (Br); HPLC: RT=1.16 min, Method: Z011_S03

Step 5:

Int-44d (141 mg, 0.32 mmol) is stirred in HCl in dioxane (4N, 0.95 mL, 3.8 mmol) at ambient temperature for 16 h. The mixture is concentrated i. vac. and the residue taken up in ACN and again concentrated i. vac. Yield: 128 mg (0.31 mmol, 97%) Int-44e MS (ESI$^+$): (M+H)$^+$ 344/346 (Br); HPLC: RT=0.98 min, Method: Z011_S03

Step 6:

To a mixture of Int-44e (125 mg, 0.30 mmol) with 5-methyl-pyrazine-2-carboxylic acid (46 mg, 0.33 mmol) and TEA (187 µL, 1.3 mmol) in 3.5 mL DMF is added TBTU (101 mg, 0.32 mmol) and the mixture stirred at ambient temperature for 1 h. The mixture is poured into water at 0° C., the mixture stirred for 10 min, the formed solid is filtered and washed with water, taken up in dioxane and freeze-dried.

Yield: 137 mg (0.28 mmol, 94%) Int-44f

MS (ESI$^+$): (M+H)$^+$ 464/466 (Br); HPLC: RT=1.08 min, Method: Z011_S03

Step 7:

A mixture of Int-44f (125 mg, 0.27 mmol) with $Zn(CN)_2$ (65 mg, 0.55 mmol) and XPhos-G1 (20 mg, 27 µmol) in 750 µL NMP under Argon is stirred at 100° C. for 1 h. After cooling, 1 drop of water is added, followed by 2 mL ACN and THF each. The mixture is filtered and purified via prep. HPLC (X-Bridge C-18, 10 µm, eluent-gradient ($H_2O$+0.15% $NH_3$):ACN 65:35→45:55). The product containing fractions are combined and freeze-dried. The residue is purified via chiral SCF.

Yield: 66 mg (0.16 mmol, 64%) example 44

---

Example 44: N-[(S)-[5-cyano-1-(2,2-difluoroethyl)-4-methyl-1H-1,3-benzodiazol-2-yl](cyclopropyl)methyl]-5-methylpyrazine-2-carboxamide HPLC-MS; Method: Z011_S03; R$_t$ [min]: 0.97    MS: 411 (M + H)$^+$
Chiral SFC Rt Method: Method I_SA_15_MEOH_NH3_001    Rt [min]: 1.91
$^1$H NMR (400 MHz, DMSO-d$_6$) δ ppm 0.40-0.66 (m, 4 H) 1.85-1.95 (m, 1 H) 2.59 (s, 3 H) 2.74 (s, 3 H) 4.85-5.11 (m, 3 H) 6.46 (m, 1 H) 7.62 (s, 2 H) 8.63 (s, 1 H) 9.03 (s, 1 H) 9.27 (d, J = 7.86 Hz, 1 H)

Example 57

Step 1:

To a mixture of 1,4,5-trifluoro-2-nitro-benzene (7 mL; 61 mmol) and TEA (21 mL; 153 mmol) in 200 mL DCM is slowly added ethylamine (2M in THF; 33.6 mL; 67 mmol) and the mixture is stirred at ambient temperature for 22 h. Ethylamine (2M in THF; 7 mL; 14 mmol) is added and the mixture stirred at ambient temperature for 6 h. The mixture is washed with water and the organic layer dried over Na$_2$SO$_4$, filtered and concentrated i. vac. The mixture is filtered, and the filtrate is concentrated i. vac. The residue is purified by chromatography (silica gel; eluent gradient petrol ether:EtOAc=90:10→80:20). Product containing fractions are combined and concentrated i. vac.

R$_f$: 0.43 (PE/EtOAc 9:1)

Yield: 5.7 g (28 mmol; 46%) Int-57a

MS (ESI$^+$): (M+H)$^+$ 203; R$_f$: 0.43 (PE/EtOAc 9:1)

Step 2:

A mixture of Int-57a (1.0 g, 4.9 mmol) with 100 mg 10% Pd on charcoal in 20 mL THF is hydrogenated at ambient temperature at 50 psi (hydrogen gas) for 15 h. Afterwards, the mixture is filtered and concentrated i. vac.

Yield: 820 mg (~90% content; 4.8 mmol; 96%) Int-57b

MS (ESI$^+$): (M+H)$^+$ 173; HPLC: RT=0.65 min, Method: Z018_S04

Step 3:

To a mixture of Int-57b (~90%, 330 mg, 1.7 mmol) and (2S)-2-Boc-amino-3-hydroxy-3-methylbutanoic acid (450 mg, 1.9 mmol) in 5 mL DCM with NMM (800 μL, 7.3 mmol) is added PPA (50 wt % in EtOAc, 1.4 mL, 2.3 mmol) at 0° C. The mixture is then stirred at 0° C. for 5 h. Water is added and the mixture concentrated i. vac. The residue is purified by prep. HPLC (XBridge C18, 50° C., eluent gradient: (H$_2$O+0.15% NH$_3$):ACN 59:41→39:61). Product containing fractions are combined and freeze-dried.

Yield: 550 mg (1.4 mmol; 81%) Int-57c

MS (ESI$^+$): (M+H)$^+$ 388; HPLC: RT=1.05 min, Method: Z018_S04

Step 4:

Int-57c (540 mg, 1.4 mmol) is stirred at 70° C. for 30 h in 10 mL AcOH. Afterwards, the mixture is purified by prep. HPLC (Sunfire C18, 50° C., eluent gradient: (H$_2$O+0.15% TFA):ACN 72:28→52:48). Product containing fractions are combined and freeze-dried.

Yield: 510 mg (1.1 mol; 76%) Int-57d

MS (ESI$^+$): (M+H)$^+$ 370; HPLC: RT=0.90 min, Method: Z018_S04

Step 5:

Int-57d (510 mg, 1.1 mmol) in HCl in dioxane (4N, 5 mL, 20 mmol) is stirred at ambient temperature for 30 min. The mixture is then concentrated i. vac., the residue taken up in MeOH, sent through an ion exchange cartridge (Agilent PL-HCO3 MP SPE) and concentrated i. vac. The residue is purified by prep. HPLC (X-Bridge C18, 50° C., eluent gradient: (H$_2$O+0.15% NH$_3$):ACN 79:21→59:41). Product containing fractions are combined and freeze-dried.

Yield: 190 mg (0.71 mmol; 67%) Int-57e

MS (ESI$^+$): (M+H)$^+$ 270; HPLC: RT=0.84 min, Method: Z011_S03

Step 6:

To 5-(difluoromethyl)-pyrazine-carboxylic acid (65 mg, 0.37 mmol) in 4 mL DMF is added Int-57e (80 mg, 0.3 mmol) and TEA (250 μL, 1.8 mmol). TBTU (100 mg, 0.31 mmol) is added and the mixture stirred at ambient temperature for 20 min. Water is added and the mixture is purified by prep. HPLC (XBridge C18, 50° C., eluent gradient: (H$_2$O+0.1% NH$_3$):ACN 58:42→38:62).

Product containing fractions are combined and freeze-dried.

Yield: 78 mg (0.18 mmol; 62%) example 57

Example 60

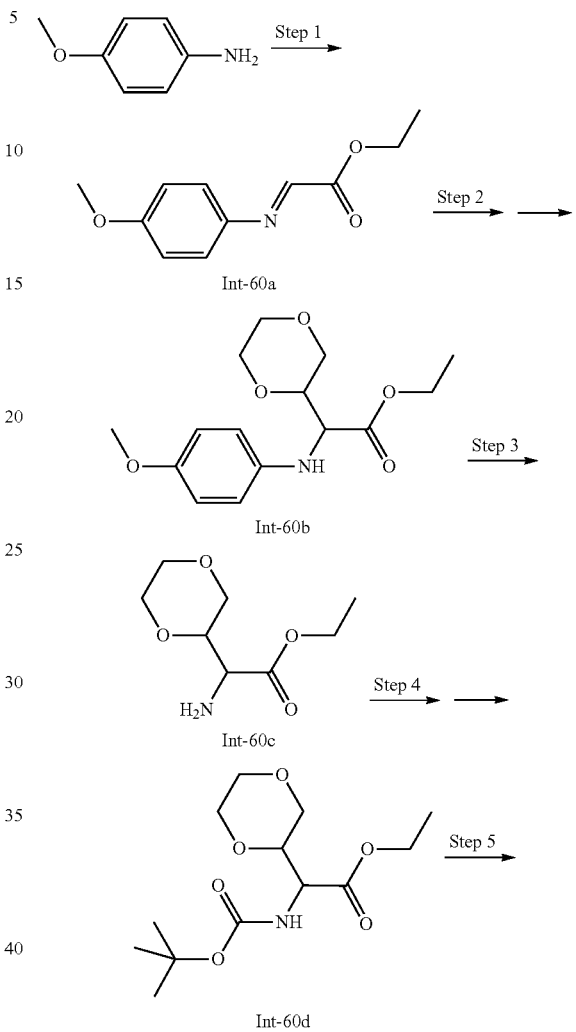

| Example 57: 5-(difluoromethyl)-N-[(1R)-1-(1-ethyl-5,6-difluoro-1H-1,3-benzodiazol-2-yl)-2-hydroxy-2-methylpropyl]pyrazine-2-carboxamide |
|---|

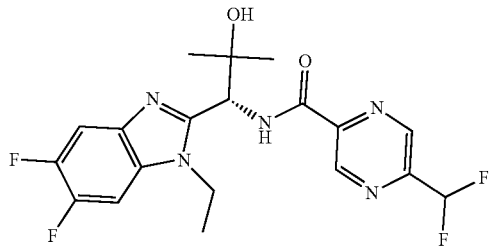 [SMILES: CCn1c([C@@H](NC(=O)c2cnc(C(F)F)cn2)C(C)(C)O)nc2cc(F)c(F)cc21]

| HPLC-MS; Method: Z018_S04; R$_t$ [min]: 0.93 | MS: 426 (M + H)$^+$ |
|---|---|
| Chiral SFC Rt Method: I_IG_15_IPA_NH3_001 | Rt [min]: 1.59 |
| $^1$H NMR (400 MHz, DMSO-d$_6$) δ ppm 1.24-1.27 (m, 6 H) 1.31-1.40 (m, 3 H) 4.37-4.60 (m, 2 H) 5.23 (s, 1 H) 5.40-5.46 (m, 1 H) 7.22 (m, 1 H) 7.73 (dd, J = 11.15, 7.48 Hz, 1 H) 7.84 (dd, J = 10.77, 7.35 Hz, 1 H) 8.80 (d, J = 9.25 Hz, 1 H) 9.11 (s, 1 H) 9.30 (s, 1 H) | |

267
-continued

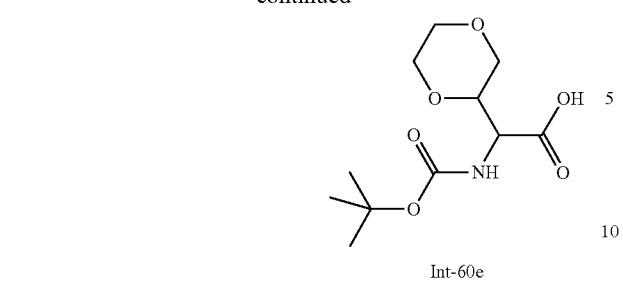
Int-60e

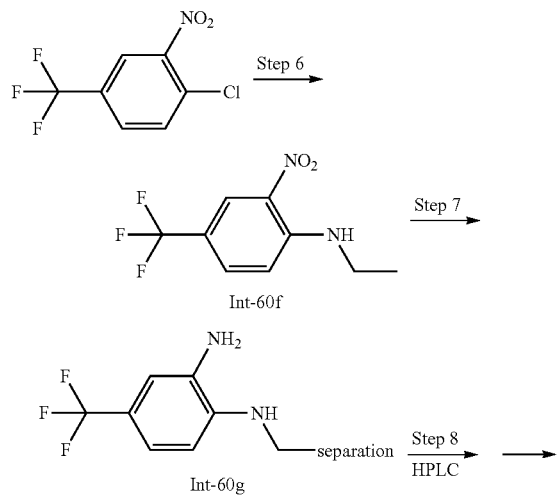
Int-60f

Int-60g

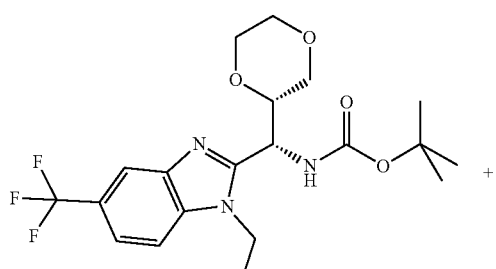

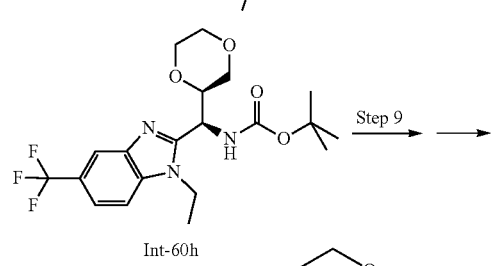
Int-60h

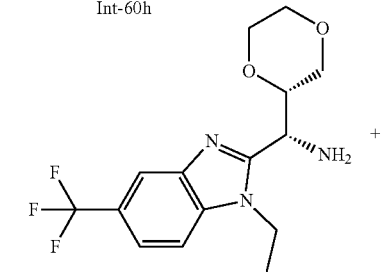

268
-continued

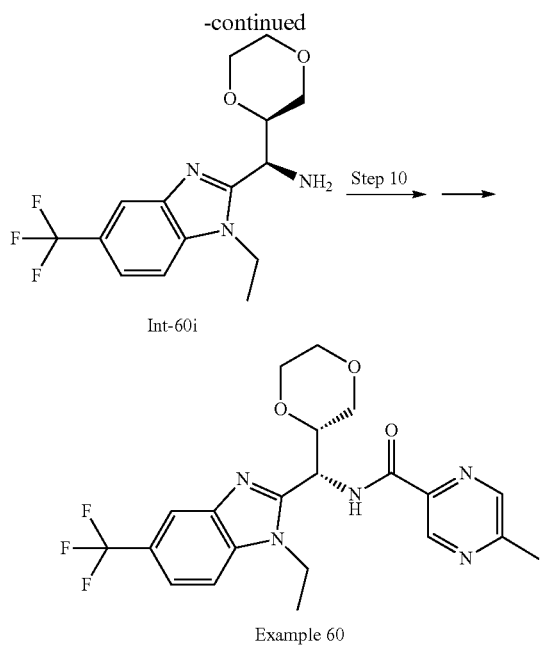
Int-60i

Example 60

Step 1:
A mixture of 4-methoxy-aniline (10 g, 81 mmol), ethyl glyoxylate polymer form (47% in toluene, 17 mL, 81 mmol) and MgSO₄ (24 g, 203 mmol) in 125 mL DCM is stirred at 40° C. for 3 h. The mixture is filtered and the filtrate is evaporated at 25° C. The residue is used without further purification.
Yield: 20.8 g (~80% content; 81 mol; quant.) Int-60a
MS (ESI⁺): (M+H)⁺ 208; HPLC: RT=0.90 min, Method: Z011_S03

Step 2:
Int-60a (21 g 80% content, 81 mmol) in 150 mL dioxane (without stabilizer) is de-gassed and kept under nitrogen. Copper(II)chloride (0.54 g, 4 mmol) and tert-butyl hydroperoxide (5.5M in decane; 17.5 mL, 96 mmol) are added and the mixture stirred at 50° C. for 16 h. The mixture is concentrated i. vac. and purified by consecutive column chromatographies (silica gel, PE/EtOAc gradient 9:1→4:1, then 7:3, then 4:1, each time product containing fractions combined and concentrated i. vac. before next purification).
Yield: 6.4 g (22 mmol; 27%) Int-60b as mixture of stereoisomers
MS (ESI⁺): (M+H)⁺ 296; HPLC: RT=0.90 min, Method: Z011_S03

Step 3:
Int-60b (300 mg, 1.02 mmol) together with ammonium cerium(IV) nitrate (835 mg, 1.6 mmol) in 10 mL ACN with 3 mL water is stirred at ambient temperature for 3 h. Afterwards, the mixture is filtered and concentrated i. vac.
Yield: 300 mg (purity: ~33%; 0.53 mmol; 52%) Int-60c as mixture of stereoisomers
MS (ESI⁺): (M+H)⁺ 190; TLC: Rf=0.5 (Eluent: DCM: MeOH 95:5)

Step 4:
Boc-anhydride (5.2 g; 24 mmol) is added to a mixture of Int-60c (3.0 g; 16 mmol) with TEA (8.0 g; 79 mmol) in 15 mL THF and the mixture stirred at ambient temperature for 18 h followed by concentration i. vac. and purification via silica gel column chromatography (eluent-gradient: hexane: EtOAc 100:0→60:40).

Yield: 1.0 g (purity: ~65%; 2.2 mmol; 9%) Int-60d as mixture of stereoisomers

MS (ESI$^+$): (M+H)$^+$ 234; TLC: Rf=0.5 (Eluent: hexane: EtOAc 7:3)

Step 5:

LiOH (100 mg; 4.2 mmol) is added to Int-60d (0.8 g, 2.8 mmol) in 10 mL MeOH with 3 mL water, and the mixture stirred at ambient temperature for 3 h, concentrated i. vac. and purified by prep. HPLC.

Yield: 0.5 g (1.9 mmol; 68%) Int-60e as mixture of stereoisomers

MS (ESI$^+$): (M+H)$^+$ 262; TLC: Rf=0.5 (Eluent: DCM: MeOH 95:5)

Step 6:

To 1-fluoro-2-nitro-4-trifluoromethyl-benzene (2.2 mL; 15.7 mmol) in 100 mL DCM is added ethylamine (2M in THF; 15.7 mL, 31.4 mmol) and the mixture stirred for 20 h at ambient temperature. 100 mL DCM are added and the mixture extracted with 100 mL water. The organic layer is collected, dried over Na$_2$SO$_4$, filtered and concentrated i. vac.

Yield: 3.30 g (14.1 mmol; 90%) Int-60f

MS (ESI$^+$): (M+H)$^+$ 235; HPLC: RT=1.10 min, Method: Z017_S04

Step 7:

Int-60f (200 mg, 0.85 mmol) is mixed with palladium on charcoal (10%, 50 mg) in 20 mL MeOH and hydrogenated for 3.5 h at 50 psi hydrogen pressure. Then the mixture is filtered and concentrated i. vac.

Yield: 170 mg (0.83 mol; 97%) Int-60 g

MS (ESI$^+$): (M+H)$^+$ 205; HPLC: RT=0.86 min, Method: Z018_S04

Step 8:

Int-60e (210 mg, 0.80 mmol), Int-60 g (170 mg, 0.83 mmol) and 350 μL NMM in 5 mL DCM are stirred at ambient temperature and PPA (50% in EtOAc; 600 μL, 1.0 mmol) is added. After stirring for 16 h at ambient temperature, water is added and the mixture stirred at ambient temperature for 20 min. Then 5 mL AcOH is added and the mixture stirred at 50° C. for 3 h, at ambient temperature for 16 h and at 80° C. for 2 h. The mixture contains four stereoisomers, which can be separated into two pairs of enantiomers by HPLC (C-18 Sunfire at 50° C., eluent gradient (water+0.15% TFA):ACN 58:42→38:62). The product containing fractions are combined and freeze-dried. Only one pair of enantiomers (Int-60 h) is used in step 9 which is depicted in the reaction scheme.

Stereoisomer Pair 1: Yield: 70 mg (0.13 mmol; 16%) Int-60 h as mixture of enantiomers MS (ESI$^+$): (M+H)$^+$ 430; HPLC: RT=1.03 min, Method: Z018_S04

Stereoisomer Pair 2: Yield: 120 mg as a mixture of enantiomers

MS (ESI$^+$): (M+H)$^+$ 430; HPLC: RT=1.04 min, Method: Z018_S04

Step 9:

Int-60 h (70 mg, 0.13 mmol) is stirred in 4 mL hydrochloric acid (4M in dioxane) at ambient temperature for 1 h. The mixture is concentrated i. vac.

Yield: 52 mg (0.13 mmol; quant.) Int-60i as mixture of enantiomers

MS (ESI$^+$): (M+H)$^+$ 330; HPLC: RT=0.77 min, Method: Z018_S04

Step 10:

A mixture from Int-60i (52 mg, 0.13 mmol), 5-methyl-pyrazine-2-carboxylic acid (22 mg, 0.16 mmol), TBTU (44 mg, 0.14 mmol) and TEA (100 μL, 0.72 mmol) in 4.0 mL DMF is stirred at ambient temperature for 15 min. Water is added and the mixture is purified by prep. HPLC (C-18 X-Bridge at 50° C., eluent gradient (water+0.15% NH$_3$): ACN 61:39→41:59). The product containing fractions are combined and freeze-dried. Afterwards chiral SFC is performed to get the desired enantiomer.

Yield: 15 mg (0.033 mol; 36%) example 60

Example 60: N-[(R)-[(2S)-1,4-dioxan-2-yl][1-ethyl-5-(trifluoromethyl)-1H-1,3-benzodiazol-2-yl]methyl]-5-methylpyrazine-2-carboxamide

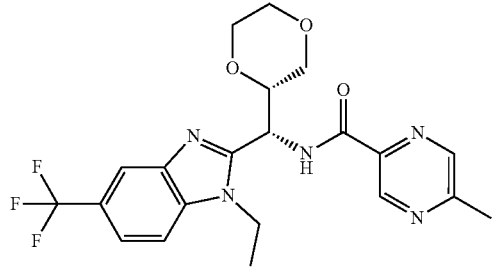 [SMILES: CCn1c([C@@H](NC(=O)c2cnc(C)cn2)[C@H]2COCCO2)nc2cc(C(F)(F)F)ccc21]

HPLC-MS; Method: Z018_S04; R$_t$ [min]: 0.99  MS: 450 (M+H)$^+$
Chiral SFC Rt Method: I_C2_15_MEOH_NH3_002  Rt [min]: 1.50
$^1$H NMR (400 MHz, DMSO-d$_6$) δ ppm 1.28-1.37 (m, 3 H) 2.60 (s, 3 H) 3.31-3.39 (m, 1 H) 3.42-3.53 (m, 1 H) 3.58-3.68 (m, 2 H) 3.77-3.86 (m, 2 H) 3.95 (s, 3 H) 4.30-4.37 (m, 1 H) 4.38-4.57 (m, 2 H) 5.64 (dd, J = 8.30, 7.29 Hz, 1 H) 7.59 (dd, J = 8.62, 1.39 Hz, 1 H) 7.83 (d, J = 8.49 Hz, 1 H) 8.03 (s, 1 H) 8.66 (d, J = 1.01 Hz, 1 H) 9.06 (d, J = 1.39 Hz, 1 H) 9.10 (d, J = 8.36 Hz, 1 H)

Example 63

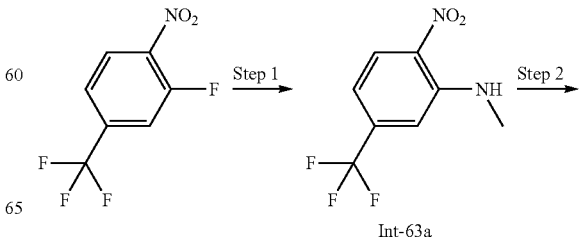

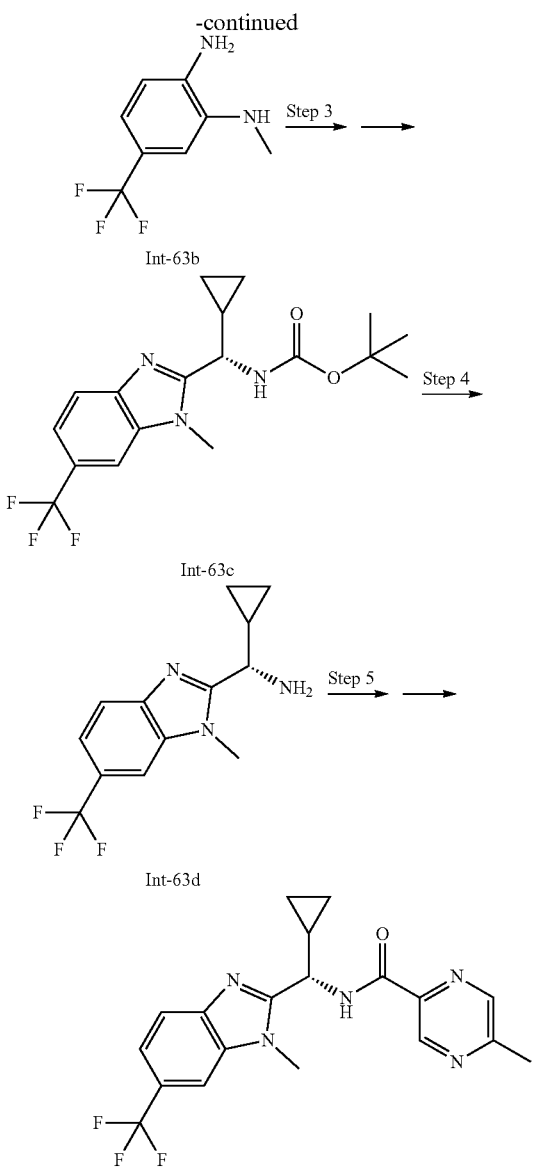

Step 1:

Methylamine (2N in THF; 36 mL, 72 mmol) is slowly added to a mixture of 3-fluoro-1-trifluoromethyl-4-nitrobenzene (10.1 g, 48 mmol) with $K_2CO_3$ (10.0 g, 72 mmol) in 60 mL DMF under stirring as slowly to keep the mixture below 35° C. Then the mixture is stirred for 1 h at ambient temperature. The mixture is poured into sat. aq. $NaHCO_3$ solution, cooled to 0° C., filtered, and the solid washed with water. The solid is dried i. vac. and used without further purification.

Yield: 10.4 g (47 mmol; 98%) Int-63a

MS (ESI$^+$): M$^+$ 220; HPLC: RT=1.03 min, Method: Z011_S03

Step 2:

Int-63a (19.9 g, 90.4 mmol) in 300 mL MeOH and 2.0 g 10% Pd/C is hydrogenated at ambient temperature for 1 h at 60 psi hydrogen pressure. The mixture is filtered, the filtrate dried over $MgSO_4$ and concentrated i. vac.

Yield: 15.7 g (82.7 mmol; 91%) Int-63b

MS (ESI$^+$): (M+H)$^+$ 191; HPLC: RT=0.78 min, Method: Z018_S04

Step 3:

A mixture of Int-63b (15.7 g, 82.7 mmol) and (2S)-2-Boc-amino-2-cyclopropyl-acetic acid (21.9 g, 102 mmol) in 150 mL pyridine is stirred at −10° C. and PPA (50% in EtOAc, 83 mL, 141 mmol) is added slowly to keep the temperature below 0° C. After 2 h at 0° C., 50 mL pyridine is added and the mixture is stirred for 18 h at ambient temperature. The mixture is poured into 3.5 L water with 20 mL conc. Aq. $NH_3$ solution and stirred vigorously. The formed solid is filtered, washed with water and dried i. vac. The solid is taken up in 125 mL AcOH and stirred at ambient temperature for 17 h. 400 mL dioxane are added and the mixture freeze-dried. The residue is taken up in ACN and 2 L water, volatile organic solvents removed i. vac., the aq. phase set to pH ~9 by adding conc. aq. $NH_3$ solution, the mixture vigorously stirred and filtered. The solid is washed with 650 mL water and dried i. vac.

Yield: 18.7 g (50.7 mmol, 65%) Int-63c

MS (ESI$^+$): (M+H)$^+$ 370; HPLC: RT=0.94 min, Method: Z018_S04

Step 4:

To Int-63c (18.7 g, 50.6 mmol) in 65 mL dioxane at 10° C. is added a HCl in dioxane (4N, 130 mL, 520 mmol) under cooling and as slowly to keep the temperature below 15° C. Afterwards, the mixture is stirred at ambient temperature for 2 h. 600 mL diethylether is added and the mixture stirred for 5 min. The formed solid is filtered and washed with diethylether. The solid is taken up in 600 mL water, set to pH 8.5 by addition of conc. aq. $NH_3$ solution and the aq. phase extracted with EtOAc. The combined organic layers are washed with half-conc. brine, dried over MgSO4 and concentrated i. vac. The residue is used without further purification.

Yield: 13.6 g (50.5 mmol, 99%) Int-63d

MS (ESI$^+$): (M+H)$^+$ 270; HPLC: RT=0.90 min, Method: Z011_S03

Step 5:

A mixture of Int-63d (13.6 g, 50.5 mmol) and 5-methyl-pyrazine-2-carboxylic acid (8.6 g, 61 mmol) in 350 mL EtOAc is stirred at 0° C. and PPA (50% in EtOAc, 39 mL, 66 mmol) is added keeping the mixture below 5° C. After 45 min at 0-10° C., 200 mL EtOAc and 500 mL water are added and the mixture set to pH ~8.5 by addition of conc. aq. $NH_3$ solution. The organic phase is washed with brine and 1.5 g charcoal is added, the mixture dried over $MgSO_4$ and filtered, washing filtered solids with 250 mL EtOAc. The filtrate is concentrated i. vac. and the residue treated with 100 mL di-isopropyl-ether. The mixture is filtered and the solid washed with 100 mL di-isopropyl-ether. The solid is dried i. vac.

Yield: 18.5 g (47.6 mmol, 94%) example 63

Example 63: N-[(S)-cyclopropyl[1-methyl-6-(trifluoromethyl)-1H-1,3-benzodiazol-2-yl]methyl]-5-methylpyrazine-2-carboxamide

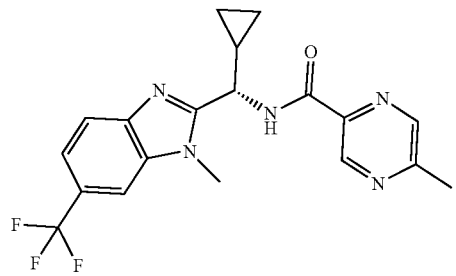 [SMILES: Cc1cnc(C(=O)N[C@H](c2nc3ccc(C(F)(F)F)cc3n2C)C2CC2)cn1]

| HPLC-MS: Method: Z011_S03; $R_t$ [min]: 1.00 | MS: 390 (M + H)$^+$ |
|---|---|
| Chiral SFC Rt Method: Method I_SA_25_IPA_NH3_001 | Rt [min]: 2.09 |

$^1$H NMR (400 MHz, DMSO-d$_6$) δ ppm 0.35-0.62 (m, 4 H) 1.68-1.78 (m, 1 H) 2.58-2.62 (m, 3 H) 3.92 (s, 3 H) 5.02 (t, J = 8.36 Hz, 1 H) 7.52 (dd, J = 8.49, 1.52 Hz, 1 H) 7.83 (d, J = 8.49 Hz, 1 H) 8.03 (s, 1 H) 8.65 (d, J = 1.01 Hz, 1 H) 9.05 (d, J = 1.39 Hz, 1 H) 9.20 (d, J = 7.98 Hz, 1 H)

Example 66

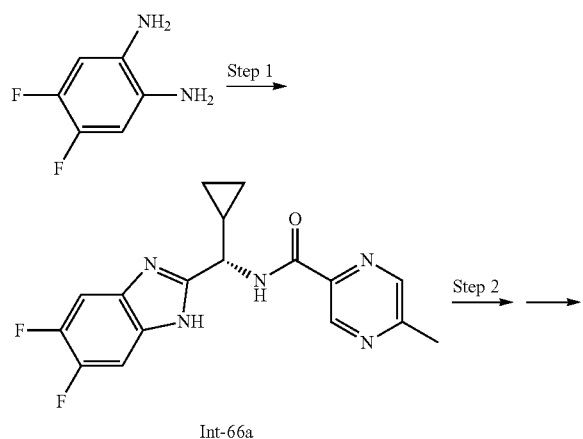

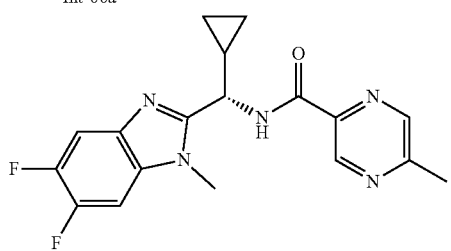

Example 66

Step 1:

1,2-diamino-4,5-difluoro-benzene (100 mg, 0.69 mmol) is mixed with Int-1c (120 mg, 0.51 mmol) and TEA (425 μL, 3.1 mmol) in 5.0 mL DCM, PPA (50% in EtOAc, 600 μL, 1.0 mmol) is added at 0° C. and the mixture stirred at 0° C. for 1 h. Afterwards, 100 μL water are added and the mixture stirred at ambient temperature for 1 h. 5.0 mL AcOH are added and the mixture stirred at ambient temperature for 16 h. The mixture is concentrated i. vac. and the residue is purified by prep. HPLC (Sunfire C-18 at 50° C., eluent-gradient (H$_2$O+0.15% TFA):ACN 88:12→68:32). The product containing fractions are combined and freeze-dried. The residue is taken up in MeOH and sent through an ion exchange cartridge (Agilent PL-HCO3 MP SPE) and concentrated i. vac.

Yield: 160 mg (0.47 mmol; 91%) Int-66a

MS (ESI$^+$): (M+H)$^+$ 344; HPLC: RT=0.75 min, Method: Z018_S04

Step 2:

Methyl-methanesulfonate (40 μL, 0.47 mmol) is added to a mixture of Int-66a (160 mg, 0.47 mmol) with Cs$_2$CO$_3$ (250 mg, 0.77 mmol) in 5 mL ACN. The mixture is stirred for 1 h at ambient temperature. Afterwards, the mixture is filtered and the filtrate is purified by prep. HPLC (X-Bridge C-18 at 50° C., eluent-gradient (H$_2$O+0.15% NH$_3$):ACN 68:32→48:52). The product containing fractions are combined and freeze-dried.

Yield: 140 mg (0.39 mmol; 84%) example 66

Example 66: N-[(S)-cyclopropyl(5,6-difluoro-1-methyl-1H-1,3-benzodiazol-2-yl)methyl]-5-methylpyrazine-2-carboxamide

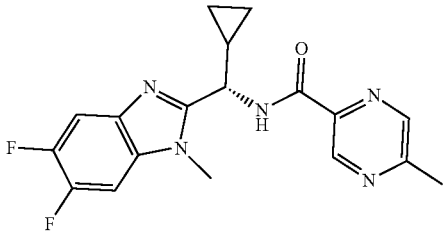 [SMILES: Cc1cnc(C(=O)N[C@H](c2nc3cc(F)c(F)cc3n2C)C2CC2)cn1]

HPLC-MS; Method: Z018_S04; R$_t$ [min]: 0.80    MS: 358 (M + H)$^+$
Chiral SFC Rt Method: Method I_SA_25_MEOH_NH3_001    Rt [min]: 2.89
$^1$H NMR (400 MHz, DMSO-d$_6$) δ ppm 0.35-0.60 (m, 4 H) 1.65-1.74 (m, 1 H) 2.60 (s, 3 H) 3.81 (s, 3 H) 4.95 (t, J = 8.36 Hz, 1 H) 7.71 (dd, J = 11.15, 7.48 Hz, 1 H) 7.74 (dd, J = 10.77, 7.35 Hz, 1 H) 8.64 (s, 1 H) 9.05 (d, J = 1.27 Hz, 1 H) 9.14 (d, J = 8.11 Hz, 1 H)

In analogy to example 66, the following products are obtained:

Example 94: N-[(1S)-2-cyclopropyl-1-(5,6-difluoro-1-methyl-1H-1,3-benzodiazol-2-yl)ethyl]-5-(difluoromethyl)pyrazine-2-carboxamide

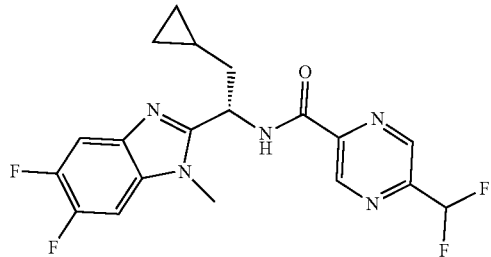 [SMILES: Cn1c([C@H](CC2CC2)NC(=O)c2cnc(C(F)F)cn2)nc2cc(F)c(F)cc21]

HPLC-MS; Method: Z011_S03; R$_t$ [min]: 1.03    MS: 408 (M + H)$^+$
Chiral SFC Rt Method: I_SC_10_IPA_NH3_001    Rt [min]: 2.11
$^1$H NMR (400 MHz, DMSO-d$_6$) δ ppm −0.06-0.04 (m, 1 H) 0.06-0.18 (m, 1 H) 0.28-0.40 (m, 2 H) 0.66-0.83 (m, 1 H) 1.96-2.07 (m, 2 H) 3.85 (s, 3 H) 5.50-5.56 (m, 1 H) 7.21 (m, 1 H) 7.66-7.79 (m, 2 H) 9.05 (s, 1 H) 9.27-9.34 (m, 2 H)

Example 111: N-[(1S)-2-cyclopropyl-1-{1-[2-(difluoromethoxy)ethyl]-5,6-difluoro-1H-1,3-benzodiazol-2-yl}ethyl]-5-(difluoromethyl)pyrazine-2-carboxamide

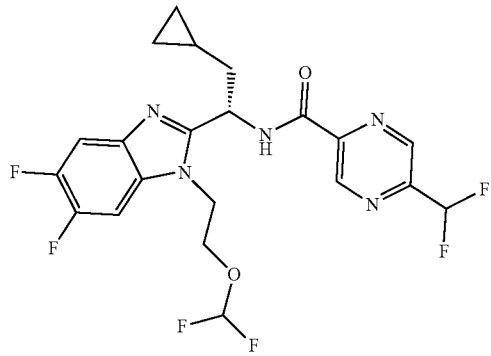 [SMILES: O=C(N[C@@H](CC1CC1)c1nc2cc(F)c(F)cc2n1CCOC(F)F)c1cnc(C(F)F)cn1]

HPLC-MS; Method: Z018_S04; R$_t$ [min]: 1.07    MS: 488 (M + H)$^+$
Chiral SFC Rt Method: I_IG_20_MEOH_NH3_001    Rt [min]: 2.62
$^1$H NMR (400 MHz, DMSO-d$_6$) δ ppm −0.03-0.06 (m, 1 H) 0.10-0.19 (m, 1 H) 0.30-0.41 (m, 2 H) 0.72-0.82 (m, 1 H) 1.93-2.14 (m, 2 H) 4.18 (t, J = 5.13 Hz, 2 H) 4.54-4.65 (m, 1 H) 4.71-4.81 (m, 1 H) 5.52-5.59 (m, 1 H) 6.56 (m, 1 H) 7.20 (m, 1 H) 7.66-7.75 (m, 1 H) 7.76-7.85 (m, 1 H) 9.03 (s, 1 H) 9.25-9.30 (m, 2 H)

Example 128: N-[(1S)-2-cyclopropyl-1-{1-[2-(difluoromethoxy)ethyl]-5,6-difluoro-1H-1,3-benzodiazol-2-yl}ethyl]-5-methylpyrazine-2-carboxamide

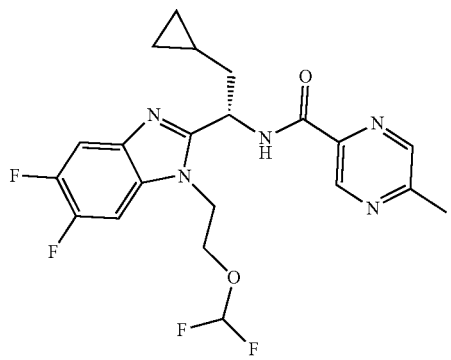 [SMILES: Cc1cnc(C(=O)N[C@@H](CC2CC2)c2nc3cc(F)c(F)cc3n2CCOC(F)F)cn1]
HPLC-MS; Method: Z018_S04; R_t [min]: 1.02  MS: 452 (M + H)+
Chiral SFC Rt Method: G_SB_IPA_NH3_001  Rt [min]: 2.62
$^1$H NMR (400 MHz, DMSO-d$_6$) δ ppm 0.01-0.17 (m, 2 H) 0.30-0.42 (m, 2 H) 0.72-0.82 (m, 1 H) 1.91-2.01 (m, 1 H) 2.09-2.18 (m, 1 H) 2.57-2.61 (m, 3 H) 4.16-4.25 (m, 2 H) 4.61-4.74 (m, 1 H) 4.77-4.88 (m, 1 H) 5.54-5.61 (m, 1 H) 6.57 (m, 1 H) 7.73-7.82 (m, 1 H) 7.89-7.97 (m, 1 H) 8.64 (d, J = 0.89 Hz, 1 H) 9.04 (d, J = 1.39 Hz, 1 H) 9.19 (d, J = 8.11 Hz, 1 H)
Example 69
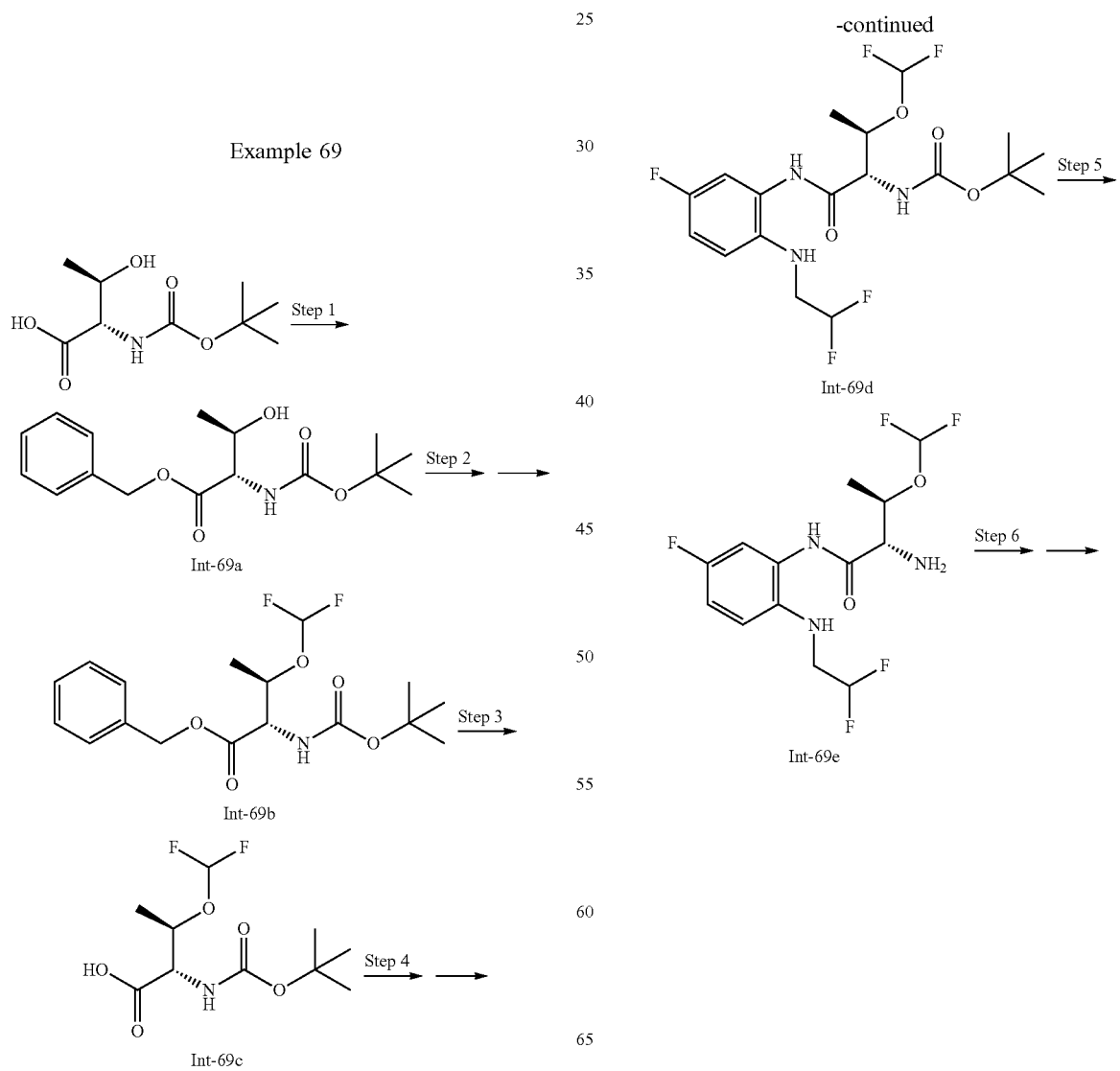

-continued

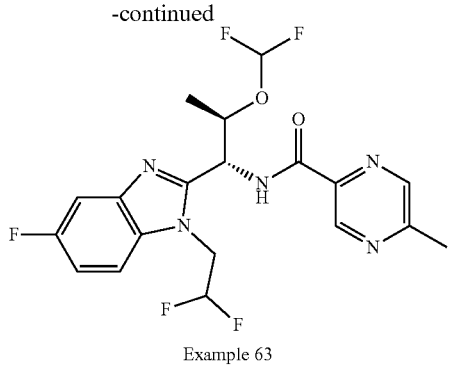

Example 63

Step 1:

A mixture from N-Boc-threonine (10 g, 46 mmol), benzylbromide (5.2 mL, 43 mmol) and NaHCO$_3$ (9 g, 107 mmol) in 80 mL DMF is stirred for 4 d at ambient temperature. The mixture is filtered and the filtrate concentrated i. vac. The residue is taken up in 500 mL water and extracted with tert-butyl-methyl-ether. The combined organic layers are dried over MgSO$_4$ and concentrated i. vac. Yield: 11.8 g (38 mmol; 88%) Int-69a MS (ESI$^+$): (M+H)$^+$ 310; HPLC: RT=0.98 min, Method: Z011_S03

Step 2:

To a mixture of Int-69a (11.8 g, 38 mmol) with CuI (3.6 g, 19 mmol) in 400 mL ACN at 50° C. is added 2,2-difluoro-2-(fluorosulfonyl)-acetic acid in 400 mL ACN over a period of 220 min. The mixture is stirred at 50° C. for further 90 min, then 30 mL TEA are added at ambient temperature and the mixture concentrated i. vac. The residue is taken up in 40 mL THF and 10 mL of conc. aq. NH$_3$ solution is added. Celite is added, the mixture filtered and the solid washed with THF. The filtrate is stored at ambient temperature for 18 h, filtered and 5 g PL-thiol resin (Agilent, 2.2 mmol/g, 100 A, 45 μm) are added, stirred and filtered. THF is added to 75 mL total volume and the mixture purified by prep. HPLC (X-Bridge C-18, 10 μm, eluent-gradient (H$_2$O+0.1% NH$_3$):ACN 52:48→32:68). The product containing fractions are combined and freeze-dried.

Yield: 4.3 g (12 mmol; 31%) Int-69b

MS (ESI$^+$): (M+H)$^+$ 360; HPLC: RT=1.10 min, Method: Z011_S03

Step 3:

Int-69b (2.2 g, 5.4 mmol) in 100 mL MeOH and 300 mg 10% Pd/C is hydrogenated at ambient temperature for 1.5 h at 60 psi hydrogen pressure. The mixture is filtered, the filtrate dried over MgSO$_4$ and concentrated i. vac.

Yield: 1.6 g (5.3 mmol; 99%) Int-69c

MS (ESI$^+$): (M+H)$^+$ 270

Step 4:

A mixture of Int-4b (885 mg, 4.2 mmol) and Int-69c (1.4 g, 4.6 mmol) in 10 mL pyridine is stirred at −10° C. and PPA (50% in EtOAc, 3.5 mL, 5.9 mmol) is added slowly to keep the temperature below 0° C. After 2.5 h at 0° C., 1 mL water is added and the mixture concentrated i. vac. The residue is purified by prep. HPLC (X-Bridge C-18, 10 μm, eluent-gradient (H$_2$O+0.1% NH$_3$):ACN 55:45→35:65). The product containing fractions are combined and freeze-dried.

Yield: 1.6 g (3.6 mmol, 86%) Int-69d

MS (ESI$^+$): (M+H)$^+$ 442; HPLC: RT=1.07 min, Method: Z011_S03

Step 5:

To Int-69d (800 mg, 1.8 mmol) in 9 mL dioxane at 0° C. is added HCl in dioxane (4N, 9 mL, 36 mmol) under cooling. Then, the mixture is stirred at ambient temperature for 2 h. The mixture is concentrated i. vac, taken up in DCM and concentrated i. vac.

Yield: 710 mg (1.7 mmol, 95%) Int-69e

MS (ESI$^+$): (M+H)$^+$ 342; HPLC: RT=0.92 min, Method: Z011_S03

Step 6:

A mixture of Int-69e (350 mg, 0.76 mmol) and 5-methylpyrazine-2-carboxylic acid (126 mg, 0.91 mmol) in 6.5 mL ACN with TEA (371 μL, 2.7 mmol) is stirred at ambient temperature and CIP (233 mg, 0.84 mmol) is added and the mixture stirred for 1 h at ambient temperature. The mixture is given into 250 mL half-conc. NaCl (aq.) and the mixture set to pH ~9 by addition of conc. aq. NH$_3$ solution. The mixture is concentrated i. vac, the solid filtered, washed with water and dried i. vac. The solid is taken up in 5 mL AcOH, stirred at 55° C. for 1 h and 15 h at 65° C. The mixture is concentrated i. vac. and the residue taken up in THF and MeOH and set to basic pH by addition of TEA. It is purified by prep. HPLC. The product containing fractions are combined and freezedried. Yield: 49 mg (0.11 mmol, 15%) example 69

Example 69: N-[(1R,2R)-1-[1-(2,2-difluoroethyl)-5-fluoro-1H-1,3-benzodiazol-2-yl]-2-(difluoromethoxy)propyl]-5-methylpyrazine-2-carboxamide

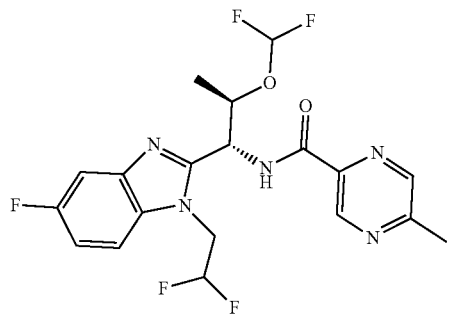 [SMILES: Cc1cnc(C(=O)N[C@H](c2nc3cc(F)ccc3n2CC(F)F)[C@@H](C)OC(F)F)cn1]

HPLC-MS; Method: Z011_S03; R$_t$ [min]: 0.99    MS: 444 (M + H)$^+$
Chiral SFC Rt Method: Method I_SC_05_IPA_NH3_001    Rt [min]: 2.76
$^1$H NMR (400 MHz, DMSO-d$_6$) δ ppm 1.25 (d, J = 6.21 Hz, 3 H) 2.56-2.61 (m, 3 H) 4.91-5.11 (m, 3 H) 5.60 (t, = 8.24 Hz, 1 H) 6.49 (m, 1 H) 6.81 (m, 1 H) 7.19 (m, 1 H)

Example 69: N-[(1R,2R)-1-[1-(2,2-difluoroethyl)-5-fluoro-1H-1,3-benzodiazol-2-yl]-2-(difluoromethoxy)propyl]-5-methylpyrazine-2-carboxamide

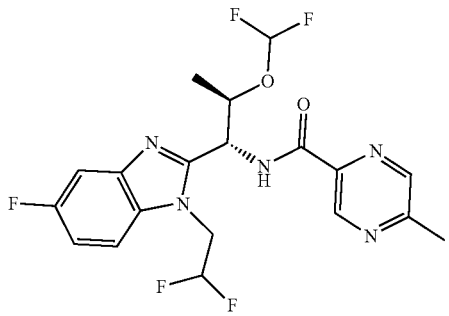

7.52 (dd, J = 9.63, 2.41 Hz, 1 H) 7.67 (dd, J = 8.87, 4.69 Hz, 1 H) 8.64 (s, 1 H) 9.07 (d, J = 1.27 Hz, 1 H) 9.17 (d, J = 8.74 Hz, 1 H)

In analogy to example 69, the following products are obtained:

Example 61: N-[(1R,2R)-2-(difluoromethoxy)-1-[1-methyl-5-(trifluoromethyl)-1H-1,3-benzodiazol-2-yl]propyl]-5-methylpyrazine-2-carboxamide

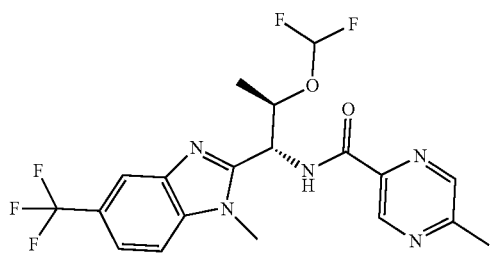 [SMILES: Cc1cnc(C(=O)N[C@H](c2nc3cc(C(F)(F)F)ccc3n2C)[C@@H](C)OC(F)F)cn1]

HPLC-MS; Method: Z011_S03; $R_t$ [min]: 1.05   MS: 444 (M + H)$^+$
Chiral SFC Rt Method: Method I_1G_15_MEOH_NH3_001   Rt [min]: 3.80
$^1$H NMR (400 MHz, DMSO-$d_6$) δ ppm 1.29 (d, J = 6.21 Hz, 3 H) 2.60 (s, 3 H) 3.95 (s, 3 H) 4.96-5.07 (m, 1 H) 5.69 (dd, J = 8.49, 6.59 Hz, 1 H) 6.81 (m, 1 H) 7.61 (d, J = 8.31 Hz, 1 H) 7.82 (d, J = 8.49 Hz, 1 H) 8.04 (s, 1 H) 8.67 (s, 1 H) 9.06-9.13 (m, 2 H)

Example 79: N-[(1R,2R)-2-(difluoromethoxy)-1-[5-(difluoromethoxy)-1-(2-methoxyethyl)-1H-1,3-benzodiazol-2-yl]propyl]-5-methylpyrazine-2-carboxamide

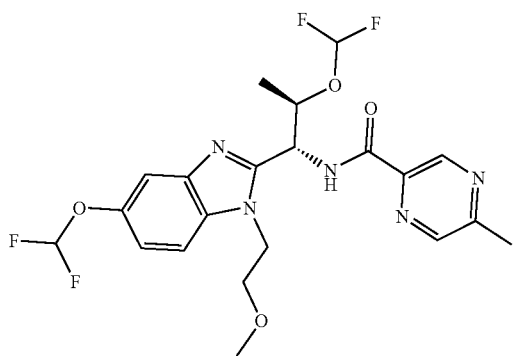 [SMILES: COCCn1c([C@@H](NC(=O)c2cnc(C)cn2)[C@@H](C)OC(F)F)nc2cc(OC(F)F)ccc21]

HPLC-MS; Method: Z011_S03; $R_t$ [min]: 1.01   MS: 486 (M + H)$^+$
Chiral SFC Rt Method: I_SB_10_IPA_NH3_001   Rt [min]: 2.65
$^1$H NMR (400 MHz, DMSO-$d_6$) δ ppm 1.26 (d, J = 6.34 Hz, 3 H) 2.59 (s, 3 H) 3.16 (s, 3 H), 3.60-3.69 (m, 2 H) 4.48-4.72 (m, 2 H) 5.00-5.10 (m, 1 H) 5.64-5.72 (m, 1 H) 6.78 (m, 1 H) 7.12 (dd, J = 8.81, 2.22 Hz, 1 H) 7.18 (m, 1 H) 7.48 (d, J = 2.15 Hz, 1 H) 7.66 (d, J = 8.87 Hz, 1 H) 8.63 (s, 1 H) 9.02 (d, J = 9.12 Hz, 1 H) 9.07 (s, 1 H)

Example 85

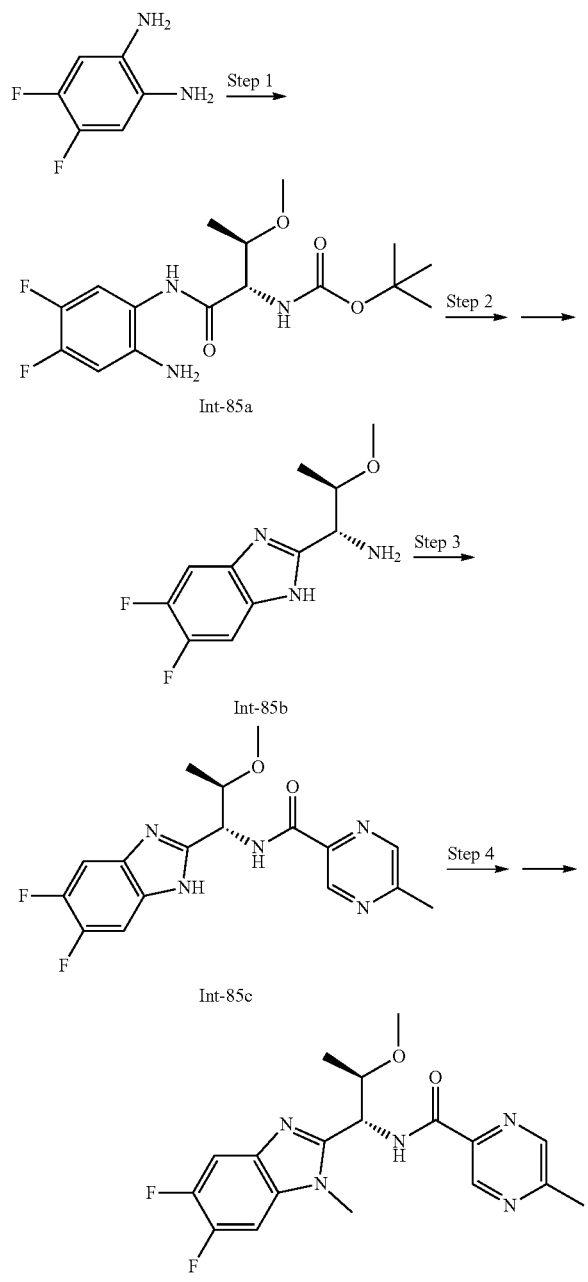

Step 1:

1,2-diamino-4,5-difluoro-benzene (500 mg, 3.5 mmol) is mixed with N-Boc-O-methyl-L-threonine (890 mg, 3.8 mmol) and NMM (2.3 mL, 21 mmol) in 50 mL DCM, PPA (50% in EtOAc, 4.1 mL, 6.9 mmol) is added at 0° C. and the mixture stirred at 0° C. for 1.8 h and at ambient temperature for 14.5 h. Afterwards, the mixture is washed with aq. Na$_2$CO$_3$ solution (0.5N) and water and the organic layer dried over MgSO$_4$ and concentrated i. vac. The residue is taken up in MeOH/THF and purified by prep. HPLC (X-Bridge C-18, 10 μm, eluent-gradient (H$_2$O+0.1% NH$_3$): ACN 66:34 →46:54). The product containing fractions are combined and freeze-dried. Yield: 361 mg (1.0 mmol; 27%) Int-85a. MS (ESI$^+$): (M+H)$^+$ 358; HPLC: RT=0.95 min, Method: Z011_S03

Step 2:

Int-85a (360 mg, 1.0 mmol) is stirred in AcOH (3.0 mL, 51 mmol) at 95° C. for 1.25 h. The mixture is concentrated i. vac. and subsequently taken up in HCl solution in dioxane (4N, 3.0 mL, 12 mmol). After stirring for 45 min at ambient temperature, the mixture is concentrated i. vac., taken up with ACN and again concentrated i. vac. Yield: 391 mg (content: ~90%, 1.0 mmol; quant.) Int-85b MS (ESI$^+$): (M+H)$^+$ 242; HPLC: RT=0.97 min, Method: Z011_S03

Step 3:

CIP (307 mg, 1.1 mmol) is added to a mixture of Int-85b (390 mg, 1.0 mmol) with 2-methylpyrazine-5-carboxylic acid (145 mg, 1.1 mmol) and TEA (0.7 mL, 5.0 mmol) in 10 mL ACN at ambient temperature and then stirred for 30 min at ambient temperature. The mixture is concentrated i. vac., THF is added, and the mixture is purified by prep. HPLC (X-Bridge C-18, 10 μm, eluent-gradient (H$_2$O+0.1% NH$_3$): ACN 74:26→54:46).

Yield: 144 mg (0.38 mmol; 38%) Int-85c

MS (ESI$^+$): (M+H)$^+$ 362; HPLC: RT=0.87 min, Method: Z011_S03

Step 4:

Methyl-methanesulfonate (35 μL, 0.42 mmol) is added to a mixture of Int-85c (125 mg, 0.35 mmol) with Cs$_2$CO$_3$ (237 mg, 0.73 mmol) in 6.5 mL ACN. The mixture is stirred for 3 h at ambient temperature. Afterwards, the mixture is concentrated i. vac., the residue taken up with DCM, washed with water, the organic layer dried over MgSO$_4$, mixed with dioxane and freeze-dried. The residue is taken up in DCM, and concentrated i. vac.

Yield: 131 mg (0.35 mmol; quant.) example 85

| Example 85: N-[(1R,2R)-1-(5,6-difluoro-1-methyl-1H-1,3-benzodiazol-2-yl)-2-methoxypropyl]-5-methylpyrazine-2-carboxamide |
|---|
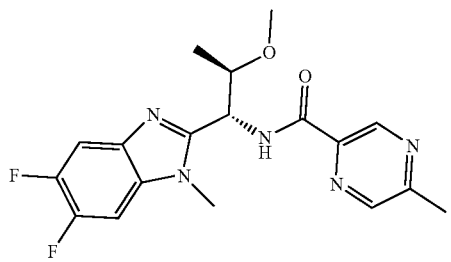 [SMILES: CO[C@H](C)[C@H](NC(=O)c1cnc(C)cn1)c1nc2cc(F)c(F)cc2n1C]
| HPL-MS; Method: Z011_S03; R$_t$ [min]: 0.93    MS: 376 (M + H)$^+$ |
|---|
| $^1$H NMR (400 MHz, DMSO-d$_6$) δ ppm 1.03-1.10 (m, 3 H) 2.56-2.66 (m, 3 H) 3.26-3.36 (m, 3 H) 3.86-3.93 (m, 3 H) 4.00-4.09 (m, 1 H) 5.48 (dd, J = 7.98, 5.32 Hz, 1 H) 7.72 (dd, J = 11.03, 7.48 Hz, 1 H) 7.78 (dd, J = 10.77, 7.22 Hz, 1 H) 8.68 (d, J = 1.01 Hz, 1 H) 8.90 (d, J = 7.98 Hz, 1 H) 9.07 (d, J = 1.39 Hz, 1 H) |
Example 14
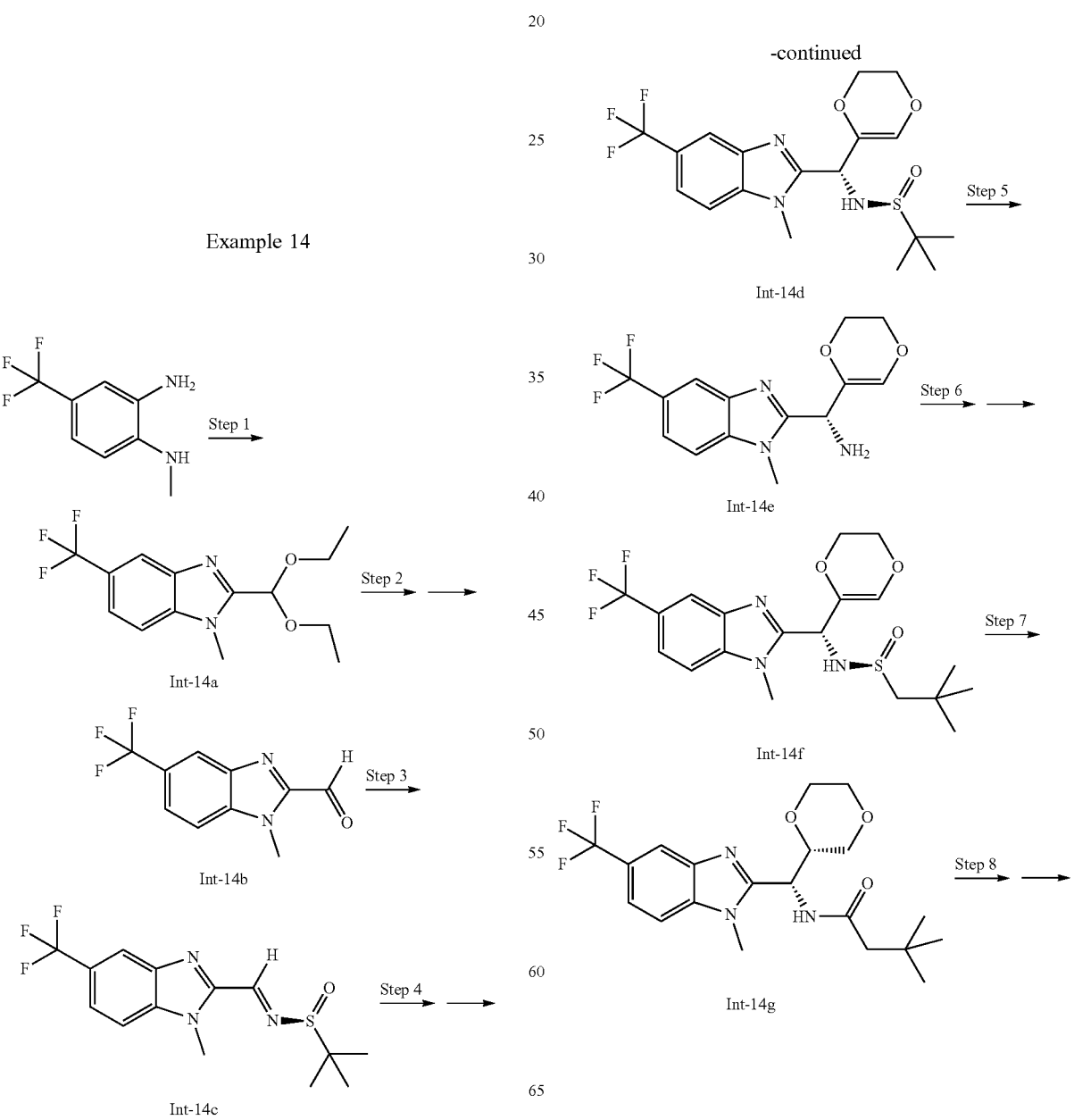

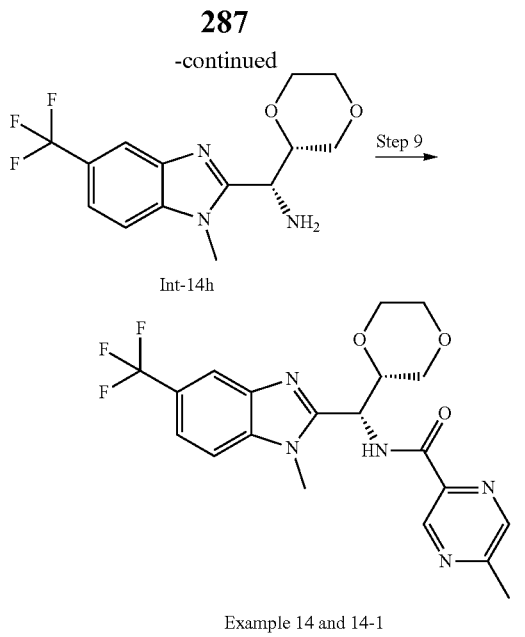

Int-14h

Example 14 and 14-1

In analogy to example 14 (see above) except step 7 the following compounds are obtained:

Example 132 and Example 133

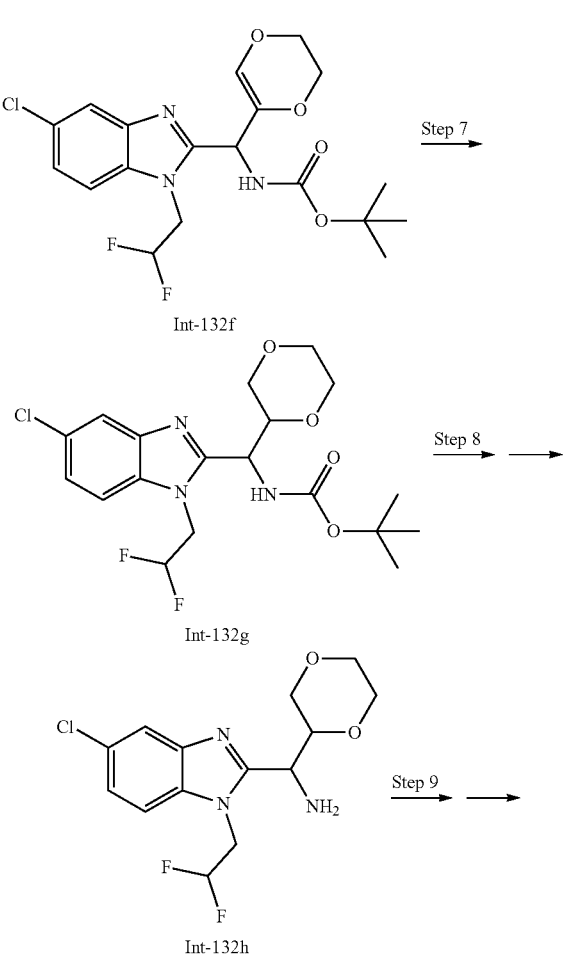

Int-132f

Int-132g

Int-132h

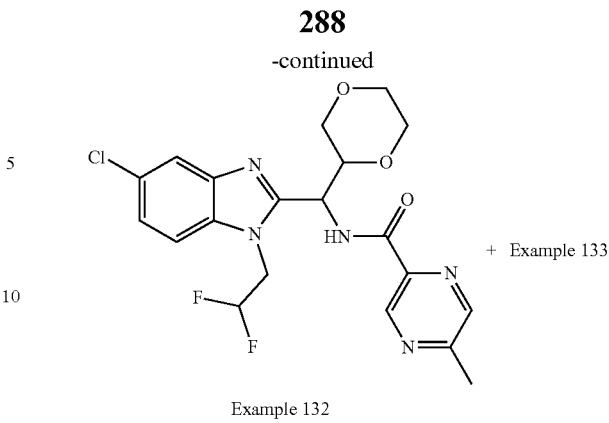

Example 132

Step 7:

A mixture of Int-132f (2.9 g, 6.75 mmol) and Wilkinsons catalyst (950 mg, 1.03 mmol) in ethanol (145 ml) is hydrogenated under a hydrogen atmosphere at 40 psi and 40° C. for 22 h. The mixture is filtered and concentrated in vacuo. The residue is dissolved in THF/MeOH and purified by column chromatography (XBridge C18.10 µm, eluent gradient: ($H_2O+0.1\%$ $NH_{40}H$): 58:42→38:62 I). The fractions containing product are combined and concentrated i.vac. The product is isolated as a mixture of stereoisomers and used as such in the following step.

Yield: 2.05 g (4.74 mmol; 70.4%) Int-132 g

MS ($ESI^+$): $(M+H)^+$ 432, HPLC: RT=1.03 min, Method: Z011_S03

Chiral SFC Rt stereoisomer 1: 0.66 min (Method: I_AC_10_IPA_NH3_002)

Chiral SFC Rt stereoisomer 2: 0.86 min (Method: I_AC_10_IPA_NH3_002)

Step 8:

Synthesized analogous to Example 14 step 8 from Inter-132 g giving the title compounds as a mixture of stereoisomers which are used as such in the next step Yield: 1.18 g (3.56 mmol; 76.8%) Int-132 h MS ($ESI^+$): $(M+H)^+$ 332; HPLC: RT=0.84 min, Method: Z011_S03

Chiral SFC Rt diastereoisomer 1: 1.23 min (Method: I_IG_20_MEOH_NH3_002)

Chiral SFC Rt diastereoisomer 2: 1.56 min (Method: I_IG_20_MEOH_NH3002)

Step 9:

Synthesized in analogy to Example 14 step 9 from Int-132 h giving example 132 and example 133 as a mixture of stereoisomers which are separated by chiral SFC.

Yield: 1.18 g (3.56 mmol; 76.8%) example 132 and 133

MS ($ESI^+$): $(M+H)^+$ 332; HPLC: RT=0.84 min, Method: Z011_S03

| Example 132: N-{[5-chloro-1-(2,2-difluoroethyl)-1H-1,3-benzodiazol-2-yl](1,4-dioxan-2-yl)methyl}-5-methylpyrazine-2-carboxamide |
|---|
| 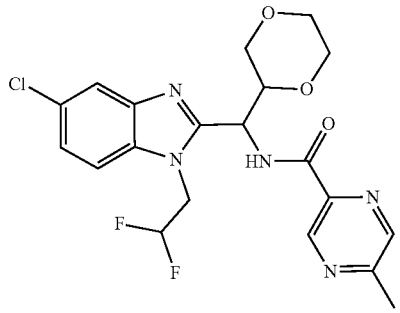 [SMILES: Cc1cnc(C(=O)NC(c2nc3cc(Cl)ccc3n2CC(F)F)C2COCCO2)cn1] |
| HPLC-MS; Method: Z011_S03; $R_t$ [min]: 0.96     MS: 452 (M + H)$^+$<br>Chiral SFC Rt Method: I_C2_20_MeOH_NH3_002     Rt [min]: 1.42<br>$^1$H NMR (400 MHz, DMSO-d$_6$) δ ppm −2.58-2.61 (m, 3 H) −3.17-3.28 (m, 1 H) −3.41-3.58 (m, 1 H) −3.58-3.70 (m, 2 H) 3.73 (dd, J = 11.41, 2.28 Hz, 1 H) 3.81 (br d, J = 11.41 Hz, 1 H) −4.37-4.43 (m, 1 H) −4.89-5.15 (m, 2 H) −5.52-6.35 (m, 1 H) −6.45-6.63 (m, 1 H) 7.34 (dd, J = 8.68, 1.96 Hz, 1 H) 7.67 (d, J = 8.74 Hz, 1 H) 7.76 (d, J = 1.90 Hz, 1 H) 8.65 (d, J = 1.01 Hz, 1 H) 9.05 (d, J = 1.39 Hz, 1 H) 9.11 (d, J = 8.24 Hz, 1 H) |
| Example 133: N-{[5-chloro-1-(2,2-difluoroethyl)-1H-1,3-benzodiazol-2-yl](1,4-dioxan-2-yl)methyl}-5-methylpyrazine-2-carboxamide |
| 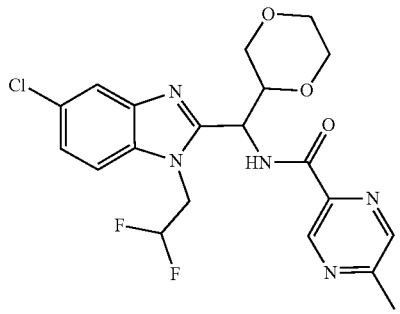 [SMILES: Cc1cnc(C(=O)NC(c2nc3cc(Cl)ccc3n2CC(F)F)C2COCCO2)cn1] |
| HPLC-MS; Method: Z011_S03; $R_t$ [min]: 0.96     MS: 452 (M + H)$^+$<br>Chiral SFC Rt Method: I_C2_20_MeOH_NH3_002     Rt [min]: 0.99<br>$^1$H NMR (400 MHz, DMSO-d$_6$) δ ppm 2.59 (s, 3 H) −3.43-3.58 (m, 3 H) −3.58-3.70 (m, 2 H) 3.98 (dd, J = 11.22, 2.22 Hz, 1 H) 4.22 (td, J = 9.47, 2.34 Hz, 1 H) −4.85-5.04 (m, 2 H) 5.48 (t, J = 8.87 Hz, 1 H) −6.30-6.60 (m, 1 H) 7.32 (dd, J = 8.62, 2.03 Hz, 1 H) 7.65 (d, J = 8.74 Hz, 1 H) 7.75 (d, J = 1.90 Hz, 1 H) 8.65 (s, 1 H) 9.03 (d, J = 1.27 Hz, 1 H) 9.28 (d, J = 8.62 Hz, 1 H) |

In analogy to example 14 the following compound is obtained. The product is a mixture of two stereoisomers. One stereoisomer is isolated: example 134

Example 134: N-[-[1-(2,2-difluoroethyl)-6-(trifluoromethyl)-1H-1,3-benzodiazol-2-yl][-1,4-dioxan-2-yl]methyl]-5-methylpyrazine-2-carboxamide

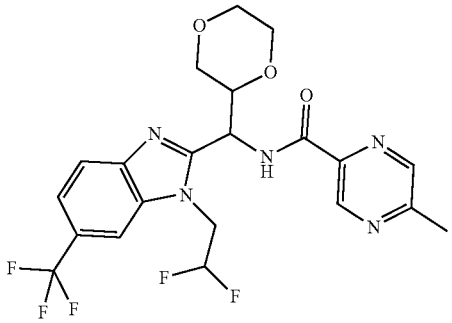 [SMILES: Cc1cnc(C(=O)NC(c2nc3ccc(C(F)(F)F)cc3n2CC(F)F)C2COCCO2)cn1]

| | |
|---|---|
| HPLC-MS; Method: Z011_S03; $R_t$ [min]: 0.99 | MS: 486 (M + H)$^+$ |
| Chiral SFC Rt Method: I_SZ_10_MeOH_NH3_003 | Rt [min]: 1.85 |

$^1$H NMR (400 MHz, DMSO-$d_6$) δ ppm −2.58-2.62 (m, 3 H) 3.31 (br s, 1 H) −3.37-3.54 (m, 1 H) −3.54-3.70 (m, 2 H) −3.70-3.84 (m, 2 H) −4.39-4.46 (m, 1 H) −5.02-5.27 (m, 2 H) −5.57-5.75 (m, 1 H) −6.36-6.67 (m, 1 H) 7.58 (dd, J = 8.62, 1.39 Hz, 1 H) 7.89 (d, J = 8.49 Hz, 1 H) 8.13 (s, 1 H) 8.66 (d, J = 1.01 Hz, 1 H) 9.06 (d, J = 1.39 Hz, 1 H) 9.15 (d, J = 8.24 Hz, 1 H)

In analogy to example 14 the following compounds are obtained. The product is a mixture of two stereoisomers which are separated by chiral SFC: examples 135, 135-1, 136, 136-1, 137, 137-1

Example 135: N-[(1,4-dioxan-2-yl)[1-methyl-6-(trifluoromethyl)-1H-1,3-benzodiazol-2-yl]methyl]-5-methylpyrazine-2-carboxamide

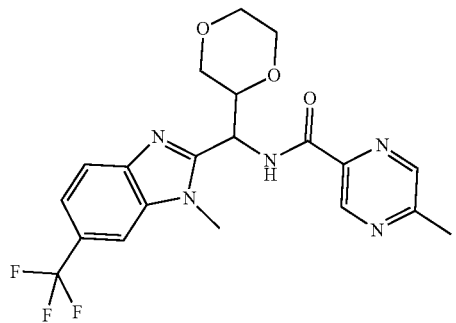 [SMILES: Cc1cnc(C(=O)NC(c2nc3ccc(C(F)(F)F)cc3n2C)C2COCCO2)cn1]

| | |
|---|---|
| HPLC-MS; Method: Z011_S03; $R_t$ [min]: 0.96 | MS: 436 (M + H)$^+$ |
| Chiral SFC Rt Method: I_IG_35_IPA_NH3_003 | Rt [min]: 2.9 |

$^1$H NMR (400 MHz, DMSO-$d_6$) δ ppm 2.61 (s, 3 H) 3.34 (dd, J = 11.47, 9.19 Hz, 1 H) −3.40-3.53 (m, 1 H) −3.53-3.73 (m, 2 H) −3.73-3.91 (m, 2 H) 3.98 (s, 3 H) 4.33 (ddd, J = 9.03, 6.56, 2.53 Hz, 1 H) 5.63 (dd, J = 8.11, 6.59 Hz, 1 H) 7.53 (dd, J = 8.49, 1.52 Hz, 1 H) 7.83 (d, J = 8.49 Hz, 1 H) 8.05 (s, 1 H) 8.67 (d, J = 1.01 Hz, 1 H) 9.06 (s, 1 H) 9.07 (d, J = 7.04 Hz, 1 H)

Example 135-1: N-[(1,4-dioxan-2-yl)[1-methyl-6-(trifluoromethyl)-1H-1,3-benzodiazol-2-yl]methyl]-5-methylpyrazine-2-carboxamide

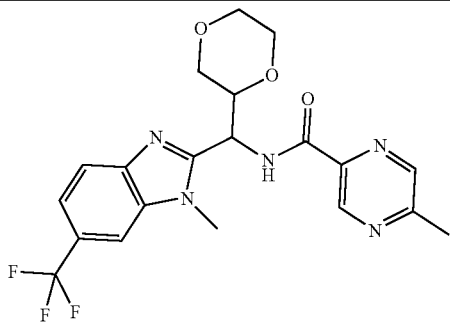

HPLC-MS; Method: Z011_S03; R$_t$ [min]: 0.96     MS: 436 (M + H)$^+$
Chiral SFC Rt Method: I_IG_35_IPA_NH3_003     Rt [min]: 4.44
$^1$H NMR (400 MHz, DMSO-d$_6$) δ ppm 2.59 (s, 3 H) −3.45-3.58 (m, 3 H) −3.58-3.80 (m, 2 H) 3.95 (s, 3 H) −3.98-4.17 (m, 1 H) 4.26 (td, J = 9.28, 2.47 Hz, 1 H) 5.49 (t, J = 8.74 Hz, 1 H) 7.52 (dd, J = 8.49, 1.52 Hz, 1 H) 7.83 (d, J = 8.49 Hz, 1 H) 8.04 (s, 1 H) 8.66 (d, J = 1.01 Hz, 1 H) 9.02 (d, J = 1.27 Hz, 1 H) 9.31 (d, J = 8.49 Hz, 1 H)

In analogy to example 14 the following compounds are obtained. The product is a mixture of two stereoisomers which are separated by chiral SFC: examples 136, 136-1

Example 136: N-[(R)-[1-(2,2-difluoroethyl)-6-fluoro-1H-1,3-benzodiazol-2-yl][(2S)-1,4-dioxan-2-yl]methyl]-5-methylpyrazine-2-carboxamide

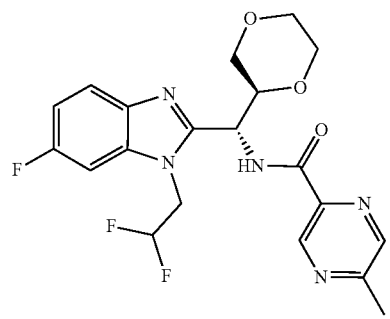 [SMILES: Cc1cnc(C(=O)N[C@H](c2nc3ccc(F)cc3n2CC(F)F)[C@H]2COCCO2)cn1]

HPLC-MS; Method: Z011_S03; R$_t$ [min]: 0.90     MS: 436 (M + H)$^+$
Chiral SFC Rt Method: I_SZ_10_MEOH_NH3_003     Rt [min]: 2.75
$^1$H NMR (400 MHz, DMSO-d$_6$) δ ppm 2.60 (s, 3 H) −3.24-3.28 (m, 1 H) −3.41-3.55 (m, 1 H) −3.55-3.68 (m, 2 H) −3.68-3.84 (m, 2 H) −4.36-4.43 (m, 1 H) −4.85-5.12 (m, 2 H) 5.54 (t, J = 7.79 Hz, 1 H) −6.32-6.62 (m, 1 H) 7.11 (ddd, J = 9.79, 8.90, 2.47 Hz, 1 H) 7.54 (dd, J = 9.38, 2.28 Hz, 1 H) 7.69 (dd, J = 8.87, 4.94 Hz, 1 H) 8.65 (d, J = 1.01 Hz, 1 H) 9.06 (d, J = 1.27 Hz, 1 H) 9.09 (d, J = 8.24 Hz, 1 H)

Example 136-1: N-{[1-(2,2-difluoroethyl)-6-fluoro-1H-1,3-benzodiazol-2-yl](1,4-dioxan-2-yl)methyl}-5-methylpyrazine-2-carboxamide

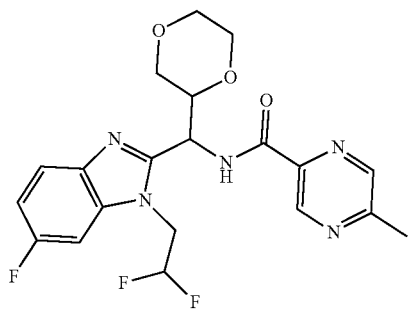 [SMILES: Cc1cnc(C(=O)NC(c2nc3ccc(F)cc3n2CC(F)F)C2COCCO2)cn1]

HPLC-MS; Method: Z011_S03; R$_t$ [min]: 0.90     MS: 436 (M + H)$^+$

Chiral SFC Rt Method: I_SZ_10_MEOH_NH3_003    Rt [min]: 2.01
¹H NMR (400 MHz, DMSO-d₆) δ ppm 2.59 (s, 3 H) −3.36-3.57 (m, 3 H) −3.57-3.91 (m, 2 H) 3.98 (dd, J = 11.34, 2.22 Hz, 1 H) 4.21 (td, J = 9.47, 2.34 Hz, 1 H) −4.82-4.99 (m, 2 H) 5.47 (t, J = 8.87 Hz, 1 H) −6.30-6.69 (m, 1 H) 7.10 (t, J = 9.21 Hz, 1 H) 7.53 (dd, J = 9.38, 2.28 Hz, 1 H) 7.68 (dd, J = 8.81, 4.88 Hz, 1 H) 8.65 (d, J = 0.89 Hz, 1 H) 9.03 (d, J = 1.27 Hz, 1 H) 9.24 (d, J = 8.62 Hz, 1 H)

In analogy to example 14 the following compounds are obtained. The product is a mixture of two stereoisomers which are separated by chiral SFC: examples 137, 137-1

Example 137: N-{[1-(2,2-difluoroethyl)-5,6-difluoro-1H-1,3-benzodiazol-2-yl](1,4-dioxan-2-yl)methyl}-5-methylpyrazine-2-carboxamide

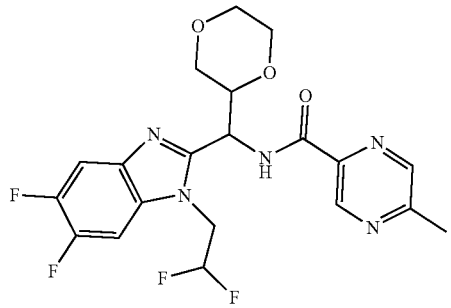 [SMILES: Cc1cnc(C(=O)NC(c2nc3cc(F)c(F)cc3n2CC(F)F)C2COCCO2)cn1]

HPLC-MS; Method: Z011_S03; R_t [min]: 0.83    MS: 454 (M + H)⁺
Chiral SFC Rt Method: I_SZ_15_MEOH_NH3_003    Rt [min]: 1.85
¹H NMR (400 MHz, DMSO-d₆) δ ppm 2.60 (s, 3 H) −3.24-3.30 (m, 1 H) −3.41-3.55 (m, 1 H) −3.55-3.69 (m, 2 H) 3.73 (dd, J = 11.41, 2.41 Hz, 1 H) 3.81 (br d, J = 11.53 Hz, 1 H) −4.36-4.42 (m, 1 H) −4.88-5.13 (m, 2 H) 5.53 (t, J = 7.73 Hz, 1 H) −6.22-6.63 (m, 1 H) −7.75-7.85 (m, 2 H) 8.65 (d, J = 1.01 Hz, 1 H) 9.05 (d, J = 1.39 Hz, 1 H) 9.11 (d, J = 8.24 Hz, 1 H)

Example 137-1: N-[(R)-[1-(2,2-difluoroethyl)-5,6-difluoro-1H-1,3-benzodiazol-2-yl][(2S)-1,4-dioxan-2-yl]methyl]-5-methylpyrazine-2-carboxamide

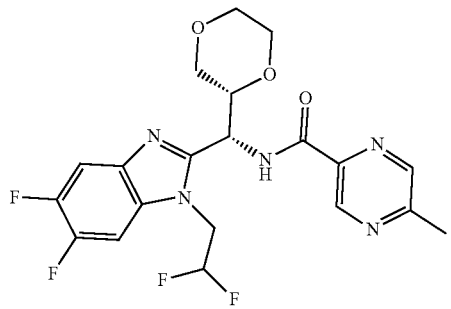 [SMILES: Cc1cnc(C(=O)N[C@H](c2nc3cc(F)c(F)cc3n2CC(F)F)[C@@H]2COCCO2)cn1]

HPLC-MS: Method: Z011_S03; R_t [min]: 0.83    MS: 454 (M + H)⁺
Chiral SFC Rt Method: I_SZ_15_MEOH_NH3_003    Rt [min]: 1.481
¹H NMR (400 MHz, DMSO-d₆) δ ppm −2.57-2.61 (m, 3 H) −3.44-3.57 (m, 3 H) −3.57-3.77 (m, 2 H) 3.97 (dd, J = 11.28, 2.28 Hz, 1 H) −4.16-4.43 (m, 1 H) 4.93 (tt, J = 15.40, 3.36 Hz, 2 H) 5.46 (t, J = 8.87 Hz, 1 H) −6.30-6.66 (m, 1 H) 7.76 (br dd, J = 10.90, 7.48 Hz, 1 H) 7.80 (br dd, J = 10.71, 7.29 Hz, 1 H) 8.65 (d, J = 1.14 Hz, 1 H) 9.03 (d, J = 1.39 Hz, 1 H) 9.26 (d, J = 8.62 Hz, 1 H)

In analogy to example 1 the following compound is obtained:

Example 138: N-[(S)-cyclopropyl[1-(2,2-difluoroethyl)-6-(trifluoromethyl)-1H-1,3-benzodiazol-2-yl]methyl]-5-methylpyrazine-2-carboxamide

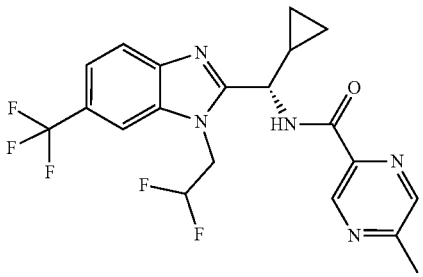 [SMILES: Cc1cnc(C(=O)N[C@H](c2nc3ccc(C(F)(F)F)cc3n2CC(F)F)C2CC2)cn1]

| HPLC-MS; Method: Z011_S03; R$_t$ [min]: 1.03 | MS: 440 (M + H)$^+$ |
|---|---|
| Chiral SFC Rt Method: I_IG_15_IPA_NH3_003 | Rt [min]: 1.48 |

$^1$H NMR (400 MHz, DMSO-d$_6$) δ ppm −0.41-0.65 (m, 4 H) −1.81-1.93 (m, 1 H) −2.58-2.61 (m, 3 H) −4.92-5.16 (m, 3 H) −6.33-6.63 (m, 1 H) 7.56 (dd, J = 8.49, 1.39 Hz, 1 H) 7.88 (d, J = 8.49 Hz, 1 H) 8.10 (s, 1 H) 8.64 (d, J = 1.39 Hz, 1 H) 9.04 (d, J = 1.27 Hz, 1 H) 9.25 (d, J = 8.11 Hz, 1 H)

In analogy to example 23 the following compounds are obtained: (redescribe the synthesis) Example 139:

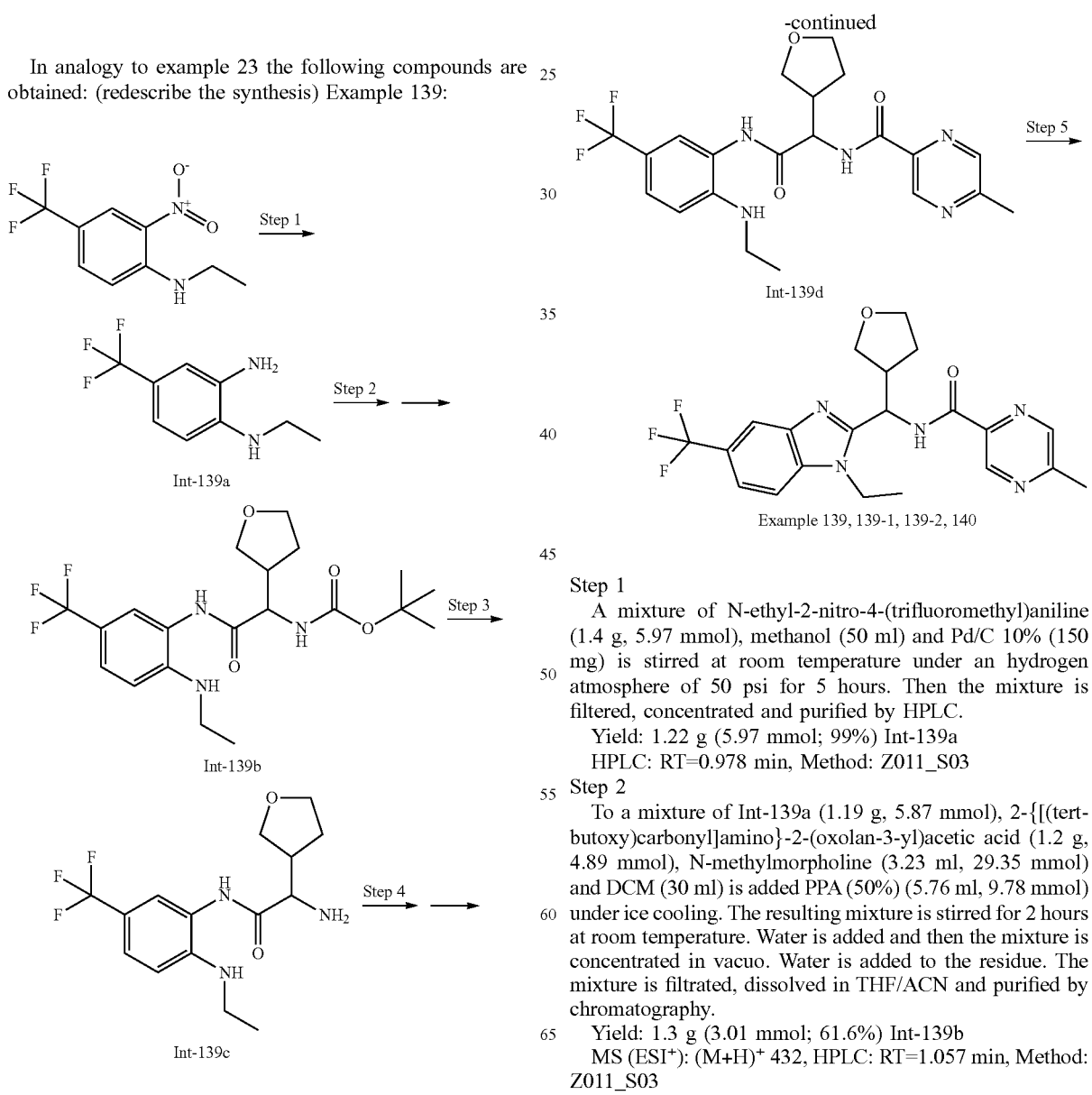

Step 1

A mixture of N-ethyl-2-nitro-4-(trifluoromethyl)aniline (1.4 g, 5.97 mmol), methanol (50 ml) and Pd/C 10% (150 mg) is stirred at room temperature under an hydrogen atmosphere of 50 psi for 5 hours. Then the mixture is filtered, concentrated and purified by HPLC.

Yield: 1.22 g (5.97 mmol; 99%) Int-139a
HPLC: RT=0.978 min, Method: Z011_S03

Step 2

To a mixture of Int-139a (1.19 g, 5.87 mmol), 2-{[(tert-butoxy)carbonyl]amino}-2-(oxolan-3-yl)acetic acid (1.2 g, 4.89 mmol), N-methylmorpholine (3.23 ml, 29.35 mmol) and DCM (30 ml) is added PPA (50%) (5.76 ml, 9.78 mmol) under ice cooling. The resulting mixture is stirred for 2 hours at room temperature. Water is added and then the mixture is concentrated in vacuo. Water is added to the residue. The mixture is filtrated, dissolved in THF/ACN and purified by chromatography.

Yield: 1.3 g (3.01 mmol; 61.6%) Int-139b
MS (ESI$^+$): (M+H)$^+$ 432, HPLC: RT=1.057 min, Method: Z011_S03

Step 3

A mixture of Int-139b and hydrochloric acid (4M in dioxane, 20 ml) is stirred 2 hours at room temperature. The mixture is concentrated and used without further purification.

Yield: 1.1 g (2.99 mmol; 99%) Int-139c
HPLC: RT=0,786 min, Method: Z011_S03

Step 4

To a mixture of Int-139c (1.1 g, 299 mmol), 5-methylpyrazine-2-carboxylic acid (0,496 g, 3,589 mmol), triethylamine (2,084 ml, 14,954 mmol) and DMF (15 ml) is added TBTU (1,056 g, 3.20 mmol). The mixture is stirred for 12 hours at room temperature. The mixture is diluted with THF and water, concentrated and purified by HPLC.

Yield: 1.1 g (3.01 mmol; 81.5%) Int-139d
MS (ESI$^+$): (M+H)$^+$ 451, HPLC: RT=0,987 min, Method: Z011_S03

Step 5

A mixture of Int-130d (1.1 g, 2,437 mmol) and acetic acid (20 ml) is stirred for 4 hours at 90° C.

Then the mixture is concentrated and THF and MEOH is added. Triethylamine is added until the mixture shows a basic pH. Then the mixture is purified by HPLC. The product is isolated as a mixture of four stereoisomers which are separated by chiral SFC.

Yield: 0.9 g (3.01 mmol; 85.2%)
MS (ESI$^+$): (M+H)$^+$ 433, HPLC: RT=1.145 min, Method: Z011_S03

---

Example 139: N-{[1-ethyl-5-(trifluoromethyl)-1H-1,3-benzodiazol-2-yl](oxolan-3-yl)methyl}-5-methylpyrazine-2-carboxamide

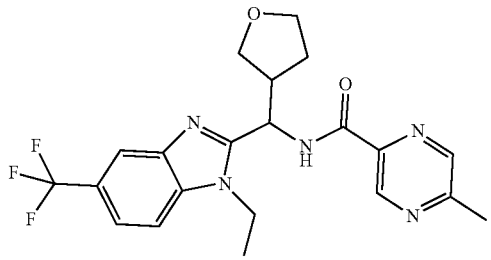 [SMILES: CCn1c(C(NC(=O)c2cnc(C)cn2)C2CCOC2)nc2cc(C(F)(F)F)ccc21]

HPLC-MS; Method: Z003_S05; R$_t$ [min]: 1.145    MS: 434 (M + H)$^+$
Chiral SFC Rt Method: I_IG_20_IPA_NH3_003    Rt [min]: 4.28

$^1$H NMR (400 MHz, DMSO-d$_6$) δ ppm 1.28 (t, J = 7.16 Hz, 3 H) 1.40 (br d, J = 5.96 Hz, 1 H) 1.49-1.61 (m, 1 H) 1.94-2.04 (m, 1 H) 2.58 (s, 3 H) 3.64 (q, J = 7.60 Hz, 1 H) 3.69-3.84 (m, 3 H) 4.33-4.54 (m, 2 H) 5.49 (t, J = 9.06 Hz, 1 H) 7.57 (dd, J = 8.55, 1.46 Hz, 1 H) 7.81 (d, J = 8.49 Hz, 1 H) 8.02 (s, 1 H) 8.61 (d, J = 1.01 Hz, 1 H) 9.06 (d, J = 1.39 Hz, 1 H) 9.29 (d, J = 8.87 Hz, 1 H)

---

Example 139-1: N-[(S)-[1-ethyl-5-(trifluoromethyl)-1H-1,3-benzodiazol-2-yl][(3R)-oxolan-3-yl]methyl]-5-methylpyrazine-2-carboxamide

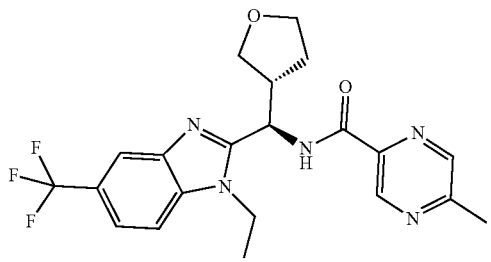 [SMILES: CCn1c([C@H](NC(=O)c2cnc(C)cn2)[C@H]2CCOC2)nc2cc(C(F)(F)F)ccc21]

HPLC-MS; Method: Z003_S05; R$_t$ [min]: 1.145    MS: 434 (M + H)$^+$
Chiral SFC Rt Method: I_IG_20_IPA_NH3_003    Rt [min]: 0.946

---

Example 139-2: N-{[1-ethyl-5-(trifluoromethyl)-1H-1,3-benzodiazol-2-yl](oxolan-3-yl)methyl}-5-methylpyrazine-2-carboxamide

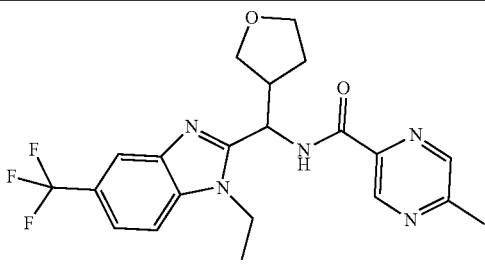

HPLC-MS; Method: Z003_S05; R$_t$ [min]: 1.145  MS: 434 (M + H)$^+$
Chiral SFC Rt Method: I_IG_20_IPA_NH3_003  Rt [min]: 3.00

Example 140: N-[(S)-[1-ethyl-5-(trifluoromethyl)-1H-1,3-benzodiazol-2-yl][(3S)-oxolan-3-yl]methyl]-5-methylpyrazine-2-carboxamide

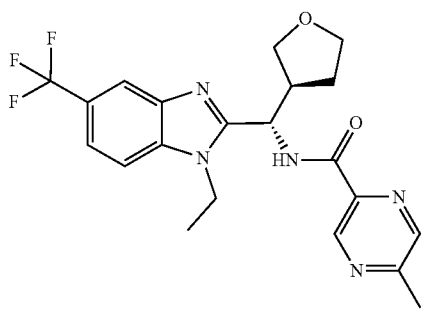 [SMILES: CCn1c([C@@H](NC(=O)c2cnc(C)cn2)[C@@H]2CCOC2)nc2cc(C(F)(F)F)ccc21]

HPLC-MS; Method: Z003_S05; R$_t$ [min]: 1.145  MS: 434 (M + H)$^+$
Chiral SFC Rt Method: I_IG_20_MEOH_NH3_002  Rt [min]: 1.52
$^1$H NMR (400 MHz, DMSO-d$_6$) δ ppm 0.15-1.29 (m, 3 H) 1.77-1.86 (m, 1 H) 1.98-2.07 (m, 1 H) 2.57-2.60 (m, 3 H) 3.34-3.44 (m, 2 H) 3.61-3.75 (m, 1 H) 3.75-3.86 (m, 2 H) 4.31-4.47 (m, 2 H) 5.45 (t, J = 9.31 Hz, 1 H) 7.57 (dd, J = 8.55, 1.46 Hz, 1 H) 7.79 (d, J = 8.49 Hz, 1 H) 8.02 (s, 1 H) 8.61 (d, J = 1.01 Hz, 1 H) 9.08 (d, J = 1.39 Hz, 1 H) 9.38 (d, J = 9.13 Hz, 1 H)

In analogy to example 139 the following compounds are obtained. The product is a mixture of four stereoisomers, which are separated by chiral SFC: examples 141, 141-1, 141-2, 142

Example 141: N-{[1-(2,2-difluoroethyl)-5-(trifluoromethyl)-1H-1,3-benzodiazol-2-yl](oxolan-3-yl)methyl}-5-methylpyrazine-2-carboxamide

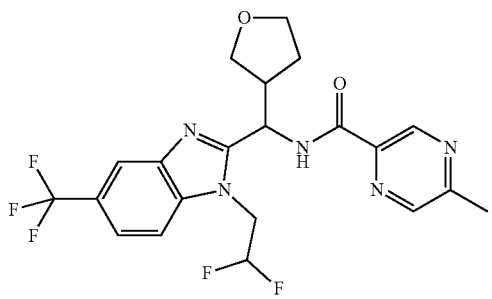 [SMILES: Cc1cnc(C(=O)NC(c2nc3cc(C(F)(F)F)ccc3n2CC(F)F)C2CCOC2)cn1]

MS: 470 (M + H)$^+$
Chiral SFC Rt Method: I_SC_10_IPA_NH3_003  Rt [min]: 2,25
$^1$H NMR (400 MHz, DMSO-d$_6$) δ ppm 1.77 (m, 1H) 2.04 (m, 1H) 2.58 (s, 3H) 3.33 (m, 1H) 3.38-3.54 (m, 1H) 3.61-3.73 (m, 1H) 3.73-3.87 (m, 2H) 4.9-5.1 (m, 1H) 4.95-5.10 (m, 2H) 5.46 (t, J = 9.44 Hz, 1H) 6.31-6.61 (m, 1H) 7.63 (dd, J = 8.62, 1.39 Hz, 1H) 7.83 (d, J = 8.49 Hz, 1H) 8.06 (s, 1H) 8.61 (d, J = 1.01 Hz, 1H) 9.07 (d, J = 1.27 Hz, 1H) 9.41 (d, J = 8.87 Hz, 1H)

-continued

Example 141-1: N-{[1-(2,2-difluoroethyl)-5-(trifluoromethyl)-1H-1,3-benzodiazol-2-yl](oxolan-3-yl)methyl}-5-methylpyrazine-2-carboxamide

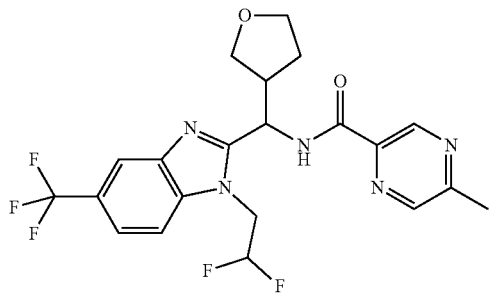 [SMILES: Cc1cnc(C(=O)NC(c2nc3cc(C(F)(F)F)ccc3n2CC(F)F)C2CCOC2)cn1]

MS: 470 (M + H)⁺
Chiral SFC Rt Method: I_IG_15_MEOH_NH3_003    Rt [min]: 1.725

Example 141-2: N-{[1-(2,2-difluoroethyl)-5-(trifluoromethyl)-1H-1,3-benzodiazol-2-yl](oxolan-3-yl)methyl}-5-methylpyrazine-2-carboxamide

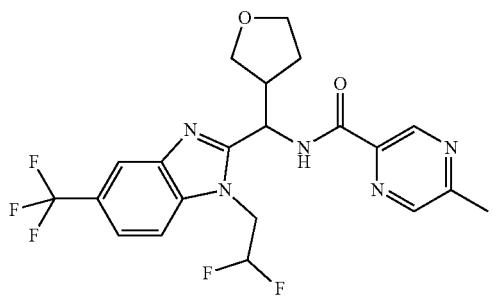 [SMILES: Cc1cnc(C(=O)NC(c2nc3cc(C(F)(F)F)ccc3n2CC(F)F)C2CCOC2)cn1]

MS: 470 (M + H)⁺
Chiral SFC Rt Method: I_IG_15_MEOH_NH3_003    Rt [min]: 1.725

Example 142: N-[(S)-[1-(2,2-difluoroethyl)-5-(trifluoromethyl)-1H-1,3-benzodiazol-2-yl][(3R)-oxolan-3-yl]methyl]-5-methylpyrazine-2-carboxamide

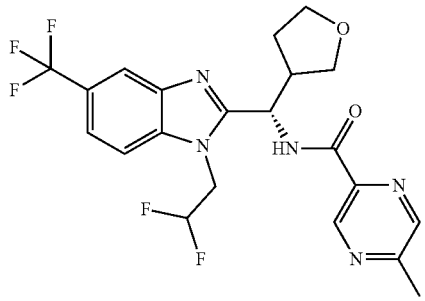 [SMILES: Cc1cnc(C(=O)N[C@H](c2nc3cc(C(F)(F)F)ccc3n2CC(F)F)C2CCOC2)cn1]

MS: 470 (M + H)⁺
Chiral SFC Rt Method: I_IG_20_IPA_NH3_003    Rt [min]: 2,90

¹H NMR (400 MHz, DMSO-d₆) δ ppm 1.52 (m, 1H) 1.96 (m, 1H) 2.57 (m, 3H) 3.37-3.52 (m, 1H) 3.59-3.85 (m, 4H) 4.83-5.21 (m, 2H) 5.46 (t, J = 9.12 Hz, 1H) 6.35-6.67 (m, 1H) 7.62 (dd, J = 8.68, 1.46 Hz, 1H) 7.84 (d, J = 8.62 Hz, 1H) 8.06 (s, 1H) 8.60 (d, J = 1.01 Hz, 1H) 9.04 (d, J = 1.27 Hz, 1H) 9.34 (d, J = 8.87 Hz, 1H)

Example 143 and Example 144

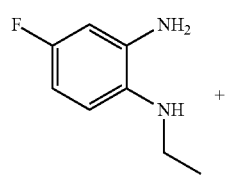

+

-continued

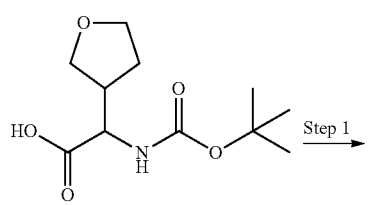

Step 1

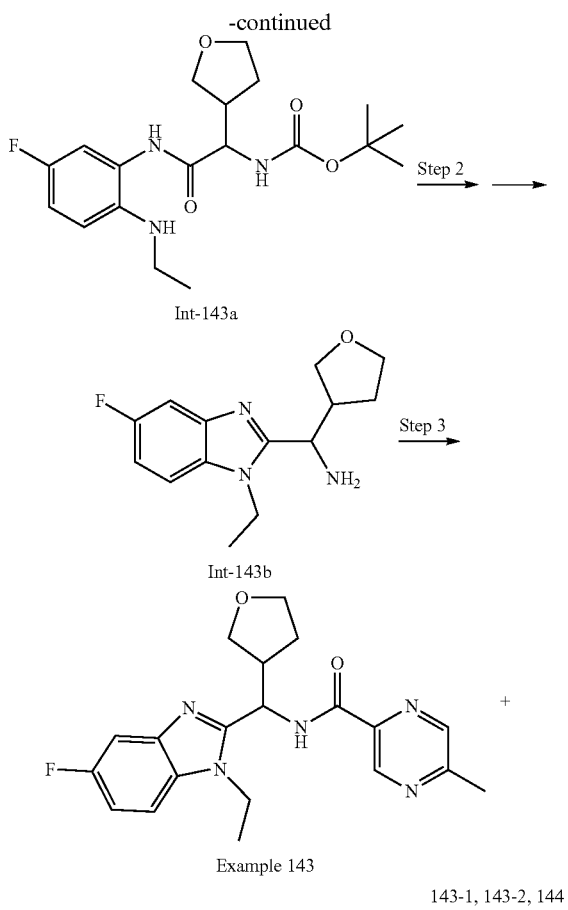

Int-143a

Int-143b

Example 143    143-1, 143-2, 144

Step 1:
PPA (50% in EtOAc, 9.72 mL, 15.88 mmol) is added to a mixture of N1-ethyl-4-fluorobenzene-1,2-diamine (1.36 g, 7.94 mmol), 2-(Boc-amino)-2-(tetrahydrofuran-3-yl)-acetic acid (2.27 g, 8.34 mmol) and NMM (5.2 mL, 47.66 mmol) in 30 mL DCM at 0° C. and then stirred for 2 h at ambient temperature. The mixture is concentrated i. vac., EtOAc and water are added and the organic layer washed with aq. NaHCO₃ solution, dried over Na₂SO₄ and concentrated i. vac. The residue is purified by prep. HPLC. The product is isolated as a mixture of stereoisomers.

Yield: 2.6 g (6.81 mmol; 86%) Int-143a

MS (ESI$^+$): (M+H)$^+$ 382; HPLC: RT=0.8 min, Method: Z011_S03

Step 2:
A mixture of Int-143a (2.6 g, 5.45 mmol) and zinc bromide (2.59 g, 11.45 mmol) in 87 ml butyl acetate is stirred at 110° C. for 22 h. The mixture is cooled and concentrated in vacuo. Ice cooled water (50 ml) is added to the residue and stirred for some minutes. Then a solution of concentrated ammonia in water (4 ml) was added. The resulting solid was filtered and dried giving the product as a mixture of stereoisomers.

Yield: 2.05 g (5.45 mmol; 99%) Int-143b

MS (ESI$^+$): (M+H)$^+$ 264; HPLC: RT=0.89 min and 0.92 min, Method: Z003_S05

Step 3:
PPA (50% in EtOAc, 4.21 mL, 7.08 mmol) is added to a mixture of Int-143b (2.05 g, 5.45 mmol) with 5-methylpyrazine-2-carboxylic acid (2.27 g, 8.34 mmol) and TEA (3.02 mL, 21.79 mmol) in 20 mL EtOAc at 0° C. and then stirred for 2 h at ambient temperature. The mixture is concentrated i. vac., DCM and water are added and the organic layer washed with aq. NaHCO₃ solution, dried over Na₂SO₄ and concentrated i. vac. The residue is purified by column chromatographie (XBridge C18, 10 µm, eluent gradient: (H2O+0.1% NH₄OH): 73:27→53:47 ACN).

Yield: 1.87 g (4.88 mmol; 89%)

The product is isolated as a mixture of four stereoisomers, which are separated by chiral SFC giving example 143, 143-1, 143-2 and example 144

---

Example 143: N-[(1-ethyl-5-fluoro-1H-1,3-benzodiazol-2-yl)(oxolan-3-yl)methyl]-5-methylpyrazine-2-carboxamide

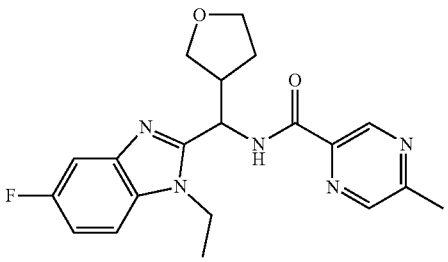 [SMILES: CCn1c(C(NC(=O)c2cnc(C)cn2)C2CCOC2)nc2cc(F)ccc21]

HPLC-MS; Method: Z011_S03; R$_t$ [min]: 0.881    MS: 384 (M + H)$^+$
Chiral SFC Rt Method: I_IG_30_MEOH_NH3_002    Rt [min]: 1,76

$^1$H NMR (400 MHz, DMSO-d₆) δ ppm 1.22 (t, J = 7.16 Hz, 3H) 1.72-1.91 (m, 1H) 2.01 (m, 1H) 2.57-2.60 (m, 3H) 3.32-3.46 (m, 2H) 3.66 (q, J = 7.35 Hz, 1H) 3.71-3.92 (m, 2H) 4.20-4.39 (m, 2H) 5.40 (t, J = 9.31 Hz, 1H) 7.11 (ddd, J = 9.70, 8.93, 2.53 Hz, 1H) 7.46 (dd, J = 9.76, 2.41 Hz, 1H) 7.58 (dd, J = 8.87, 4.82 Hz, 1H) 8.61 (d, J = 0.89 Hz, 1H) 9.08 (d, J = 1.39 Hz, 1H) 9.30 (d, J = 9.13 Hz, 1H)

Example 143-1: N-[(1-ethyl-5-fluoro-1H-1,3-benzodiazol-2-yl) (oxolan-3-yl)methyl]-5-methylpyrazine-2-carboxamide

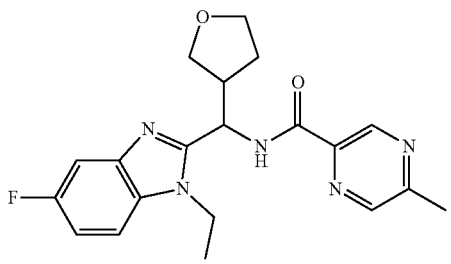 [SMILES: CCn1c(C(NC(=O)c2cnc(C)cn2)C2CCOC2)nc2cc(F)ccc21]

HPLC-MS; Method: Z011_S03; R<sub>t</sub> [min]: 0.881     MS: 384 (M + H)⁺
Chiral SFC Rt Method: I_IG_30_MEOH_NH3_002     Rt [min]: 1,24
Example 143-2: N-[(1-ethyl-5-fluoro-1H-1,3-benzodiazol-2-yl)(oxolan-3-yl)methyl]-5-methylpyrazine-2-carboxamide

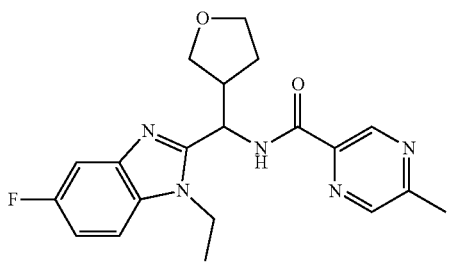 [SMILES: CCn1c(C(NC(=O)c2cnc(C)cn2)C2CCOC2)nc2cc(F)ccc21]

HPLC-MS; Method: Z011_S03; $R_t$ [min]: 0.881     MS: 384 (M + H)⁺
Chiral SFC Rt Method: I_SC_15_MEOH_NH3_003     Rt [min]: 4.63
Example 144: N-[(S)-(1-ethyl-5-fluoro-1H-1,3-benzodiazol-2-yl)[(3R)-oxolan-3-yl]methyl]-5-methylpyrazine-2-carboxamide

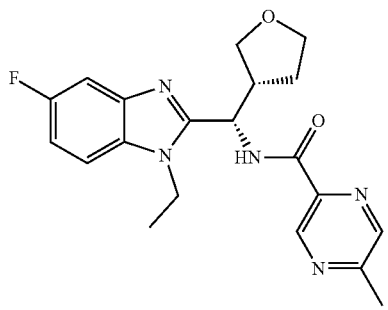 [SMILES: CCn1c([C@@H](NC(=O)c2cnc(C)cn2)[C@H]2CCOC2)nc2cc(F)ccc21]

HPLC-MS; Method: Z011_S03; $R_t$ [min]: 0.881     MS: 384 (M + H)⁺
Chiral SFC Rt Method: I_SC_15_MEOH_NH3_003     Rt [min]: 4,13
¹H NMR (400 MHz, DMSO-$d_6$) δ ppm 1.26 (t, J = 7.16 Hz, 3H) 1.44-1.59 (m, 1H) 1.98 (m 1H) 2.56-2.60 (m, 3H) 3.24-3.33 (m, 1H) 3.63 (q, J = 7.60 Hz, 1H) 3.68-3.82 (m, 3H) 4.29-4.48 (m, 2H) 5.44 (t, J = 9.12 Hz, 1H) 7.11 (ddd, J = 9.70, 8.93, 2.53 Hz, 1H) 7.46 (dd, J = 9.82, 2.47 Hz, 1H) 7.59 (dd, J = 8.87, 4.69 Hz, 1H) 8.61 (d, J = 0.89 Hz, 1H) 9.06 (d, J = 1.39 Hz, 1H) 9.21 (d, J = 9.00 Hz, 1H)

Example 145 and 146

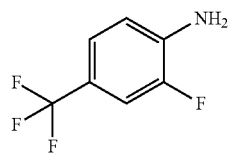

Step 1 ⟶

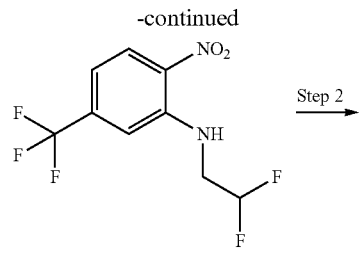

Int-145a

Step 2 ⟶

309

-continued

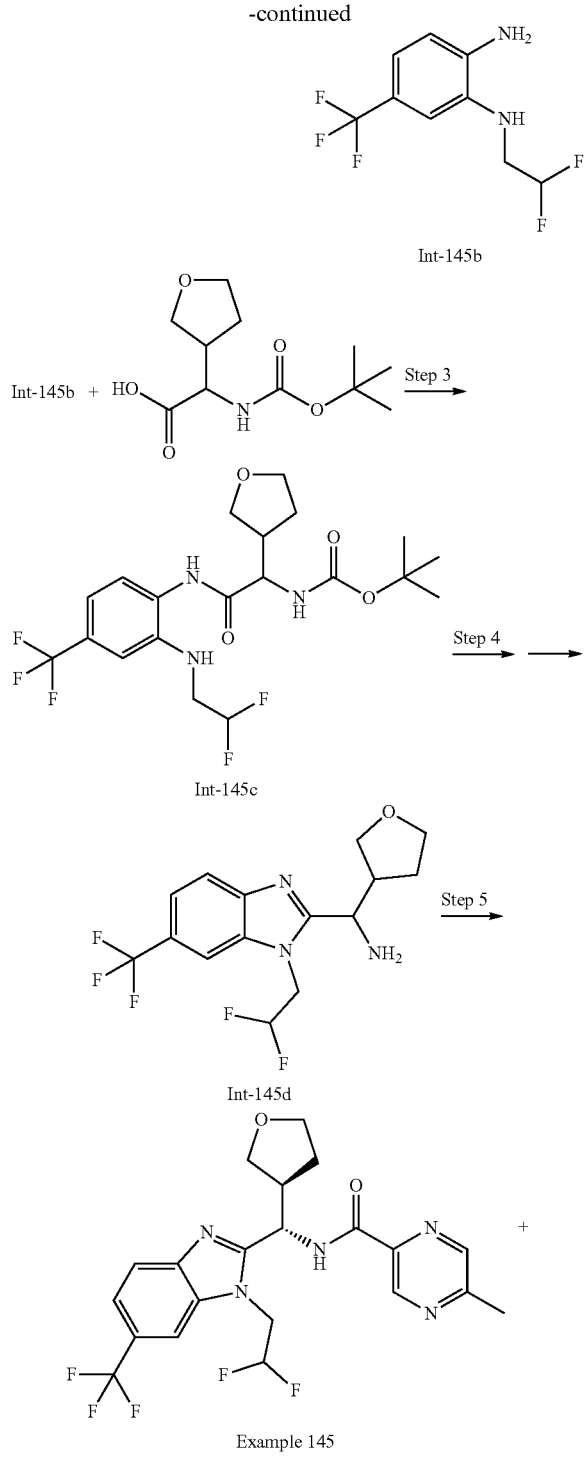

310

Step 1

A mixture of 2-fluoro-1-nitro-4-(trifluoromethyl) benzene (9.65 g, 45.22 mmol) and 2,2-difluorethylamine (4.93 ml, 67.84 mmol) and potassium carbonate (9.38 g, 67.84 mmol) in 110 ml ACN is stirred for 36 h at 60° C. The mixture is poured in 500 ml water and then concentrated in vacuo. The mixture is filtrated and the remaining solid is washed with 500 ml of water. The solid is dried.

Yield: 11.98 g (44.34 mmol; 98%) Int-145a

MS (ESI$^+$): (M+H)$^+$ 271; HPLC: RT=1.1 min, Method: Z018_S04

Step 2:

A mixture of Int-145a (1.34 g, 4.95 mmol) and palladium on charcoal (10%) in 27 ml THF is hydrogenated for 2 h in a Parr apparatus at 60 psi and 25° C. Then the mixture is filtrated. The filtrate is evaporated in vacuo. The residue is used in the next step without further purification.

Yield: 1.19 g (44.34 mmol; 100%) Int-145b

HPLC: RT=0.94 min, Method: Z011_S03

Step 3:

Prepared analogously to example 143 step 1 from Int-145b and 2-(Boc-amino)-2-(tetrahydrofuran-3-yl)-acetic acid.

Yield: 2.55 g (4.92 mmol; 99%) Int-145c

MS (ESI$^+$): (M+H)$^+$ 468

Step 4:

Prepared analogously to example 143 step 2 from Int-145c and zinc bromide.

Yield: 1.78 g (4.08 mmol; 83%) Int-145d

MS (ESI$^+$): (M+H)$^+$ 350 HPLC: RT=1.04 min and 1.02 min, Method: Z011_S03

Step 5:

Prepared analogously to example 143 step 3 from Int-145d and 5-methylpyrazine-2-carboxylic acid.

Yield: 0.83 g (1.76 mmol; 43%)

The product is isolated as a mixture of four stereoisomers, which are separated by chiral SFC giving example 145, 145-1, 145-2, 146

Example 145: N-[(S)-[1-(2,2-difluoroethyl)-6-(trifluoromethyl)-1H-1,3-benzodiazol-2-yl][(3S)-oxolan-3-yl]methyl]-5-methylpyrazine-2-carboxamide -continued

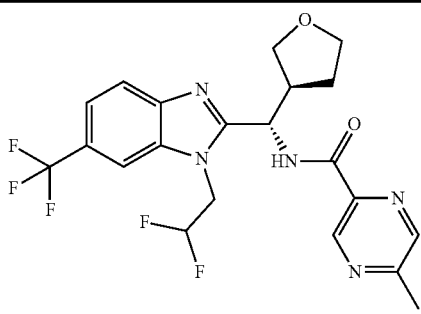

HPLC-MS; Method: Z011_S03; R$_t$ [min]: 0.976     MS: 470 (M + H)$^+$
Chiral SFC Rt Method: I_IG10_MEOH_NH3_003     Rt [min]: 2,8
$^1$H NMR (400 MHz, DMSO-d$_6$) δ ppm 1.73-1.83 (m, 1H) 2.04 (m, 1H) 2.58 (s, 3H) 3.32-3.39 (m, 1H) 3.39-3.57 (m, 1H) 3.57-3.72 (m, 1H) 3.72-3.84 (m, 2H) 4.94-5.15 (m, 2H) 5.46 (t, J = 9.44 Hz, 1H) 6.23-6.62 (m, 1H) 7.56 (dd, J = 8.55, 1.33 Hz, 1H) 7.88 (d, J = 8.49 Hz, 1H) 8.10 (s, 1H) 8.61 (d, J = 1.01 Hz, 1H) 9.07 (d, J = 1.39 Hz, 1H) 9.41 (d, J = 9.00 Hz, 1H)
Example 145-1: N-[(S)-[1-(2,2-difluoroethyl)-6-(trifluoromethyl-1H-1,3-benzodiazol-2-yl][(3S)-oxolan-3-yl]methyl]-5-methylpyrazine-2-carboxamide

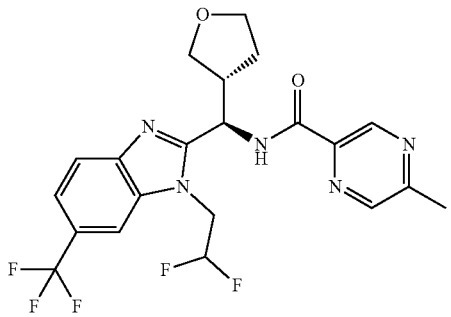 [SMILES: Cc1cnc(C(=O)N[C@@H](c2nc3ccc(C(F)(F)F)cc3n2CC(F)F)[C@H]2CCOC2)cn1]

HPLC-MS; Method: Z011_S03; R$_t$ [min]: 0.976     MS: 470 (M + H)$^+$
Chiral SFC Rt Method: I_IG10_MEOH_NH3_003     Rt [min]: 1.97
Example 145-2: N-{[1-(2,2-difluoroethyl)-6-(trifluoromethyl)-1H-1,3-benzodiazol-2-yl](oxolan-3-yl)methyl}-5-methylpyrazine-2-carboxamide

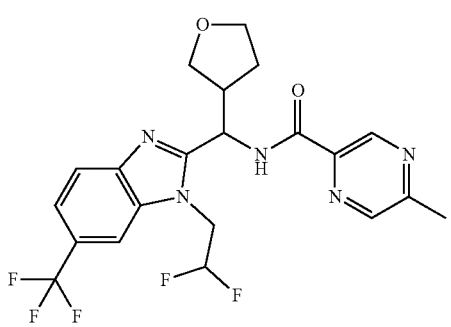

HPLC-MS; Method: Z011_S03; R$_t$ [min]: 0.976     MS: 470 (M + H)$^+$
Chiral SFC Rt Method: I_SZ_10_IPA_NH3_003     Rt [min]: 2.52
Example 146: N-{[1-(2,2-difluoroethyl)-6-(trifluoromethyl)-1H-1,3-benzodiazol-2-yl](oxolan-3-yl)methyl}-5-methylpyrazine-2-carboxamid

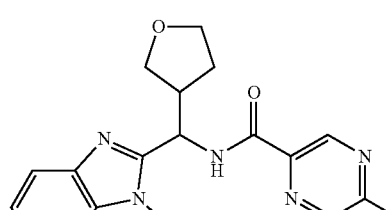

The following examples are prepared in analogy to example 1 as mixtures of four stereoisomers, which are separated by chiral SFC giving examples 147, 147-1, 147-2, 148.

Example 147: N-{[1-ethyl-6-(trifluoromethyl)-1H-1,3-benzodiazol-2-yl](oxolan-3-yl)methyl}-5-methylpyrazine-2-carboxamide

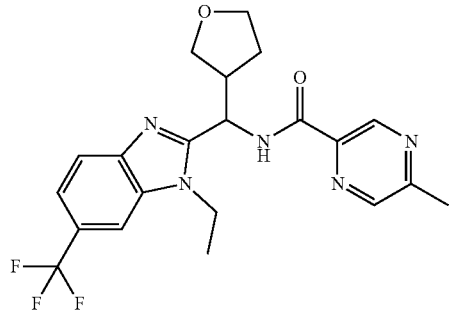

HPLC-MS; Method: Z011_S03; R$_t$ [min]: 0.973        MS: 434 (M + H)$^+$
Chiral SFC Rt Method: I_SB_10_IPA_NH3_003            Rt [min]: 3,04

$^1$H NMR (400 MHz, DMSO-d$_6$) δ ppm 1.28 (t, J = 7.10 Hz, 3H) 1.47-1.66 (m, 1H) 1.99 (m, 1H) 2.58 (m, 3H) 3.33-3.36 (m, 1H) 3.64 (q, J = 7.56 Hz, 1H) 3.69-3.84 (m, 3H) 4.39-4.59 (m, 2H) 5.49 (t, J = 9.06 Hz, 1H) 7.52 (dd, J = 8.55, 1.33 Hz, 1H) 7.84 (d, J = 8.49 Hz, 1H) 8.04 (s, 1H) 8.61 (d, J = 1.01 Hz, 1H) 9.06 (d, J = 1.39 Hz, 1H) 9.30 (d, J = 8.87 Hz, 1H)

Example 147-1: N-[(S)-[1-ethyl-6-(trifluoromethyl)-1H-1,3-benzodiazol-2-yl][(3R)-oxolan-3-yl]methyl]-5-methylpyrazine-2-carboxamide

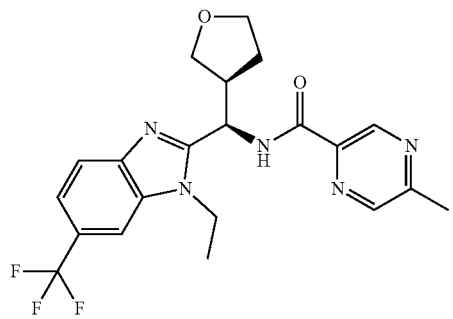 [SMILES: CCn1c([C@H](NC(=O)c2cnc(C)cn2)[C@@H]2CCOC2)nc2ccc(C(F)(F)F)cc21]

HPLC-MS; Method: Z011_S03; R$_t$ [min]: 0.973        MS: 434 (M + H)$^+$
Chiral SFC Rt Method: I_SB_10_IPA_NH3_003            Rt [min]: 2.31

Example 147-2: N-{[1-ethyl-6-(trifluoromethyl)-1H-1,3-benzodiazol-2-yl](oxolan-3-yl)methyl}-5-methylpyrazine-2-carboxamide

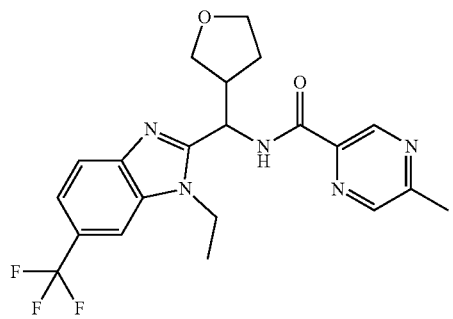

HPLC-MS; Method: Z011_S03; R$_t$ [min]: 0.973        MS: 434 (M + H)$^+$
Chiral SFC Rt Method: I_SB_10_IPA_NH3_003            Rt [min]: 1.82

Example 148: N-{[1-ethyl-6-(trifluoromethyl)-1H-1,3-benzodiazol-2-yl](oxolan-3-yl)methyl}-5-methylpyrazine-2-carboxamide -continued
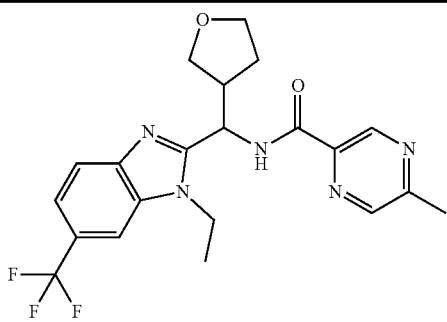
HPLC-MS; Method: Z011_S03; R$_t$ [min]: 0.973  MS: 434 (M + H)$^+$
Chiral SFC Rt Method: I_SB_10_IPA NH3_003  Rt [min]: 2,05
$^1$H NMR (400 MHz, DMSO-d$_6$) δ ppm 1.21 (m, 3H) 1.73-1.91 (m, 1H) 1.91-2.07 (m, 1H) 2.59 (s, 3H) 3.34-3.46 (m, 2H) 3.57-3.73 (m, 1H) 3.73-3.86 (m, 2H) 4.31-4.57 (m, 2H) 5.42-5.51 (m, 1H) 7.52 (dd, J = 8.55, 1.33 Hz, 1H) 7.84 (d, J = 8.49 Hz, 1H) 8.03 (s, 1H) 8.62 (d, J = 1.01 Hz, 1H) 9.05-9.09 (m, 1H) 9.38 (d, J = 9.13 Hz, 1H)
Example 149
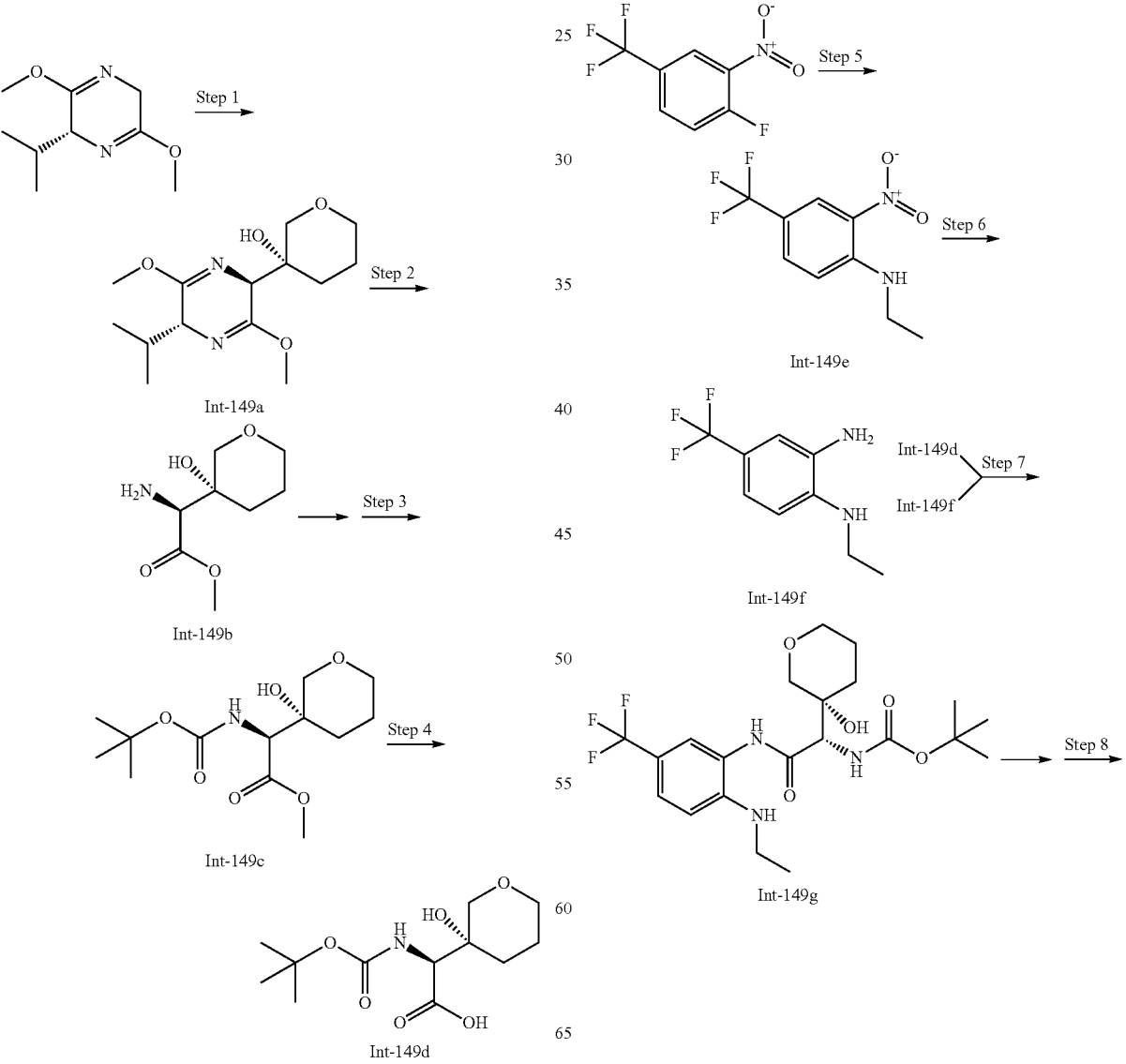

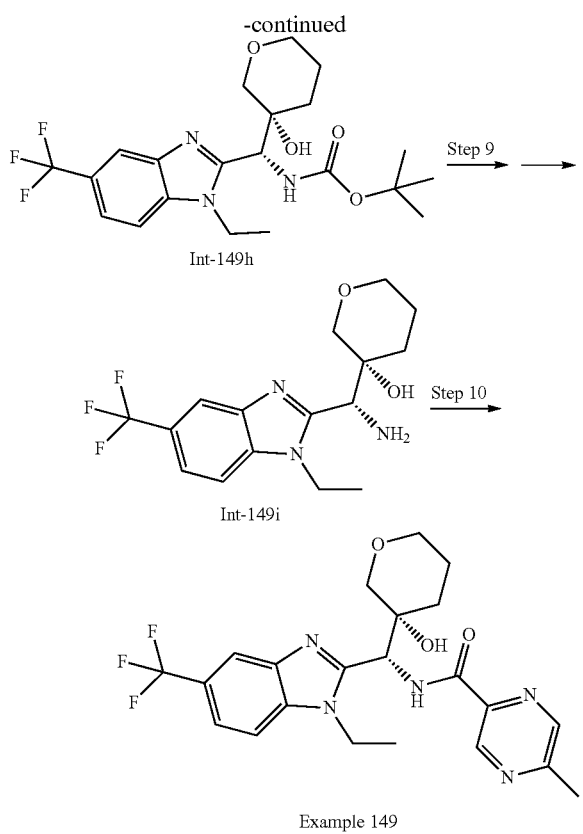

Example 149

Step 1:
To a stirred solution of R-2-Isopropyl-3,6-dimethoxy-2,5-dihydro-pyrazine (5 g, 27 mmol) in THF (50 ml) is added at −78° C. n-butyllithium 2.5 M in hexane (1.91 g, 30 mmol) over a period of 15 min and the mixture is stirred at −78° C. for 1 h. Then dihydro-pyran-3-one (2.72 g, 27 mmol) in 30 ml THF is added dropwise and the mixture is stirred at −25° C. for 30 min. The mixture is quenched by addition of acetic acid (dissolved in THF), diluted with water (30 ml) and extracted with ethyl acetate (2×50 ml). The combined organic layers are washed with brine solution, dried over sodium sulfate and concentrated. The residue is purified by column chromatography using silica gel (eluent; 30% EtOAc in petrolether).
Yield: 5.5 g (19 mmol; 71%) Int-149a Step 2:
To a mixture of Int-149a (15 g, 53 mmol) in THF (50 ml) is added 0.2 N hydrochloric acid solution (150 ml) slowly dropwise at 0° C. and the mixture is stirred at room temperature for 16 h. The pH of the reaction mixture is adjusted to 7.5 with sodium hydroxide solution and lyophilized. The crude product is used without further purification.
Yield: 9.5 g (19 mmol; 95%) Int-149b Step 3:
To a mixture of Int-149b (8 g, 42 mmol) in THF (80 ml) is added triethylamine (6.42 g, 63 mmol) and di-tert-butyl diacetate (9.23 g, 42 mmol) at room temperature. The mixture is stirred for 2 h at room temperature. Then the mixture is diluted with water and extracted with EtOAc (2×50 ml). The combined organic phases are washed with brine solution, dried over sodium sulfate and concentrated. The residue is purified by chromatography using silica gel with 50% EtOAc in petrolether. Yield: 2.8 g (10 mmol; 23%) Int-149c Step 4:
To a stirred solution of Int-149c (5.2 g, 18 mmol) in THF (50 ml) and water (10 ml) is added lithium hydroxide monohydrate (1.51 g, 36 mmol). The mixture is stirred at room temperature for 4 h. The reaction mixture is concentrated, diluted with water and extracted with EtOAc (2×30 ml). The aqueous layer is acidified with citric acid (pH 6) and extracted with EtOAc (2×60 ml). The combined organic layers are washed with brine solution, dried over sodium sulfate and concentrated in vacuo. The residue is purified by chromatography using silica gel with 80% EtOAc in petrolether. Yield: 4.2 g (15 mmol; 85%) Int-149d.

Step 5:
To a solution of 1-fluoro-2-nitro-4-(trifluoromethyl)benzene (10 ml, 71.45 mmol) in DCM (300 ml) is added dropwise ethylamine solution 2M in THF (71.45 ml, 142.9 mmol). The mixture is stirred over night. Then DCM (100 ml) is added and the mixture is extracted with water (250 ml). The organic phase is dried over sodium sulfate and concentrated in vacuo.
Yield: 16.6 g (70.88 mmol; 99%) Int-149e
MS (ESI$^+$): (M+H)$^+$ 235; HPLC: RT=1.1 min, Method: Z017_S04

Step 6:
A mixture of Int-149e (1.4 g, 5.97 mmol) and palladium on charcoal 10% (150 mg) in methanol (50 ml) is hydrogenated at 50 psi at room temperature. The mixture is filtrated and the filtrate is concentrated in vacuo. Yield: 1.22 g (5.97 mmol; 99%) Int-149f HPLC: RT=0.97 min, Method: Z011_S03

Step 7:
To a mixture of Int-149f (0.51 g, 2.51 mmol), Int-149d (0.6 g, 2.09 mmol) and N-methylmorpholine in DCM (20 ml) is added PPA 50% (2.47 ml, 4.19 mmol) at 0° C. The mixture is then stirred for 2 h at room temperature. The mixture is concentrated, EtOAc is added and extracted with water. The organic layer is washed with saturated sodium hydrogencarbonate solution, dried over sodium sulfate and concentrated in vacuo. The residue is purified by column chromatography.
Yield: 1.22 g (5.97 mmol; 99%) Int-149 g
MS (ESI$^+$): (M+H)$^+$ 462; HPLC: RT=1.06 min, Method: Z011_S03

Step 8
A mixture of Int-149 g (0.51 g, 1.11 mmol) and acetic acid (10 ml, 174.5 mmol) is stirred for 24 h at 50° C. and 24 h at 90° C. The mixture is concentrated in vacuo. THF and methanol are added to the residue and TEA is added until the mixture is basic. This mixture is purified by HPLC.
Yield: 1.22 g (5.97 mmol; 99%) Int-149 h
MS (ESI$^+$): (M+H)$^+$ 444; HPLC: RT=1.13 min, Method: Z011_S03

Step 9
A mixture of Int-149 h (0.2 g, 45 mmol) and hydrochloric acid 4M in dioxane (5 ml) is stirred for 2 h at room temperature. The mixture is concentrated and used without further purification.
Yield: 1.22 g (5.97 mmol; 99%) Int-149i
HPLC: RT=0.91 min, Method: Z011_S03

Step 10
To a mixture of Int-149i (0,085 g, 0.22 mmol), 5-methylpyrazine-2-carboxylic acid (0,037 g, 0.27 mmol) and TEA (0.16 ml, 1.12 mmol) in 5 ml DMF is added TBTU (0,079 g, 0.25 mmol). The mixture is stirred for 2 h at room temperature. Water and acetonitrile are added. The mixture is filtrated and concentrated. The residue is purified by HPLC.

Yield: 0,081 g (0.17 mmol; 78%) Example 149

Example 149: N-[(R)-[1-ethyl-5-(trifluoromethyl)-1H-1,3-benzodiazol-2-yl][(3R)-3-hydroxyoxan-3-yl]methyl]-5-methylpyrazine-2-carboxamide

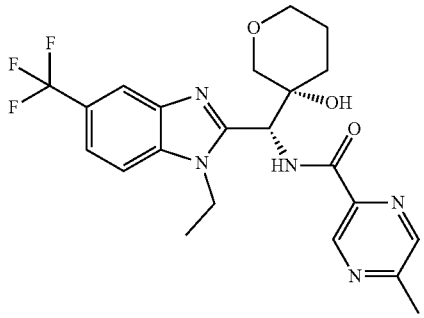 [SMILES: CCn1c([C@@H](NC(=O)c2cnc(C)cn2)[C@]2(O)CCCOC2)nc2cc(C(F)(F)F)ccc21]

HPLC-MS; Method: Z011_S03; $R_t$ [min]: 1.053   MS: 464 (M + H)$^+$
Chiral SFC Rt Method: I_IH_05_MEOH NH3 003   Rt [min]: 1,74
$^1$H NMR (400 MHz, DMSO-$d_6$) δ ppm 1.37 (t, J = 7.16 Hz, 3H) 1.55-1.75 (m, 3H) 1.90 (m, 1H) 2.60 (s, 3H) 3.29 (m, 1H) 3.35-3.43 (m, 1H) 3.49 (m, 1H) 3.58-3.68 (m, 1H) 4.48-4.62 (m, 2H) 5.57 (s, 1H) 5.74 (d, J = 9.51 Hz, 1H) 7.60 (dd, J = 8.62, 1.39 Hz, 1H) 7.86 (d, J = 8.49 Hz, 1H) 8.05 (s, 1H) 8.67 (s, 1H) 8.83 (d, J = 9.50 Hz, 1H) 9.08 (d, J = 1.27 Hz, 1H)

The following examples are obtained in analogy to example 149.

Example 150: N-[(R)-(1-ethyl-5-fluoro-1H-1,3-benzodiazol-2-yl)[(3R)-3-hydroxyoxan-3-yl]methyl]-5-methylpyrazine-2-carboxamide

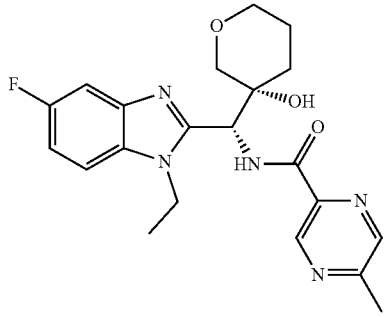 [SMILES: CCn1c([C@@H](NC(=O)c2cnc(C)cn2)[C@]2(O)CCCOC2)nc2cc(F)ccc21]

HPLC-MS; Method: Z011_S03; $R_t$ [min]: 0.969   MS: 414 (M + H)$^+$
Chiral SFC Rt Method: I_IH_10_IPA_NH3_003   Rt [min]: 2,12
$^1$H NMR (400 MHz, DMSO-$d_6$) δ ppm 1.35 (t, J = 7.16 Hz, 3H) 1.47-1.79 (m, 3H) 1.79-2.08 (m, 1H) 2.60 (s, 3H) 3.25-3.30 (m, 1H) 3.33-3.41 (m, 1H) 3.48 (dt, J = 11.22, 5.42 Hz, 1H) 3.57-3.68 (m, 1H) 4.41-4.56 (m, 2H) 5.66 (s, 1H) 5.71 (d, J = 9.63 Hz, 1H) 7.15 (td, J = 9.31, 2.41 Hz, 1H) 7.49 (dd, J = 9.63, 2.41 Hz, 1H) 7.66 (dd, J = 8.87, 4.69 Hz, 1H) 8.66 (s, 1H) 8.77 (d, J = 9.63 Hz, 1H) 9.09 (s, 1H)

Example 151: N-[(R)-[1-(2,2-difluoroethyl)-5-fluoro-1H-1,3-benzodiazol-2-yl][(3R)-3-hydroxyoxan-3-yl]methyl]-5-methylpyrazine-2-carboxamide

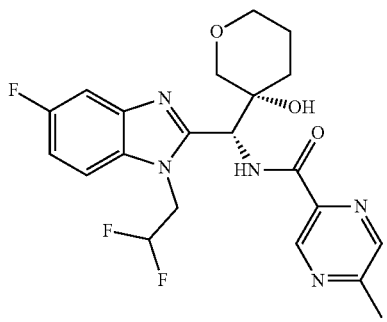 [SMILES: Cc1cnc(C(=O)N[C@H](c2nc3cc(F)ccc3n2CC(F)F)[C@]2(O)CCCOC2)cn1]

HPLC-MS; Method: Z011_S03; $R_t$ [min]: 0.943   MS: 450 (M + H)$^+$

-continued

| | |
|---|---|
| Chiral SFC Rt Method: I_IG_15_MEOH_NH3_003 | Rt [min]: 3,06 |

¹H NMR (400 MHz, DMSO-d₆) δ ppm 1.55-1.78 (m, 3H) 1.78-1.87 (m, 1H) 2.60 (s, 3H) 3.33-3.46 (m, 2H) 3.46-3.58 (m, 2H) 4.93-5.14 (m, 2H) 5.52 (s, 1H) 5.60 (1, J = 9.25 Hz, 1H) 6.32-6.61 (m 1H) 7.18 (td, J = 9.28, 2.47 Hz, 1H) 7.53 (dd, J = 9.57, 2.47 Hz, 1H) 7.68 (dd, J = 8.87, 4.69 Hz, 1H) 8.68 (d, J = 1.01 Hz, 1H) 8.82 (d, J = 9.12 Hz, 1H) 9.08 (d, J = 1.27 Hz, 1H)

Example 152: N-[(R)-[1-ethyl-6-(trifluoromethyl)-1H-1,3-benzodiazol-2-yl][(3R)-3-hydroxyoxan-3-yl]methyl]-5-methylpyrazine-2-carboxamide

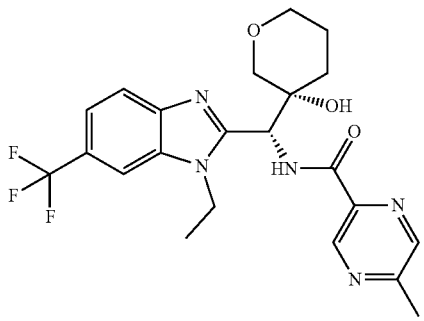 [SMILES: CCn1c([C@@H](NC(=O)c2cnc(C)cn2)[C@]2(O)CCCOC2)nc2ccc(C(F)(F)F)cc21]

| | |
|---|---|
| HPLC-MS; Method: Z011_S03; R_t [min]: 1.054 | MS: 464 (M + H)⁺ |
| Chiral SFC Rt Method: I_IH_10_IPA_NH3_003 | Rt [min]: 1,48 |

1.83-1.94 (m, 1H) 2.60 (s, 3H) 3.25-3.34 (m, 1H) 3.34-3.42 (m, 1H) 3.49 (dt, J = 10.93, 5.24 Hz, 1H) 3.58-3.68 (m, 1H) 4.60 (q, J = 7.05 Hz, 2H) 5.58 (s, 1H) 5.74 (d, J = 9.50 Hz, 1H) 7.54 (d, J = 8.49 Hz, 1H) 7.86 (d, J = 8.36 Hz, 1H) 8.11 (s, 1H) 8.67 (s, 1H) 8.83 (d, J = 9.50 Hz, 1H) 9.08 (s, 1H)

Example 153: N-[(R)-(1-ethyl-6-fluoro-1H-1,3-benzodiazol-2-yl)[(3R)-3-hydroxyoxan-3-yl]methyl]-5-methylpyrazine-2-carboxamide

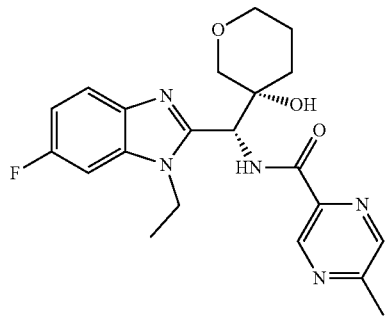

| | |
|---|---|
| HPLC-MS; Method: Z011_S03; R_t [min]: 0.973 | MS: 414 (M + H)⁺ |
| Chiral SFC Rt Method: I_IH_10_IPA_NH3_003 | Rt [min]: 2,11 |

¹H NMR (400 MHz, DMSO-d₆) δ ppm 1.33 (t, J = 7.16 Hz, 3H) 1.57-1.79 (m, 3H) 1.79-1.91 (m, 1H) 2.60 (s, 3H) 3.24-3.32 (m, 1H) 3.32-3.41 (m, 1H) 3.41-3.53 (m, 1H) 3.60-3.68 (m, 1H) 4.39-4.50 (m, 2H) 5.64 (s, 1H) 5.70 (d, J = 9.63 Hz, 1H) 7.08 (ddd, J = 9.79, 8.90, 2.47 Hz, 1H) 7.55 (dd, J = 9.32, 2.47 Hz, 1H) 7.67 (dd, J = 8.81, 4.88 Hz, 1H) 8.65 (d, J = 1.01 Hz, 1H) 8.74 (d, J = 9.63 Hz, 1H) 9.08 (d, J = 1.39 Hz, 1H)

Example 154

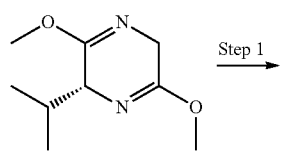

Step 1 →

-continued

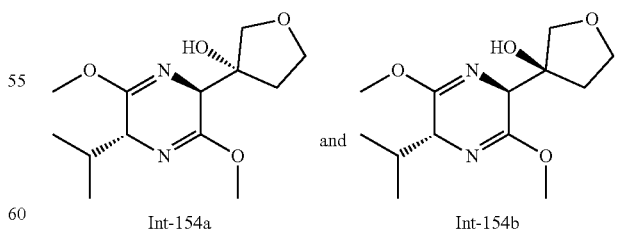

Int-154a   and   Int-154b

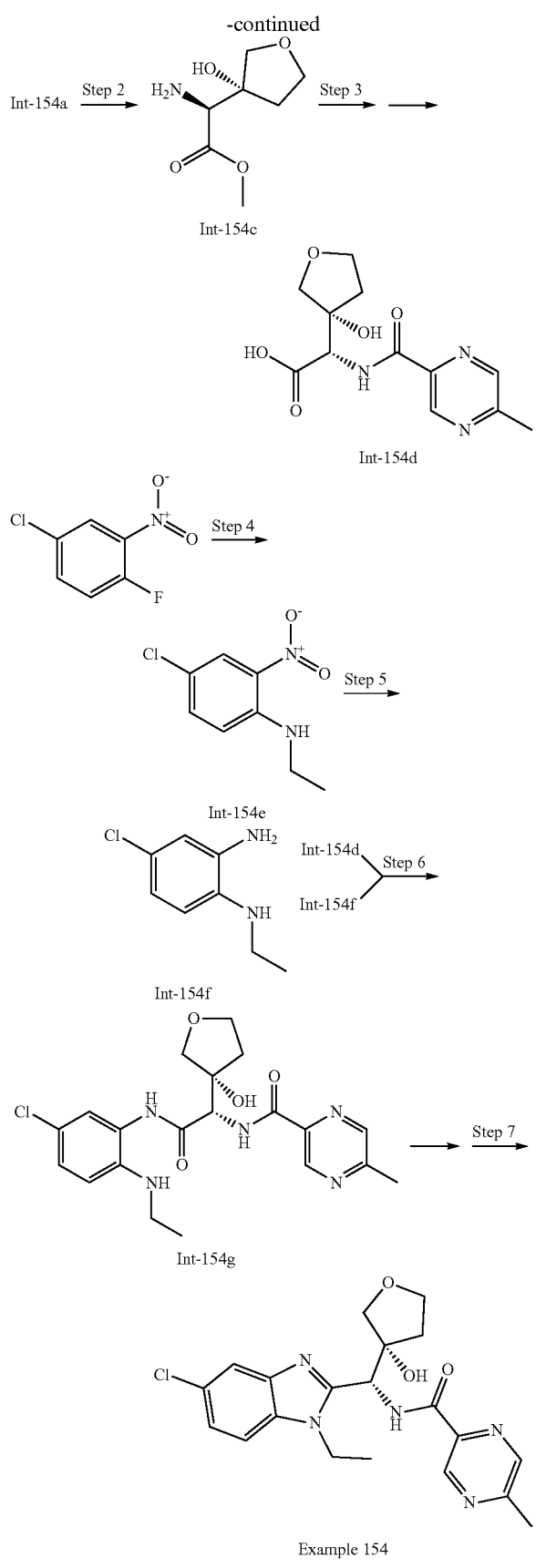

Step 1

To a mixture of (2R)-3,6-dimethoxy-2-(propan-2-yl)-2,5-dihydropyrazine (11,948 ml, 60 mmol) in waterfree THF (250 ml) cooled to −75° C. is added n-butyllithium solution (39,375 ml, 63 mmol, 1.6N in n-hexane) dropwise at a temperature below −65° C. The resulting mixture is stirred for 1 h at this temperature. Then a mixture of oxolan-3-one (4,571 ml, 60 mmol) in waterfree THF (80 ml) is added dropwise while the temperature is kept below −55° C. The mixture is stirred for 1 h at this temperature. Then glacial acetic acid (3.61 ml, 63 mmol) dissolved in THF (30 ml) is added dropwise. The mixture is diluted with diethylether (500 ml) and extracted two times with sodium bicarbonate (2%, 250 ml each time). The combined organic phases are dried over sodiumsulfate and concentrated in vacuo. Purification is achieved by column chromatography on silica gel (eluent: cyclohexane/acetic acid ethylester). Yield: 6.35 g (23.5 mmol; 39%) Int-154a and 2.48 g (9.17 mmol, 15.3%) Int-154b Step 2

A mixture of Int-154a (2 g, 7,399 mmol), hydrochloric acid (0.2N, 73.98 ml, 14,797 mmol) and THF (50 ml) is stirred for 18 hours at room temperature. The mixture is concentrated in vacuo, freeze-dried and used without further purification for the next step.

Yield: 3.24 g (purity 40%) Int-154c

Step 3

To a mixture of Int-154c (3.24 g, purity 40%, 7.3 mmol), THF (75 ml) and triethylamine (6,187 ml, 44.38 mmol) is added 5-methylpyrazine-2-carboxylic acid (2,146 g, 15,536 mmol) and the mixture is cooled in an ice bath. Then CIP (4,328 g, 15,536 mmol) is added. The mixture is stirred 5 min under ice cooling and 1 h at room temperature. The mixture is concentrated in vacuo. The residue is taken up in methanol (20 ml), filtered and purified by HPLC (XBridge C18, water/NH₄OH/CAN, flow 50 ml, T column=60° C.). Product containing fractions are combined and stirred for 2 hours at the rotavap (bath temperature 45° C.). After concentration in vacuo the residue is freeze-dried. Yield: 0.8 g (2,844 mmol, 38.4%) Int-154d Step 4

To a mixture of 1-fluoro-4-methyl-2-nitrobenzene (15 g, 82,885 mmol), potassium carbonate (22,911 g, 165,769 mmol) and THF (150 ml) is added ethylamine solution in THF (2N, 82,885 ml, 165,769 mmol). The resulting mixture is stirred for 16 h at room temperature and filtered. The mixture is concentrated in vacuo, diethyl ether is added and the mixture is concentrated in vacuo again. Yield: 16.75 g (83.49 mmol, 100%) Int-154e Step 5

A mixture of Int-154e, THF (30 ml) and Raney-nickel (300 mg) is hydrogenated at 60 psi and room temperature for 7 h. After 1 h additional Raney-nickel (300 mg) is added. Then the mixture is filtered and concentrated in vacuo.

Yield: 2.1 g (12,307 mmol, 98.8%) Int-154f

Step 6

To an ice-cooled mixture of Int-154f (180 mg 1,055 mmol), Int-154d (370.8 mg, 1,055 mmol) and DMF (12 ml) is added diisopropylethylamine (0,735 ml, 4,219 mmol) and T3P (1,243 ml, 2.11 mmol). The mixture is stirred under ice-cooling for 1 h. Then the mixture is allowed to reach room temperature and it is stirred for 20 h. After that time methanol is added, the mixture is filtered and purified by HPLC (XBridge C18, water/NH₄OH/ACN, flow 50 ml, T column=60° C.). Product containing fractions are combined, concentrated in vacuo and freeze dried.

Yield: 43 mg (0,099 mmol, 9.4%) Int-154 g

Step 7

A mixture of Int-154 g (58 mg, 0,134 mmol) and glacial acetic acid (3 ml) is stirred for 3 h at 85° C. At room temperature ethyl acetate (30 ml) and potassium carbonate solution are added. The organic phase is separated and dried over sodium sulfate.

Example 154: N-[(R)-(5-chloro-1-ethyl-1H-1,3-benzodiazol-2-yl)[(3R)-3-hydroxyoxolan-3-yl]methyl]-5-methylpyrazine-2-carboxamide

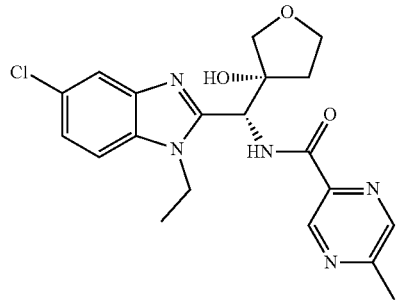 [SMILES: CCn1c([C@@H](NC(=O)c2cnc(C)cn2)[C@]2(O)CCOC2)nc2cc(Cl)ccc21]

HPLC-MS; Method: Z011_S03; R$_t$ [min]: 0.975  MS: 416 (M + H)$^+$
Chiral SFC Rt Method: I_SZ_20_MEOH_NH3_003  Rt [min]: 3,6

The following compounds are obtained in analogy to example 154

Example 155: N-[(R)-[1-ethyl-6-(trifluoromethyl)-1H-1,3-benzodiazol-2-yl][(3R)-3-hydroxyoxolan-3-yl]methyl]-5-methylpyrazine-2-carboxamide

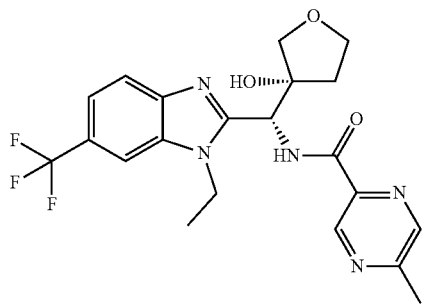 [SMILES: CCn1c([C@@H](NC(=O)c2cnc(C)cn2)[C@]2(O)CCOC2)nc2ccc(C(F)(F)F)cc21]

HPLC-MS; Method: Z011_S03; R$_t$ [min]: 1.00  MS: 450 (M + H)$^+$
Chiral SFC Rt Method: I_AC_15_IPA_NH3_002  Rt [min]: 0,69

Example 156: N-[(R)-[1-ethyl-5-(trifluoromethyl)-1H-1,3-benzodizaol-2-yl][(3R-3-hydroxyoxolan-3-yl]methyl]-5-methylpyrazine-2-carboxamide

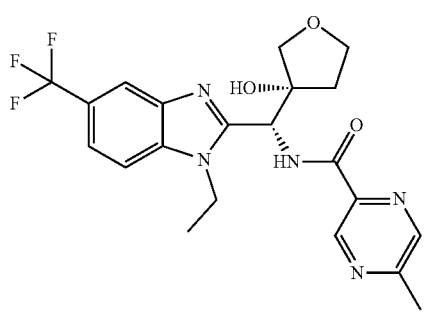 [SMILES: CCn1c([C@@H](NC(=O)c2cnc(C)cn2)[C@]2(O)CCOC2)nc2cc(C(F)(F)F)ccc21]

HPLC-MS; Method: Z011_S03; R$_t$ [min]: 1.01  MS: 450 (M + H)$^+$
Chiral SFC Rt Method: I_AC_15_IPA_NH3_002  Rt [min]: 0,74

The following examples are obtained in analogy to example 143:

Example 157 : N-[(S)-[6-chloro-1-(2,2-difluoroethyl)-1H-1,3-benzodiazol-2-yl](cyclopropyl)methyl]-5-methylpyrazine-2-carboxamid

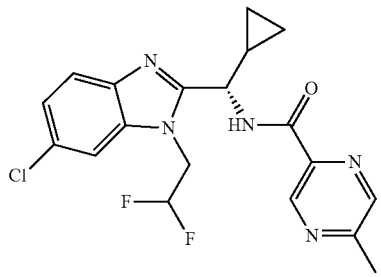 [SMILES: Cc1cnc(C(=O)N[C@H](c2nc3ccc(Cl)cc3n2CC(F)F)C2CC2)cn1]

HPLC-MS; Method: Z011_S03; $R_t$ [min]: 1.00     MS: 406 (M + H)$^+$
Chiral SFC Rt Method: I_SB_10_IPA_NH3_003     Rt [min]: 0,69
$^1$H NMR (400 MHz, DMSO-d$_6$) δ ppm 0.36-0.52 (m, 2H) 0.52-0.67 (m, 2H) 1.78-1.99 (m, 1H) 2.59 (s, 3H) 4.73-5.09 (m, 3H) 6.29-6.47 (m, 1H) 7.26 (dd, J = 8.62, 2.03 Hz, 1H) 7.68 (d, J = 8.62 Hz, 1H) 7.77 (s, 1H) 8.63 (d, J = 1.01 Hz, 1H) 9.04 (d, J = 1.39 Hz, 1H) 9.19 (d, J = 8.24 Hz, 1H)

Example 158: N-[(S)-[5-chloro-1-(2,2-difluoroethyl)-1H-1,3-benzodiazol-2-yl](cyclopropyl)methyl]-5-methylpyrazine-2-carboxamide

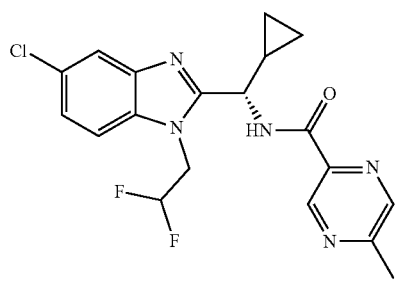 [SMILES: Cc1cnc(C(=O)N[C@H](c2nc3cc(Cl)ccc3n2CC(F)F)C2CC2)cn1]

HPLC-MS; Method: Z011_S03; $R_t$ [min]: 0.99     MS: 406 (M + H)$^+$
Chiral SFC Rt Method: I_SC_15_IPA_NH3_003     Rt [min]: 2,64
$^1$H NMR (400 MHz, DMSO-d$_6$) δ ppm 0.39-0.52 (m, 2H) 0.52-0.63 (m, 2H) 1.80-1.88 (m, 1H) 2.59 (s, 3H) 4.81-5.04 (m, 3H) 6.28-6.48 (m, 1H) 7.32 (dd, J = 8.74, 2.03 Hz, 1H) 7.64 (d, J = 8.74 Hz, 1H) 7.75 (d, J = 1.90 Hz, 1H) 8.63 (d, J = 1.01 Hz, 1H) 9.04 (d, J = 1.39 Hz, 1H) 9.20 (d, J = 8.11 Hz, 1H)

The following examples are obtained in analogy to example 143: examples 159, 159-1, 159-2, 160

Example 159: N-[(1-ethyl-5,6-difluoro-1H-1,3-benzodiazol-2-yl) (oxolan-3-yl)methyl]-5-methylpyrazine-2-carboxamide

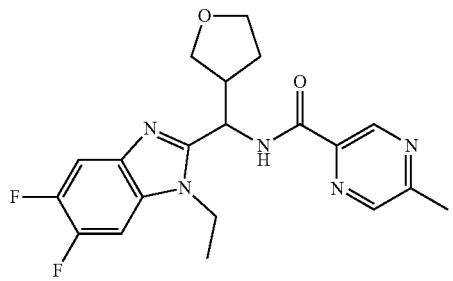 [SMILES: CCn1c(C(NC(=O)c2cnc(C)cn2)C2CCOC2)nc2cc(F)c(F)cc21]

HPLC-MS; Method: Z011_S03; $R_t$ [min]: 0.92     MS: 402 (M + H)$^+$
Chiral SFC Rt Method: I_IG_25_IPA_NH3_002     Rt [min]: 1,01
$^1$H NMR (400 MHz, DMSO-d$_6$) δ ppm 1.24 (t, J = 7.16 Hz, 3H) 1.43-1.59 (m, 1H) 1.98 (dtd, J = 12.69, 7.98, 7.98, 4.94 Hz, 1H) 2.58 (s, 3H) 3.16-3.28 (m, 1H) 3.63 (q, J = 7.60 Hz, 1H) 3.71 (dd, J = 8.87, 5.96 Hz, 1H) 3.73-3.82 (m, 2H) 4.27-4.45 (m, 2H) 5.43 (t, J = 9.06 Hz, 1H) 7.72 (dd, J = 11.15, 7.48 Hz, 1H) 7.78 (dd, J = 10.77, 7.22 Hz, 1H) 8.61 (d, J = 1.01 Hz, 1H) 9.05 (d, J = 1.39 Hz, 1H) 9.23 (d, J = 8.87 Hz, 1H)

Example 159-1: N-[(1-ethyl-5,6-difluoro-1H-1,3-benzodiazol-2-yl) (oxolan-3-yl)methyl]-5-methylpyrazine-2-carboxamide

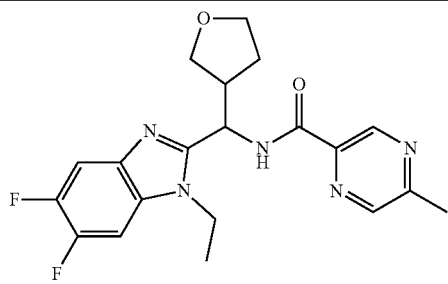

HPLC-MS; Method: Z011_S03; R$_t$ [min]: 0.92     MS: 402 (M + H)$^+$
Chiral SFC Rt Method: I_C4_20_MEOH_NH3_002     Rt [min]: 0.77
Example 159-2: N-[(1-ethyl-5,6-difluoro-1H-1,3-benzodiazol-2-yl) (oxolan-3-yl)methyl]-5-methylpyrazine-2-carboxamide

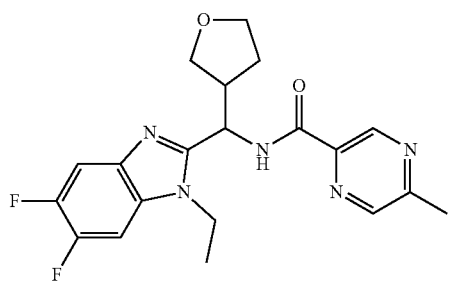 [SMILES: CCn1c(C(NC(=O)c2cnc(C)cn2)C2CCOC2)nc2cc(F)c(F)cc21]

HPLC-MS; Method: Z011_S03; R$_t$ [min]: 0.92     MS: 402 (M + H)$^+$
Chiral SFC Rt Method: I_IG_25_IPA_NH3_002     Rt [min]: 1,10
Example 160: N-[(1-ethyl-5,6-difluoro-1H-1,3-benzodiazol-2-yl) (oxolan-3-yl)methyl]-5-methylpyrazine-2-carboxamide

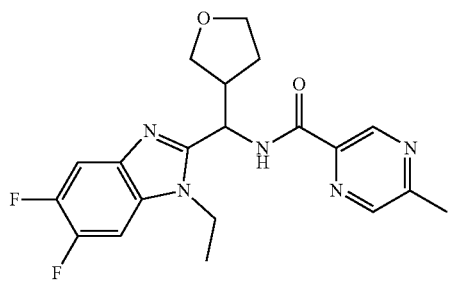 [SMILES: CCn1c(C(NC(=O)c2cnc(C)cn2)C2CCOC2)nc2cc(F)c(F)cc21]

HPLC-MS; Method: Z011_S03; R$_t$ [min]: 0.92     MS: 402 (M + H)$^+$
Chiral SFC Rt Method: I_C4_20_MEOH_NH3_00     Rt [min]: 1,43
$^1$H NMR (400 MHz, DMSO-d$_6$) δ ppm 1.20 (t, J = 7.16 Hz, 3H) 1.75-1.84 (m, 1H) 1.96-2.05 (m, 1H) 2.59 (s, 3H) 3.32-3.55 (m, 2H) 3.65 (q, J = 7.35 Hz, 1H) 3.72-3.84 (m, 2H) 4.22-4.38 (m, 2H) 5.40 (t, J = 9.25 Hz, 1H) 7.69-7.80 (m, 2H) 8.61 (d, J = 1.01 Hz, 1H) 9.08 (d, J = 1.39 Hz, 1H) 9.32 (d, J = 9.12 Hz, 1H)

The following examples are obtained in analogy to example 143: examples 161, 161-1, 161-2, 162

Example 161: N-[(5-chloro-1-ethyl-1H-1,3-benzodiazol-2-yl) (oxolan-3-yl)methyl]-5-methylpyrazine-2-carboxamide -continued

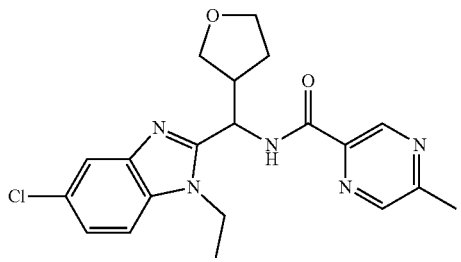 [SMILES: CCn1c(C(NC(=O)c2cnc(C)cn2)C2CCOC2)nc2cc(Cl)ccc21]

HPLC-MS; Method: Z011_S03; R$_t$ [min]: 0.94  MS: 400 (M + H)$^+$
Chiral SFC Rt Method: I_C4_25_IPA_NH3_002  Rt [min]: 1,11
$^1$H NMR (400 MHz, DMSO-d$_6$) δ ppm 1.25 (t, J = 7.16 Hz, 3H) 1.42-1.71 (m, 1H) 1.90-2.04 (m, 1H) 2.58 (s, 3H) 3.25-3.29 (m, 1H) 3.60-3.65 (m, 1H) 3.65-3.75 (m, 1H) 3.75-3.87 (m, 2H) 4.38 (ddt, J = 22.38, 14.81, 7.32, 7.32 Hz, 2H) 5.44 (br d, J = 7.35 Hz, 1H) 7.27 (dd, J = 8.62, 2.03 Hz, 1H) 7.61 (d, J = 8.62 Hz, 1H) 7.71 (d, J = 2.03 Hz, 1H) 8.60 (d, J = 1.14 Hz, 1H) 9.05 (d, J = 1.39 Hz, 1H) 9.24 (br s, 1H)
Example 161-1: N-[(5-chloro-1-ethyl-1H-1,3-benzodiazol-2-yl) (oxolan-3-yl)methyl]-5-methylpyrazine-2-carboxamide

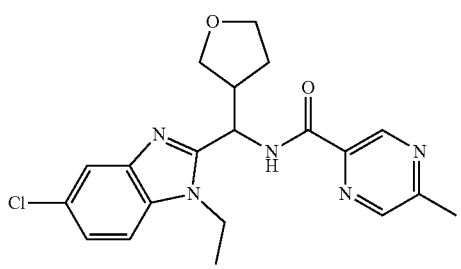 [SMILES: CCn1c(C(NC(=O)c2cnc(C)cn2)C2CCOC2)nc2cc(Cl)ccc21]

HPLC-MS; Method: Z011_S03; R$_t$ [min]: 0.94  MS: 400 (M + H)$^+$
Chiral SFC Rt Method: I_C4_25_IPA_NH3_002  Rt [min]: 0.74
Example 161-2: N-[(5-chloro-1-ethyl-1H-1,3-benzodiazol-2-yl) (oxolan-3-yl)methyl]-5-methylpyrazine-2-carboxamide

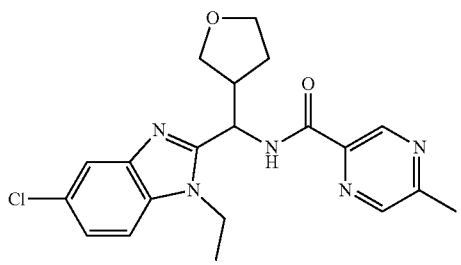 [SMILES: CCn1c(C(NC(=O)c2cnc(C)cn2)C2CCOC2)nc2cc(Cl)ccc21]

HPLC-MS; Method: Z011_S03; R$_t$ [min]: 0.94  MS: 400 (M + H)$^+$
Chiral SFC Rt Method: I_C4_25_IPA_NH3_002  Rt [min]: 1,00
Example 162: N-[(5-chloro-1-ethyl-1H-1,3-benzodiazol-2-yl) (oxolan-3-yl)methyl]-5-methylpyrazine-2-carboxamide

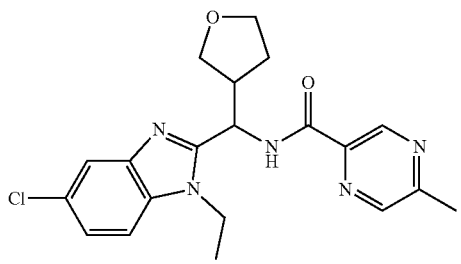 [SMILES: CCn1c(C(NC(=O)c2cnc(C)cn2)C2CCOC2)nc2cc(Cl)ccc21]

HPLC-MS; Method: Z011_S03; R$_t$ [min]: 0.94  MS: 400 (M + H)$^+$
Chiral SFC Rt Method: I_C4_25_IPA_NH3_002  Rt [min]: 1,25
$^1$H NMR (400 MHz, DMSO-d$_6$) δ ppm 1.22 (t, J = 7.16 Hz, 3H) 1.67-1.91 (m, 1H) 1.91-2.07 (m, 1H) 2.58 (s, 3H) 3.33-3.59 (m, 2H) 3.65 (q, J = 7.35 Hz, 1H) 3.72-3.89 (m, 2H) 4.33 (ddt, J = 18.17, The following examples are obtained in analogy to example 143: examples 163, 163-1, 163-2, 164

Example 163: N-[(6-chloro-1-ethyl-1H-1,3-benzodiazol-2-yl) (oxolan-3-yl)methyl]-5-methylpyrazine-2-carboxamide

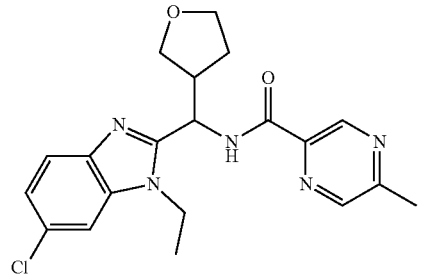 [SMILES: CCn1c(C(NC(=O)c2cnc(C)cn2)C2CCOC2)nc2ccc(Cl)cc21]

HPLC-MS; Method: Z011_S03; R$_t$ [min]: 0.95    MS: 400 (M + H)$^+$
Chiral SFC Rt Method: I_SB_15_MEOH_NH3_002    Rt [min]: 0,96

$^1$H NMR (400 MHz, DMSO-d$_6$) δ ppm 1.25 (t, J = 7.10 Hz, 3H) 1.36-1.60 (m, 1H) 1.99 (dtd, J = 12.67, 7.95, 7.95, 5.01 Hz, 1H) 2.57-2.60 (m, 3H) 3.17-3.29 (m, 1H) 3.59-3.69 (m, 1H) 3.69-3.76 (m, 1H) 3.76-3.83 (m, 2H) 4.30-4.47 (m, 2H) 5.45 (t, J = 9.12 Hz, 1H) 7.22 (dd, J = 8.62, 2.03 Hz, 1H) 7.65 (d, J = 8.62 Hz, 1H) 7.74 (d, J = 1.90 Hz, 1H) 8.61 (d, J = 1.01 Hz, 1H) 9.06 (d, J = 1.39 Hz, 1H) 9.22 (d, J = 9.00 Hz, 1H)

Example 163-1: N-[(6-chloro-1-ethyl-1H-1,3-benzodiazol-2-yl) (oxolan-3-yl)methyl]-5-methylpyrazine-2-carboxamide

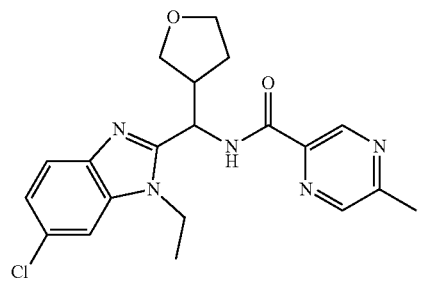 [SMILES: CCn1c(C(NC(=O)c2cnc(C)cn2)C2CCOC2)nc2ccc(Cl)cc21]

HPLC-MS; Method: Z011_S03; R$_t$ [min]: 0.95    MS: 400 (M + H)$^+$
Chiral SFC Rt Method: I_IG_25_IPA_NH3_002    Rt [min]: 1.522

Example 163-2: N-[(6-chloro-1-ethyl-1H-1,3-benzodiazol-2-yl) (oxolan-3-yl)methyl]-5-methylpyrazine-2-carboxamide

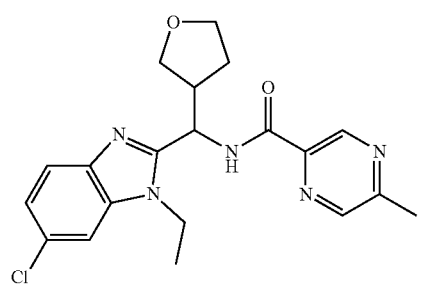 [SMILES: CCn1c(C(NC(=O)c2cnc(C)cn2)C2CCOC2)nc2ccc(Cl)cc21]

HPLC-MS; Method: Z011_S03; R$_t$ [min]: 0.95    MS: 400 (M + H)$^+$
Chiral SFC Rt Method: I_SB_15_MEOH_NH3_002    Rt [min]: 0.69

Example 164: N-[(6-chloro-1-ethyl-1H-1,3-benzodiazol-2-yl) (oxolan-3-yl)methyl]-5-methylpyrazine-2-carboxamide -continued

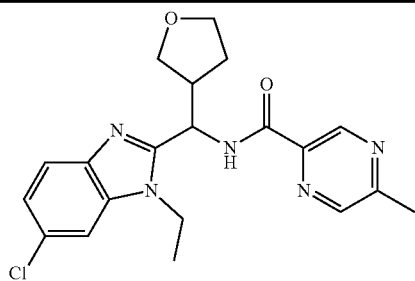

HPLC-MS; Method: Z011_S03; R$_t$ [min]: 0.95  MS: 400 (M + H)$^+$
Chiral SFC Rt Method: I_IG_25_IPA_NH3_002  Rt [min]: 1,25
$^1$H NMR (400 MHz, DMSO-d$_6$) δ ppm 1.21 (t, J = 7.16 Hz, 3H) 1.37-1.91
(m, 1H) 1.91-2.05 (m, 1H) 2.52-2.65 (m, 3H) 3.32-3.55 (m, 2H) 3.66 (q,
J = 7.44 Hz, 1H) 3.72-3.85 (m, 2H) 4.22-4.42 (m, 2H) 5.41 (t, J = 9.25 Hz, 1H) 7.22 (dd, J = 8.62, 2.03
Hz, 1H) 7.65 (d, J = 8.62 Hz, 1H) 7.72 (d, J = 1.90 Hz, 1H) 8.61 (d, J = 1.01 Hz, 1H) 9.08 (d, J = 1.39
Hz, 1H) 9.31 (d, J = 9.12 Hz, 1H)

The following compounds are obtained in analog to example 14 except step 8. In step 8 the product, consisting of 2 stereoisomers, is purified by crystallization resulting in one single stereoisomer.

Example 14

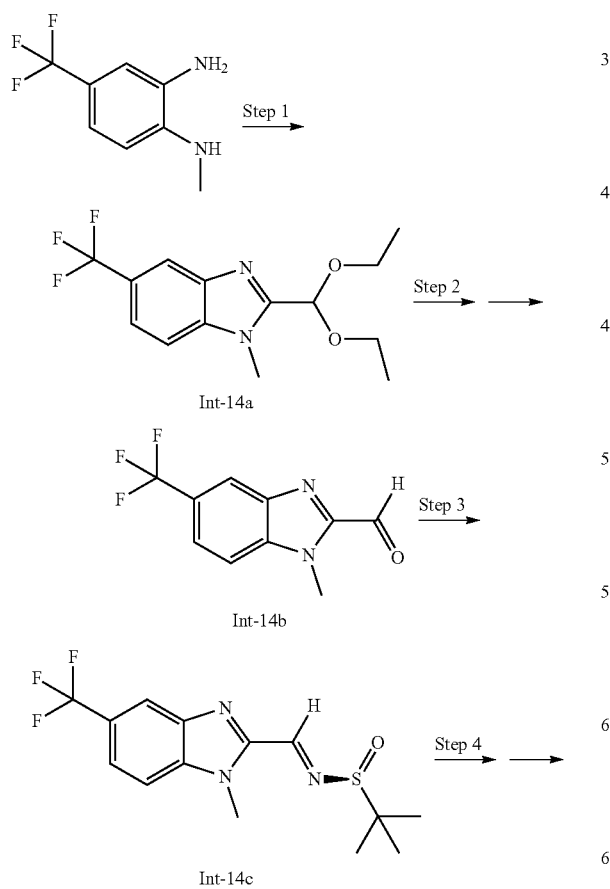

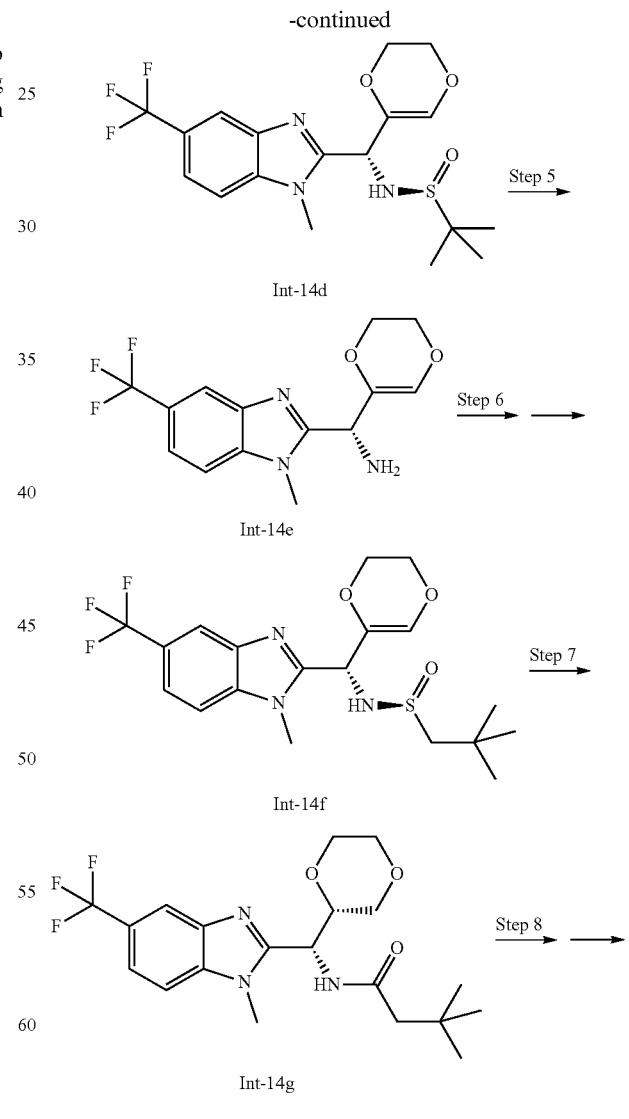

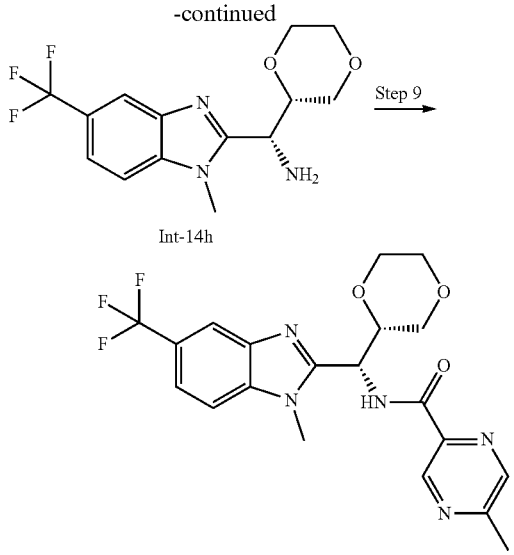

Int-14h

Example 14 and 14-1

Example 165 and 166

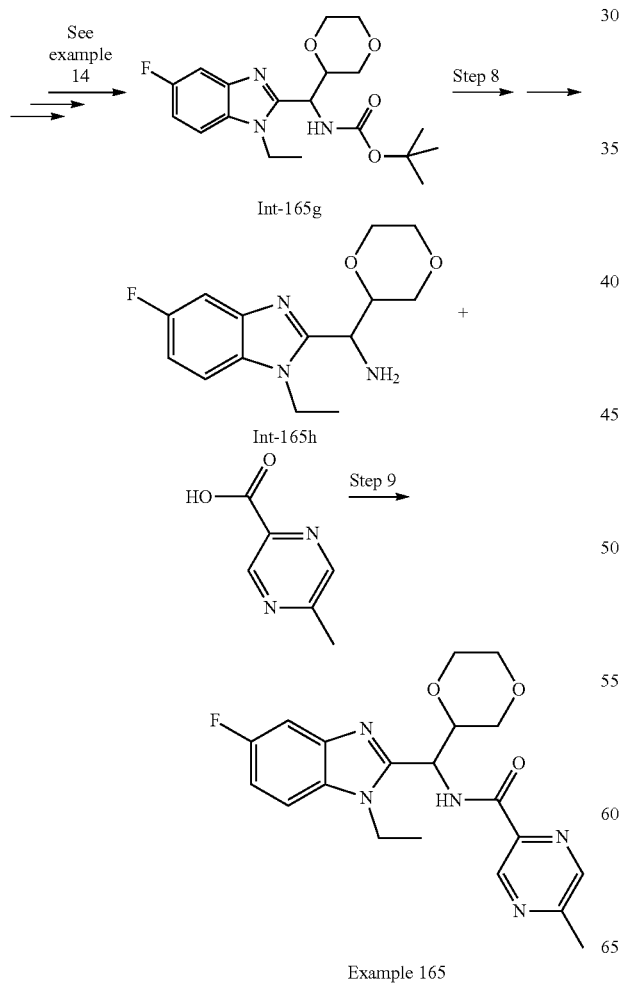

Int-165g

Int-165h

Example 165

Step 8:

TFA (5.083 ml, 65.88 mmol) is added to Int-165 g (2.5 g, 6.589 mmol) in 30 ml DCM at 5° C. Cooling is removed and the mixture stirred for 6.5 h at ambient temperature. DCM (50 ml) is added to the mixture and then water (150 ml) is added. The organic phase is extracted two times with water (100 ml). The combined water phases are adjusted to pH ~10 by addition of conc. aq. $NH_3$ solution. The aqueous layer is extracted with ethyl acetate (250 ml). The combined organic layers are dried over $MgSO_4$ and concentrated i. vac. To the residue (1.67 g) is added ethanol (11.75 ml) and water (0.62 ml). The mixture is heated at 70° C. Then 5-methylpyrazine-2-carboxylic acid (0.775 g, 5.612 mmol) is added. To this mixture ethanol (5.87 ml) and water (0.31 ml) is added and the mixture is heated for 1 hour at 70° C. After that the mixture is slowly cooled to room temperature. The mixture is then cooled within 1 minute to 20° C. The mixture is filtrated, washed with ethanol (3 ml) and dried in a dry gun at 50° C.

Yield: 1.81 g (4.33 mmol; 73%) Int-165 h as a salt with 5-methylpyrazine-2-carboxylic acid Step 9:

A mixture of Int-165 h as a salt with 5-methylpyrazine-2-carboxylic acid (0.55 g, 1.32 mmol), NMM (0.581 mL, 5.27 mmol) in 5.5 ml EtOAc and 5-methylpyraine-2-carboxylic acid (90.9 mg, 0.66 mmol) is cooled to 0° C. under stirring. Then PPA (50% in EtOAc; 1.165 mL, 1.97 mmol) is added. Cooling is removed after 10 min and the mixture stirred at ambient temperature for 45 min. Ethyl acetate (20 ml) is added to the mixture, which is then extracted two times sodium bicarbonate solution. The combined organic phases are dried over $MgSO_4$. After filtration the mixture is concentrated i. vac., the residue taken up in THF/MeOH and purified via chromatography (XBridge C18, 10, ($H_2O$+0.1% $NH_4OH$+28-48% ACN). The product containing fractions are combined and concentrated i. vac. The product is obtained as a single stereoisomer.

Yield: 0.461 mg (1.15 mmol; 87%) example 165.

Example 165: N-[(1,4-dioxan-2-yl) (1-ethyl-5-fluoro-1H-1,3-benzodiazol-2-yl)methyl]-5-methylpyrazine-2-carboxamide

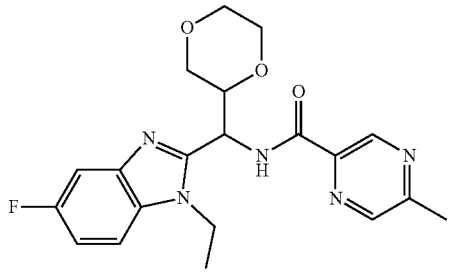 [SMILES: CCn1c(C(NC(=O)c2cnc(C)cn2)C2COCCO2)nc2cc(F)ccc21]

HPLC-MS; Method: Z011_S03; R$_t$ [min]: 0.89  MS: 400 (M + H)$^+$
Chiral SFC Rt Method: I_SC_20_IPA_NH3_003  Rt [min]: 3,59
$^1$H NMR (400 MHz, DMSO-d$_6$) δ ppm 1.31 (t, J = 7.16 Hz, 3H) 2.60 (s, 3H) 3.32-3.42 (m, 1H) 3.42-3.57 (m, 1H) 3.57-3.73 (m, 2H) 3.73-3.84 (m, 2H) 4.28-4.36 (m, 1H) 4.36-4.50 (m, 2H) 5.59 (dd, J = 8.36, 7.22 Hz, 1H) 7.13 (ddd, J = 9.70, 8.87, 2.47 Hz, 1H) 7.46 (dd, J = 9.76, 2.41 Hz, 1H) 7.62 (dd, J = 8.87, 4.69 Hz, 1H) 8.66 (d, J = 1.01 Hz, 1H) 9.04 (d, J = 8.49 Hz, 1H) 9.07 (d, J = 1.39 Hz, 1H)

In analogy to example 165 the following compound is obtained.

Example 166: N-[(1,4-dioxan-2-yl)(1-ethyl-5-fluoro-1H-1,3-benzodiazol-2-yl)methyl]-5-methylpyrazine-2-carboxamide

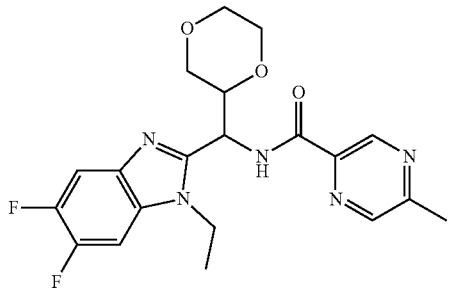 [SMILES: CCn1c(C(NC(=O)c2cnc(C)cn2)C2COCCO2)nc2cc(F)c(F)cc21]

HPLC-MS; Method: Z011_S03; R$_t$ [min]: 0.92  MS: 418 (M + H)$^+$
Chiral SFC Rt Method: I_SB_10_MEOH_NH3_003  Rt [min]: 2,39
$^1$H NMR (400 MHz, DMSO-d$_6$) δ ppm 1.29 (t, J = 7.16 Hz, 3H) 2.60 (s, 3H) 3.32-3.41 (m, 1H) 3.41-3.55 (m, 1H) 3.55-3.71 (m, 2H) 3.71-3.84 (m, 2H) 4.27-4.48 (m, 3H) 5.58 (dd, J = 8.49, 7.22 Hz, 1H) 7.72 (dd, J = 11.03, 7.48 Hz, 1H) 7.81 (dd, J = 10.77, 7.35 Hz, 1H) 8.65 (d, J = 1.01 Hz, 1H) 9.04 (d, J = 8.49 Hz, 1H) 9.06 (d, J = 1.27 Hz, 1H)

Example 167 is prepared analogously to example 154 starting from Int-154b.

Example 167: N-[(R)-[1-ethyl-5-(trifluoromethyl)-1H-1,3-benzodiazol-2-yl][(3S)-3-hydroxyoxolan-3-yl]methyl]-5-methylpyrazine-2-carboxamide

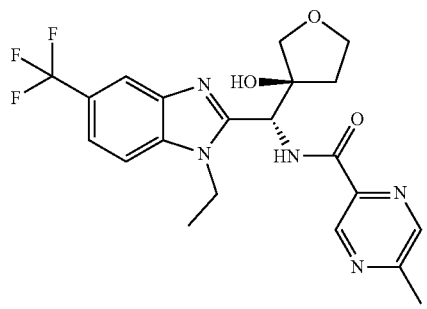 [SMILES: CCn1c([C@@H](NC(=O)c2cnc(C)cn2)[C@@]2(O)CCOC2)nc2cc(C(F)(F)F)ccc21]

-continued
| HPLC-MS; Method: Z011_S03; R, [min]: | MS: 450 (M + H)+ |
| Chiral SFC Rt Method: I_AC_10_IPA_NH3_002 | Rt [min]: 1,73 |
$^1$H NMR (400 MHz, DMSO-$d_6$) δ ppm 1.36 (t, J = 7.22 Hz, 3H) 1.91 (ddd, J = 12.71, 6.62, 3.61 Hz, 1H) 2.17 (dt, J = 12.86, 8.84 Hz, 1H) 2.60 (s, 3H) 3.54 (d, J = 9.63 Hz, 1H) 3.77-4.01 (m, 2H) 4.13 (d, J = 9.63 Hz, 1H) 4.31-4.60 (m, 2H) 5.67-5.75 (m, 2H) 7.59 (dd, J = 8.62, 1.52 Hz, 1H) 7.85 (d, J = 8.49 Hz, 1H) 8.05 (s, 1H) 8.66 (d, J = 1.01 Hz, 1H) 8.86 (d, J = 9.13 Hz, 1H) 9.08 (d, J = 1.39 Hz, 1H)
The invention claimed is:
1. A compound selected from the group consisting of
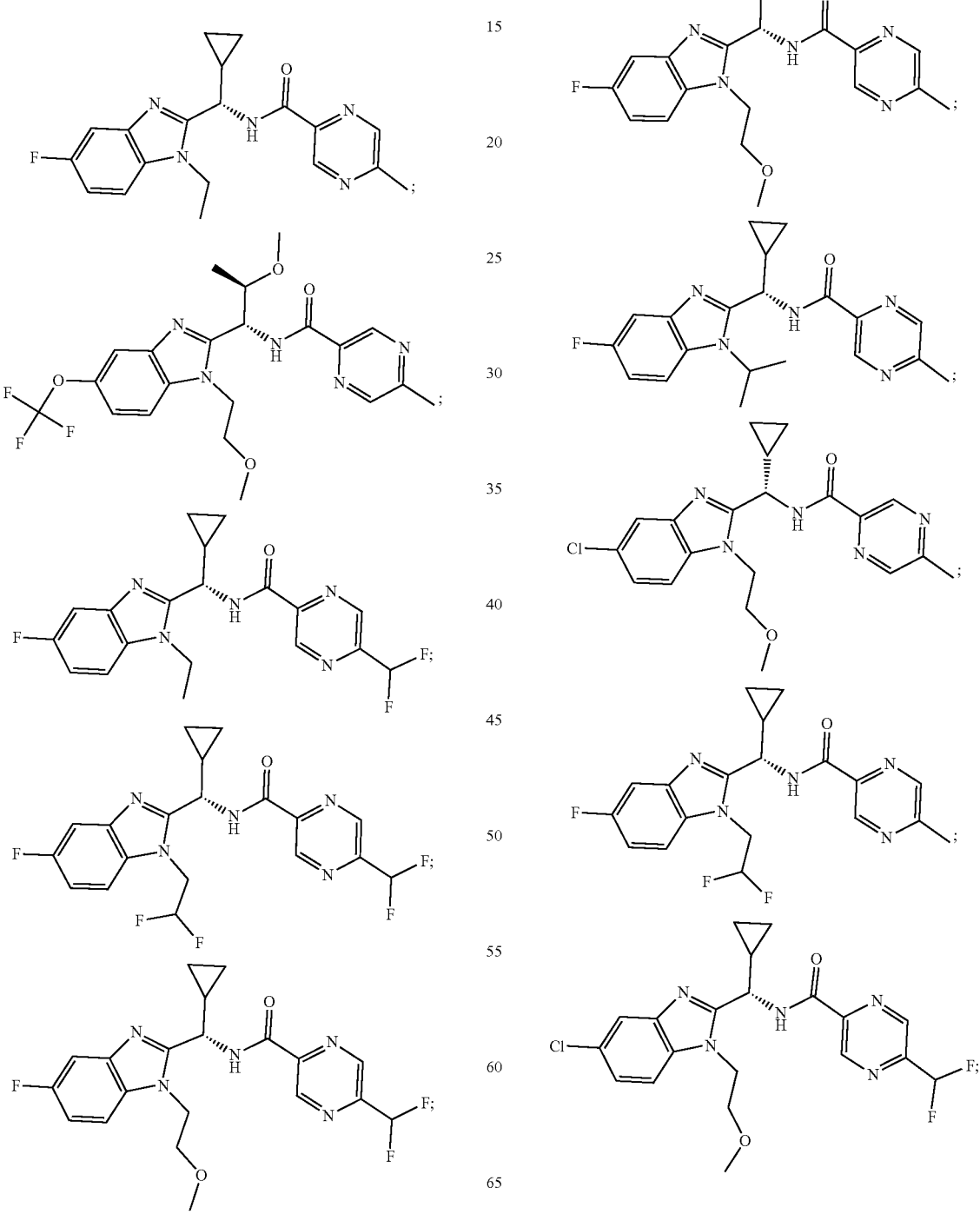

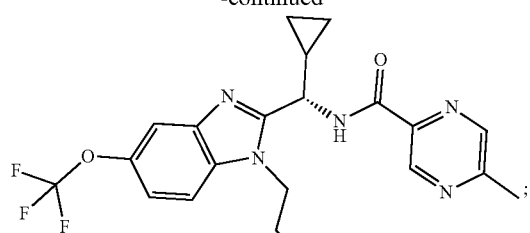
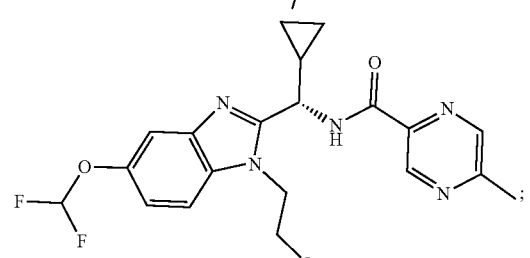
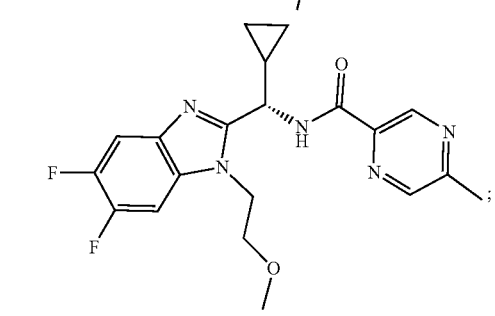
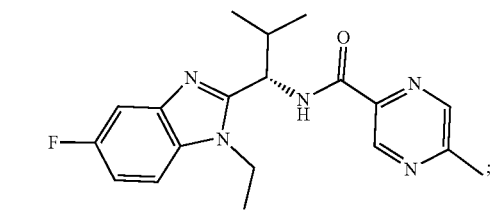
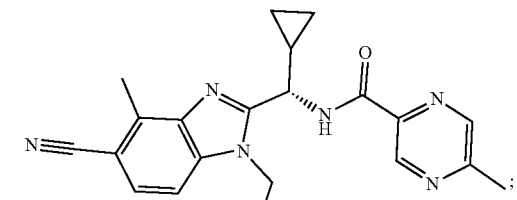
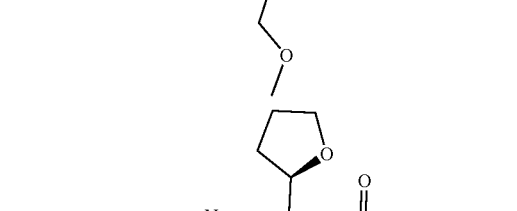
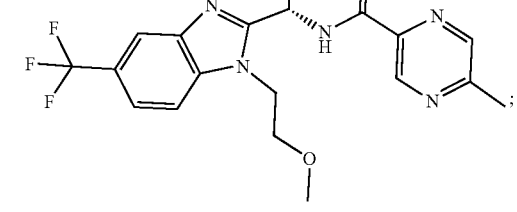
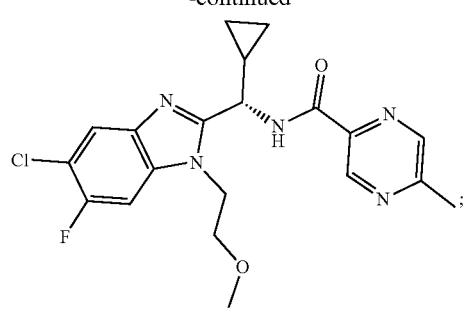
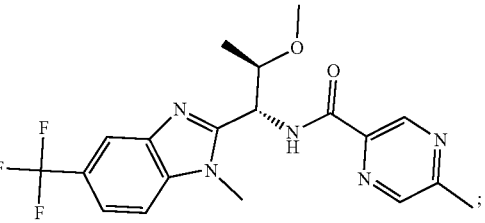
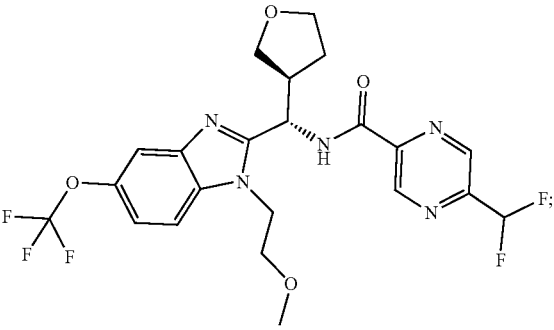
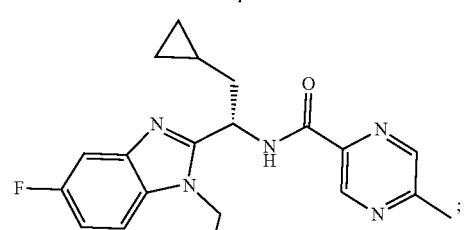
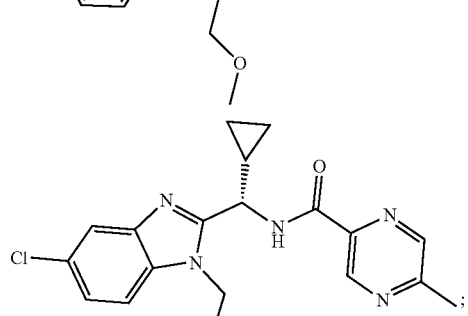
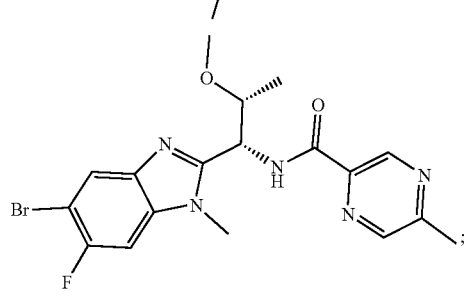

345
-continued
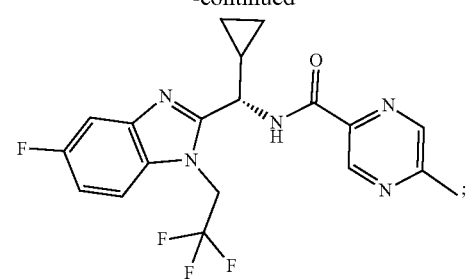
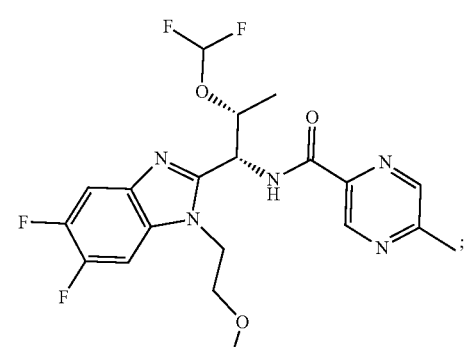
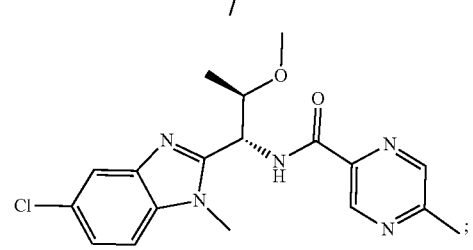
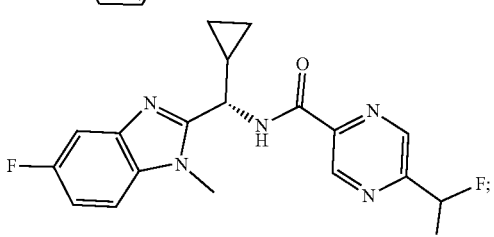
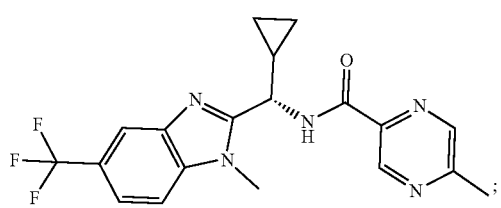
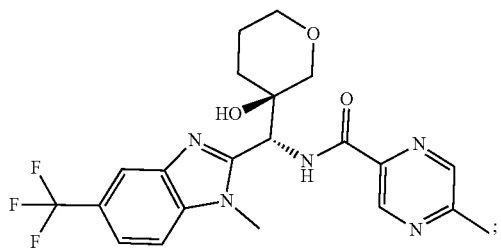
346
-continued
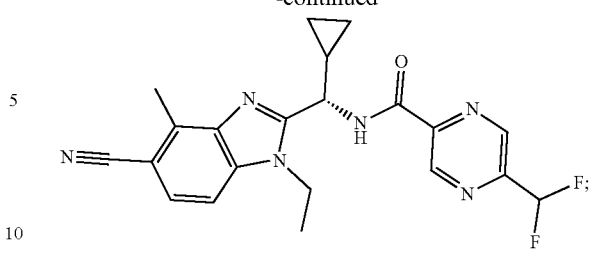
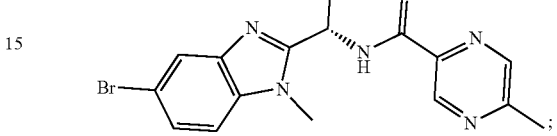
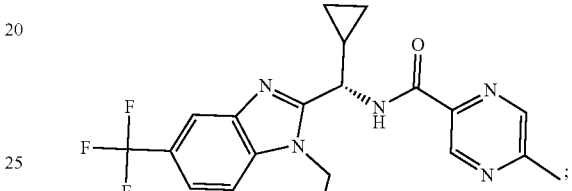
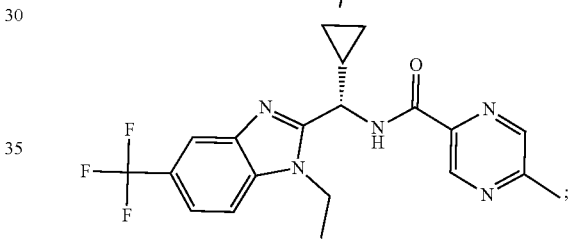
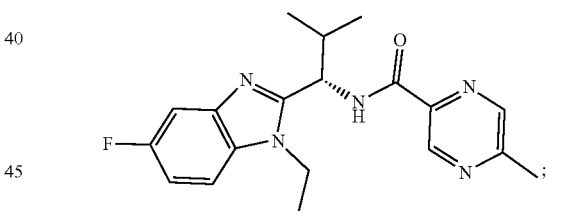
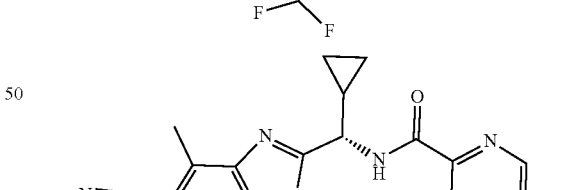
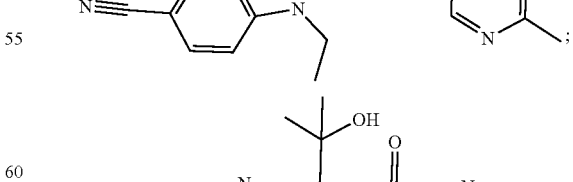
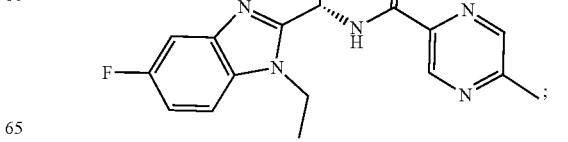

347
-continued
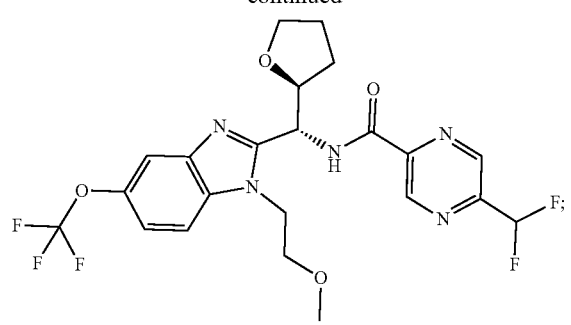
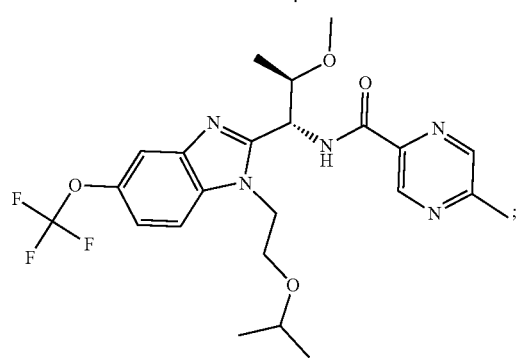
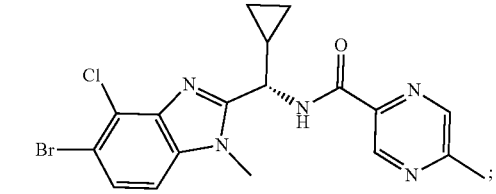
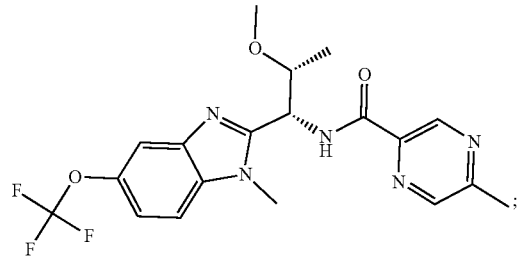
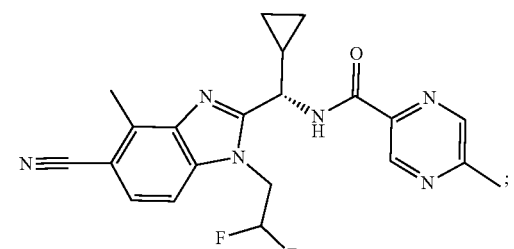
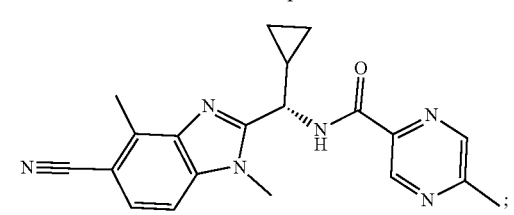
348
-continued
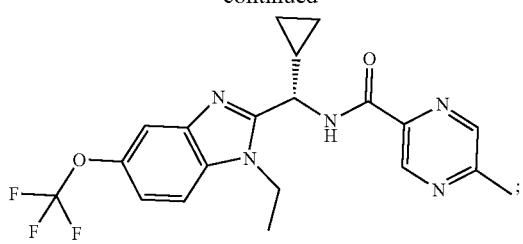
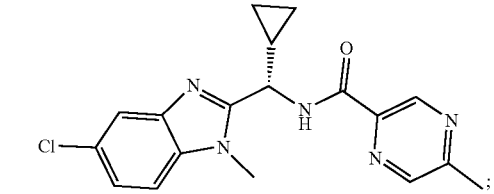
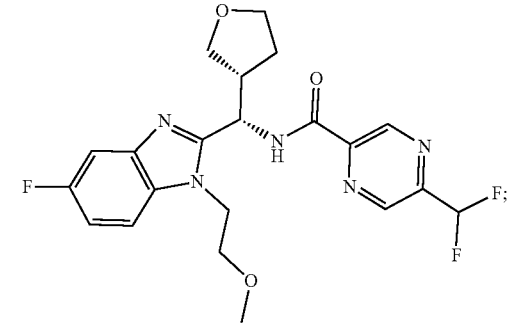
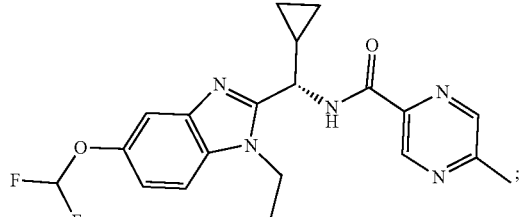
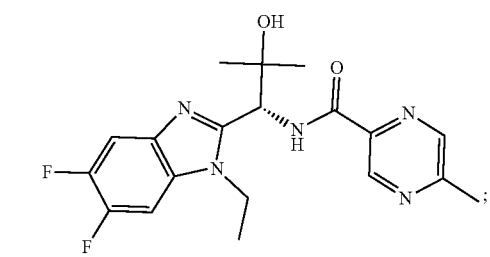
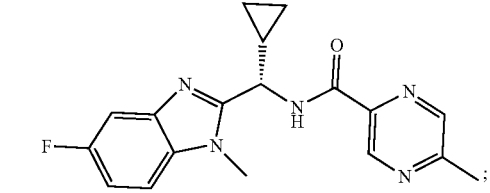
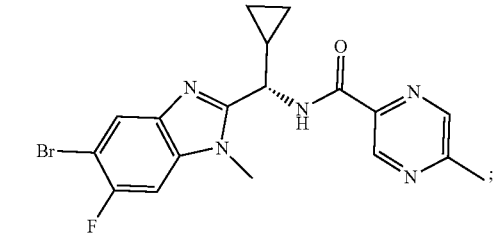

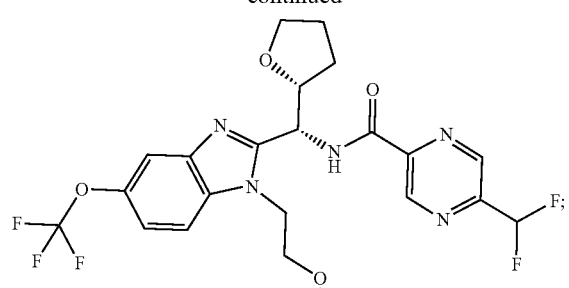
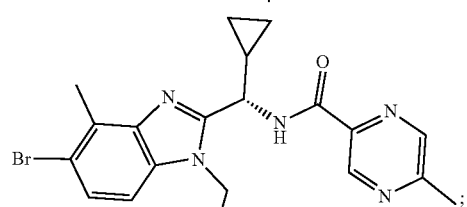
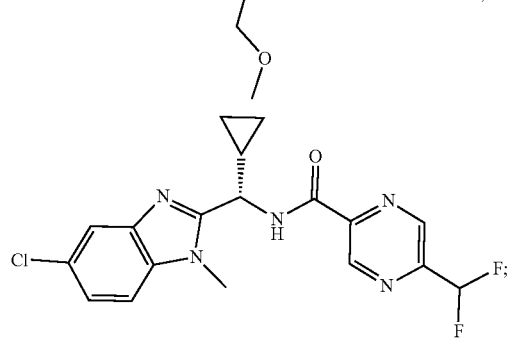
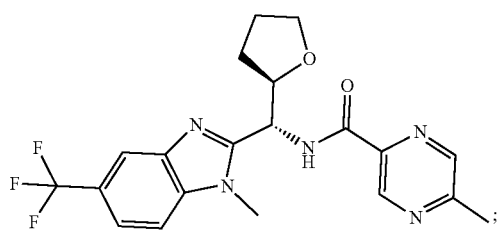
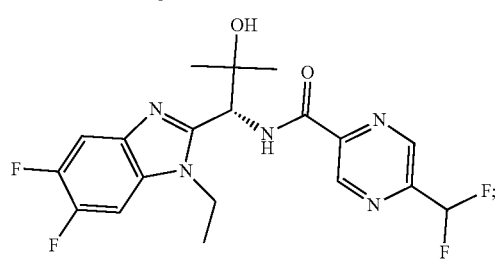
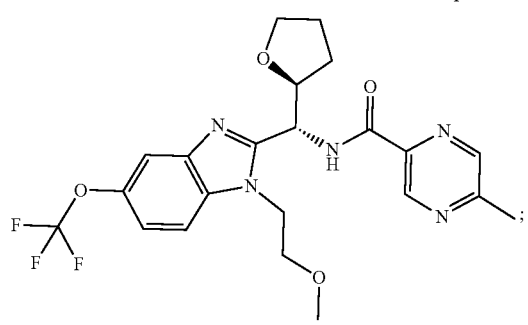
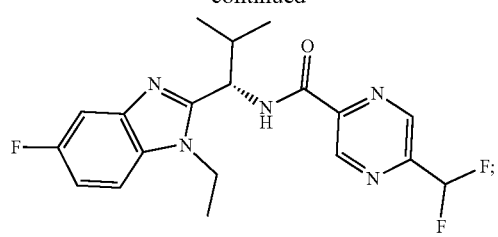
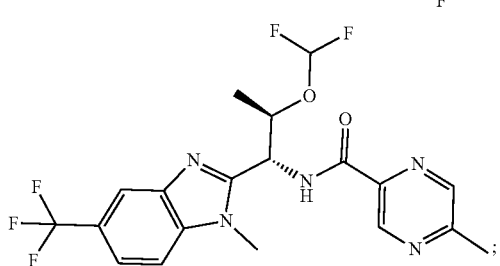
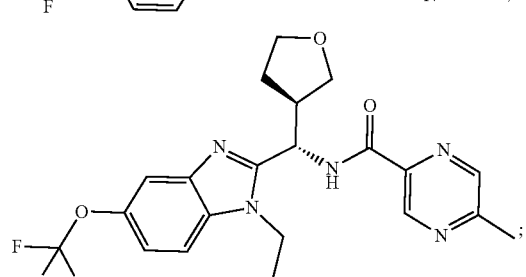
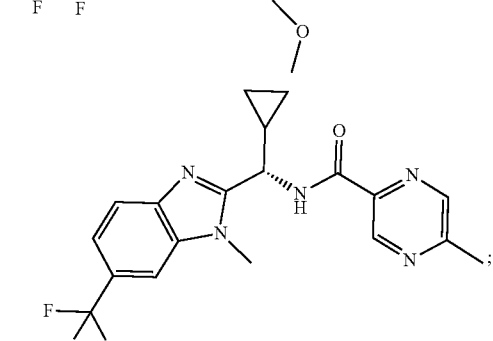
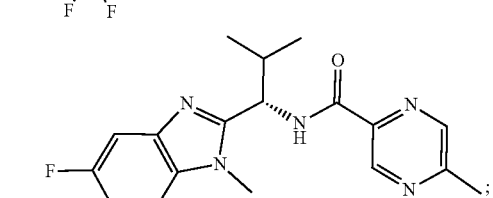
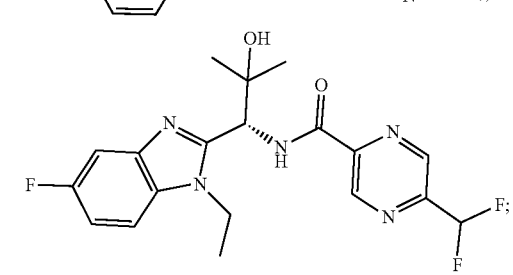

-continued
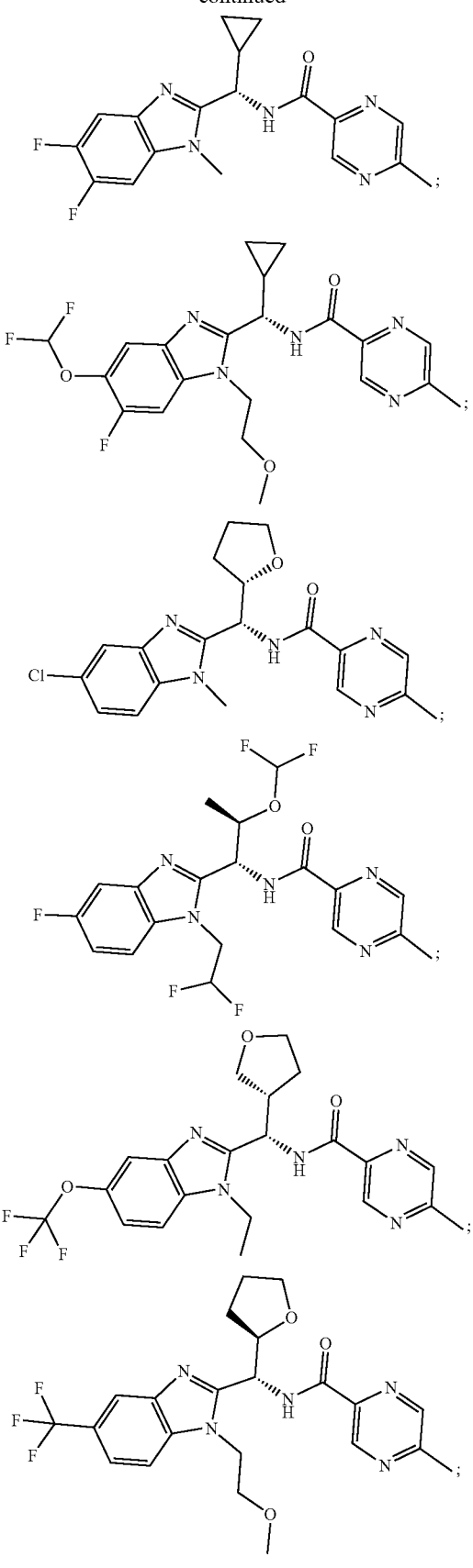
-continued
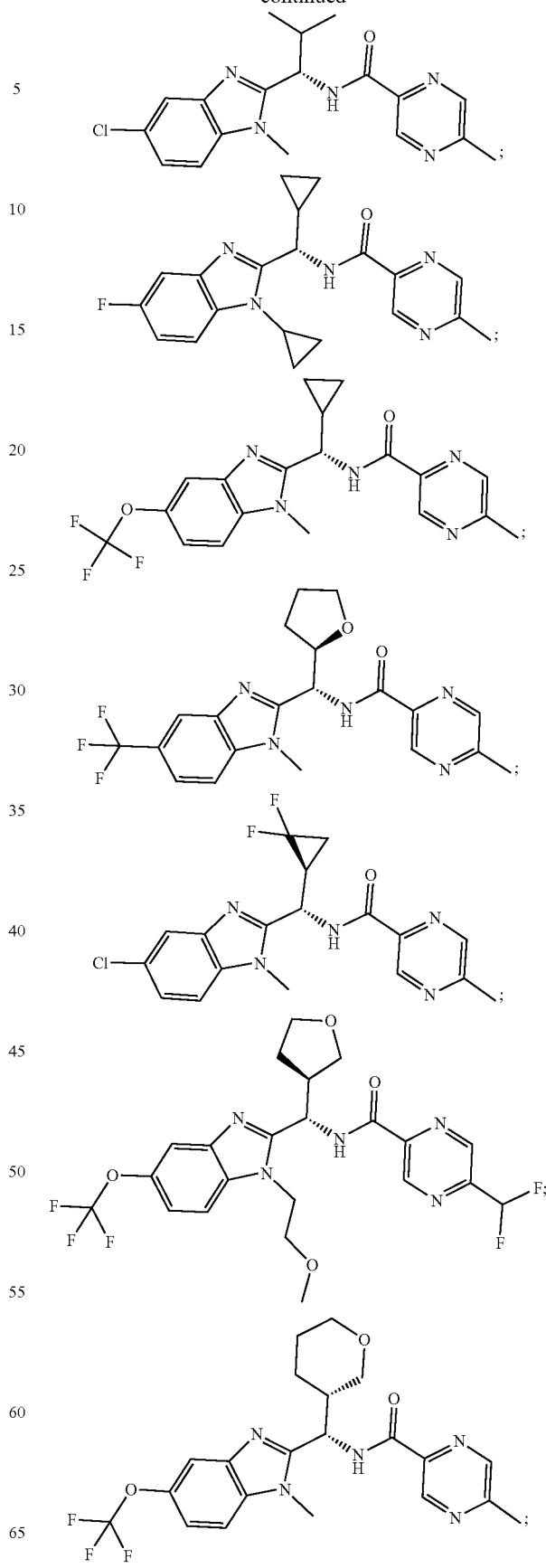

353
-continued
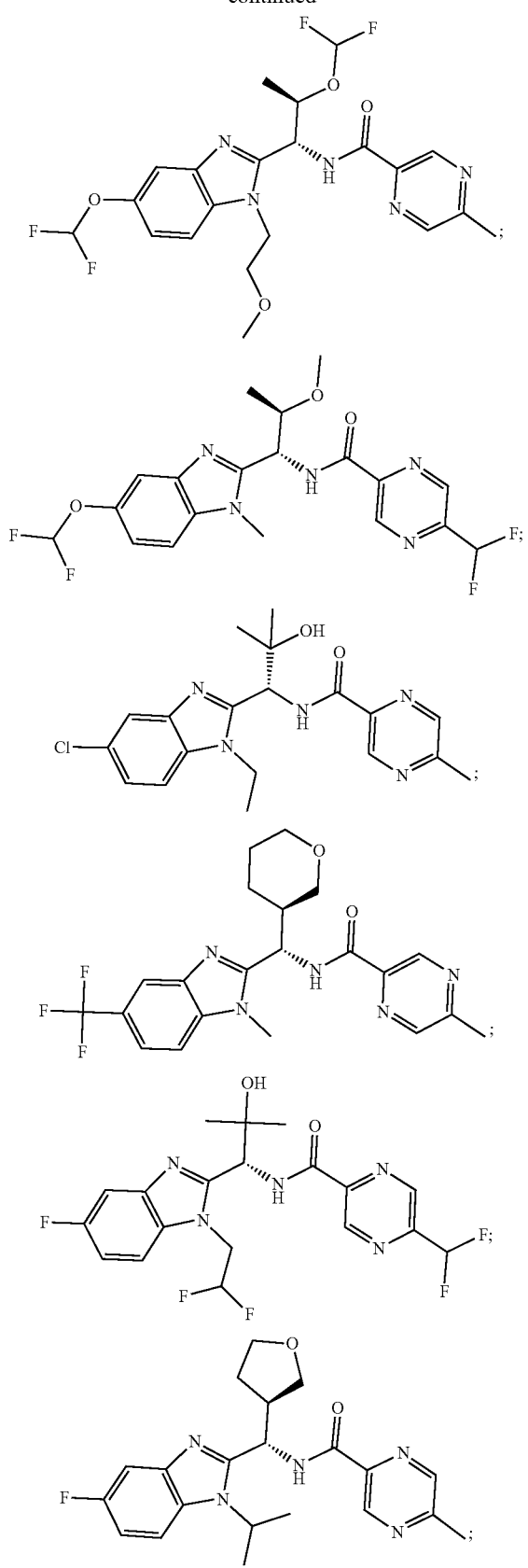
354
-continued
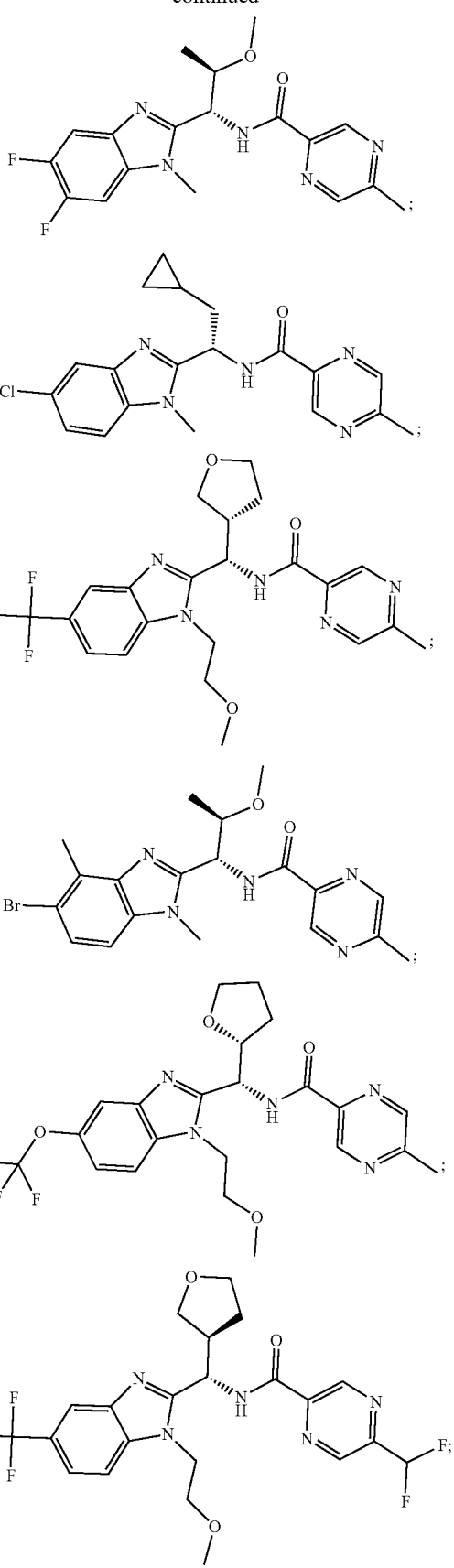

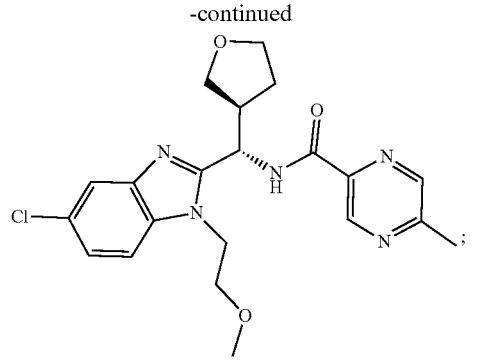
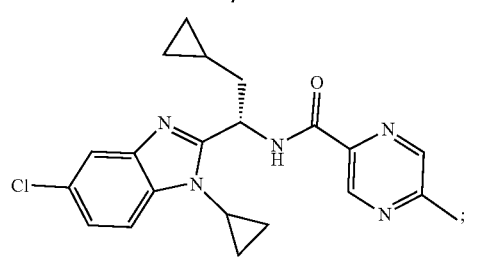
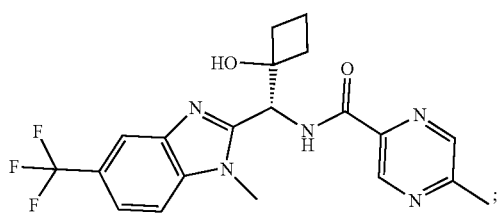
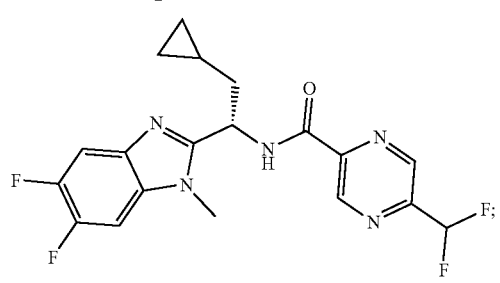
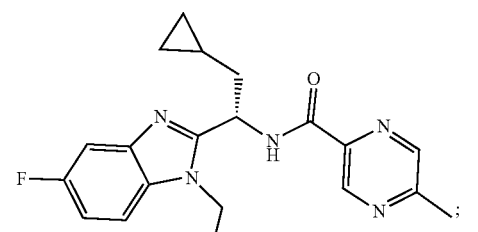
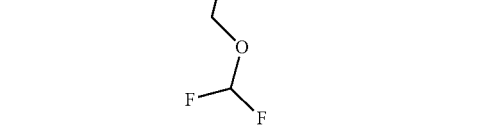
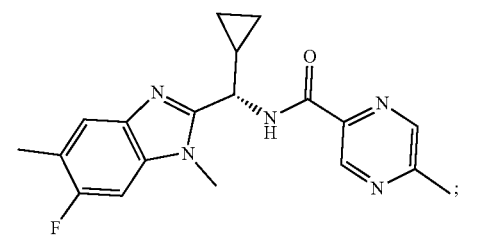
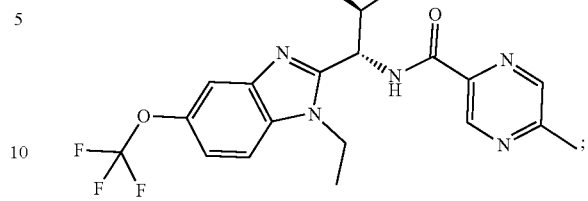
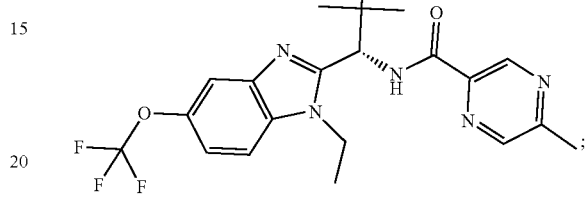
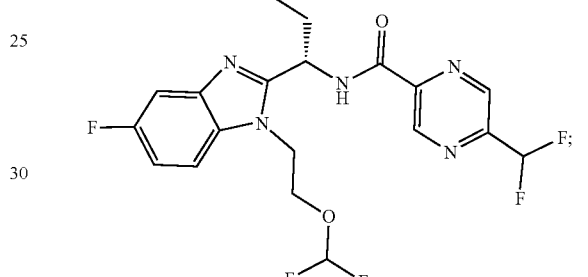
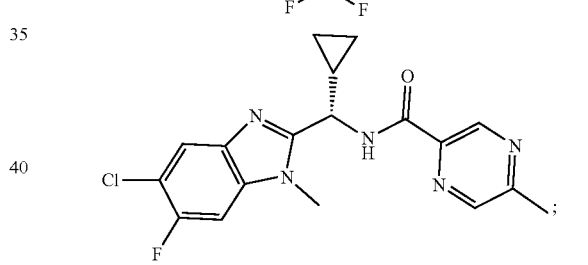
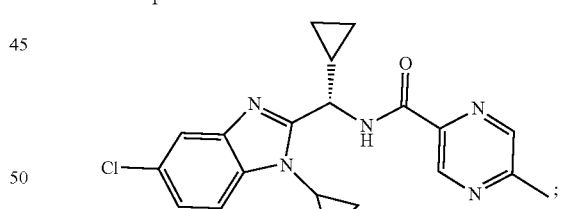
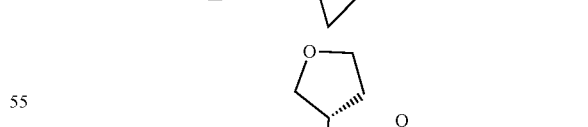
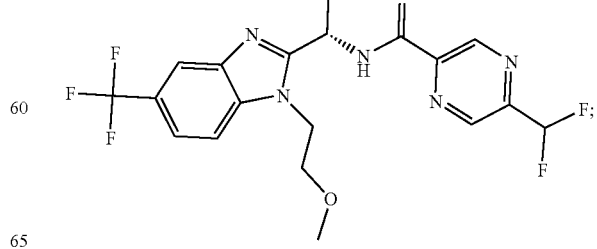

357
-continued
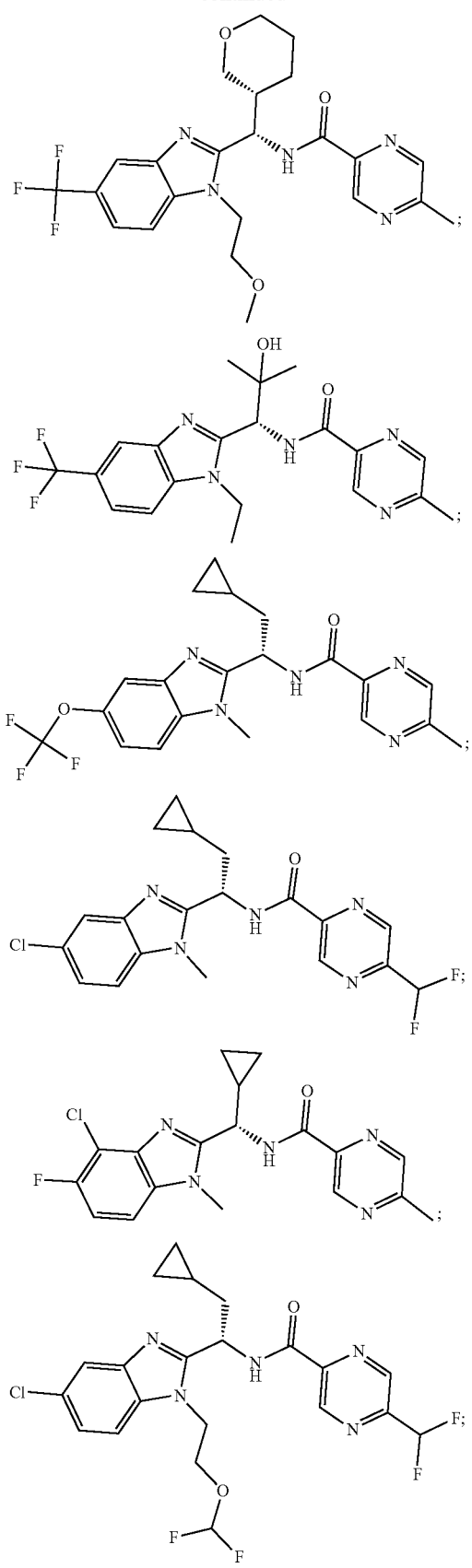
358
-continued
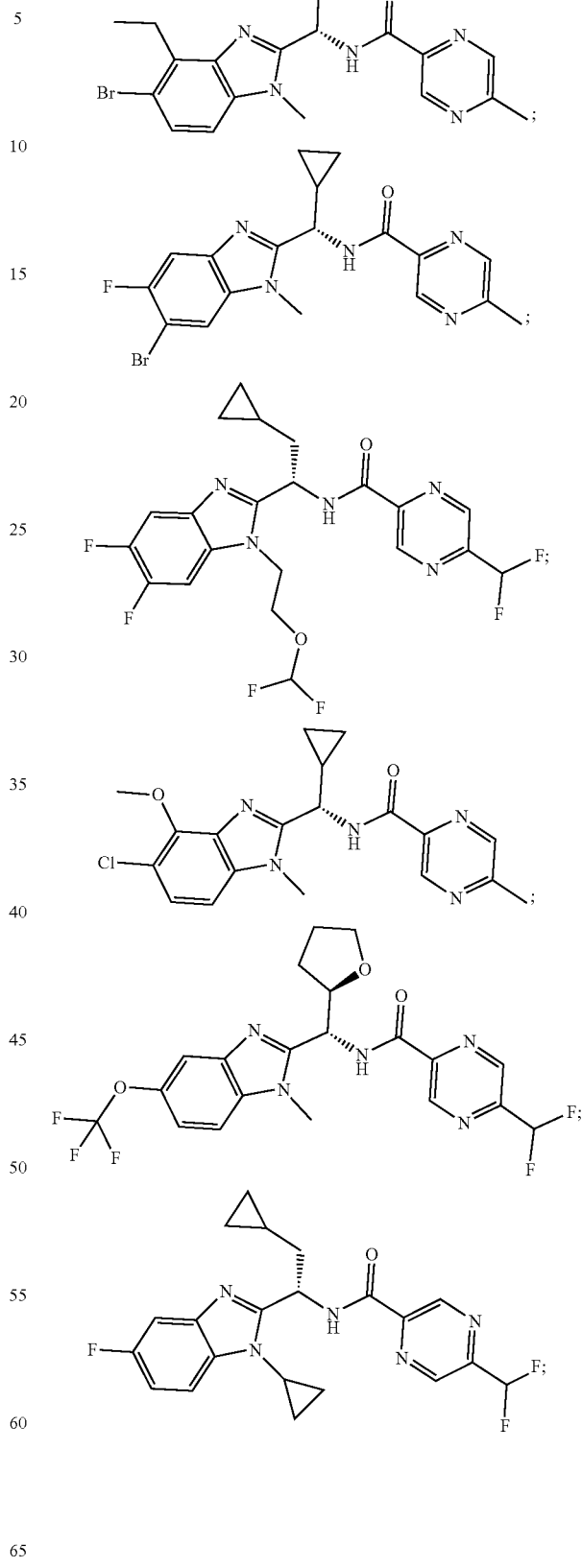

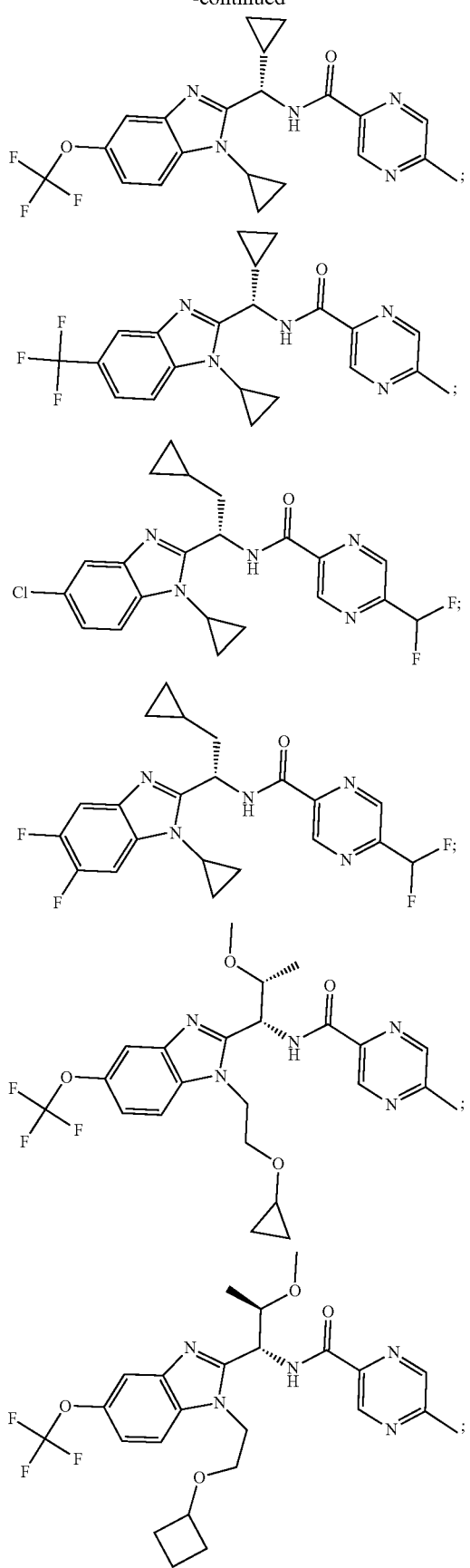
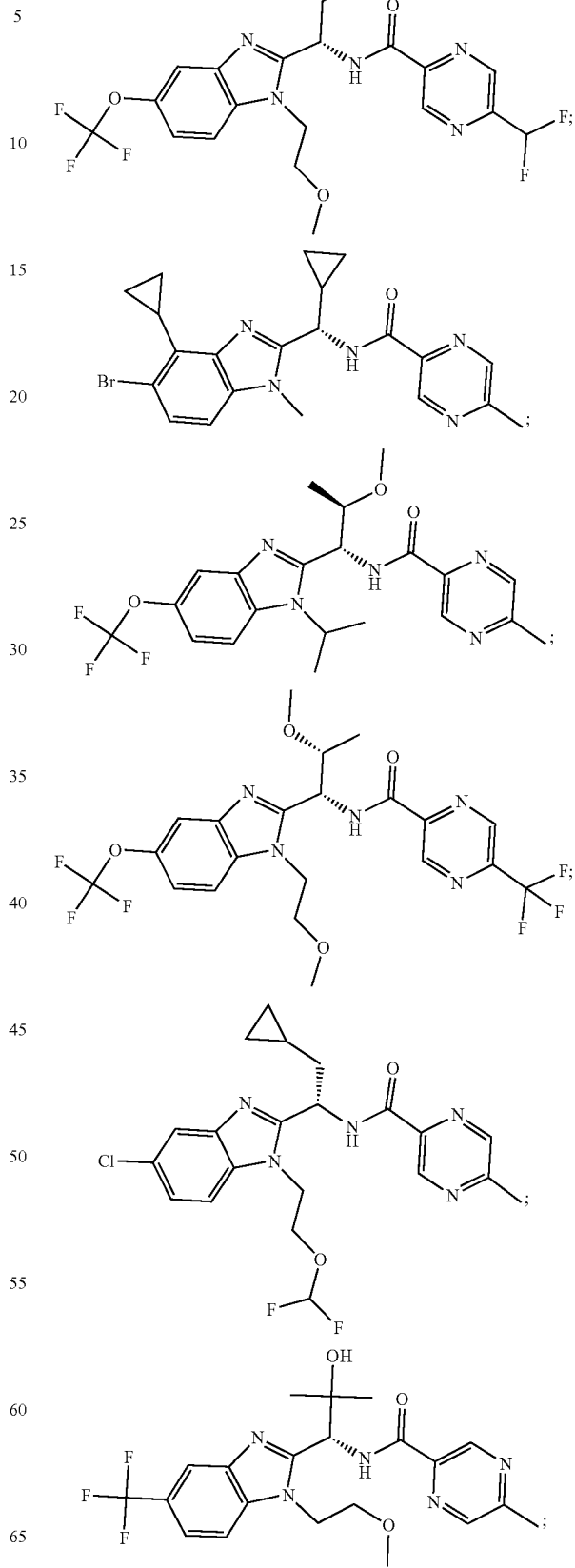

361
-continued
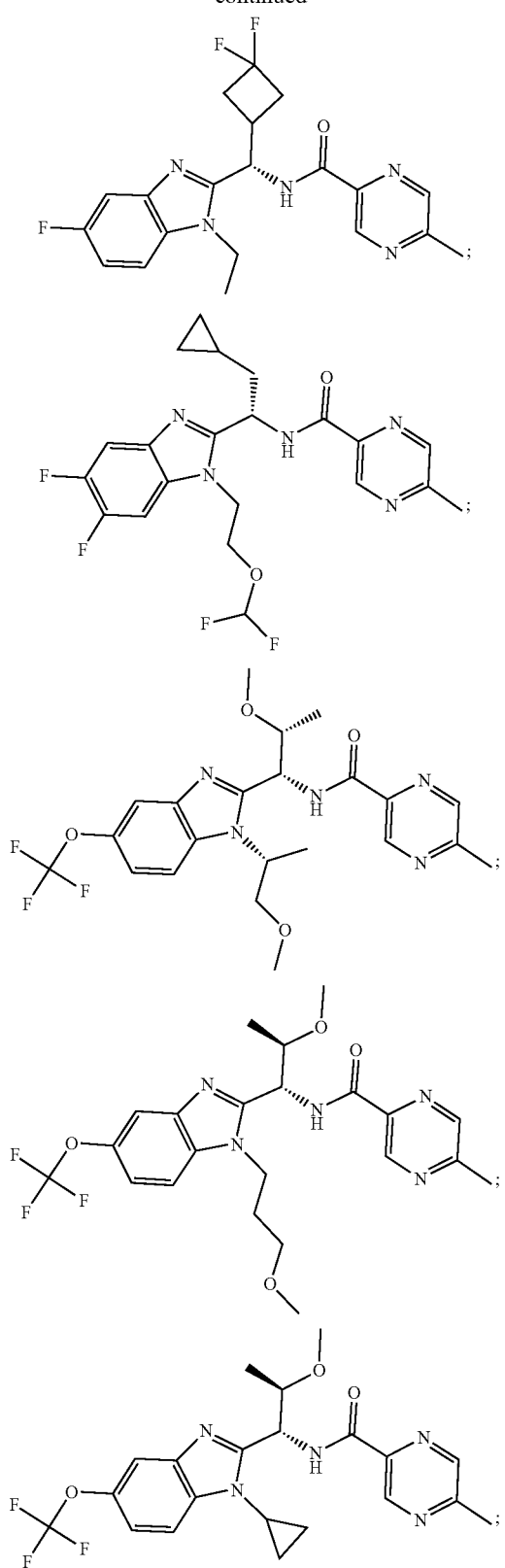
362
-continued
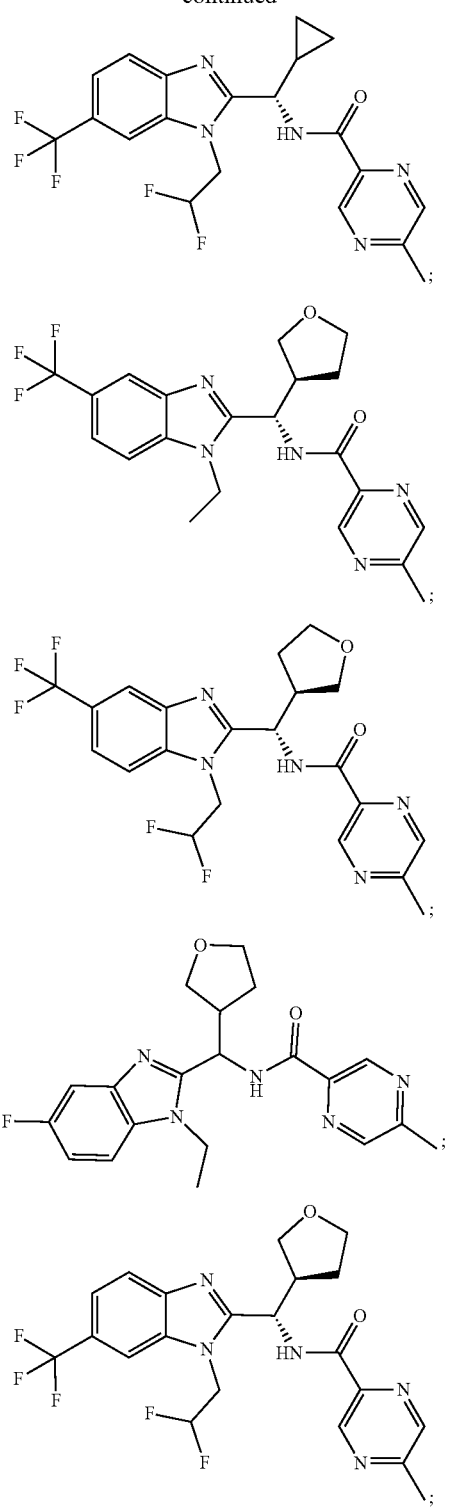

363
-continued
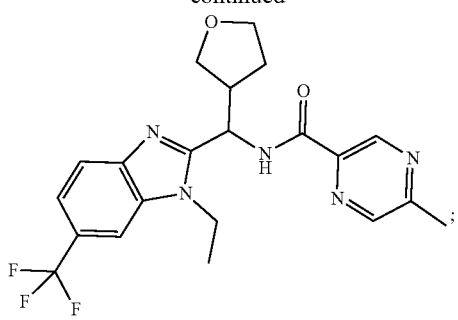
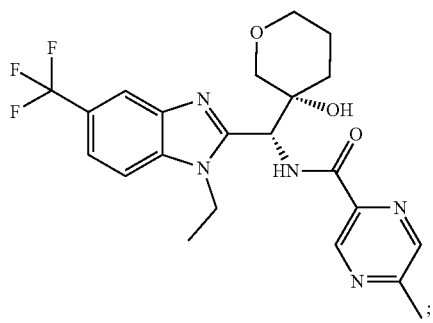
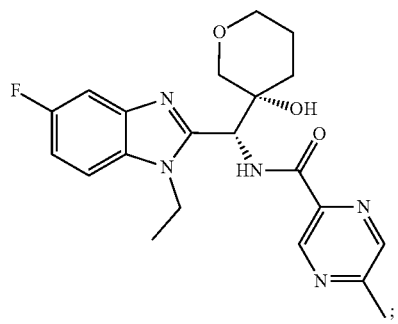
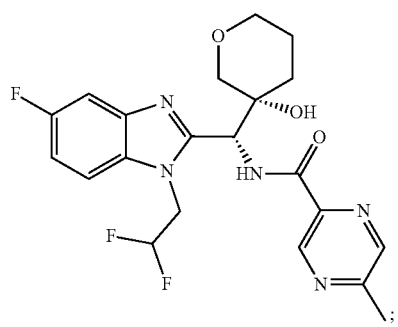
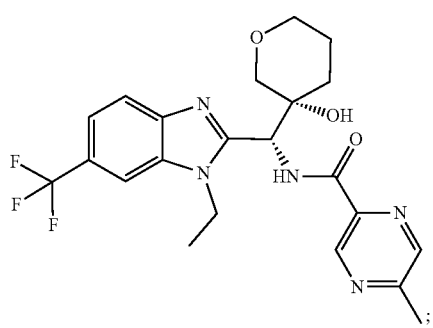
364
-continued
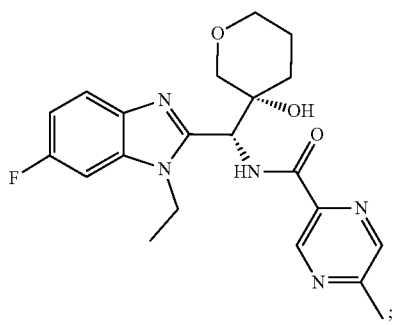
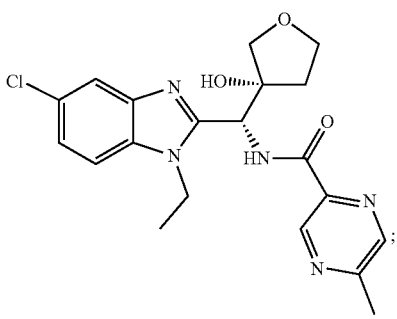
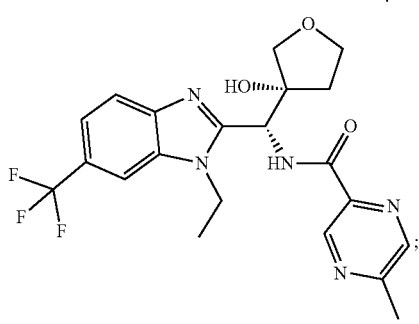
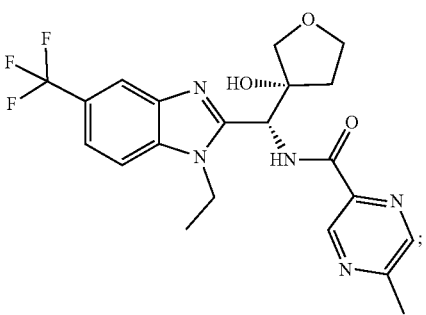
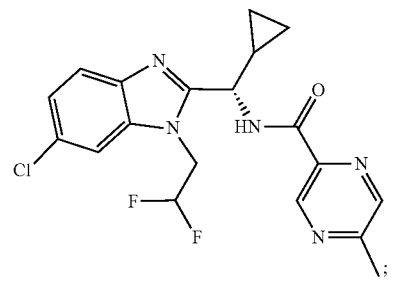

365
-continued

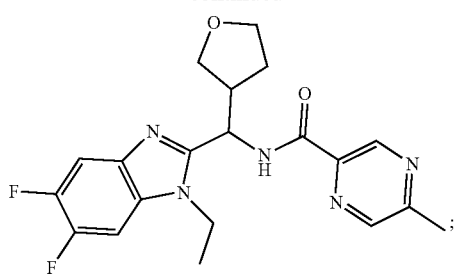

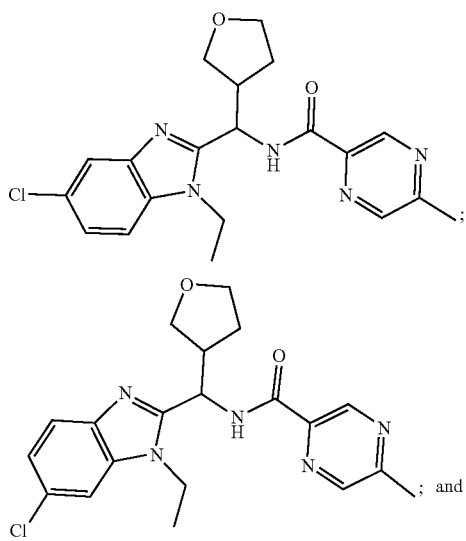

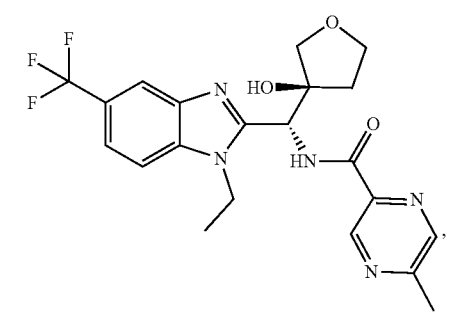

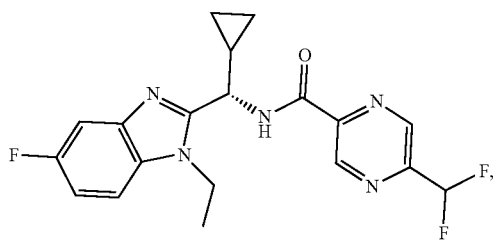 [SMILES: CCn1c([C@@H](NC(=O)c2cnc(C(F)F)cn2)C2CC2)nc2cc(F)ccc21]

or a pharmaceutically acceptable salt thereof.

2. The compound of claim 1 having the structure:

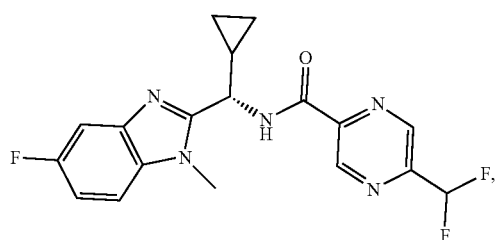

or a pharmaceutically acceptable salt thereof.

3. The compound of claim 1 having the structure:

366

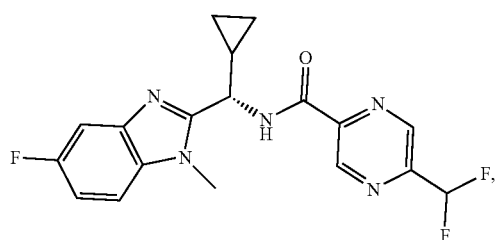

or a pharmaceutically acceptable salt thereof.

4. The compound of claim 1 having the structure:

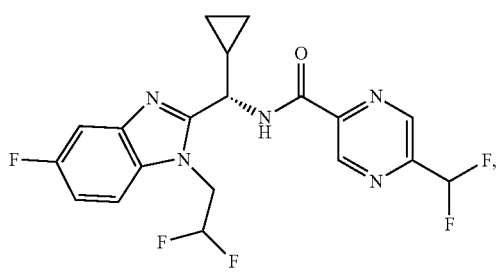

or a pharmaceutically acceptable salt thereof.

5. The compound of claim 1 having the structure:

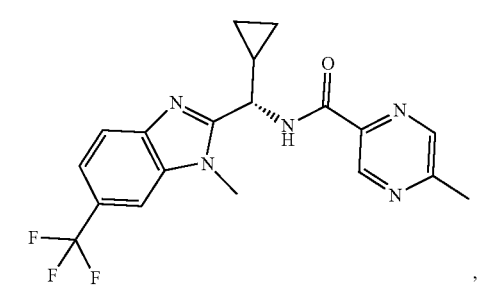 [SMILES: Cc1cnc(C(=O)N[C@H](c2nc3ccc(C(F)(F)F)cc3n2C)C2CC2)cn1]

or a pharmaceutically acceptable salt thereof.

6. A compound having the structure:

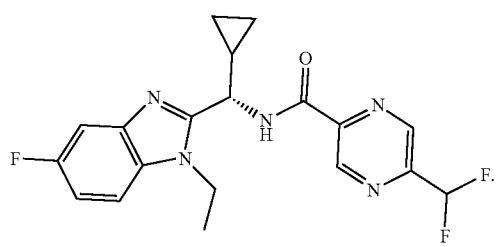

7. A compound having the structure:

367

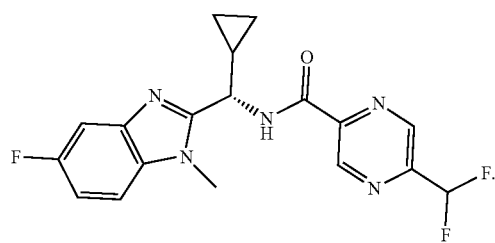 [SMILES: Cn1c([C@@H](NC(=O)c2cnc(C(F)F)cn2)C2CC2)nc2cc(F)ccc21]

8. A compound having the structure:

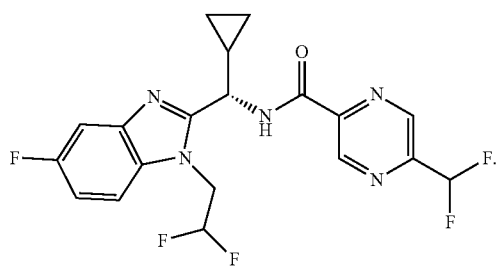 [SMILES: O=C(N[C@H](c1nc2cc(F)ccc2n1CC(F)F)C1CC1)c1cnc(C(F)F)cn1]

9. A compound having the structure:

368

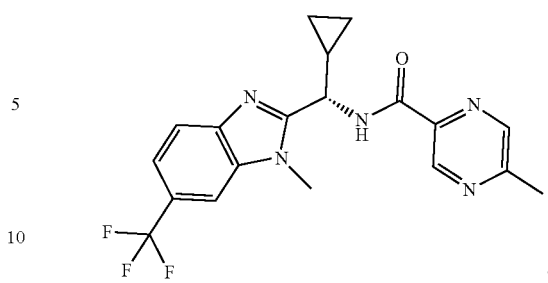

10. A pharmaceutical composition comprising the compound according to claim 1, or a pharmaceutically acceptable salt thereof.

11. A pharmaceutical composition comprising the compound according to claim 6.

12. A pharmaceutical composition comprising the compound according to claim 7.

13. A pharmaceutical composition comprising the compound according to claim 8.

14. A pharmaceutical composition comprising the compound according to claim 9.

* * * * *